United States Patent
Fang et al.

(10) Patent No.: US 8,497,278 B2
(45) Date of Patent: Jul. 30, 2013

(54) IMIDAZO[1,2-A]PYRIDINE COMPOUNDS

(75) Inventors: Qun Kevin Fang, Wellesley, MA (US);
Frank Xinhe Wu, Shrewsbury, MA (US); Paul T. Grover, Plainville, MA (US); Seth C. Hopkins, Clinton, MA (US); Una Campbell, Marlborough, MA (US); Milan Chytil, Clinton, MA (US); Kerry L. Spear, Concord, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 12 days.

(21) Appl. No.: 12/993,679

(22) PCT Filed: May 19, 2009

(86) PCT No.: PCT/US2009/044525
§ 371 (c)(1),
(2), (4) Date: Feb. 9, 2011

(87) PCT Pub. No.: WO2009/143156
PCT Pub. Date: Nov. 26, 2009

(65) Prior Publication Data
US 2011/0166146 A1 Jul. 7, 2011

Related U.S. Application Data

(60) Provisional application No. 61/054,432, filed on May 19, 2008, provisional application No. 61/054,437, filed on May 19, 2008.

(51) Int. Cl.
C07D 249/08 (2006.01)
C07D 271/06 (2006.01)
C07D 403/12 (2006.01)
A61K 31/506 (2006.01)
A61K 31/4245 (2006.01)

(52) U.S. Cl.
USPC ........... 514/275; 514/361; 514/383; 544/331; 548/262.2; 548/131

(58) Field of Classification Search
USPC ................... 544/331; 546/121; 514/300, 275, 514/361, 383; 548/262.2, 131
See application file for complete search history.

(56) References Cited

U.S. PATENT DOCUMENTS

| | | | |
|---|---|---|---|
| 4,650,796 A * | 3/1987 | George et al. | 514/212.08 |
| 5,459,132 A * | 10/1995 | Bru-Magniez et al. | 514/46 |
| 6,514,969 B2 * | 2/2003 | Briem et al. | 514/233.2 |
| 6,552,037 B2 * | 4/2003 | Cai et al. | 514/303 |
| 7,666,880 B2 * | 2/2010 | Lee et al. | 514/300 |
| 2009/0163545 A1 * | 6/2009 | Goldfarb | 514/312 |
| 2011/0281863 A1 * | 11/2011 | Bearss et al. | 514/233.2 |

FOREIGN PATENT DOCUMENTS

| | | | |
|---|---|---|---|
| EP | 0172096 A | | 2/1986 |
| EP | 0234970 A | | 9/1987 |
| EP | 1845098 A1 | | 10/2007 |
| GB | 991589 | * | 5/1965 |
| IN | 179789 | * | 12/1997 |
| WO | 02/02557 A | | 1/2002 |
| WO | 02/14313 A2 | | 2/2002 |
| WO | WO 02066477 | * | 8/2002 |
| WO | 2005/044818 A2 | | 5/2005 |
| WO | 2005/080355 A1 | | 9/2005 |
| WO | 2006/051063 A | | 5/2006 |
| WO | 2006/101455 A1 | | 9/2006 |
| WO | 2006/128692 A2 | | 12/2006 |
| WO | WO 2007067511 | * | 12/2006 |
| WO | WO 2007019416 | * | 2/2007 |
| WO | 2008/116665 A1 | | 10/2008 |

OTHER PUBLICATIONS

Nutt, et al., B. J. Psych., (2001)179: 390-396.*
Miczek, et al., J. Stud. Alcohol Suppl., Sep. 1993;11:170-9.*
Cotter, et al., Biol. Psychiatry, 2002: 51: 377-386.*
Enna, et al., Adv Pharmacol. 2006;54:1-27.*
Narwade, et al., Indian J. Chem., Section B: Org. Chem. Including Med. Chem. (2006), 45B(12), 2776-2780.*
Geronikaki, et al., Bioorg. & Med. Chem. (2004), 12(24), 6559-6568.*
Muro, et al., Yakugaku Zasshi (1977), 97(8), 835-48.*
Almirante, et al., J. Med. Chem. (1965), 8(3), 305-12.*
Kerns, Edward et al, Drug-like Properties: Concepts, Structure Design and Methods: from ADME to Toxicity Optimization, (Elsevier, 2008) pp. 92-93.*
Goosen et al., Pharm. Res., vol. 19, No. 1, 13-19 (Jan. 2002).*
Fourie, International J. Pharmaceutics, vol. 279, Nos. 1-2, 26, Jul. 2004, 59-66.*

(Continued)

*Primary Examiner* — Susanna Moore
*Assistant Examiner* — Cecilia M Jaisle
(74) *Attorney, Agent, or Firm* — Heslin Rothenberg Farley & Mesiti P.C.

(57) ABSTRACT

Imidazo[1,2-a]pyridines are disclosed. Compounds of the invention are useful therapeutic agents and their inclusion in pharmaceutical formulations and use in methods of treatment are disclosed. Many of the compounds disclosed herein may be represented by the following generic formula:

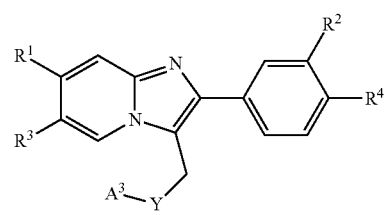

in which Y is a direct bond or heteroatom and $A^3$ is usually a nitrogenous heterocycle.

10 Claims, No Drawings

OTHER PUBLICATIONS

Edwards, J. Med. Chem. 39 (1996), pp. 1112-1124.*
Rautio, Eur. J. Pharm. Sci., 11:157-163 (2000).*
Marcelo Zaldini Hernandes et al., "Halogen Atoms in the Modern Medicinal Chemistry: Hints for the Drug Design" http://azevedolab.dominiotemporario.com/doc/Hernandes_CDT_11_3.pdf.*
Purser et al., Chem. Soc. Rev., 2008, 37, 320-330, http://pubs.rsc.org/en/content/articlepdf/2008/CS/B610213C.*
Hagmann, J. Med. Chem., Aug. 14, 2008;51(15):4359-69, http://pubs.acs.org/doi/pdfplus/10.1021/jm800219f.*
Enguehard, Cecile et al: "Synthesis of diaryl-substituted imidazo[1,2-a]pyridines designed as potential aromatase inhibitors", Chemical & Pharmaceutical Bulletin, 48 (7), 935-940 CODEN: CPTBAL; ISSN: 0009-2363, 2000.
Collins, Jon L. et al: "N-(2-Benzoylphenyl)-L-tyrosine PPAR.gamma. Agonists. 2. Structure-Activity Relationship and Optimization of the Phenyl Alkyl Ether Moiety", Journal of Medicinal Chemistry, 41(25), 5037-5054, 1998.
Zhai, Zin et al.: "Synthesis and antibacterial activity of novel oxazolidinone analogs containing substituted thiazole/fused-bicyclic groups", Databas Caplus [Online] Chemical Abstracts Service, Columbus, Ohio, US, 2006.
Barlin, Gordon B et al: "Imidazo[1,2-a]pyridazines. X. Syntheses and central nervous system activities of some 3-(acetamido, benzamido, substituted benzamido or dimethylamino)methyl-2-(phenyl or substituted phenyl)-6-(halo, alkylthio, alkoxy, phenylthio, phenoxy, behzylthio or benzyloxy)imidazo[1,2-b]pyridazines", Database Caplus [Online] Chemical Abstracts Service, Columbus, Ohio, US, 1992.
International Search Report for PCT/US2009/044525 dated Dec. 1, 2009.

* cited by examiner

IMIDAZO[1,2-A]PYRIDINE COMPOUNDS

CROSS REFERENCE TO RELATED APPLICATIONS

This application is a national phase filing under 35 U.S.C. §371 of PCT International Application PCT/US2009/044525, filed May 19, 2009, and published under PCT Article 21(2) in English as WO 2009/143156 on Nov. 26, 2009. PCT/US2009/044525 claimed priority under 35 U.S.C. §119 (e) to U.S. Provisional Patent Application No. 61/054,432 filed on May 19, 2008 and U.S. Provisional Patent Application No. 61/054,437 filed on May 19, 2008, the disclosures of which are incorporated herein by reference in their entirety for all purposes.

FIELD OF THE INVENTION

The invention relates to imidazo[1,2-a]pyridines and the use of such compounds in treating and preventing various conditions, including anxiety.

BACKGROUND OF THE INVENTION

Gamma-aminobutyric acid (GABA) is the major inhibitory neurotransmitter within the central nervous system (CNS). $GABA_A$ receptors are ligand gated ion channels that are made up from a large range of different subunits (α1-6, β1-3, γ1-3, δ, ε, π, and θ). Each receptor complex comprises five subunits, with the dominant in vivo combination thought to be 2α2β1γ. Several therapeutic agents exert their effects by modulating this receptor complex, but adverse effects, particularly sedation, are common and, in part, a consequence of poor subunit selectivity. The existence of a large number of different GABA-A receptors resulting from subunit heterogeneity indicates that there are excellent prospects for developing more selective drugs for the treatment of CNS disorders with reduced side effects. To date, the majority of the ligands that have been identified bind to α subunits that are sensitive to classical benzodiazepines, namely α1, β2, α3 and α5. Without exception, these ligands bind allosterically to the receptor, rather than by occupying the orthosteric (GABA) site and can exert a range of pharmacological activities including agonists, antagonists, partial agonists, and inverse agonists.

Agents that bind or interact with the modulatory sites on the $GABA_A$ receptor complex, such as the benzodiazepine receptor, can have either an enhancing effect on the action of GABA, i.e. a positive modulatory effect of the receptor (agonists, partial agonists), an attenuating effect on the action of GABA, i.e. negative modulation of the receptor (inverse agonists, partial inverse agonists), or they can block the effect of both agonists and inverse agonists by competitive block (antagonists or ligands without intrinsic activity).

SUMMARY OF THE INVENTION

In various embodiments, the present invention provides a compound having a structure according to Formula I:

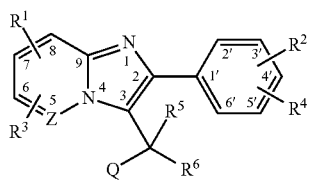

(I)

In Formula I, $R^1$, $R^2$, $R^3$ and $R^4$ are each independently selected from H, D, halogen, hydroxyl, dialkylamino, cyano, sulfonamide, acyl, substituted or unsubstituted alkyl, substituted or unsubstituted alkoxy, substituted or unsubstituted heterocycloalkyl, substituted or unsubstituted aryl and substituted or unsubstituted heteroaryl. The symbols $R^5$ and $R^6$ represent members independently selected from H; F; hydroxyl; substituted or unsubstituted alkoxy and lower alkyl. Q is selected from:

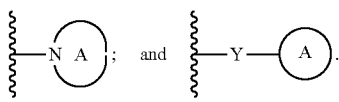

Ring system A is an optionally substituted 4, 5, 6 or 7 member monocyclic or 8, 9, 10, 11 or 12 member bicyclic ring comprising 0, 1, 2, 3 or 4 heteroatoms independently selected from N, O and S. The symbol X represents O, S or $NR^7$. $R^7$ is selected from H; substituted or unsubstituted alkyl; substituted or unsubstituted heteroalkyl; substituted or unsubstituted cycloalkyl; substituted or unsubstituted heterocycloalkyl; substituted or unsubstituted aryl and substituted or unsubstituted heteroaryl. Y is a member selected from a bond, $(CR^8R^9)_n$, O, S, $NR^{10}R^{11}$, S(O), $S(O)_2$, $S(O)pNR^{10}R^{11}$, $(CR^8R^9)_nG(CR^8R^9)_m$. G is a member selected from a bond and O. The indeces m and n are independently selected integers from 0 to 4. Each $R^8$, $R^9$ and $R^{10}$ are independently selected from H, D, substituted or unsubstituted alkyl, acyl, $SO_2R^{8a}$, $OR^{8a}$, $COOR^{8a}$, and $CONR^{8a}R^{8b}$. $R^{8a}$ and $R^{8b}$ are independently selected from H, D, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. A member selected from $R^8$ and $R^9$, $R^{8a}$ and $R^{8b}$ and a combination thereof are optionally joined in a ring. The index n is the integer 0, 1, 2, 3 or 4. $R^8$, $R^9$ and $R^{10}$ are independently H, D, substituted or unsubstituted alkyl, acyl, $SO_2R^{8a}$, $OR^{8a}$, $COOR^{8a}$, or $CONR^{8a}R^{8b}$. The symbols $R^{8a}$ and $R^{8b}$ independently represent H, D, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{11}$ is a bond or NH. Z is $CR^{12}$ or N. $R^{12}$ is H; substituted or unsubstituted alkyl; substituted or unsubstituted heteroalkyl; substituted or unsubstituted cycloalkyl; substituted or unsubstituted heterocycloalkyl; substituted or unsubstituted aryl or substituted or unsubstituted heteroaryl. The compounds of the present invention are capable of modulating the benzodiazepine receptor. In various embodiments, the compounds of the present invention are capable of modulating $GABA_A$ receptor subtypes. In some embodiments, the compounds of the present invention are capable of selectively modulating $GABA_A$ receptor subtypes.

In various embodiments, the invention also provides salts of the compounds of Formula I, including pharmaceutically acceptable salts, pharmaceutical formulations including the salts and methods of using the salts and pharmaceutical formulations including the salts to treat, ameliorate and prevent various diseases, syndromes and conditions.

In various embodiments, the present invention also provides pharmaceutical compositions comprising a pharmaceutically acceptable carrier and any compound described herein.

The present invention also provides methods for treating or preventing a disease or condition. Exemplary conditions include, but are not limited to anxiety disorders, psychiatric disorders, convulsive disorders, aggressive behavior, muscle spasms or tension, depressive or bipolar disorders, cognitive disorders, sleeping disorders, neurodegenerative eye diseases, neurodegeneration, pain, schizophrenia, emesis, and eating disorders, comprising administering to a patient a therapeutically effective amount of any compound described herein.

Other embodiments, objects and advantages of the present invention are set forth in the detailed description that follows

DETAILED DESCRIPTION OF THE INVENTION

I. Definitions

Where substituent groups are specified by their conventional chemical formulae, written from left to right, they optionally encompass substituents resulting from writing the structure from right to left, e.g., —$CH_2$O— optionally also recites —O$CH_2$—.

The symbol "H" represents hydrogen and, optionally, deuterium and tritium. When H is a component of a chemical formula it represents deuterium and tritium as well. Replacement of hydrogen with its heavier isotopes is well within the abilities of those of skill in the art.

The term "alkyl," by itself or as part of another substituent, means, unless otherwise stated, a straight or branched chain, or cyclic hydrocarbon radical, or combination thereof, which can be fully saturated, mono- or polyunsaturated and can include mono-, di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butyryl, and the higher homologs and isomers. Alkyl groups that are limited to hydrocarbon groups are termed "homoalkyl". "Lower alkyl" refers to alkyl groups having 1, 2, 3, 4, 5, 6, 7 or 8 carbon atoms. Examples of lower alkyl groups include methyl, ethyl, propyl, isopropyl, butyl, s- and t-butyl and the like.

The term "alkenyl" by itself or as part of another substituent is used in its conventional sense, and refers to a radical derived from an alkene, as exemplified, but not limited by, substituted or unsubstituted vinyl and substituted or unsubstituted propenyl. Typically, an alkenyl group will have from 1 to 24 carbon atoms, with those groups having from 1 to 10 carbon atoms being generally preferred.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkylene" is a short chain group, generally having, for example, 1, 2, 3, 4, 5, 6, 7 or 8 carbon atoms.

The terms "alkoxy," "alkylamino" and "alkylthio" (or thioalkoxy) are used in their conventional sense, and refer to those alkyl groups attached to the remainder of the molecule via an oxygen atom, a nitrogen atom, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P, B, and S, and wherein the nitrogen, phosphorus and sulfur atoms can optionally be oxidized and the nitrogen heteroatom can optionally be quaternized. The heteroatom(s) O, N and S and Si can be placed at any interior position of the heteroalkyl group or at the position at which the alkyl group is attached to the remainder of the molecule. Examples of heteroalkyl groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms can be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$ —S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. A "cycloalkyl" or "heterocycloalkyl" substituent can be attached to the remainder of the molecule directly or through a linker, wherein the linker is preferably alkylene. An cycloalkyl or heterocycloalkyl group can be attached to the remainder of the molecule through a linkage to an atom that forms part of the cycloalkyl or heterocycloalkyl ring or through a linkage to a substituent of the cycloalkyl or heterocycloalkyl ring. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "halo" or "halogen," by itself or as part of another substituent, means, unless otherwise stated, a fluorine, chlorine, bromine, or iodine atom. Additionally, terms such as "haloalkyl," are meant to include monohaloalkyl, polyhaloalkyl and perhaloalkyl. For example, the term "halo($C_1$-$C_4$) alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (e.g., 1, 2 or 3 rings), which are fused together, linked covalently or a combination thereof. The term "heteroaryl" refers to aryl groups that containing 1, 2, 3, 4, 5 or 6 heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. An aryl or heteroaryl group can be attached to the remainder of the molecule through a linkage to an atom that forms part of the aryl or heteroaryl ring or through a linkage to a substituent of the aryl or heteroaryl ring. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) optionally includes both aryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

"Ring" or "ring system" as used herein means a substituted or unsubstituted cycloalkyl, substituted or unsubstituted heterocycloalkyl, substituted or unsubstituted aryl, or substituted or unsubstituted heteroaryl. A ring can include fused ring moieties. The number of atoms in a ring is typically defined by the number of members in the ring. For example, a "5- to 8-member ring" means there are 5, 6, 7 or 8 atoms in the encircling arrangement. The ring optionally includes at least one heteroatom. Thus, the term "5- to 8-member ring" includes heterocycloalkyl and heteroaryl systems, for example, pyridinyl and piperidinyl. The term "ring" further includes a ring system comprising more than one "ring", wherein each "ring" is independently defined as above.

Each of the above terms (e.g., "alkyl," "heteroalkyl," "aryl," "arylalkyl," "heteroaryl," "heteroarylalkyl") includes both substituted and unsubstituted forms of the indicated radical. Exemplary substituents for each type of radical are provided below. It will be understood that "substitution", "substituted" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

The term "perfluoro lower alkyl" refers to a lower alkyl fluorocarbon in which all hydrogen atoms directly attached to the carbon atoms are replaced by fluorine.

The term "lower alkyl sulfonamido" refers to a residue of formula (lower alkyl-SO$_2$NR—), wherein R is hydrogen or a $C_1$ to $C_{20}$ hydrocarbon, and the point of attachment is through N.

Two of the substituents on adjacent atoms of the aryl or heteroaryl ring can optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed can optionally be replaced with a double bond. Alternatively, two of the substituents on adjacent atoms of the aryl or heteroaryl ring can optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, D, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems" can include aromatic as well as nonaromatic rings. Examples of "fused ring systems" are naphthalenes, indoles, quinolines, chromenes and the like.

As used herein, the term "heteroatom" includes oxygen (O), nitrogen (N), sulfur (S) and silicon (Si), boron (B) and phosphorus (P).

The symbol "R" is a general abbreviation that represents a substituent group, e.g., one that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups. Superscripted variants, such as R', R", and the like, are used similarly.

Certain compounds of the present invention can exist in unsolvated forms as well as solvated forms, including hydrated forms. Certain compounds of the present invention can exist in multiple crystalline or amorphous forms ("polymorphs"). In general, all physical forms are of use in the methods contemplated by the present invention and are intended to be within the scope of the present invention. "Compound or a pharmaceutically acceptable salt, hydrate, polymorph or solvate of a compound" intends the inclusive meaning of "or", in that materials meeting more than one of the stated criteria are included, e.g., a material that is both a salt and a solvate is encompassed.

Many of the compounds described herein contain one or more asymmetric centers and can thus give rise to enantiomers, diastereomers, and other stereoisomeric forms that can be defined, in terms of absolute stereochemistry, as (R)- or (S)-. The present invention is meant to include all such possible isomers, as well as their racemic and optically pure forms. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, *J. Chem. Ed.*, 62, 114-120 (1985): Solid and broken wedges are used to denote the absolute configuration of a chiral element; solid and broken bold lines are geometric descriptors indicating the relative configuration shown but denoting racemic character; and wedge outlines and dotted or broken lines denote enantiomerically pure compounds of indeterminate absolute configuration. Thus, the formula X encompasses both of the pure enantiomers of that pair:

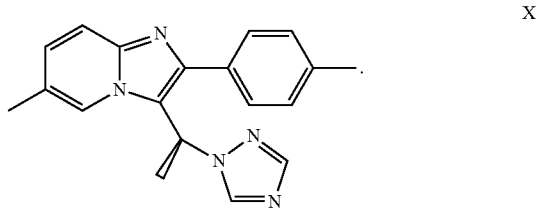

The compounds falling within the foregoing parent genus and their subgenera can be useful as inhibitors of the neurotransmitter Gamma-aminobutyric acid (GABA).

It will be recognized that the compounds of this invention can exist in radiolabeled form, i.e., the compounds can contain one or more atoms containing an atomic mass or mass number different from the atomic mass or mass number usually found in nature. Radioisotopes of hydrogen, carbon, phosphorous, fluorine, chlorine and iodine include $^3$H, D, $^{14}$C, $^{35}$S, $^{18}$F, $^{36}$Cl and $^{125}$I, respectively. Compounds that contain those radioisotopes and/or other radioisotopes of other atoms are within the scope of this invention. Tritiated, i.e., $^3$H, D, and carbon-14, i.e., $^{14}$C, radioisotopes are particularly preferred for their ease in preparation and detectability. Radiolabeled compounds of this invention can generally be prepared by methods well known to those skilled in the art. Conveniently, such radiolabeled compounds can be prepared by carrying out the procedures disclosed in the Examples by substituting a readily available radiolabeled reagent for a non-radiolabeled reagent. Because of the high affinity for the GABA receptor, radiolabeled compounds of the invention are useful for GABA assays.

The phrase "therapeutically effective amount" as used herein means that amount of a compound, material, or composition comprising a compound of the present invention which is effective for producing some desired therapeutic effect by inhibition of DAAO in at least a sub-population of cells in an animal and thereby blocking the biological consequences of that pathway in the treated cells, at a reasonable benefit/risk ratio applicable to any medical treatment.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein.

In various embodiments, the compounds of the invention also include pharmaceutically acceptable salts of the structures set forth herein. The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

When a residue is defined as "O−", then the formula is meant to optionally include an organic or inorganic cationic counterion. Preferably, the resulting salt form of the compound is pharmaceutically acceptable. The radicals —COOH, D, SO$_3$H include both the protonated and salt forms of the acid.

The neutral forms of the compounds are optionally regenerated by contacting the salt with a base or acid and isolating the parent compound in the conventional manner. The parent form of the compound can differ from the various salt forms with respect to certain physical properties, e.g., solubility in polar solvents. For exemplary compounds of the invention, the salts are equivalent to the parent form of the compound in terms of their general therapeutic utility.

The term "neurological disorder" refers to any condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. Schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

"Somatic" pain, as described above, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

"Neuropathic pain" is a heterogeneous group of neurological conditions that result from damage to the nervous system. "Neuropathic" pain, as described above, refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis. Other types of pain that are meant to be included in the definition of neuropathic pain include pain from spinal cord injury, neuropathic cancer pain, HIV/AIDS induced pain, phantom limb pain, and complex regional pain syndrome. In a preferred embodiment, the compounds of the invention are of use for treating neuropathic pain. An exemplary compound of use in this embodiment is a compound according to Formula I in which each of R$^1$-R$^3$ is hydrogen, and R$^4$ is selected such that the compound is a free acid or salt thereof.

Common clinical features of neuropathic pain include sensory loss, allodynia (non-noxious stimuli produce pain), hyperalgesia and hyperpathia (delayed perception, summation, and painful aftersensation). Pain is often a combination of nociceptive and neuropathic types, for example, mechanical spinal pain and radiculopathy or myelopathy.

"Acute pain" is the normal, predicted physiological response to a noxious chemical, thermal or mechanical stimulus typically associated with invasive procedures, trauma and disease. It is generally time-limited, and can be viewed as an appropriate response to a stimulus that threatens and/or produces tissue injury. "Acute pain", as described above, refers to pain which is marked by short duration or sudden onset.

"Chronic pain" occurs in a wide range of disorders, for example, trauma, malignancies and chronic inflammatory diseases such as rheumatoid arthritis. Chronic pain usually lasts more than about six months. In addition, the intensity of chronic pain can be disproportionate to the intensity of the noxious stimulus or underlying process. "Chronic pain", as described above, refers to pain associated with a chronic disorder, or pain that persists beyond resolution of an underlying disorder or healing of an injury, and that is often more intense than the underlying process would predict. It may be subject to frequent recurrence.

"Inflammatory pain" is pain in response to tissue injury and the resulting inflammatory process. Inflammatory pain is adaptive in that it elicits physiologic responses that promote healing. However, inflammation may also affect neuronal function. Inflammatory mediators, including $PGE_2$ induced by the COX2 enzyme, bradykinins, and other substances, bind to receptors on pain-transmitting neurons and alter their function, increasing their excitability and thus increasing pain sensation. Much chronic pain has an inflammatory component. "Inflammatory pain", as described above, refers to pain which is produced as a symptom or a result of inflammation or an immune system disorder.

"Visceral pain", as described above, refers to pain which is located in an internal organ.

"Mixed etiology" pain, as described above, refers to pain that contains both inflammatory and neuropathic components.

"Dual mechanism" pain, as described above, refers to pain that is amplified and maintained by both peripheral and central sensitization.

"Causalgia", as described above, refers to a syndrome of sustained burning, allodynia, and hyperpathia after a traumatic nerve lesion, often combined with vasomotor and sudomotor dysfunction and later trophic changes.

"Central" pain, as described above, refers to pain initiated by a primary lesion or dysfunction in the central nervous system.

"Hyperesthesia", as described above, refers to increased sensitivity to stimulation, excluding the special senses.

"Hyperpathia", as described above, refers to a painful syndrome characterized by an abnormally painful reaction to a stimulus, especially a repetitive stimulus, as well as an increased threshold. It can occur with allodynia, hyperesthesia, hyperalgesia, or dysesthesia.

"Dysesthesia", as described above, refers to an unpleasant abnormal sensation, whether spontaneous or evoked. Special cases of dysesthesia include hyperalgesia and allodynia, "Hyperalgesia", as described above, refers to an increased response to a stimulus that is normally painful. It reflects increased pain on suprathreshold stimulation.

"Allodynia", as described above, refers to pain due to a stimulus that does not normally provoke pain.

The term "Diabetic Peripheral Neuropathic Pain" (DPNP, also called diabetic neuropathy, DN or diabetic peripheral neuropathy) refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

The term "Post-Herpetic Neuralgia", also called "Postherpetic Neuralgia" (PHN), is a painful condition affecting nerve fibers and skin. It is a complication of shingles, a second outbreak of the varicella zoster virus (VZV), which initially causes chickenpox.

The term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

The term "HIV/AIDS peripheral neuropathy" or "HIV/AIDS-related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

The term "Phantom Limb Pain" refers to pain appearing to come from where an amputated limb used to be. Phantom limb pain can also occur in limbs following paralysis. It is usually chronic in nature. It is similar in nature to the limb pain experienced by patients with paralysis following spinal cord injury.

The term "Trigeminal Neuralgia" (TN) refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

The term "Complex Regional Pain Syndrome (CRPS)," formerly known as Reflex Sympathetic Dystrophy (RSD), is a chronic pain condition. The key symptom of CRPS is continuous, intense pain out of proportion to the severity of the injury, which gets worse rather than better over time. CRPS is divided into type 1, which includes conditions caused by tissue injury other than peripheral nerve, and type 2, in which the syndrome is provoked by major nerve injury, and is sometimes called causalgia.

The term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

The term "convulsion" refers to a CNS disorder and is used interchangeably with "seizure;" there are many types of seizure, some of which have subtle or mild symptoms instead of convulsions. Seizures of all types may be caused by disorganized and sudden electrical activity in the brain. Convulsions are a rapid and uncontrollable shaking During convulsions, the muscles contract and relax repeatedly.

The term "method of treating pain" means a method providing to a subject a measure of relief from the symptoms or the prevention of pain, which includes the descriptions of pain provided herein. Additional examples include, but are not limited to, migraine, chronic back pain, phantom limb pain, neuropathic pain such as diabetic neuropathy, and post herpetic neuropathy.

The term "method of treating anxiety disorders" as used herein means a method of providing to a subject a measure of relief from the symptom of anxiety, or a method preventing anxiety. Anxiety disorders include, but are not limited to, panic disorder with or without agoraphobia, agoraphobia without history of panic disorder, animal or other phobias including social phobias, obsessive-compulsive disorder, stress disorders including post-traumatic and acute stress disorder, situational anxiety, generalized anxiety disorder and substance-induced anxiety disorder.

The term "method of treating psychotic disorders" as used herein means a method of providing to a subject a measure of relief from the symptoms of a psychotic disorder, or preventing a psychotic disorder. Psychotic disorders include, but are not limited to, schizophrenia, schizophreniform disorder, schizoaffective disorder, delusional disorder, brief psychotic disorder, shared psychotic disorder, psychotic disorder due to general medical condition, substance-induced psychotic disorder, or psychotic disorder not otherwise specified (*Diagnostic and Stastistical Manual of Mental Disorders*, (Ed. 4$^{th}$) American Psychiatric Association, Washington, D.C. (1994)).

The term "method of treating convulsive disorders" means a method of providing to a subject a measure of relief from the symptoms of a convulsive disorder, e.g., epilepsy, or preventing a convulsive disorder. Convulsive disorders include, but are not limited to, altered consciousness, altered motor activity, autonomic responses, inappropriate behavior patterns seizures including tonic or clonic jerking of extremities, emotional stress, sense of terror, uneasiness, nervousness, headache, fatigue, auditory hallucinations, aggressive outbursts, acute skeletal muscle spasm, and spasticity.

The term "method of treating depressive or bipolar disorders", as used herein, means a method of providing a measure of relief to a subject from the symptoms of, or preventing, depressive disorders, which include, but are not limited to, single-episode or recurrent major depressive disorder, seasonal affective disorder (SAD), dysthymic disorder, bipolar I and bipolar II manic disorders, and cyclothymic disorder.

The term "method of treating cognitive disorders" means a method of providing to a subject a measure of relief from the symptoms of a cognitive disorder, or of preventing a cognitive disorder. Cognitive disorders include, but are not limited to delirium, dementia, amnesic disorders, and cognitive deficits, memory deficits, including age-related memory deficits, and deficits due to traumatic injury, stroke, Parkinson's disease, attention deficit disorder and Downs Syndrome. Cognitive disorders may also be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV virus, head trauma, Parkinson's disease or Creutzfeld-Jakob disease.

The term "method of treating sleeping disorders", as used herein, means a method providing to a subject a measure of relief from the symptoms of, or preventing, sleep disorders or states that affect a subject's ability to sleep, which includes, but are not limited to, insomnia, sleep apnea, REM sleep interruptions, parasomnia, jet-lag syndrome, hypersomnia, shift workers' sleep disturbances, dysomnias, night terror, narcolepsy, disturbed sleep patterns, disturbed biological or circadian rhythms, sleep disturbances associated with such diseases as neurological disorders, neuropathic pain and restless leg syndrome, or providing sleep induction before surgical procedures or in disturbed or anxious states.

The term "method of treating neurodegenerative eye diseases", as used herein, means a method providing to a subject a measure of relief of symptoms of, or preventing, neurodegenerative eye diseases, which include, but are not limited to retinoschisis, vascular diseases of the retina, diseases caused by venous and/or arterial vascular occlusions, macular degenerations, traumatic retinal changes such as contusion of the eye, perforating eye injuries, siderosis/hemidosis, chalcosis, burns, retinopathia traumatica and/or injury to the retina from light, diseases of the choroid, diseases of the optic nerve, anterior ischemic optic neuropathy, optic atrophy, glaucoma, glaucoma simplex, secondary glaucoma and/or ocular hypertension.

The term "method of treating emesis" means a method of providing a subject a measure of relief from the symptoms of, or preventing, emesis, which includes, but is not limited to, acute, delayed and anticipatory emesis, emesis induced by chemotherapy or radiation, as well as motion sickness, and post-operative nausea and vomiting.

The term "method of treating eating disorders" means relief from the symptoms of, or preventing, eating disorders, which include, but are not limited to, anorexia nervosa, bulimia nervosa, obesity, weight-gain after smoking cessation, snacking and binge eating.

The term "benzodiazepine receptor" as used herein, includes the benzodiazepine receptor/GABA receptor/chloride channel complex (benzodiazepine receptor complex) and benzodiazepine receptor-agonist binding sites at or near the receptor complex. Both central nervous system ("central") and peripheral benzodiazepine receptors ("peripheral") are encompassed by the use of this term.

The term "$IC_{50}$" refers to the concentration causing a 50% inhibition of the specific binding of the control substance.

II. Compounds

In various embodiments, the present invention provides a compound having a structure according to Formula I:

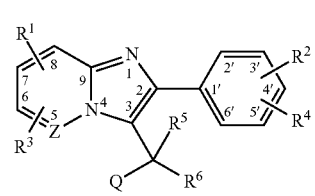

(I)

In Formula I, $R^1$, $R^2$, $R^3$ and $R^4$ are each independently selected from H, D, halogen, hydroxyl, dialkylamino, cyano, sulfonamide, acyl, substituted or unsubstituted alkyl, substituted or unsubstituted alkoxy, substituted or unsubstituted heterocycloalkyl, substituted or unsubstituted aryl and substituted or unsubstituted heteroaryl. The symbols $R^5$ and $R^6$ represent members independently selected from H; F; hydroxyl; substituted or unsubstituted alkoxy and lower alkyl. Q is selected from:

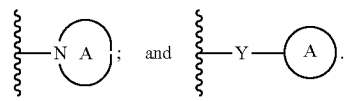

Ring system A is an optionally substituted 4, 5, 6 or 7 member monocyclic or 8, 9, 10, 11 or 12 member bicyclic ring comprising 0, 1, 2, 3 or 4 heteroatoms independently selected from N, O and S. The symbol X represents O, S or $NR^7$. $R^7$ is selected from H; substituted or unsubstituted alkyl; substituted or unsubstituted heteroalkyl; substituted or unsubstituted cycloalkyl; substituted or unsubstituted heterocycloalkyl; substituted or unsubstituted aryl and substituted or unsubstituted heteroaryl. Y is a member selected from a bond, $(CR^8R^9)_n$, O, S, $NR^{10}R^{11}$, S(O), $S(O)_2$, $S(O)pNR^{10}R^{11}$, $(CR^8R^9)_nG(CR^8R^9)_m$. G is a member selected from a bond and O. The indeces m and n are independently selected integers from 0 to 4. Each $R^8$, $R^9$ and $R^{10}$ are independently selected from H, D, substituted or unsubstituted alkyl, acyl, $SO_2R^{8a}$, $OR^{8a}$, $COOR^{8a}$, and $CONR^{8a}R^{8b}$. $R^{8a}$ and $R^{8b}$ are independently selected from H, D, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^8$ and $R^9$, $R^{8a}$ and $R^{8b}$ are optionally joined in a ring, or both these pairs of radicals are optionally joined into rings. The index n is the integer 0, 1, 2, 3 or 4. $R^8$, $R^9$ and $R^{10}$ are independently H, D, substituted or unsubstituted alkyl, acyl, $SO_2R^{8a}$, $OR^{8a}$, $COOR^{8a}$, or $CONR^{8a}R^{8b}$. The symbols $R^{8a}$ and $R^{8b}$ independently represent H, D, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{11}$ is selected from a bond and $NR^{11a}$. $R^{11a}$ is selected from H, D, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. Z is $CR^{12}$ or N. $R^{12}$ is H, D, halogen, substituted or unsubstituted alkyl; substituted or unsubstituted heteroalkyl; substituted or unsubstituted cycloalkyl; substituted or unsubstituted heterocycloalkyl; substituted or unsubstituted aryl or substituted or unsubstituted heteroaryl.

Exemplary compounds according to Formula I can be conveniently divided into subgenera based on the identity of Q. The structures of these exemplary subgenera are shown below:

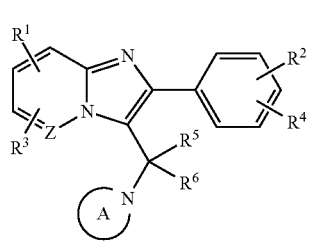

(II)

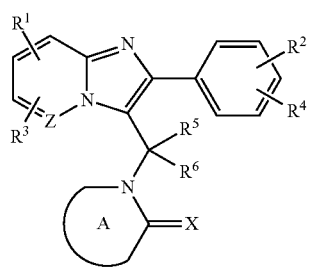

(III)

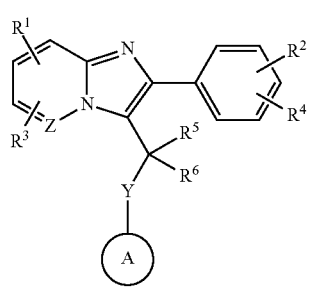

(IV)

in which the substituents are as set forth above in the description of Formula I.

In an exemplary embodiment A comprises at least two endocyclic nitrogen atoms. In exemplary embodiments, A comprises 2 or 3 endocyclic nitrogen atoms. In various embodiments, A is a a six-member ring system with two endocyclic nitrogen atoms, a five-member ring system with two endocyclic nitrogen atoms, a five-member ring with two endocyclic nitrogen atoms and an endocyclic oxygen atom, or a five-member ring system with three endocyclic nitrogen atoms.

In various embodiments according to Formula I, ring system A is selected from substituted or unsubstituted thiadiazolyl; substituted or unsubstituted pyridazinyl; substituted or unsubstituted oxadiazolyl; substituted or unsubstituted triazinyl; substituted or unsubstituted pyrazolyl; substituted or unsubstituted pyrimidinyl; substituted or unsubstituted triazolyl; substituted or unsubstituted benzoimidazolyl; substituted or unsubstituted indolinyl; substituted or unsubstituted furopyrrolyl; substituted or unsubstituted indolyl; substituted or unsubstituted benzotriazolyl; substituted or unsubstituted benzooxazolyl; substituted or unsubstituted pyridinyl; substituted or unsubstituted tetrazolyl; substituted or unsubstituted thiazolyl; substituted or unsubstituted indazolyl; substituted or unsubstituted diazolyl; substituted or unsubstituted purinyl; substituted or unsubstituted pyrazinyl; substituted or unsubstituted imidazopyridinyl; substituted or unsubstituted benzooxazinyl; substituted or unsubstituted oxazolyl; substituted or unsubstituted benzyl; substituted or unsubstituted benzothiadiazonyl; substituted or unsubstituted thiopheneyl; substituted or unsubstituted quinolinyl; substituted or unsubstituted quinazolinyl; substituted or unsubstituted oxazolidinyl; substituted or unsubstituted imidazolidinyl and substituted or unsubstituted azetidinyl.

In an exemplary embodiment, ring system A comprises at least one substituent selected from $OCH_3$; $CH_2CH_3$; $NHCH_3$; $CH_3$; H; =O; Cl; C=OOCH$_2$CH$_3$; —CN; Br; F; CF$_3$; NH$_2$; SCH$_3$; S=OCH$_3$; CHCH$_2$; NCH$_3$CH$_3$; OCH$_2$CH$_2$NCH$_3$CH$_3$; NHCH$_2$CH$_2$NCH$_3$CH$_3$; C(H)(OCH$_3$)(OCH$_3$); OCH$_2$CH$_3$; OCH$_2$CH$_2$NHCH$_3$; CH$_2$NCH$_3$CH$_3$; NHC=OCH$_3$; 4-methylpiperazinyl; 1-(t-butoxycarbonyl)azetidin-3-oxy; azetidin-3-oxy; pyrrolidinaminyl; NHNCH$_3$CH$_3$; CH$_2$SCH$_3$; (S)—(N-methylpyrrolidin-2-yl)methoxy; (N-methylpyrrolidin-3-yl)methoxy; CH$_2$OH; NHNH$_2$; N-methylpiperidinyloxy; NNH$_2$CH$_3$; CH$_2$C=ONHCH$_3$; N(C=OCH$_3$)(NHC=OCH$_3$); piperidin-4-ol-1-yl; (N-methylpyrrolidin-2-yl)methoxy; OCHCH$_3$CH$_2$NCH$_3$CH$_3$; piperidin-4-oxy; N-methylpyrrolidin-3-yl; CH$_2$NHCH$_2$CH$_3$; CH$_2$NCH$_3$CH$_2$CH$_3$; 1-t-butoxycarbonylpyrrolidin-2-yl; pyrrolidin-2-yl; pyrrolidinylmethyl; S-2-hydroxymethylpyrrolidinyl; 3-hydroxypyrrolidinyl; R—N-pyrrolidin-3-yloxy; S—N-pyrrolidin-3-yloxy; 4-hydroxy-4-methyl-piperidinyl; =S; CH$_2$C=OOCH$_3$; CH$_2$CH$_2$NCH$_3$CH$_3$; C=OOCH$_3$; C=OCH$_2$CH$_3$; phenyl; C=ONCH$_3$CH$_3$; CHCH$_3$CH$_3$; C=OH; C=OOCHCH$_3$; C=ONHCH$_3$; C=ONH$_2$; 3-methyl-1,2,4-diazole-5-yl; C=ONHCH$_2$CH$_2$NCH$_3$CH$_3$; C=OCH$_2$; 2-pyridinyl; =NH; 2-furanyl; 3-pyridyl; p-methylbenzyl; C=OOH; =ONCH$_3$OCH$_3$; C=OOC(H)(CH$_3$)(CH$_3$); C(OH)(CH$_3$)(CH$_3$); CH$_3$OH; C=OCH$_3$; C=OOCCH$_3$CH$_3$CH$_3$; C=OOCCCH$_3$CH$_3$CH$_3$; COOCH$_3$; CH$_2$NHCH$_3$; =ONHCH$_2$CH$_2$NCH$_3$CH$_3$; 3-hydroxypyrrolidinyl; NCH$_3$CH$_2$CH$_2$OH; NHNHCH$_3$; 3-pyrrolidinoxy; 1,2,4-triazolyl; pyrrolidinyl and NHCH$_2$CH$_3$.

In various embodiments, A is substituted with a moiety having the formula:

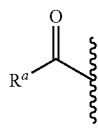

In the formula above, $R^a$ is $OR^b$, $NR^bR^c$, or $NHNH_2$, wherein $R^b$ is H, D, or substituted or unsubstituted alkyl. The symbol $R^c$ represents H, D, $OR^d$ or substituted or unsubstituted alkyl. $R^d$ is H or substituted or unsubstituted alkyl. In various embodiments, at least one of $R^a$ and $R^b$ is other than H.

In certain embodiments according to Formula I, the invention provides a compound having a structure according to Formula VI:

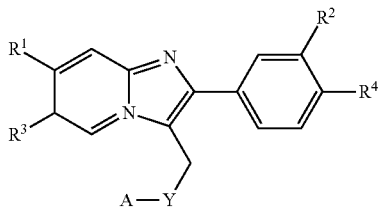

(VI)

$R^1$, $R^2$, $R^3$ and $R^4$ are each members independently selected from H, D, halogen, hydroxyl, dialkylamino, cyano, sulfonamide, acyl, substituted or unsubstituted alkyl, substituted or unsubstituted alkoxy, substituted or unsubstituted heterocycloalkyl, substituted or unsubstituted aryl and substituted or unsubstituted heteroaryl. The symbol Y represents a bond, NH, D, S, and O such that when Y is a bond, it binds A directly to the methylene moiety pendant from the ring. The symbol A is as described hereinabove.

In certain embodiments, according to Formula VI, $R^2$ is H, D and $R^4$ is H, D, substituted or unsubstituted alkyl or halogen. In various embodiments, $R^1$ is H, D and $R^3$ is H, D, substituted or unsubstituted alkyl or halogen. In exemplary embodiments, $R^4$ is halogen and $R^3$ is H, D, methyl or halogen.

In various embodiments according to Formula I, the invention provides a compound having a structure according to Formula VII:

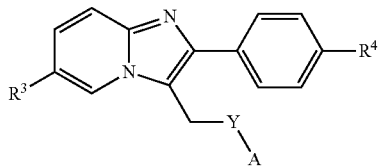

(VII)

in which the substituents are as described for Formula VI.

In exemplary embodiments according to Formula I, in compounds according to Formula VI and VII, Y-A has a formula selected from Table 1:

TABLE 1

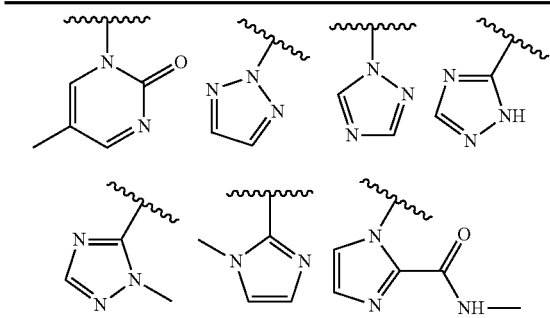

TABLE 1-continued

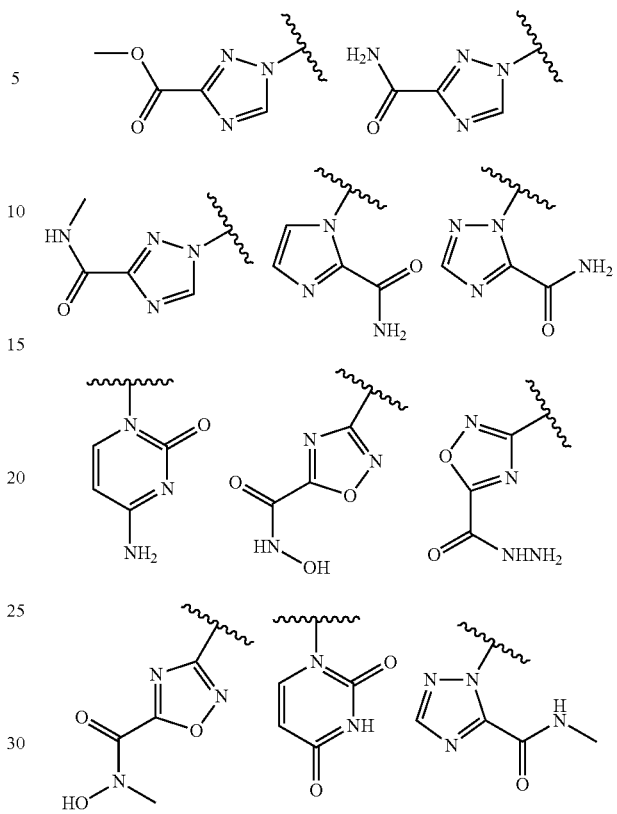

In exemplary compounds of Formula I, $R^5$ and $R^6$ are hydrogen. Q is

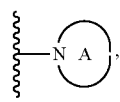

and A is imidazol-1-yl, 2-methylimidazol-1-yl, 2-ethylimidazol-1-yl, 2-isopropylimidazol-1-yl, 2-phenylimidazol-1-yl, 2-(N,N-dimethyl)aminocarbonylimidazol-1-yl, 2-methoxycarbonylimidazol-1-yl, 2-ethoxycarbonylimidazol-1-yl, 4,5-dichloroimidazol-1-yl, pyrazol-1-yl, 3,5-dimethylpyrazol-1-yl, 1,2,3-triazol-1-yl, 1,2,3-triazol-2-yl, 1,2,4-triazol-1-yl, 3-methoxycarbonyl-1,2,4-triazol-1-yl, 5-methoxycarbonyl-1,2,4-triazol-1-yl, 5-isopropyloxycarbonyl-1,2,4-triazol-1-yl, 5-hydroxycarbonyl-1,2,4-triazol-1-yl, 5-methylaminocarbonyl-1,2,4-triazol-1-yl, 5-methyl(methoxy)aminocarbonyl-1,2,4-triazol-1-yl, 5-aminocarbonyl-1,2,4-triazol-1-yl, 5-dimethylaminocarbonyl-1,2,4-triazol-1-yl, 5-methyltetrazol-1-yl, 5-methyltetrazol-2-yl, 6-(N,N-dimethylamino)-purin-9-yl, 2-methylbenzimidazol-1-yl, benzotriazol-2-yl, imidazopyridin-1-yl, azetidin-2-one-1-yl, pyrrolidin-2-one-1-yl, 3-ethyl-4-methyl-pyrrol-2(5H)-one-1-yl, 4-methoxypyrrol-2(5H)-one-1-yl, 1,2-dihydro-5-methylpyrazol-3-one-2-yl, oxazolidin-2-one-3-yl, piperidin-2-one-1-yl, 4,5-dimethylpyridazin-3-one-2-yl, pyridine-2-one-1-yl, 3-methyl-pyridine-2-one-1-yl, 6-methylpyridine-2-one-1-yl, 5-chloropyridine-2-one-1-yl, 6-methylpyridazin-3-one-2-yl, pyrimidin-2-one-1-yl, pyrimidin-4-one-3-yl, pyrimidin-2-thione-1-yl, 5,5-dimethyloxazolidin-2,4-dione-3-yl, 1-methylimidazolidine-2,4-dione-3-yl, thiazol-2-one- 3-yl, 4,5-dimethylthiazol-2-one-3-yl, 3-(methylthio)-1,2,4-thiadiazol-5-one-4-yl, isoindolin-1,3-dione-2-yloxy, benzo[1,2,3]triazol-1-yloxy, pyrimidin-2-ylamino, 4,6-dimethylpyrimidin-2-ylamino, 4,6-dichloropyrimidin-2-ylamino, 5-bromopyrimidin-2-ylamino, 4-methylpyrimidin-2-ylamino, pyrazin-2-ylamino, 1,3,5-triazin-2-ylamino, 1,2,4-triazin-3-ylamino, pyridin-2-ylamino, 3-chloropyridin-6-ylamino, 3,5-dichloropyridin-2-ylamino, 1,3,4-thiadiazol-2-ylamino, thiazol-2ylamino, 3-methyl-thiazol-5ylamino, 3-methylisothiazol-5-ylamino, isoxazol-3ylamino, 1,2,4-triazol-4-ylamino, imidazolin-2-ylamino, 4-methyl-1,2,4-triazol-3-ylthio, 2-methyl-1,3,4-thiadizol-5-ylthio, 1,3,4-thiadizol-2-ylthio, 4,6-dimethylpyrimidin-2-ylthio, 1-methylbenzimidazol-2-ylthio, oxazolo[4,5-b]pyridine-2-ylthio, 1,2,4-triazol-3-ylthio or phenylthio.

In various exemplary compounds according to Formula I, $R^4$ is hydrogen and $R^2$ is at the 4'-position and is selected from the group consisting of methyl, chloro, fluoro, bromo or H.

In various exemplary compounds according to Formula I, $R^1$ is at the 6-position of the H-imidazol[1,2-a]pyridine ring and is selected from the group consisting of methyl, chloro, fluoro, bromo or H. In an exemplary embodiment, and Z is CH In some embodiments according to Formula I, $R^3$ is at the 8-position of the H-imidazo[1,2-a]pyridine ring and is selected from the group consisting of chloro; fluoro and H. In an exemplary embodiment, and Z is CH.

In various embodiments according to Formula I, compounds are provided in which Q is a member selected from:

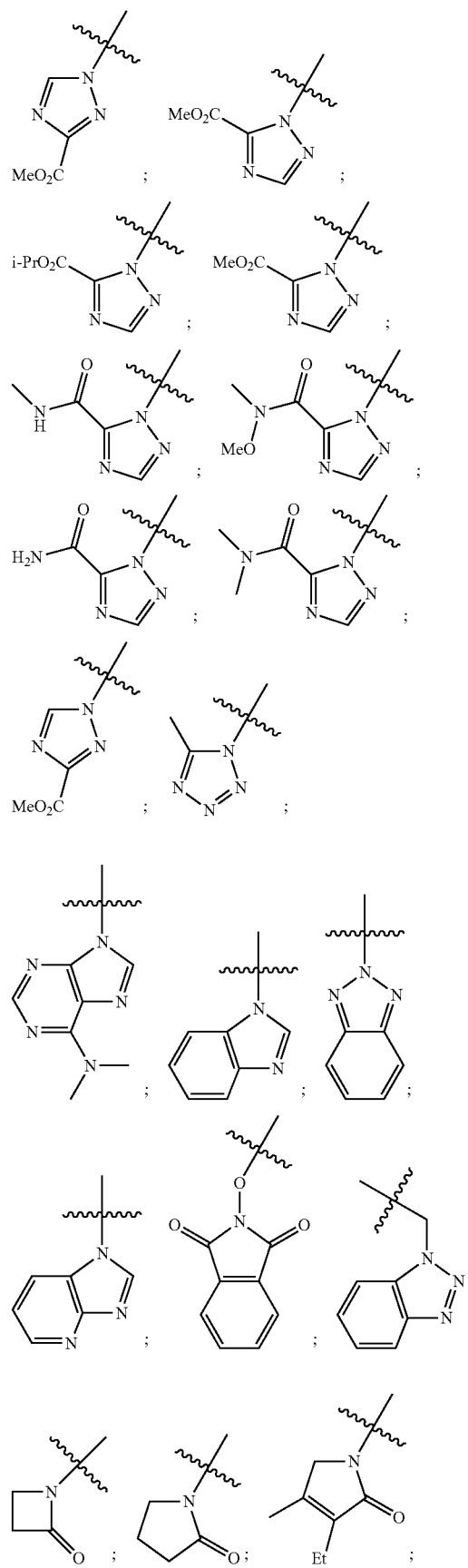

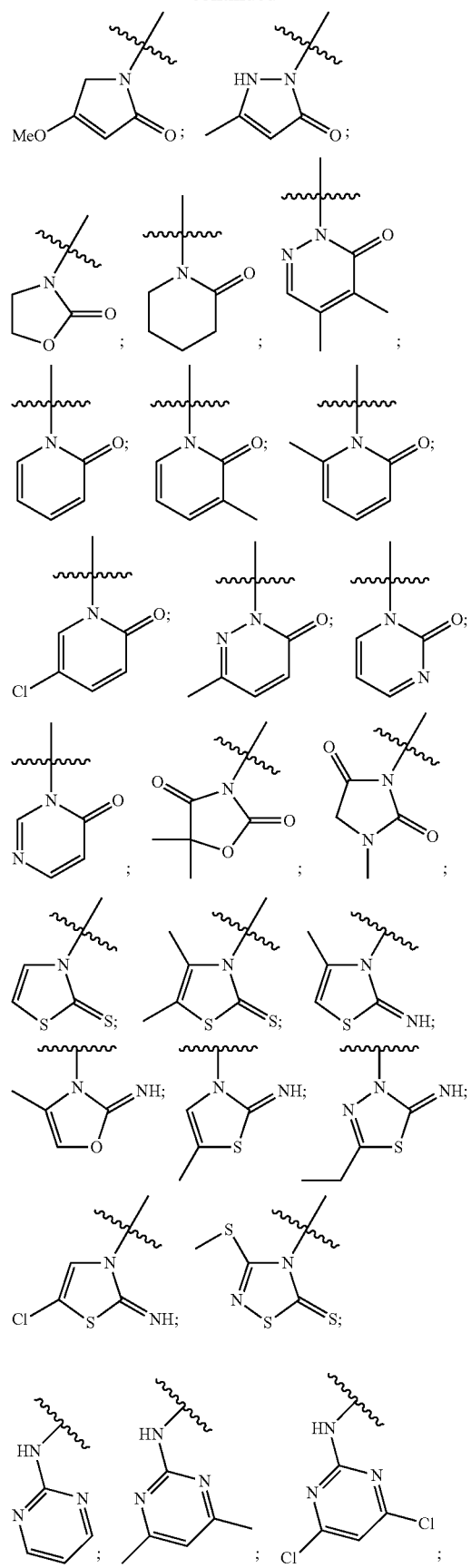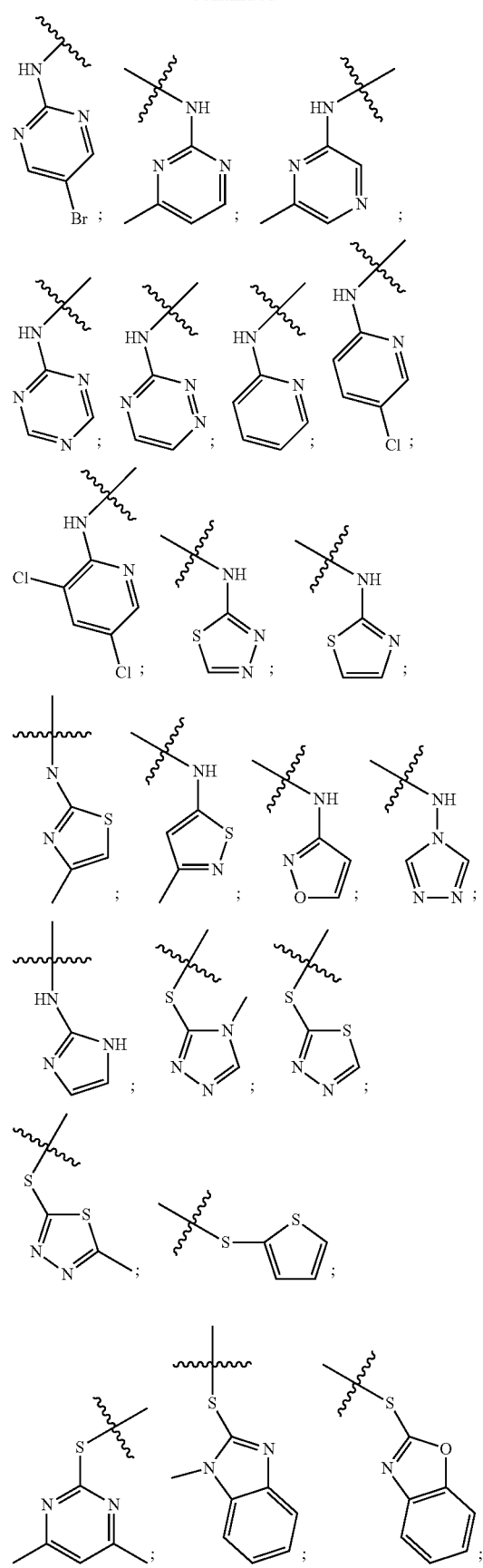

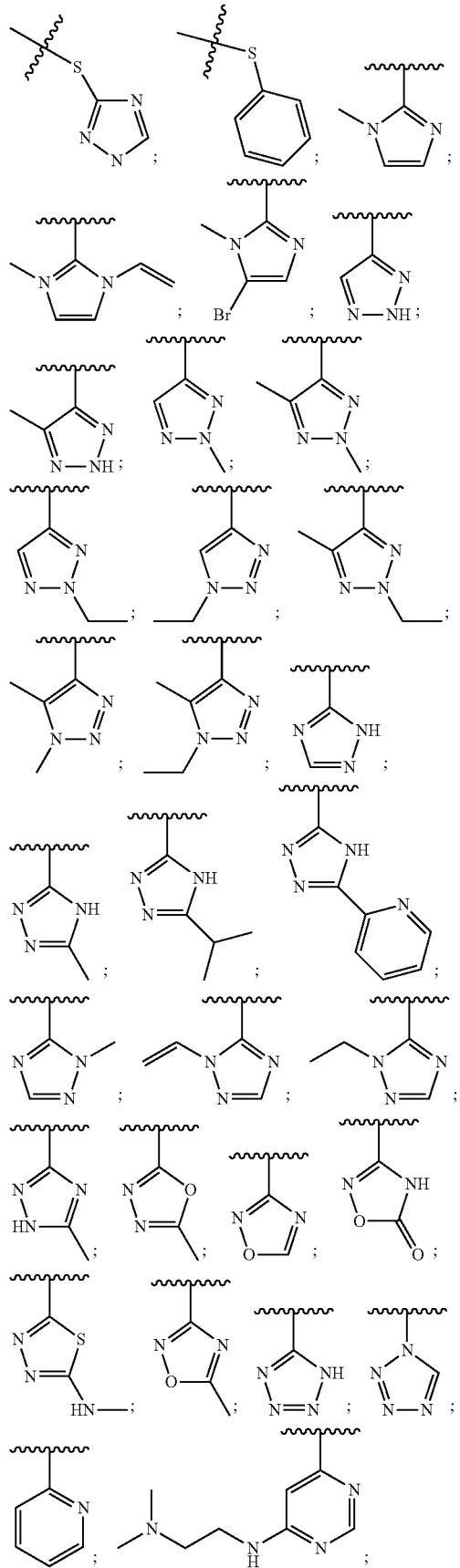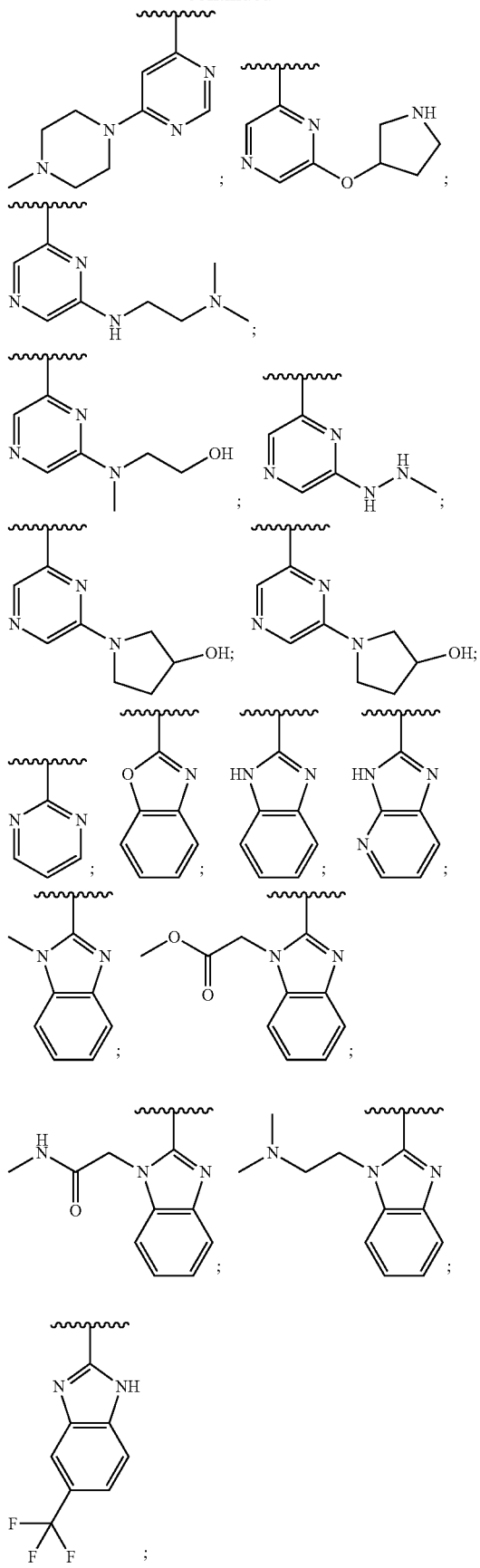

-continued
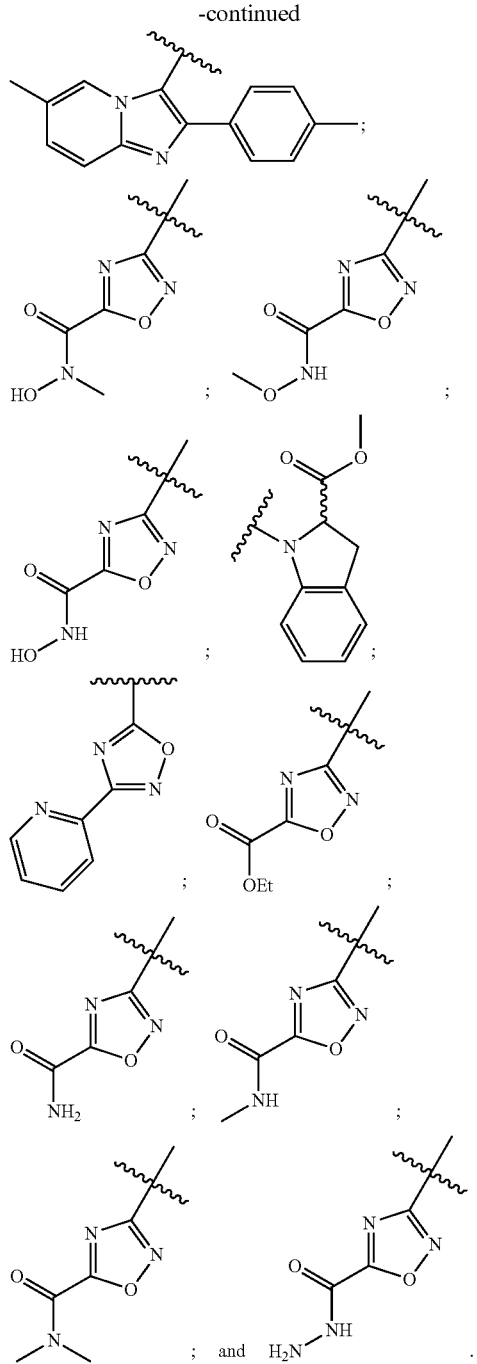
In various embodiments according to Formula I, the invention provides compounds having the structure:
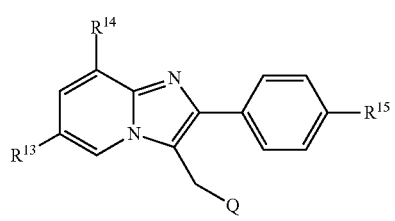
in which $R^{13}$, $R^{14}$ and $R^{15}$ are members independently selected from methyl; chlorine; fluorine; bromine and hydrogen, and Q is as described above.
In various embodiments according to this formula, Q is selected from:
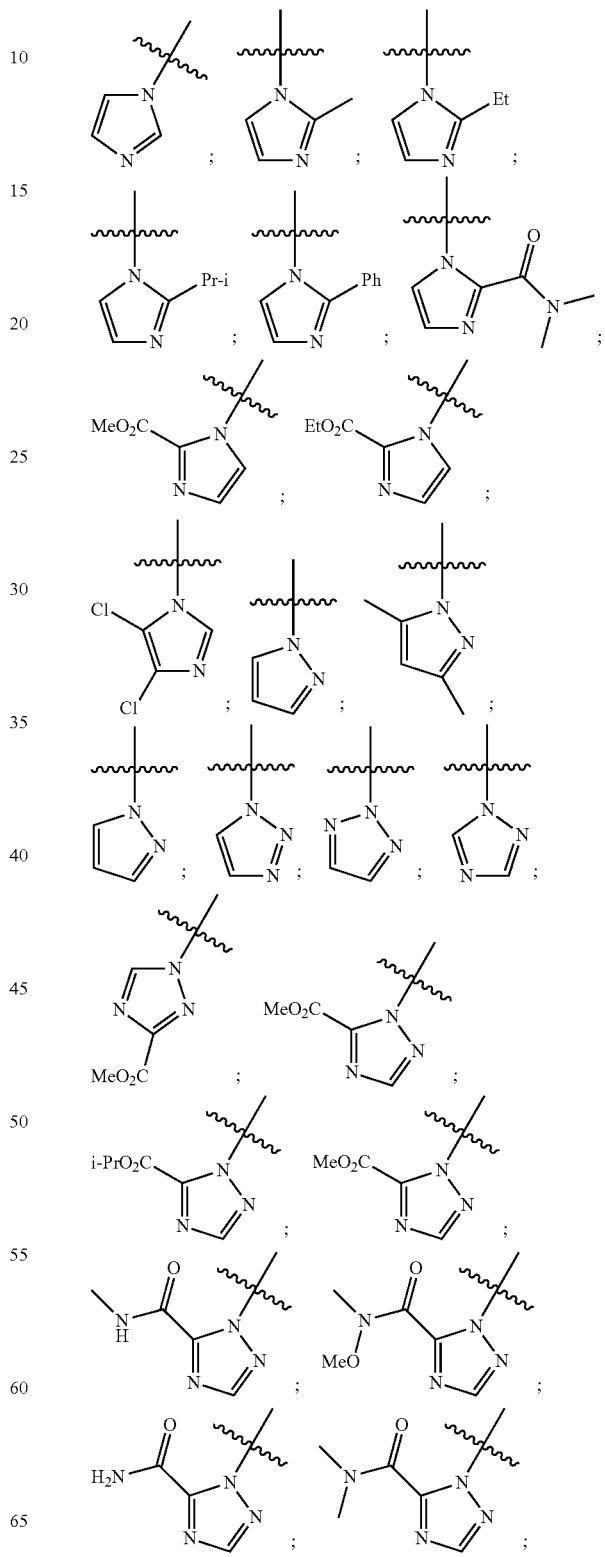

-continued
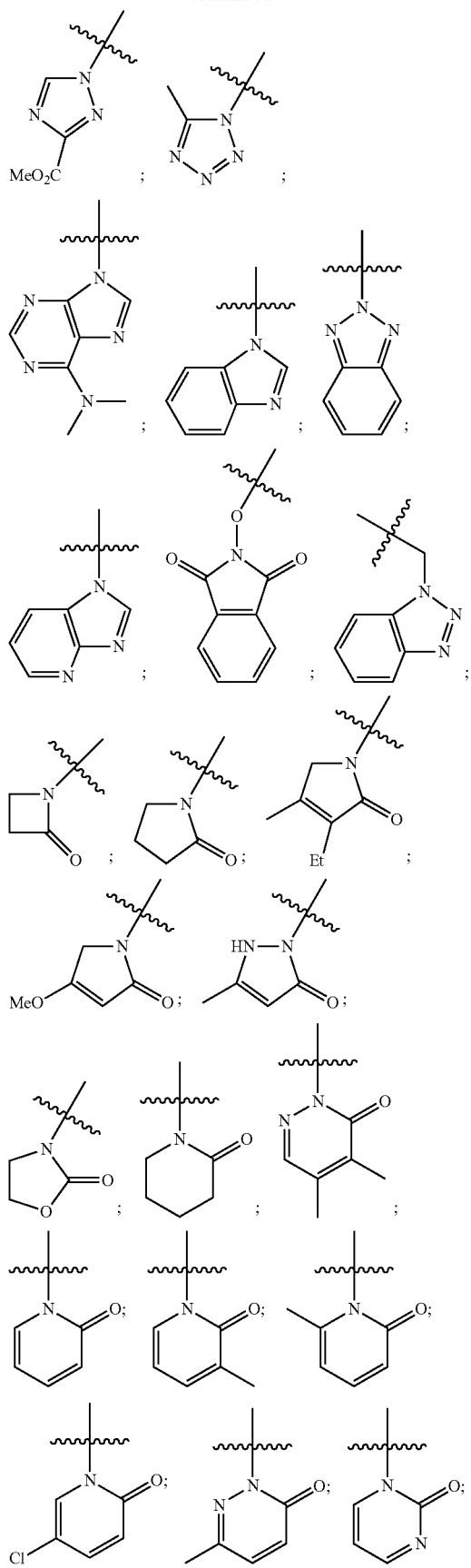
-continued
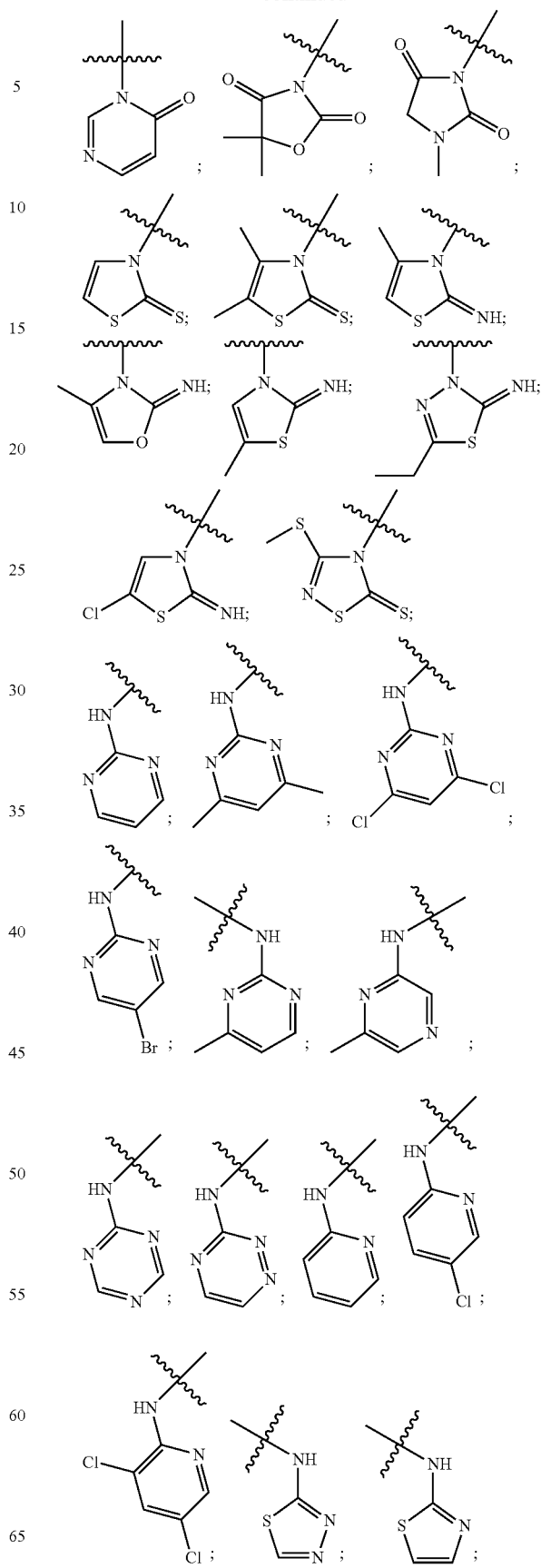

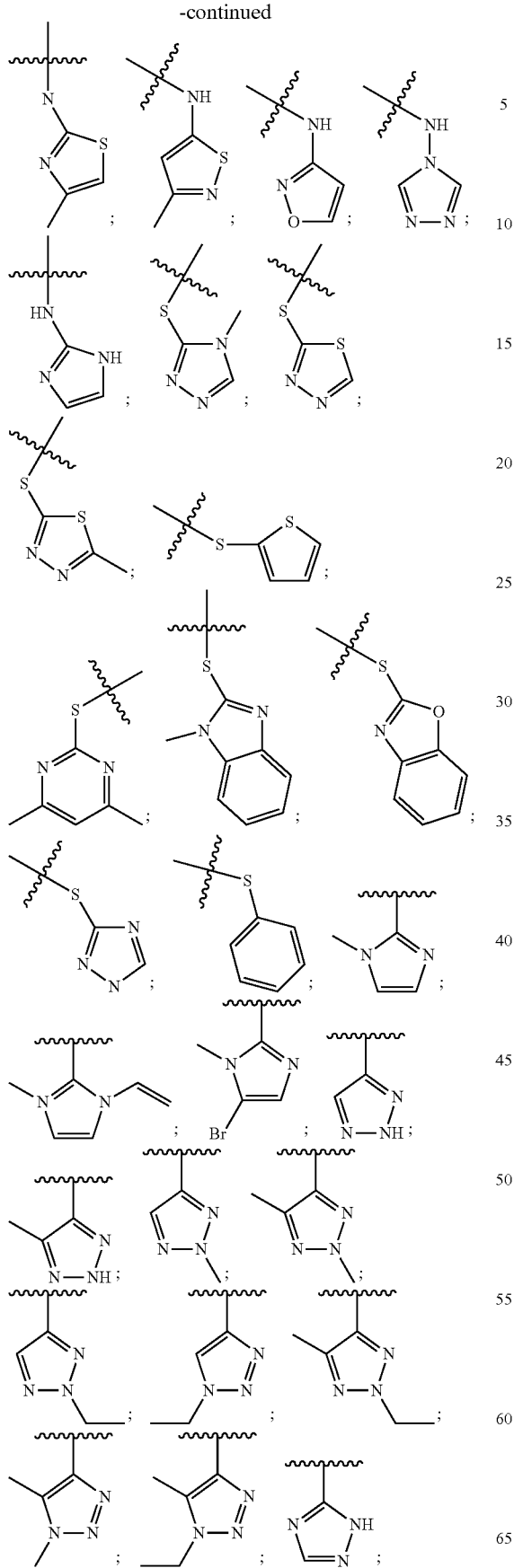
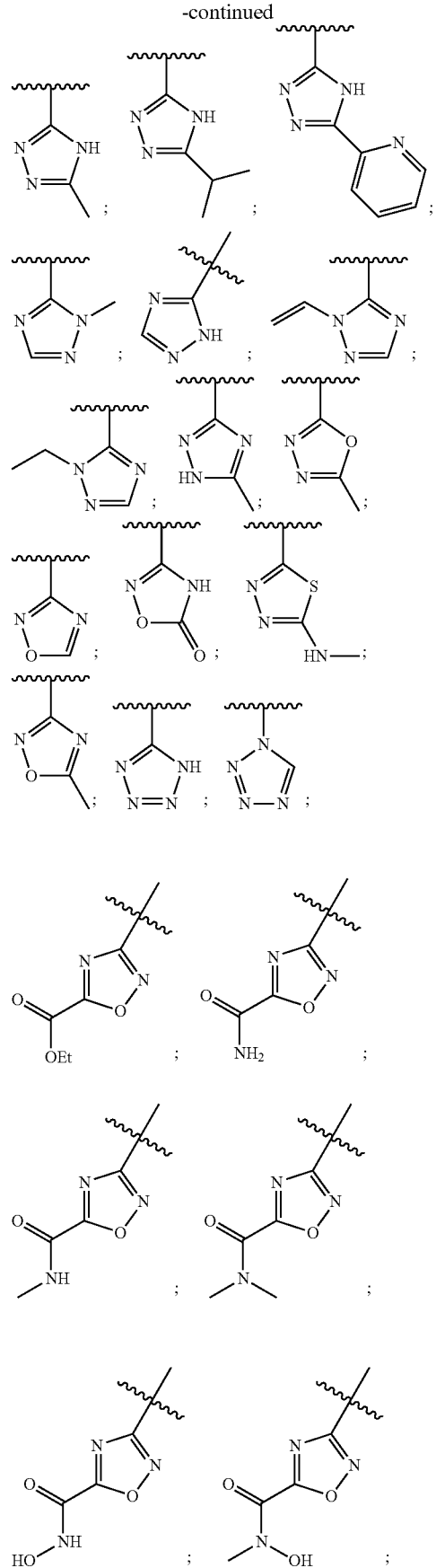

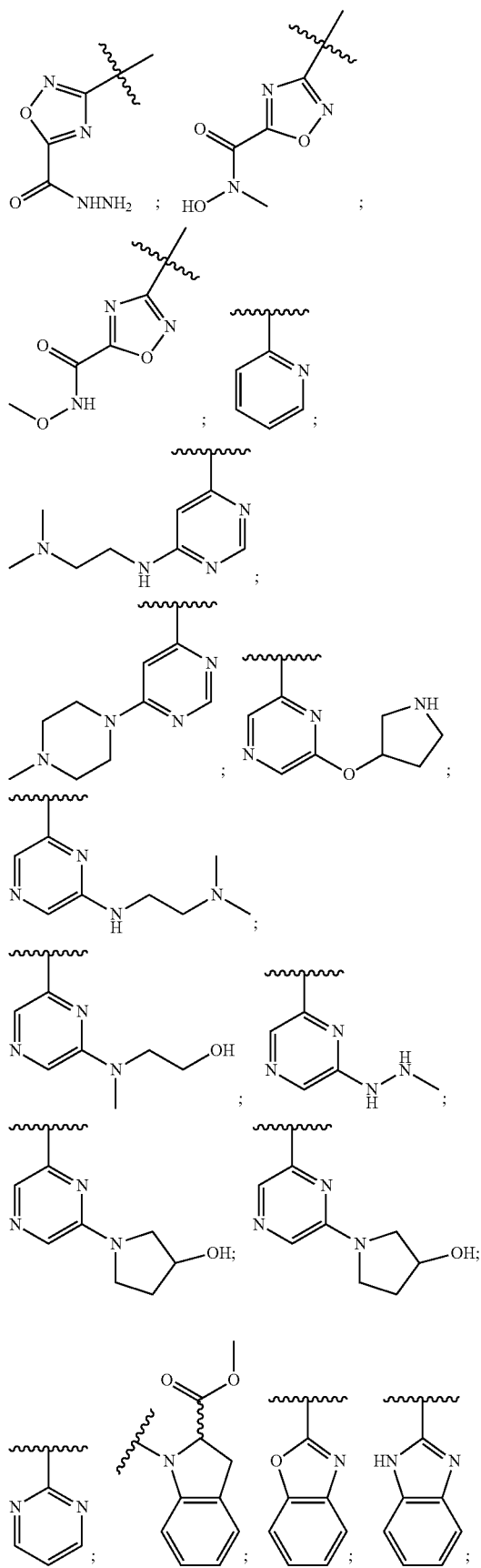

In an exemplary embodiment according to Formula I, Y is a bond. Thus, in exemplary compounds, the C-3 carbon of the imidazo[1,2-a]pyridine is directly attached to the carbon of $CR^5R^6$, which carbon is directly attached to an atom of the backbone ring A. In various embodiments, the C-3 carbon of the imidazo[1,2-a]pyridine is directly attached to the carbon of $CR^5R^6$, which carbon is directly attached to a carbon of the backbone ring A as disclosed herein.

In various embodiments according to Formula I, Y is a bond and Q is substituted or unsubstituted pyrrolyl, diazolyl, triazolyl or tetrazolyl. In an exemplary embodiment, Q is substituted or unsubstituted 1,2,4-triazol-5-yl. In an exemplary embodiment, Q is 1,2,4-triazol-5-yl subsituted with an alkyl group. In an exemplary embodiment, Q is 1-methyl-1,2,4-triazol-5-yl.

In an exemplary embodiment according to Formula I, Z is CH, D, Q is a structure as set forth herein, $R^1$ and $R^2$ are H, D and $R^3$ and $R^4$ are independently selected halogen. In an exemplary embodiment according to Formula I, Z is CH, D, Q is a structure as set forth herein, $R^1$ and $R^2$, $R^5$ and $R^6$ are H, D, $R^3$ and $R^4$ and are independently selected halogen. In an exemplary embodiment according to Formula I, Z is CH, D, Q is a structure as set forth herein, $R^1$, $R^2$, $R^5$ and $R^6$ are H, D, and $R^3$ and $R^4$ are F. In an exemplary embodiment according to Formula I, Z is CH, D, Q is 1-methyl-1,2,4-triazol-5-yl, $R^1$, $R^2$, $R^5$ and $R^6$ are H, D, $R^3$ is F at position 6, and $R^4$ is F at position 4'.

The invention also provides compounds having a structure selected from:

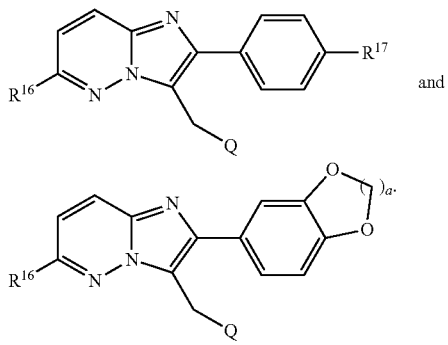

$R^{16}$ and $R^{17}$ are independently selected from H, D, halogen, substituted or unsubstituted alkyl, substituted or unsubstituted heteroalkyl and $NR^{18}R^{19}$, wherein $R^{18}$ and $R^{19}$ are substituted or unsubstituted alkyl. The index a is 1, 2 or 3. Q is selected from substituted or unsubstituted heterocycloalkyl and substituted or unsubstituted heteroaryl. $R^{18}$ and $R^{19}$ are optionally joined in a ring. Exemplary rings include 5- and 6-member rings.

In one embodiment, Q has the structure

wherein $R^{20}$ is selected from a bond and NH; and $R^{21}$ is selected from substituted or unsubstituted heterocycloalkyl and substituted or unsubstituted heteroaryl.

In one embodiment, Q has a structure selected from

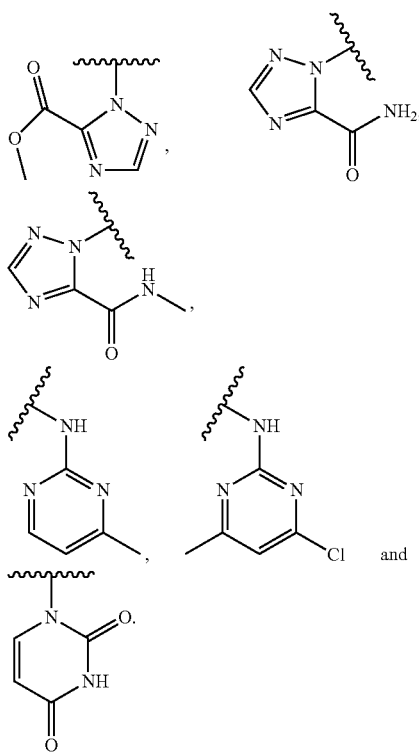

The present invention also provides compounds of having a structure:

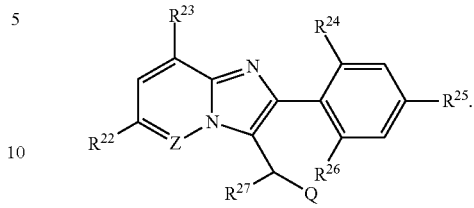

$R^{22}$ is selected from H; halogen and substituted or unsubstituted alkyl; $R^{23}$, $R^{24}$ and $R^{26}$ is selected from H, D and halogen; $R^{25}$ is selected from H; halogen; substituted or unsubstituted alkyl; substituted or unsubstituted heteroalkyl and substituted or unsubstituted aryl; $R^{27}$ is selected from H; substituted or unsubstituted alkyl and $OR^{28}$, wherein $R^{28}$ is selected from H, D and substituted or unsubstituted alkyl; and Q is selected from substituted or unsubstituted cycloalkyl; substituted or unsubstituted heterocycloalkyl; substituted or unsubstituted aryl; substituted or unsubstituted heteroaryl; substituted or unsubstituted arylalkyl and substituted or unsubstituted heteroarylalkyl. Z is selected from $CR^{12}$ and N, wherein $R^{12}$ is selected from H; substituted or unsubstituted alkyl; substituted or unsubstituted heteroalkyl; substituted or unsubstituted cycloalkyl; substituted or unsubstituted heterocycloalkyl; substituted or unsubstituted aryl and substituted or unsubstituted heteroaryl.

In one embodiment, Q has the structure

$R^{29}$ is selected from a bond, substituted or unsubstituted alkyl, S, O, C(O), S(O) and $NR^{29a}R^{29b}$. $R^{29a}$ is selected from H, D and alkyl. $R^{29b}$ is selected from a bond and $NR^{29c}$. $R^{29}$ and $R^{29c}$ are optionally joined in a ring. Exemplary rings include 5- and 6-member rings. $R^{30}$ is selected from substituted or unsubstituted cycloalkyl; substituted or unsubstituted heterocycloalkyl; substituted or unsubstituted aryl; substituted or unsubstituted heteroaryl; substituted or unsubstituted arylalkyl and substituted or unsubstituted heteroarylalkyl.

In one embodiment, $R^{30}$ has the structure:

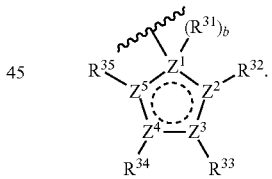

The symbols $Z^1$, $Z^2$, $Z^3$, $Z^4$ and $Z^5$ independently represent C, N, O, and S. The index b is 0 or 1. The symbols $R^{31}$, $R^{32}$, $R^{33}$, $R^{34}$ and $R^{35}$ independently represent nil, H, D, heteroatom, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, =NH, D, =O, =S, $C(O)R^{36}$ or $SR^{37}$. $R^{34}$ and $R^{35}$ are optionally joined in a ring. An exemplary ring is a 5-member or a 6-member ring. $R^{36}$ is a group selected from H; substituted or unsubstituted alkyl, $NR^{36a}R^{36b}$ and $OR^{36c}$. $R^{36a}$ and $R^{36b}$ are independently H, D, substituted or unsubstituted alkyl or substituted or unsubstituted heteroalkyl. $R^{36a}$ and $R^{36b}$ are optionally joined in a ring. An exemplary ring is a 5- or 6-member ring. $R^{36c}$ is H or substituted or unsubstituted alkyl. $R^{37}$ is substituted or unsubstituted alkyl. $R^{32}$ and $R^{33}$, together with the atoms to which they are attached are optionally joined to form a 5- or 6-member ring. $R^{33}$ and $R^{34}$, together with the atoms to which they are attached, are optionally joined to form a 5- or 6-member ring.

In one embodiment, $R^{30}$ has the structure

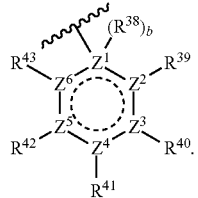

$Z^1$, $Z^2$, $Z^3$, $Z^4$, $Z^5$, and $Z^6$ are independently selected from C, N, O and S. The index b is 0 or 1. $R^{38}$, $R^{39}$, $R^{40}$, $R^{41}$, $R^{42}$ and $R^{43}$ are independently selected from nil, H, D, heteroatom, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, =NH, =O, =S, C(O)$R^{44}$ and S$R^{45}$. $R^{42}$ and $R^{43}$ are optionally joined in a ring, e.g., a 5- or 6-member ring. $R^{44}$ is selected from H, D, substituted or unsubstituted alkyl, N$R^{44a}R^{44b}$ and O$R^{44c}$, wherein $R^{44a}$ and $R^{44b}$ are independently selected from H, D, substituted or unsubstituted alkyl and substituted or unsubstituted heteroalkyl, and $R^{44c}$ is selected from H, D and substituted or unsubstituted alkyl, and $R^{45}$ is selected from substituted or unsubstituted alkyl. $R^{39}$ and $R^{40}$ are optionally joined to form a 5- or 6-member ring including the atoms to which they are attached. $R^{40}$ and $R^{41}$ are optionally joined to form a 5 or 6 membered ring including the atoms to which they are attached. $R^{41}$ and $R^{42}$ are optionally joined to form a 5- or 6-member ring including the atoms to which they are attached.

In one embodiment, $R^{30}$ comprises at least one substituent selected from the group OCH$_3$, CH$_2$CH$_3$, NHCH$_3$, CH$_3$, H, D, =O, Cl, C=OOCH$_2$CH$_3$, —CN, Br, F, CF$_3$, NH$_2$, SCH$_3$, S=OCH$_3$, CHCH$_2$, NCH$_3$CH$_3$, OCH$_2$CH$_2$NCH$_3$CH$_3$, NHCH$_2$CH$_2$NCH$_3$CH$_3$, OCH$_2$CH$_3$, OCH$_2$CH$_2$NHCH$_3$, CH$_2$NCH$_3$CH$_3$, NHC=OCH$_3$, 4-methylpiperazinyl, 1-(t-butoxycarbonyl)azetidin-3-oxy, azetidin-3-oxy, pyrrolidinaminyl, NHNCH$_3$CH$_3$, CH$_2$SCH$_3$, (S)—(N-methylpyrrolidin-2-yl)methoxy, (N-methylpyrrolidin-3-yl)methoxy, CH$_2$OH, NHNH$_2$, N-methylpiperidinyloxy, NHNHCH$_3$, CH$_2$C=ONHCH$_3$, N(C=OCH$_3$)(NHC=OCH$_3$), piperidin-4-ol-1-yl, (N-methylpyrrolidin-2-yl)methoxy, OCHCH$_3$CH$_2$NCH$_3$CH$_3$, piperidin-4-oxy, N-methylpyrrolidin-3-yl, CH$_2$NHCH$_2$CH$_3$, CH$_2$NCH$_3$CH$_2$CH$_3$, 1-t-butoxycarbonylpyrrolidin-2-yl, pyrrolidin-2-yl, pyrrolidinylmethyl, S-2-hydroxymethylpyrrolidinyl, 3-hydroxypyrrolidinyl, R—N-pyrrolidin-3-yloxy, S—N-pyrrolidin-3-yloxy, 4-hydroxy-4-methyl-piperidinyl, =S, CH$_2$C=OOCH$_3$, CH$_2$CH$_2$NCH$_3$CH$_3$, C=OOCH$_3$, C=OCH$_2$CH$_3$, phenyl, C=ONCH$_3$CH$_3$, CHCH$_3$CH$_3$, C=OH, C=OOCHCH$_3$, C=ONHCH$_3$, C=ONH$_2$, 3-methyl-1,2,4-diazole-5-yl, C=ONHCH$_2$CH$_2$NCH$_3$CH$_3$, C=OCH$_2$, 2-pyridinyl, =NH, 2-furanyl, 3-pyridyl, p-methylbenyl, C=OOH, =ONCH$_3$OCH$_3$, C=OOC(H)(CH$_3$)(CH$_3$), C(OH)(CH$_3$)(CH$_3$), CH$_3$OH, C=OCH$_3$, C=OOCCH$_3$CH$_3$CH$_3$, C=OOCCCH$_3$CH$_3$CH$_3$, COOCH$_3$, CH$_2$NHCH$_3$, =ONHCH$_2$CH$_2$NCH$_3$CH$_3$, NCH$_3$CH$_2$CH$_2$OH, NHNHCH$_3$, 3-pyrrolidinoxy, 1,2,4-triazolyl, pyrrolidinyl and NHCH$_2$CH$_3$, C=ON(OH)CH$_3$, C=ONHOH, C=ONHNH$_2$, and C=ONHNCH$_3$CH$_3$.

In an exemplary embodiment, Q is selected from substituted or unsubstituted azetidine and substituted or unsubstituted imidazolidine.

The following compounds are illustrative of compounds of Formula II, but the invention is not limited to the compounds listed herein: 3-((1H-imidazol-1-yl)methyl)-6-methyl-2-p-tolylH-imidazo[1,2-a]pyridine, 6-methyl-3-((2-methyl-1H-imidazol-1-yl)methyl)-2-p-tolylH-imidazo[1,2-a]pyridine, 3-((1H-pyrazol-1-yl)methyl)-6-methyl-2-p-tolylH-imidazo[1,2-a]pyridine, 6-methyl-3-((3,5-dimethyl-1H-pyrazol-1-yl)methyl)-2-p-tolylH-imidazo[1,2-a]pyridine, 3-((1H-1,2,3-triazol-1-yl)methyl)-6-methyl-2-p-tolylH-imidazo[1,2-a]pyridine, 3-((1H-1,2,4-triazol-1-yl)methyl)-6-methyl-2-p-tolylH-imidazo[1,2-a]pyridine, N,N-dimethyl-9-((6-methyl-2-p-tolylH-imidazo[1,2-a]pyridin-3-yl)methyl)-9H-purin-6-amine, 1-((6-methyl-2-p-tolylH-imidazo[1,2-a]pyridin-3-yl)methyl)-1H-imidazo[4,5-b]pyridine, 6-methyl-3-((5-methyl-2H-tetrazol-2-yl)methyl)-2-p-tolylH-imidazo[1,2-a]pyridine, 6-methyl-3-((5-methyl-1H-tetrazol-1-yl)methyl)-2-p-tolylH-imidazo[1,2-a]pyridine, 3-((2-isopropyl-1H-imidazol-1-yl)methyl)-6-methyl-2-p-tolylH-imidazo[1,2-a]pyridine, 3-((4,5-dichloro-1H-imidazol-1-yl)methyl)-6-methyl-2-p-tolylH-imidazo[1,2-a]pyridine, 3-((2-ethyl-1H-imidazol-1-yl)methyl)-6-methyl-2-p-tolylH-imidazo[1,2-a]pyridine, 6-methyl-3-((2-phenyl-1H-imidazol-1-yl)methyl)-2-p-tolylH-imidazo[1,2-a]pyridine, N,N-dimethyl-1-((6-methyl-2-p-tolylH-imidazo[1,2-a]pyridin-3-yl)methyl)-1H-imidazole-2-carboxamide, 2-((6-methyl-2-p-tolylH-imidazo[1,2-a]pyridin-3-yl)methyl)-2H-benzo[d][1,2,3]triazole, 1-((6-methyl-2-p-tolylH-imidazo[1,2-a]pyridin-3-yl)methyl)-1H-benzo[d]imidazole, 3-((1H-1,2,4-triazol-1-yl)methyl)-6-chloro-2-(4-chlorophenyl)H-imidazo[1,2-a]pyridine, 3-((1H-1,2,3-triazol-1-yl)methyl)-6-chloro-2-(4-chlorophenyl)H-imidazo[1,2-a]pyridine, methyl 1-((6-chloro-2-(4-chlorophenyl)H-imidazo[1,2-a]pyridin-3-yl)methyl)-1H-1,2,4-triazole-3-carboxylate, methyl 2-((6-chloro-2-(4-chlorophenyl)H-imidazo[1,2-a]pyridin-3-yl)methyl)-2H-1,2,4-triazole-3-carboxylate, 3-((1H-pyrazol-1-yl)methyl)-6,8-dichloro-2-p-tolylH-imidazo[1,2-a]pyridine, 3-((1H-1,2,3-triazol-1-yl)methyl)-2-(4-chlorophenyl)H-imidazo[1,2-a]pyridine, 3-((2H-1,2,3-triazol-2-yl)methyl)-2-(4-chlorophenyl)H-imidazo[1,2-a]pyridine, 3-((1H-1,2,3-triazol-1-yl)methyl)-6-chloro-2-phenylH-imidazo[1,2-a]pyridine, 3-((2H-1,2,3-triazol-2-yl)methyl)-6-chloro-2-phenylH-imidazo[1,2-a]pyridine, 3-((2H-1,2,3-triazol-2-yl)methyl)-6-chloro-2-(4-chlorophenyl)H-imidazo[1,2-a]pyridine, 2-((6-chloro-2-(4-chlorophenyl)H-imidazo[1,2-a]pyridin-3-yl)methyl)-N-methyl-2H-1,2,4-triazole-3-carboxamide, methyl 2-((6-methyl-2-p-tolylH-imidazo[1,2-a]pyridin-3-yl)methyl)-2H-1,2,4-triazole-3-carboxylate, methyl 1-((6-methyl-2-p-tolylH-imidazo[1,2-a]pyridin-3-yl)methyl)-1H-1,2,4-triazole-3-carboxylate, methyl 1-((2-(4-chlorophenyl)H-imidazo[1,2-a]pyridin-3-yl)methyl)-1H-1,2,4-triazole-3-carboxylate, methyl 2-((6-chloro-2-phenylH-imidazo[1,2-a]pyridin-3-yl)methyl)-2H-1,2,4-triazole-3-carboxylate, methyl 1-((6-chloro-2-phenylH-imidazo[1,2-a]pyridin-3-yl)methyl)-1H-1,2,4-triazole-3-carboxylate, 2-((2-(4-chlorophenyl)H-imidazo[1,2-a]pyridin-3-yl)methyl)-N-methyl-2H-1,2,4-triazole-3-carboxamide, methyl 2-((2-(4-chlorophenyl)H-imidazo[1,2-a]pyridin-3-yl)methyl)-2H-1,2,4-triazole-3-carboxylate, 2-(6-chloro-2-(4-chlorophenyl)H-imidazo[1,2-a]pyridin-3-yl)methyl)-N-methoxy-N-methyl-2H-1,2,4-triazole-3-carboxamide, ethyl 1-((6-chloro-2-(4-chlorophenyl)H-imidazo[1,2-a]pyridin-3-yl)methyl)-1H-imidazole-2-carboxylate, 2-((6-chloro-2-(4-chlorophenyl)H-imidazo[1,2-a]pyridin-3-yl)methyl)-2H-1,2,4-triazole-3-carboxamide, 2-((6-chloro-2-(4- chlorophenyl)H-imidazo[1,2-a]pyridin-3-yl)methyl)-N,N-dimethyl-2H-1,2,4-triazole-3-carboxamide, ethyl 1-((6-methyl-2-p-tolylH-imidazo[1,2-a]pyridin-3-yl)methyl)-1H-imidazole-2-carboxylate, N-methyl-2-((6-methyl-2-p-tolylH-imidazo[1,2-a]pyridin-3-yl)methyl)-2H-1,2,4-triazole-3-carboxamide, N,N-dimethyl-2-((6-methyl-2-p-tolylH-imidazo[1,2-a]pyridin-3-yl)methyl)-2H-1,2,4-triazole-3-carboxamide, 2-((6-methyl-2-p-tolylH-imidazo[1,2-a]pyridin-3-yl)methyl)-2H-1,2,4-triazole-3-carboxamide, isopropyl 2-((6-chloro-2-(4-chlorophenyl)H-imidazo[1,2-a]pyridin-3-yl)methyl)-2H-1,2,4-triazole-3-carboxylate, and 3-(1-(1H-1,2,4-triazol-1-yl)ethyl)-6-methyl-2-p-tolylH-imidazo[1,2-a]pyridine, 3-((2-(4-chlorophenyl)-6-fluoroimidazo[1,2-a]pyridin-3-yl)methyl)-1,2,4-oxadiazole-5-carbohydrazide, 3-((2-(4-chlorophenyl)-6-fluoroimidazo[1,2-a]pyridin-3-yl)methyl)-1,2,4-oxadiazole-5-carboxamide, 3-((2-(4-chlorophenyl)-6-fluoroimidazo[1,2-a]pyridin-3-yl)methyl)-1,2,4-oxadiazole-5-carboxamide, ethyl 3-((2-(4-chlorophenyl)imidazo[1,2-a]pyridin-3-yl)methyl)-1,2,4-oxadiazole-5-carboxylate, ethyl 3-((2-(4-chlorophenyl)-6-fluoroimidazo[1,2-a]pyridin-3-yl)methyl)-1,2,4-oxadiazole-5-carboxylate, ethyl 3-((6-fluoro-2-(4-fluorophenyl)imidazo[1,2-a]pyridin-3-yl)methyl)-1,2,4-oxadiazole-5-carboxylate, 3-((2-(4-chlorophenyl)-6-fluoroimidazo[1,2-a]pyridin-3-yl)methyl)-N-methyl-1,2,4-oxadiazole-5-carboxamide, 3-((6-fluoro-2-(4-fluorophenyl)imidazo[1,2-a]pyridin-3-yl)methyl)-1,2,4-oxadiazole-5-carboxamide, 3-((6-fluoro-2-(4-fluorophenyl)imidazo[1,2-a]pyridin-3-yl)methyl)-N-methyl-1,2,4-oxadiazole-5-carboxamide, 3-((2-(4-chlorophenyl)-6-fluoroimidazo[1,2-a]pyridin-3-yl)methyl)-N-hydroxy-1,2,4-oxadiazole-5-carboxamide, 3-((6-fluoro-2-(4-fluorophenyl)imidazo[1,2-a]pyridin-3-yl)methyl)-N-hydroxy-1,2,4-oxadiazole-5-carboxamide, 3-((6-fluoro-2-(4-fluorophenyl)imidazo[1,2-a]pyridin-3-yl)methyl)-N-methoxy-1,2,4-oxadiazole-5-carboxamide, 3-((6-fluoro-2-(4-fluorophenyl)imidazo[1,2-a]pyridin-3-yl)methyl)-N-hydroxy-N-methyl-1,2,4-oxadiazole-5-carboxamide, and 3-((2-(4-chlorophenyl)imidazo[1,2-a]pyridin-3-yl)methyl)-N-hydroxy-1,2,4-oxadiazole-5-carboxamide.

The following compounds are illustrative of compounds of Formula III, however, the invention is not limited to the compounds listed herein: 1-((6-methyl-2-p-tolylH-imidazo[1,2-a]pyridin-3-yl)methyl)pyrrolidin-2-one, 3-ethyl-4-methyl-1-((6-methyl-2-p-tolylH-imidazo[1,2-a]pyridin-3-yl)methyl)-1H-pyrrol-2(5H)-one, 4-methoxy-1-((6-methyl-2-p-tolylH-imidazo[1,2-a]pyridin-3-yl)methyl)-1H-pyrrol-2(5H)-one, 1,2-dihydro-3-methyl-1-((6-methyl-2-p-tolylH-imidazo[1,2-a]pyridin-3-yl)methyl)pyrazol-5-one, 3-((6-methyl-2-p-tolylH-imidazo[1,2-a]pyridin-3-yl)methyl)oxazolidin-2-one, 1-methyl-3-((6-methyl-2-p-tolylH-imidazo[1,2-a]pyridin-3-yl)methyl)imidazolidin-2-one, 1-((6-methyl-2-p-tolylH-imidazo[1,2-a]pyridin-3-yl)methyl)piperidin-2-one, 1-((6-methyl-2-p-tolylH-imidazo[1,2-a]pyridin-3-yl)methyl)pyridin-2(1H)-one, 3-methyl-1-((6-methyl-2-p-tolylH-imidazo[1,2-a]pyridin-3-yl)methyl)pyridin-2(1H)-one, 6-methyl-2-((6-methyl-2-p-tolylH-imidazo[1,2-a]pyridin-3-yl)methyl)pyridazin-3(2H)-one, 4,5-dichloro-2-((6-methyl-2-p-tolylH-imidazo[1,2-a]pyridin-3-yl)methyl)pyridazin-3(2H)-one, 3-((6-methyl-2-p-tolylH-imidazo[1,2-a]pyridin-3-yl)methyl)pyrimidin-4(3H)-one, 1-((6-methyl-2-p-tolylH-imidazo[1,2-a]pyridin-3-yl)methyl)pyrimidin-2(1H)-one, 1-((6-chloro-2-(4-chlorophenyl)H-imidazo[1,2-a]pyridin-3-yl)methyl)pyrrolidin-2-one, 1-((6-chloro-2-(4-chlorophenyl)H-imidazo[1,2-a]pyridin-3-yl)methyl)-4-methoxy-1H-pyrrol-2(5H)-one, 3-((6-chloro-2-(4-chlorophenyl)H-imidazo[1,2-a]pyridin-3-yl)methyl)oxazolidin-2-one, 1-((6-chloro-2-(4-chlorophenyl)H-imidazo[1,2-a]pyridin-3-yl)methyl)pyridin-2(1H)-one, 1-((6-chloro-2-(4-chlorophenyl)H-imidazo[1,2-a]pyridin-3-yl)methyl)-3-methylpyridin-2(1H)-one, 1-((6-chloro-2-(4-chlorophenyl)H-imidazo[1,2-a]pyridin-3-yl)methyl)-6-methylpyridin-2(1H)-one, 2-((6-chloro-2-(4-chlorophenyl)H-imidazo[1,2-a]pyridin-3-yl)methyl)-6-methylpyridazin-3(2H)-one, 5-chloro-1-((6-chloro-2-(4-chlorophenyl)H-imidazo[1,2-a]pyridin-3-yl)methyl)pyridin-2(1H)-one, 1-((6-chloro-2-(4-chlorophenyl)H-imidazo[1,2-a]pyridin-3-yl)methyl)-4-methoxy-1H-pyrrol-2(5H)-one, 1-methyl-3-((6-methyl-2-p-tolylH-imidazo[1,2-a]pyridin-3-yl)methyl)imidazolidine-2,4-dione, 1-((6-methyl-2-p-tolylH-imidazo[1,2-a]pyridin-3-yl)methyl)azetidin-2-one, 5,5-dimethyl-3-((6-methyl-2-p-tolylH-imidazo[1,2-a]pyridin-3-yl)methyl)oxazolidine-2,4-dione, 3-((6-methyl-2-p-tolylH-imidazo[1,2-a]pyridin-3-yl)methyl)thiazole-2(3H)-thione, 4,5-dimethyl-3-((6-methyl-2-p-tolylH-imidazo[1,2-a]pyridin-3-yl)methyl)thiazole-2(3H)-thione, 4-((6-methyl-2-p-tolylH-imidazo[1,2-a]pyridin-3-yl)methyl)-3-(methylthio)-1,2,4-thiadiazole-5(4H)-thione, 1-((6-methyl-2-p-tolylH-imidazo[1,2-a]pyridin-3-yl)methyl)pyrimidine-2(1H)-thione, 2-((6,8-dichloro-2-p-tolylH-imidazo[1,2-a]pyridin-3-yl)methyl)-6-methylpyridazin-3(2H)-one, 1-((6,8-dichloro-2-p-tolylH-imidazo[1,2-a]pyridin-3-yl)methyl)pyrrolidin-2-one, 1-((2-(4-chlorophenyl)H-imidazo[1,2-a]pyridin-3-yl)methyl)pyridin-2(1H)-one, 1-((6-chloro-2-phenylH-imidazo[1,2-a]pyridin-3-yl)methyl)pyridin-2(1H)-one, and 1-((6-chloro-2-(4-chlorophenyl)H-imidazo[1,2-a]pyridin-3-yl)methyl)azetidin-2-one.

The following compounds are illustrative of compounds of Formula IV, however, the invention is not limited to the compounds listed herein: N-((6-methyl-2-p-tolylH-imidazo[1,2-a]pyridin-3-yl)methyl)-1,2,4-triazin-3-amine, 4-methyl-N-((6-methyl-2-p-tolylH-imidazo[1,2-a]pyridin-3-yl)methyl)pyrimidin-2-amine, N-((6-methyl-2-p-tolylH-imidazo[1,2-a]pyridin-3-yl)methyl)pyrazin-2-amine, N-((6-methyl-2-p-tolylH-imidazo[1,2-a]pyridin-3-yl)methyl)pyrimidin-2-amine, 4,6-dimethyl-N-((6-methyl-2-p-tolylH-imidazo[1,2-a]pyridin-3-yl)methyl)pyrimidin-2-amine, 4,6-dichloro-N-((6-methyl-2-p-tolylH-imidazo[1,2-a]pyridin-3-yl)methyl)pyrimidin-2-amine, 5-bromo-N-((6-methyl-2-p-tolylH-imidazo[1,2-a]pyridin-3-yl)methyl)pyrimidin-2-amine, 3,5-dichloro-N-((6-methyl-2-p-tolylH-imidazo[1,2-a]pyridin-3-yl)methyl)pyridin-2-amine, N-((6-methyl-2-p-tolylH-imidazo[1,2-a]pyridin-3-yl)methyl)pyridin-2-amine, N-((6-chloro-2-(4-chlorophenyl)H-imidazo[1,2-a]pyridin-3-yl)methyl)pyrimidin-2-amine, N-((6-methyl-2-p-tolylH-imidazo[1,2-a]pyridin-3-yl)methyl)isoxazol-3-amine, N-((6-methyl-2-p-tolylH-imidazo[1,2-a]pyridin-3-yl)methyl)thiazol-2-amine, 3-methyl-N-((6-methyl-2-p-tolylH-imidazo[1,2-a]pyridin-3-yl)methyl)isothiazol-5-amine, (6-methyl-2-p-tolylH-imidazo[1,2-a]pyridin-3-yl)-N-(4H-1,2,4-triazol-4-yl)methanamine, 1-methyl-N-((6-methyl-2-p-tolylH-imidazo[1,2-a]pyridin-3-yl)methyl)-1H-benzo[d]imidazol-2-amine, 5-chloro-N-((6-methyl-2-p-tolylH-imidazo[1,2-a]pyridin-3-yl)methyl)pyridin-2-amine, N-((6-methyl-2-p-tolylH-imidazo[1,2-a]pyridin-3-yl)methyl)-1H-imidazol-2-amine, 1-((6-methyl-2-p-tolylH-imidazo[1,2-a]pyridin-3-yl)methoxy)-1H-benzo[d][1,2,3]triazole, 2-((6-methyl-2-p-tolylH-imidazo[1,2-a]pyridin-3-yl)methoxy)isoindoline-1,3-dione, 3-((4-methyl-4H-1,2,4-triazol-3-ylthio)methyl)-6-methyl-2-p-tolylH-imidazo[1,2-a]pyridine, 3-((1-methyl-1H-benzo[d]imidazol-2-ylthio)methyl)-6-methyl-2-p-tolylH-imidazo[1,2-a]pyridine, 3-((4H-1,2,4-triazol-3-ylthio)methyl)-6-methyl-2-p-tolylH-imidazo[1,2-a]pyridine, 6-methyl-3-((phenylthio)methyl)-2- p-tolylH-imidazo[1,2-a]pyridine, N-((6-methyl-2-p-tolylH-imidazo[1,2-a]pyridin-3-yl)methyl)-1H-imidazol-2-amine, 3-((5-methyl-1,3,4-thiadiazol-2-ylthio)methyl)-6-methyl-2-p-tolylH-imidazo[1,2-a]pyridine, 3-((1,3,4-thiadiazol-2-ylthio)methyl)-6-methyl-2-p-tolylH-imidazo[1,2-a]pyridine, N-((6-methyl-2-p-tolylH-imidazo[1,2-a]pyridin-3-yl)methyl)-1H-pyrazol-5-amine, ethyl 5-((6-methyl-2-p-tolylH-imidazo[1,2-a]pyridin-3-yl)methylamino)-1H-pyrazole-4-carboxylate, N-((6-chloro-2-(4-chlorophenyl)H-imidazo[1,2-a]pyridin-3-yl)methyl)-4-methylpyrimidin-2-amine, N-((6-chloro-2-(4-chlorophenyl)H-imidazo[1,2-a]pyridin-3-yl)methyl)-4,6-dimethylpyrimidin-2-amine, 5-((6-chloro-2-(4-chlorophenyl)H-imidazo[1,2-a]pyridin-3-yl)methylamino)-1H-pyrazole-4-carbonitrile, N-((6-chloro-2-(4-chlorophenyl)H-imidazo[1,2-a]pyridin-3-yl)methyl)-4-methoxy-6-methylpyrimidin-2-amine, N-((6-chloro-2-(4-chlorophenyl)H-imidazo[1,2-a]pyridin-3-yl)methyl)-4,6-dimethoxypyrimidin-2-amine, N-((6-chloro-2-(4-chlorophenyl)H-imidazo[1,2-a]pyridin-3-yl)methyl)benzo[c][1,2,5]thiadiazol-4-amine, 6-methyl-3-(((thiophen-2-ylthio)methyl)-2-p-tolylH-imidazo[1,2-a]pyridine, 6-methyl-3-((pyridin-3-yloxy)methyl)-2-p-tolylH-imidazo[1,2-a]pyridine, N-((6,8-dichloro-2-p-tolylH-imidazo[1,2-a]pyridin-3-yl)methyl)-4,6-dimethylpyrimidin-2-amine, N-((6,8-dichloro-2-p-tolylH-imidazo[1,2-a]pyridin-3-yl)methyl)-1H-imidazol-2-amine, 3-((4,6-dimethylpyrimidin-2-ylthio)methyl)-6-methyl-2-p-tolylH-imidazo[1,2-a]pyridine, 3-((benzo[d]oxazol-2-ylthio)methyl)-6-methyl-2-p-tolylH-imidazo[1,2-a]pyridine, N-((2-(4-chlorophenyl)H-imidazo[1,2-a]pyridin-3-yl)methyl)-4-methylpyrimidin-2-amine, N-((6-chloro-2-phenylH-imidazo[1,2-a]pyridin-3-yl)methyl)-4-methylpyrimidin-2-amine, 4-methyl-N-((6-methyl-2-p-tolylH-imidazo[1,2-a]pyridin-3-yl)methyl)thiazol-2-amine, N-((6-methyl-2-p-tolylH-imidazo[1,2-a]pyridin-3-yl)methyl)-1,2,4-triazin-3-amine, N-((6-methyl-2-p-tolylH-imidazo[1,2-a]pyridin-3-yl)methyl)-1,3,5-triazin-2-amine, and 2-((6-methyl-2-p-tolylH-imidazo[1,2-a]pyridin-3-yl)methylamino)-3-methylisoquinolin-1(2H)-one.

In exemplary embodiments, the invention provides compounds having a structure set forth in Table 2:

TABLE 2

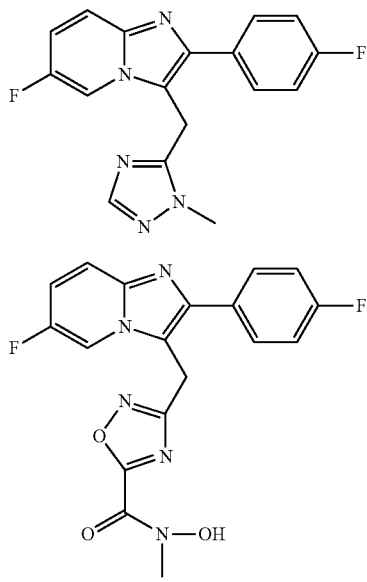

TABLE 2-continued

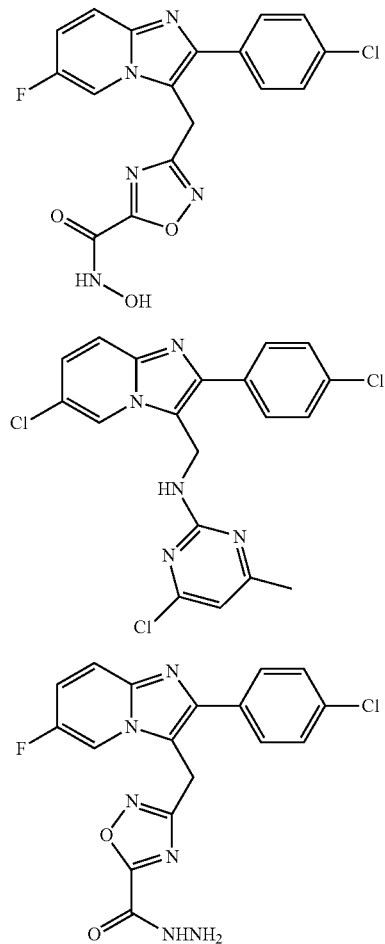

In various embodiments, the compounds of the invention are active against one or more benzodiazepine receptor. In various embodiments of the invention, the compounds of the invention have activity versus the benzodiazepine central and/or benzodiazepine peripheral receptor of at least 40% inhibition at 10 μM. In certain embodiments, the compounds have an activity versus the benzodiazepine central and/or benzodiazepine peripheral receptor with an $IC_{50}$ less than or equal to 1 μM. In various embodiments, the compounds of the invention have an activity versus the benzodiazepine central and/or benzodiazepine peripheral receptor with an $IC_{50}$ less than or equal to 0.3 μM. In certain embodiments the invention provides compounds having activity versus the benzodiazepine central and/or benzodiazepine peripheral receptor with an $IC_{50}$ less than or equal to 0.1 μM.

In an exemplary embodiment, the invention provides compounds that are two-fold selective for the benzodiazepine central receptor over the benzodiazepine peripheral receptor. In various embodiments compounds of the invention are ten-fold selective for the benzodiazepine central receptor over the benzodiazepine peripheral receptor. In certain embodiments, the compounds of the invention are 50-fold selective for the benzodiazepine central receptor over the benzodiazepine peripheral receptor. In an exemplary embodiment, compounds of the present invention can have similar activity, defined as less than two-fold difference, versus both the benzodiazepine central and peripheral receptors. One skilled in the art will recognize that subtypes contribute to the effects of GABA-A modulators. Such that compounds favoring different subtypes can have different therapeutic effects. The magnitude of modulation, for example, partial modulators can influence the effects in vivo. Modulation favoring alpha 1 relative to alpha2 and/or alpha 3 can have sedative hypnotic effects (e.g., zolpedem, zaleplon). Compounds with reduced selectivity of alpha 1 can express anxiolytic effects with less sedation. Compounds with selectivity for alpha 5 can have memory/cognition enhancing effects.

The present invention further provides pharmaceutical compositions comprising as active agents, the compounds described herein.

As used herein a "pharmaceutical composition" refers to a preparation of one or more of the compounds described herein, or physiologically acceptable salts or solvates (including hydrates) thereof, with other chemical components such as physiologically suitable carriers and excipients.

Pharmaceutical compositions containing compounds of Formulae I, II, III, IV and any compound described herein can be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, a dose ranges from about 0.1 mg to about 7000 mg, for example, about 1 mg to about 100 mg, or about, about 25 mg to about 50 mg, in single or divided doses. In some embodiments, a dose can range from about 50 mg to about 500 mg, for example, about 100 mg to about 500 mg in single or divided doses. The compounds of the invention can be provided in unit dosage format. The doses of compounds of the invention can be administered 1, 2, 3, 4, 5, 6 or more times in a day. It may be recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

In one embodiment, the pharaceutical composition comprises a compound acccording to formula I wherein Z is CH, D, Q is 1-methyl-1,2,4-triazol-5-yl, $R^1$ and $R^2$ are H, D, $R^3$ is F at position 6, $R^4$ is F at position 4', and $R^5$ and $R^6$ are H.

One aspect of the present invention relates to combination therapy. This type of therapy is advantageous because the co-administration of active ingredients achieves a therapeutic effect that is greater than the therapeutic effect achieved by administration of only a single therapeutic agent. In one embodiment, the co-administration of two or more therapeutic agents achieves a synergistic effect, i.e., a therapeutic affect that is greater than the sum of the therapeutic effects of the individual components of the combination. In another embodiment, the co-administration of two or more therapeutic agents achieves an augmentation effect.

The active ingredients that comprise a combination therapy can be administered together via a single dosage form or by separate administration of each active agent. In certain embodiments, the first and second therapeutic agents are administered in a single dosage form. The agents can be formulated into a single tablet, pill, capsule, or solution for parenteral administration and the like.

Alternatively, the first therapeutic agent and the second therapeutic agents can be administered as separate compositions, e.g., as separate tablets or solutions. The first active agent can be administered at the same time as the second active agent or the first active agent can be administered intermittently with the second active agent. The length of time between administration of the first and second therapeutic agent can be adjusted to achieve the desired therapeutic effect. In certain instances, the second therapeutic agent can be administered only a few minutes (e.g., 1, 2, 5, 10, 30, or 60 min) after administration of the first therapeutic agent. Alternatively, the second therapeutic agent can be administered several hours (e.g., 2, 4, 6, 10, 12, 24, or 36 hr) after administration of the first therapeutic agent. In certain embodiments, it can be advantageous to administer more than one dosage of the second therapeutic agent between administrations of the first therapeutic agent. For example, the second therapeutic agent can be administered at 2 hours and then again at 10 hours following administration of the first therapeutic agent. Alternatively, it can be advantageous to administer more than one dosage of the first therapeutic agent between administrations of the second therapeutic agent. Importantly, it is preferred that the therapeutic effects of each active ingredient overlap for at least a portion of the duration of each therapeutic agent so that the overall therapeutic effect of the combination therapy is attributable in part to the combined or synergistic effects of the combination therapy.

The dosage of the active agents will generally be dependent upon a number of factors including pharmacodynamic characteristics of each agent of the combination, mode and route of administration of active agent(s), the health of the patient being treated, the extent of treatment desired, the nature and kind of concurrent therapy, if any, and the frequency of treatment and the nature of the effect desired. In general, dosage ranges of the active agents often range from about 0.001 to about 250 mg/kg body weight per day. For example, for a normal adult having a body weight of about 70 kg, a dosage in the range of from about 0.1 to about 25 mg/kg body weight is typically preferred. However, some variability in this general dosage range can be required depending upon the age and weight of the subject being treated, the intended route of administration, the particular agent being administered and the like. Since two or more different active agents are being used together in a combination therapy, the potency of each agent and the interactive effects achieved using them together must be considered. Importantly, the determination of dosage ranges and optimal dosages for a particular mammal is also well within the ability of one of ordinary skill in the art having the benefit of the instant disclosure.

In certain embodiments, it can be advantageous for the pharmaceutical combination to have a relatively large amount of the first component compared to the second component. In certain instances, the ratio of the first active agent to second active agent is 30:1, 20:1, 15:1, 10:1, 9:1, 8:1, 7:1, 6:1, or 5:1. In certain embodiments, it can be preferable to have a more equal distribution of pharmaceutical agents. In certain instances, the ratio of the first active agent to the second active agent is 4:1, 3:1, 2:1, 1:1, 1:2, 1:3, or 1:4. In certain embodiments, it can be advantageous for the pharmaceutical combination to have a relatively large amount of the second component compared to the first component. In certain instances, the ratio of the second active agent to the first active agent is 30:1, 20:1, 15:1, 10:1, 9:1, 8:1, 7:1, 6:1, or 5:1. Importantly, a composition comprising any of the above-identified combinations of first therapeutic agent and second therapeutic agent can be administered in divided doses 1, 2, 3, 4, 5, 6, or more times per day or in a form that will provide a rate of release effective to attain the desired results. In a preferred embodiment, the dosage form contains both the first and second active agents. In a more preferred embodiment, the dosage form only has to be administered one time per day and the dosage form contains both the first and second active agents.

For example, a formulation intended for oral administration to humans can contain from 0.1 mg to 5 g of the first therapeutic agent and 0.1 mg to 5 g of the second therapeutic agent, both of which are compounded with an appropriate and convenient amount of carrier material varying from about 5 to about 95 percent of the total composition. Unit dosages will generally contain between from about 0.5 mg to about 1500 mg of the first therapeutic agent and 0.5 mg to about 1500 mg of the second therapeutic agent. In a preferred embodiment, the dosage comprises 0.5 mg, 1 mg, 2 mg, 3 mg, 4 mg, 5 mg, 10 mg, 25 mg, 50 mg, 100 mg, 200 mg, 300 mg, 400 mg, 500 mg, 600 mg, 800 mg, or 1000 mg, etc., up to 1500 mg of the first therapeutic agent. In a preferred embodiment, the dosage comprises 0.5 mg, 1 mg, 2 mg, 3 mg, 4 mg, 5 mg, 10 mg, 25 mg, 50 mg, 100 mg, 200 mg, 300 mg, 400 mg, 500 mg, 600 mg, 800 mg, or 1000 mg, etc., up to 1500 mg of the second therapeutic agent.

The optimal ratios of the first and second therapeutic agent can be determined by standard assays known in the art. For example, the phenyl-p-benzoquinone test can be used to establish analgesic effectiveness. The phenyl-p-benzoquinone induced writhing test in mice (H. Blumberg et al., 1965, Proc. Soc. Exp. Med. 118:763-766) and known modifications thereof is a standard procedure which can be used for detecting and comparing the analgesic activity of different classes of analgesic drugs with a good correlation with human analgesic activity. Data for the mouse, as presented in an isobologram, can be translated to other species where the orally effective analgesic dose of the individual compounds are known or can be estimated. The method consists of reading the percent ED50 dose for each dose ratio on the best fit regression analysis curve from the mouse isobologram, multiplying each component by its effective species dose, and then forming the ratio of the amount of COX-2 inhibitor and opioid analgesic. This basic correlation for analgesic properties enables estimation of the range of human effectiveness (E. W. Pelikan, 1959, The Pharmacologist 1:73). Thus, application of an equieffective dose substitution model and a curvilinear regression analysis utilizing all the data for the individual compounds and various dose ratios for the combinations can be used to establish the existence of unexpectedly enhanced analgesic activity of combinations of active agents, i.e., the resulting activity is greater than the activity expected from the sum of the activities of the individual components.

The toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of RT production from infected cells compared to untreated control as determined in cell culture. Such information can be used to more accurately determine useful doses in humans. Levels in plasma can be measured, for example, by high performance liquid chromatography (HPLC).

Synergism and Augmentation

The term "synergistic" refers to a combination which is more effective than the additive effects of any two or more single agents. A synergistic effect permits the effective treatment of a disease using lower amounts (doses) of either individual therapy. The lower doses result in lower toxicity without reduced efficacy. In addition, a synergistic effect can result in improved efficacy, e.g., improved binding activity. Finally, synergy can result in an improved avoidance or reduction of disease as compared to any single therapy.

Combination therapy can allow for the use of lower doses of the first therapeutic or the second therapeutic agent (referred to as "apparent one-way synergy" herein), or lower doses of both therapeutic agents (referred to as "two-way synergy" herein) than would normally be required when either drug is used alone.

In certain embodiments, the synergism exhibited between the second therapeutic agent and the first therapeutic agent is such that the dosage of the first therapeutic agent would be sub-therapeutic if administered without the dosage of the second therapeutic agent. Alternatively, the synergism exhibited between the second therapeutic agent and the first therapeutic agent is such that the dosage of the second therapeutic agent would be sub-therapeutic if administered without the dosage of the first therapeutic agent.

The terms "augmentation" or "augment" refer to combination where one of the compounds increases or enhances therapeutic effects of another compound or compounds administered to a patient. In some instances, augmentation can result in improving the efficacy, tolerability, or safety, or any combination thereof, of a particular therapy.

In certain embodiments, the present invention relates to a pharmaceutical composition comprising a therapeutically effective dose of a first therapeutic agent together with a dose of a second therapeutic agent effective to augment the therapeutic effect of the first therapeutic agent. In other embodiments, the present invention relates to methods of augmenting the therapeutic effect in a patient of a first therapeutic agent by administering the second therapeutic agent to the patient. In various embodiments, the present invention relates to a pharmaceutical composition comprising a therapeutically effective dose of a second therapeutic agent together with a dose of a first therapeutic agent effective to augment the therapeutic effect of the second therapeutic agent. In selected embodiments, the present invention relates to methods of augmenting the therapeutic effect in a patient of a second therapeutic agent by administering the first therapeutic agent to the patient.

In certain preferred embodiments, the invention is directed in part to synergistic combinations of the first therapeutic agent in an amount sufficient to render a therapeutic effect together with a second therapeutic agent. For example, in certain embodiments a therapeutic effect is attained which is at least about 2 (or at least about 4, 6, 8, or 10) times greater than that obtained with the dose of the first therapeutic agent alone. In certain embodiments, the synergistic combination provides a therapeutic effect which is up to about 20, 30 or 40 times greater than that obtained with the dose of first therapeutic agent alone. In such embodiments, the synergistic combinations display what is referred to herein as an "apparent one-way synergy", meaning that the dose of second therapeutic agent synergistically potentiates the effect of the first therapeutic agent, but the dose of first therapeutic agent does not appear to significantly potentiate the effect of the second therapeutic agent.

In certain embodiments, the combination of active agents exhibit two-way synergism, meaning that the second therapeutic agent potentiates the effect of the first therapeutic agent, and the first therapeutic agent potentiates the effect of the second therapeutic agent. Thus, various embodiments of the invention relate to combinations of a second therapeutic agent and a first therapeutic agent where the dose of each drug is reduced due to the synergism between the drugs, and the therapeutic effect derived from the combination of drugs in reduced doses is enhanced. The two-way synergism is not always readily apparent in actual dosages due to the potency ratio of the first therapeutic agent to the second therapeutic agent. For instance, two-way synergism can be difficult to detect when one therapeutic agent displays much greater therapeutic potency relative to the other therapeutic agent.

The synergistic effects of combination therapy can be evaluated by biological activity assays. For example, the therapeutic agents can be mixed at molar ratios designed to give approximately equipotent therapeutic effects based on the EC90 values. Then, three different molar ratios are used for each combination to allow for variability in the estimates of relative potency. These molar ratios are maintained throughout the dilution series. The corresponding monotherapies are also evaluated in parallel to the combination treatments using the standard primary assay format. A comparison of the therapeutic effect of the combination treatment to the therapeutic effect of the monotherapy gives a measure of the synergistic effect. Further details on the design of combination analyses can be found in B E Korba (1996) Antiviral Res. 29:49. Analysis of synergism, additivity, or antagonism can be determined by analysis of the aforementioned data using the CalcuSyn™ program (Biosoft, Inc.). This program evaluates drug interactions by use of the widely accepted method of Chou and Talalay combined with a statistically evaluation using the Monte Carlo statistical package. The data are displayed in several different formats including median-effect and dose-effects plots, isobolograms, and combination index [CI] plots with standard deviations. For the latter analysis, a CI greater than 1.0 indicates antagonism and a CI less than 1.0 indicates synergism.

Compositions of the invention present the opportunity for obtaining relief from moderate to severe cases of disease. Due to the synergistic and/or additive effects provided by the inventive combination of the first and second therapeutic agent, it can be possible to use reduced dosages of each of therapeutic agent. By using lesser amounts of other or both drugs, the side effects associated with each may be reduced in number and degree. Moreover, the inventive combination avoids side effects to which some patients are particularly sensitive.

One aspect of the present invention relates to a pharmaceutical composition of the present invention, or a pharmaceutically acceptable salt, solvate, clathrate, polymorpH, D, or co-crystal thereof, and an antidepressant. Nonlimiting examples of antidepressants include without limitation selective serotonin reuptake inhibitors, serotonin reuptake inhibitors, norepinephrine reuptake inhibitors, dopamine reuptake inhibitors, 5-HT 2A receptor modulators, triple reuptake inhibitors, and double reuptake inhibitors. In another aspect, the present invention discloses a method of treating a patient suffering from a mood discorder, comprising the step of co-administering to a patient in need thereof a therapeutically effective amount of a compound of the present invention, or a pharmaceutically acceptable salt, and an antidepressant.

Nonlimiting examples of 5-HT 2A receptor modulators include MDL 100907, SR 46349B, YM 992, fananserin, oxazolidine compounds A, phenylindole compounds A, piperidinyl compounds B, spiroazacyclic compounds C, or azacyclic compounds D, or a pharmaceutically acceptable salt, clathrate, polymorpH, D, or co-crystal of any one of them.

Nonlimiting examples of serotonin reuptake inhibitors include citalopram, duloxetine, escitalopram, fluoxetine, fluvoxamine, milnacipran, paroxetine, sertraline, clominpramine, femoxetine, indapline, alaprolclate, cericlamine, or ifoxetine, or a pharmaceutically acceptable salt, clathrate, polymorpH, D, or co-crystal of any one of them.

Nonlimiting examples of norepinephrine reuptake inhibitors include desipramine, maprotiline, lofepramine, reboxetine, oxaprotiline, fezolamine, tomoxetine, or (S,S)-hydroxybupropion, or a pharmaceutically acceptable salt, clathrate, polymorpH, D, or co-crystal of any one of them.

Pharmaceutical compositions for use in accordance with the present invention can be formulated in a conventional manner using one or more physiologically acceptable carriers comprising excipients and auxiliaries, which facilitate processing of the active compounds into preparations whicH, D, can be used pharmaceutically. The carriers must be acceptable in the sense of being compatible with the other ingredients of the formulation and not deleterious to the recipient thereof. Proper formulation is dependent upon the route of administration chosen. As will be understood by those of skill in the art, the carrier must be of a toxicity suitably low to be appropriate for administration to a subject.

Compounds that inhibit GABA can be formulated as pharmaceutical compositions and administered to a mammalian subject, such as a human patient in a variety of forms adapted to the chosen route of administration, i.e., orally, rectal, topical (including dermal, buccal, sublingual, and intraocular), or parenterally, by intravenous, intramuscular, topical, transdermal, intradermal, intraarticular, or subcutaneous routes.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starcH, D, wheat starcH, D, rice starcH, D, potato starcH, D, gelatin, gum tragacantH, D, methyl cellulose, hydroxypropylmethyl-cellulose, sodium carbomethylcellulose; and/or physiologically acceptable polymers such as polyvinylpyrrolidone (PVP). If desired, disintegrating agents can be added, such as cross-linked polyvinyl pyrrolidone, agar or alginic acid or a salt thereof such as sodium alginate.

In addition, an enteric coating may be useful as it is may be desirable to prevent exposure of the compounds of the invention to the gastric environment.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

Compositions for topical administration in the moutH, D, for example buccally or sublingually, include lozenges comprising the active ingredient in a flavored basis such as sucrose and acacia or tragacantH, D, and pastilles comprising the active ingredient in a basis such as gelatin and glycerin or sucrose and acacia. All formulations for oral administration should be in dosages suitable for the chosen route of administration.

For injection, the compounds of the invention can be formulated in aqueous solutions, preferably in physiologically compatible buffers such as Hank's or Ringer's solution or physiological saline buffer. For transmucosal and transdermal administration, penetrants appropriate to the barrier to be permeated can be used in the composition. Such penetrants, including for example DMSO or polyethylene glycol, are known in the art.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Pharmaceutical compositions for parenteral administration include aqueous and non-aqueous sterile injection solutions, which can contain anti-oxidants, buffers, bacteriostats and solutes, which render the formulation isotonic with the blood of the intended recipient. Compositions also include aqueous and non-aqueous sterile suspensions, which can include suspending agents and thickening agents. Pharmaceutical compositions for parenteral administration in an aqueous solution contain the active ingredients in water-soluble form. Additionally, suspensions of the active compounds can be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents, which increase the solubility of the compounds, to allow for the preparation of highly concentrated solutions.

The formulations can be presented in unit-dose of multi-dose containers, for example sealed ampoules and vials, and can be stored in a freeze-dried (lyophilized) condition requiring only the addition of a sterile liquid carrier, for example saline, phosphate-buffered saline (PBS) or the like, immediately prior to use. Extemporaneous injection solutions and suspensions can be prepared from sterile powders, granules and tablets of the kind previously described.

The compounds of the present invention can also be formulated in rectal compositions such as suppositories or retention enemas, using, e.g., conventional suppository bases such as cocoa butter, polyethylene glycol, or other glycerides.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compounds of the invention can be administered orally or via injection at a dose from 0.001 to 250 mg/kg per day. The dose range for adult humans is generally from 0.5 mg to 10 g/day. Tablets or other forms of presentation provided in discrete units can conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration can vary depending on the condition and its severity.

As used herein, and as would be understood by the person of skill in the art, the recitation of "a compound" is intended to include salts, solvates and inclusion complexes of that compound. The term "solvate" refers to a compound described herein and/or according to Formula I, II, III, or IV in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts can be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

It should be understood that in addition to the ingredients particularly mentioned above, the formulations of this invention can include other agents conventional in the art having regard to the type of formulation in question, for example those suitable for oral administration can include flavoring agents.

The compositions can be presented in a packaging device or dispenser, which can contain one or more unit dosage forms containing the active ingredient. Examples of a packaging device include metal or plastic foil, such as a blister pack and a nebulizer for inhalation. The packaging device or dispenser can be accompanied by instructions for administration. Compositions comprising a compound of the present invention formulated in a compatible pharmaceutical carrier can also be placed in an appropriate container and labeled for treatment of an indicated condition.

III. Chemical Synthesis

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the *Journal of Organic Chemistry*. The list, which is typically presented in a table entitled "Standard List of Abbreviations", is incorporated herein by reference.

In general, the compounds of the present invention can be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or can be obtained by the methods well known to persons of skill in the art.

Starting materials of structure type W, for some of the compounds of the invention, are prepared as follows:

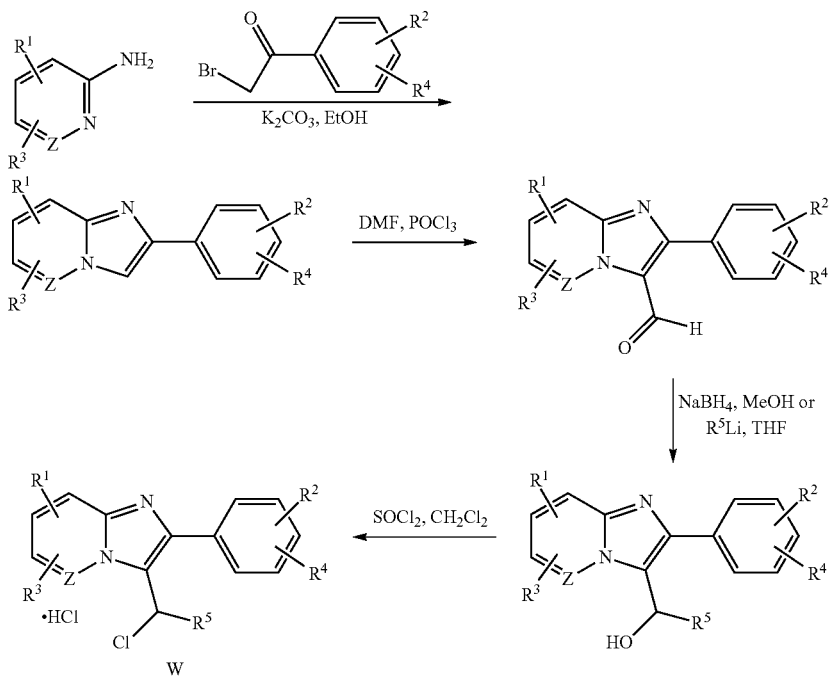

Some of the compounds of the invention are prepared according to Method A (for the synthesis of Formulae II and IV)

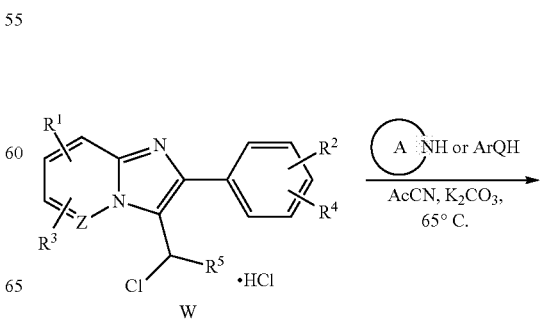

-continued

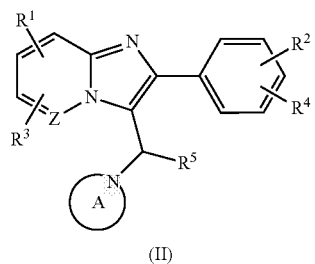

(II)

or

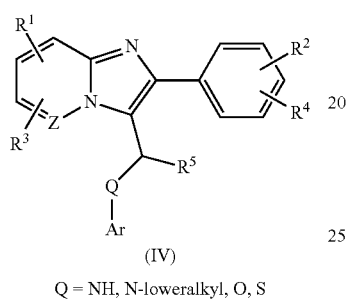

(IV)

Q = NH, N-loweralkyl, O, S

Some of the compounds of the invention are prepared according to Method B (for the synthesis of compounds of Formula III)

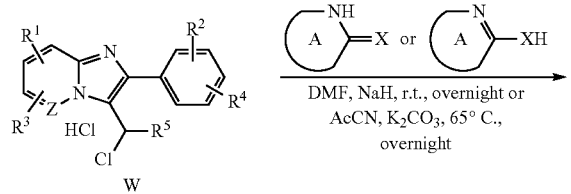

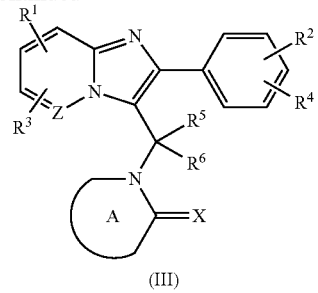

(III)

X = O, S

Some of the compounds of the invention are prepared according to Method C (General procedure for nucleophilic addition to aldehyde and dehydroxylations (for the synthesis of formula IV where Y is nil)

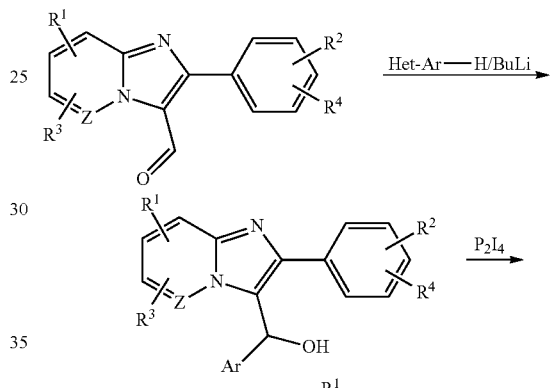

Some of the compounds of the invention are prepared according to Method D (Preparation of imidazopyridines with carbon-carbon bonded 6-membered aromatic side chains, formula IV where Y is nil).

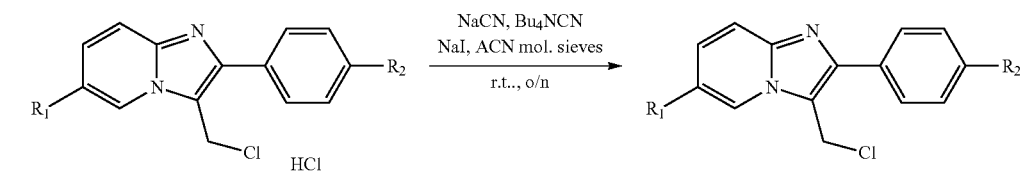

1. KOBu, RT, O/N
2. TFA, 150° C., uW, 5 min

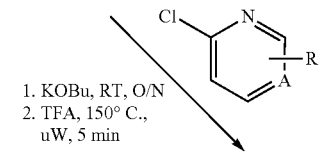

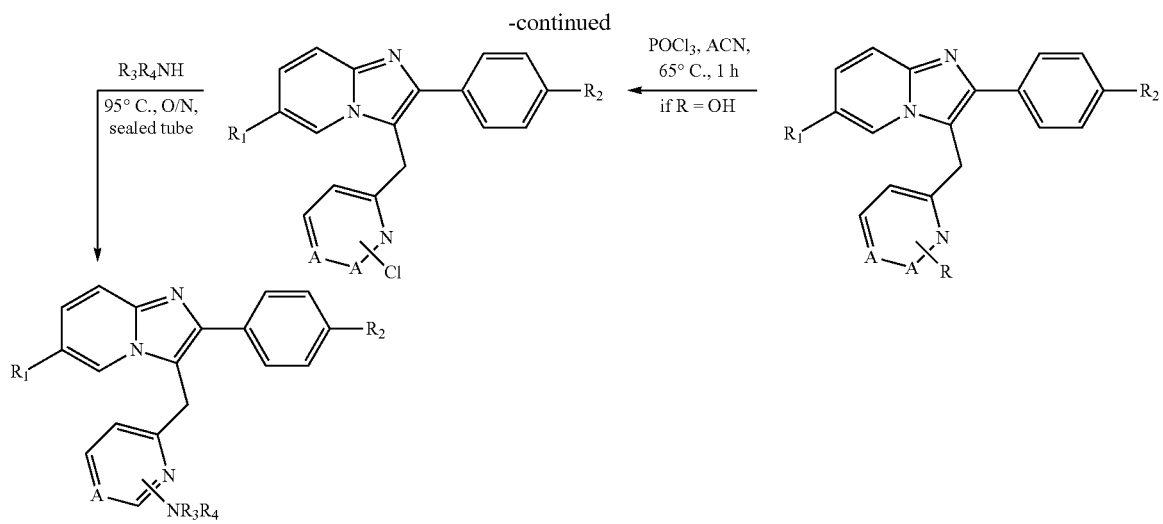

Other compounds of the invention not prepared by the above Methods are described as appropriate in the corresponding sections.

IV. Indications

The compounds of the present invention are useful in modulating the activity of GABA receptor complex or in modulating GABA mediated activity and are useful for treatment of and preventing central nervous system (CNS) disorders such as anxiety disorders (e.g., GAD and panic disorder) and a number of conditions in which GABA is believed to exert a physiologic role. These conditions include psychiatric disorders, convulsive disorders, aggressive behavior disorders, muscle spasms or tensing, depressive or bipolar disorders, cognitive disorders, sleeping disorders, neurodegenerative eye diseases, neurodegeneration, pain, emesis, or eating disorders and of complications arising therefrom.

The compounds described supra and to be described infra are useful in treating and/or preventing anxiety disorders, which can have their etiology in both psychologic and physiologic factors. Emotional stress can precipitate anxiety neurosis which represents the individual's fear of losing control of such emotional drives as aggressive or dependency needs, and losing control of his resulting actions. Physiologically, anxiety is associated with autonomic nervous system discharge and the related neurohumoral processes. In acute anxiety attacks, lasting from a few minutes to an hour, the individual experiences a subjective sense of terror, for no evident reason, and perhaps a haunting dread of catastrophe. Chronic anxiety displays less intense symptoms of longer duration, characterized by uneasiness, nervousness, nagging uncertainty about future events, headache, fatigue, and subacute autonomic symptoms.

Furthermore, the compounds described herein are useful in treating and/or preventing psychotic disorders, which tend towards chronicity, which impair functioning, and which are characterized by psychotic symptoms of disturbed thinking, feeding, and general behavior. Clear, goal-directed behavior becomes difficult, while blunting and inappropriate affect are the most characteristic emotional changes. Auditory hallucinations can be common, and delusions of persecution are frequent, as are threats of violence, minor aggressive outbursts and aggressive behavior. Disturbances of movement can range from significant over activity and excitement to retardation and stupor. Treatment has often included tranquilizers with the pharmacologic profile of compounds of the current invention, and other antipsychotic drugs, either orally or by long-acting depot injection to offset problems of patient compliance.

In addition, the compounds described herein are useful for treating and/or preventing other disorders such as convulsive disorders like epilepsy. Seizure disorders or epilepsy represent a broad group of central nervous system disorders of function that are characterized by recurrent, sudden, often brief attacks, which may alter consciousness, motor activity, sensory phenomena, and autonomic responses, and which may prompt inappropriate behavior. Recurrent seizure patterns of either an idiopathic or symptomatic etiology are termed epilepsy. The most common form of these recurrent but transient episodes are convulsive seizures, which may include loss of consciousness, motor function and control, and which may produce tonic or clonic jerking of the extremities. Pharmacological treatment of epilepsy has been directed to control based on seizure type, rather than etiology. Accordingly, the convulsions have been grouped in broad, but rather distinct types, including Tonic-clonic (Grand Mal), Partial (Focal) seizures, psychomotor (Complex partial) seizures, pyknoepileptic or Absence (Petit Mal) and the less frequent Myoclonic seizures.

The compounds described herein are also useful in the treatment and/or prevention of spasticity and acute muscle spasm. Spasticity represents not a single disorder, but rather a range of abnormalities of regulation of skeletal muscle that result from problems at various levels of the central nervous system. A predominant component is heightened muscle tone or hyper-excitability of tonic stretch muscle reflexes. While the pathophysiology of these disorders remains rather poorly understood, it often includes dysfunction of the descending spinal pathways. Presynaptic inhibition of motorneurons, as may be induced by GABA, or agents that in some respects resemble and/or exhibit the pharmacology of GABA provides some antispastic affect. Additionally, benzodiazepines, or drugs like compounds of the present invention that bind to the benzodiazepine receptor, can enhance the efficiency of inhibitory GABA-ergic transmission, and thus can provide some efficacy in the treatment or conditions of spasticity, particularly those due to spinal cord lesions. Acute muscle spasm can be associated with a variety of conditions including trauma, inflammation, anxiety, and pain.

The compounds described herein are useful for the treatment and/or prevention of sleep disorders. Difficulties in falling asleep, remaining asleep, sleeping for adequate lengths of time, or abnormal sleep behavior are common symptoms for those suffering with a sleep disorder. A number of sleep disorders, e.g., insomnia or sleep apnea, are described in the online *Merck Manual of Medical Information*. Insomnia is characterized by difficulty in sleeping or disturbed sleep patterns. Insomnia can be of a primary nature with little apparent relationship to intermediate somatic or psychic events, or secondary to some acquired pain, anxiety, or depression. Where possible, treatment is directed to the underlying cause of the condition; hypnotic medication is generally reserved for insomnia of emotional disturbances and for refractory cases due to more common causes.

In exemplary embodiments, the invention provides a method for treating or preventing a disease or condition selected from the group consisting of anxiety disorders; psychiatric disorders; convulsive disorders; aggressive behavior; muscle spasms or tension; depressive or bipolar disorders; cognitive disorders; sleeping disorders; neurodegenerative eye diseases; neurodegeneration; pain; epilepsy; schizophrenia; emesis and eating disorders; comprising administering to a patient a therapeutically effective amount of one or more compounds of the present invention, or a pharmaceutically acceptable salt thereof.

The following examples will further describe the invention, and are used for purposes of illustration only, and should not be considered as limiting the invention being disclosed. In general, the compounds of the present invention can be prepared by the methods illustrated in the reaction schemes as, for example, described below, or by modifications thereof, using readily available starting materials, reagents and conventional synthesis procedures. In these reactions, it is also possible to make use of variants that are in themselves known, but are not mentioned here. Compounds of the invention can be synthesized as follows.

The invention is illustrated by the following Examples, but is not limited to the specific embodiments contained therein.

EXAMPLES

General Procedure: Flash chromatography was performed on EM Science silica gel 60. Thin layer chromatography was performed using silica gel 60 $F_{254}$ plates, and compound visualization was effected using a UV light or with 10% $H_2SO_4$ containing 5% ammonium molybdate and 0.2% ceric sulfate. $^1$H Nuclear Magnetic Resonance (NMR) and $^{13}$C NMR spectroscopy were performed on a 400 MHz Varian instrument. Tetramethylsilane (TMS), deuterated chloroform ($CDCl_3$) or deuterated dimethyl sulfoxide (DMSO-$d_6$) were used as internal standards for $^1$H, D and $^{13}$C spectra, respectively. J values are given in hertz.

Example 1

3-((1H-imidazol-1-yl)methyl)-6-methyl-2-p-tolylimidazo[1,2-a]pyridine (1)

Step 1: 6-Methyl-2-(4-methylphenyl)-imidazo[1,2-a]-pyridine

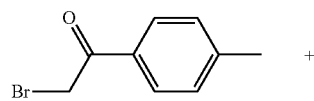

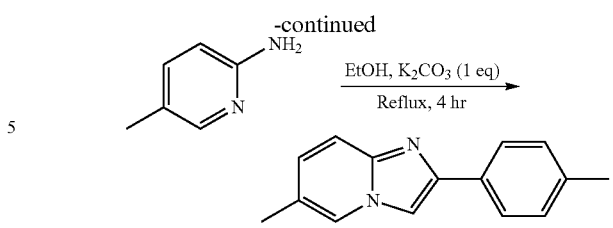

A mixture of 2-bromo-4'-methylacetophenone (90% pure, 10.21 g, 43.11 mmol), 2-amino-5-methyl picoline (4.66 g, 43.11 mmol) and $K_2CO_3$ (6.6 g, 47.75 mmol) in absolute EtOH (70 ml) was heated at 93° C. overnight. After cooled to 40° C., ether (100 mL) was added. The mixture was stirred for 30 minutes and cooled by ice-water bath. After removal of solvent through filtration, the solid was stirred with water (50 ml) for 30 minutes and filtered, rinsed with water and dried under vacuum at 80° C. for 2 hr to give 6.33 g of white solid (66.1% yield). m/e$^+$ 223.4 for $C_{15}H_{15}N_2$ (M+H)$^+$; $^1$H-NMR (400 MHz, $CDCl_3$, δ) 7.84 (m, 3H), 7.71 (d, J=9.531 Hz, 1), 7.51 (d, J=9.165 Hz, 1H), 7.24 (m, 2H), 7.00 (m, 1), 2.38 (s, 3H), 2.29 (d, J=6.23 Hz, 3H) ppm. $^{13}$C-NMR (100 MHz, $CDCl_3$ δ) 145.065, 144.444, 137.991, 130.696, 130.635, 129.642, 129.483, 128.391, 128.262, 126.018, 123.652, 122.476, 116.486, 107.857, 21.520, 18.259 ppm.

Step 2: 6-Methyl-2-p-tolyl-H-imidazo[1,2-a]pyridine-3-carbaldehyde

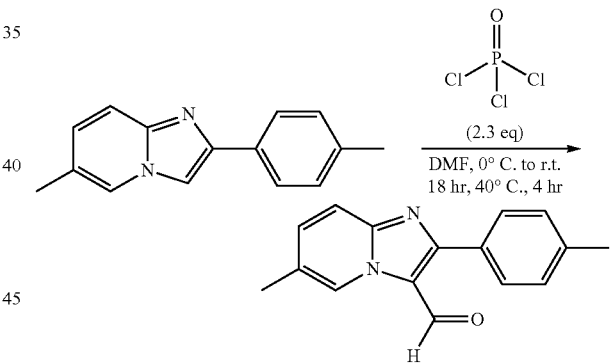

DMF (50 ml) was cooled to 0° C. and phosphorus oxotrichloride (3.54 ml, 38.6 mmol) was added dropwise. After addition, the mixture was warmed to room temperature and stirred for 10 min. To this solution, the starting material (6-methyl-2-p-tolylH-imidazo[1,2-a]pyridine, 4.29 g, 19.32 mmol) was added in a few portions. The resulting mixture was stirred at room temperature until the reaction was complete as monitored by TLC and LC-mass analysis (18-24 hr). The reaction mixture was then poured into ice-cooled water (200 ml). The pH was adjusted to 7 with concentrated ammonium hydroxide. The mixture was extracted with $CH_2Cl_2$ (2×100 ml). The combined organic solution was washed with brine and dried with $Na_2SO_4$. After removal of most of the solvent, ether was added to precipitate out a white solid. The white solid was collected by filtration. The mother liquid was concentrated and the white solid was collected again. (3.89 g, 80.5%). m/e$^+$ 251 for $C_{16}H_{15}N_2O$ (M+H)$^+$; $^1$H-NMR (300 MHz, $CDCl_3$, δ) 10.025 (s, 1H), 9.48 (d, J=0.9 Hz, 1H), 7.72

(m, 3H), 7.43 (dd, $J_1$=9.3 Hz, $J_2$=1.8 Hz, 1H), 7.32 (d, J=8.1 Hz, 2H), 2.441 (s, 6H, D, 2×$CH_3$) ppm.

Step 3: (6-Methyl-2-p-tolylH-imidazo[1,2-a]pyridin-3-yl)methanol

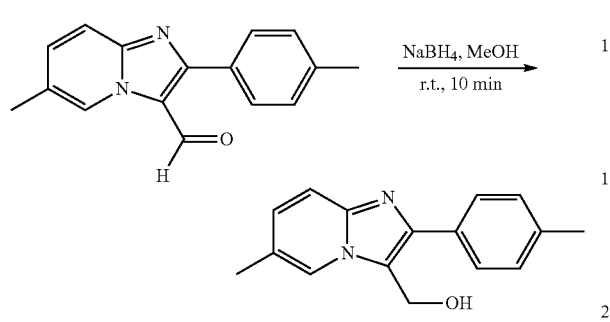

To a suspension of 6-methyl-2-p-tolylH-imidazo[1,2-a]pyridine-3-carbaldehyde (1.50 g, 6.0 mmol) in MeOH (30 ml) and THF (10 ml) at 0° C. was added $NaBH_4$ (265 mg, 7.0 mmol). The mixture was stirred for 10 min and concentrated under reduced pressure to give a white solid, which was stirred with water (30 ml) for 30 min and collected by filtration. After rinsed several times with water, the white solid was dried under vacuum. (1.47 g, 97.3%). m/e$^+$ 253.5 for $C_{16}H_{17}N_2O$ (M+H)$^+$; $^1$H-NMR (300 MHz, $CDCl_3$—$CD_3OD$, 6) 7.989 (s, 1H), 7.55 (d, J=8.1 Hz, 2H), 7.42 (d, J=9.3 Hz, 1H), 7.16 (d, J=8.10 Hz, 2H), 7.05 (d, J=9.3 Hz, 1H), 5.01 (s, $CH_2$), 2.35 (s, 3H, D, $CH_3$), 2.30 (s, 3H, D, $CH_3$) ppm; $^{13}$C-NMR (100 MHz, $CDCl_3$—$CD_3OD$, δ) 144.049, 137.991, 130.893, 129.377, 128.876, 128.550, 122.552, 122.302, 115.887, 53.519, 21.178, 18.183 ppm. Note: the compound is not very soluble in EtOAc, $CH_2Cl_2$, $CHCl_3$. It is soluble in MeOH.

Step 4: 3-(Chloromethyl)-6-methyl-2-p-tolyl-H-imidazo[1,2-a]pyridine hydrochloride

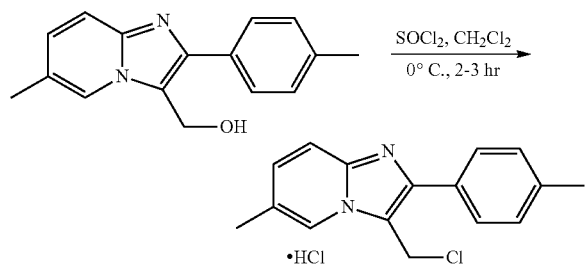

To a suspension of (6-methyl-2-p-tolylH-imidazo[1,2-a]pyridin-3-yl)methanol (1.47 g, 5.83 mmol) in $CH_2Cl_2$ (15 ml) was at 0° C. was added thionyl chloride ($SOCl_2$, 2.0 ml). The suspension became a clear solution. Then white solid was formed again in the reaction solution. After stirred at 0° C. for 3 hrs, the reaction mixture was poured into ether (100 ml). The white solid was collected by filtration and rinsed with ether and dried under reduced pressure. The product is not soluble in most organic solvents and is reactive towards nucleophilic solvents such as alcohols and water. However, it is stable in solid state and can be kept at room temperature for months without decomposition.

Step 5: 3-((1H-imidazol-1-yl)methyl)-6-methyl-2-p-tolylimidazo[1,2-a]pyridine

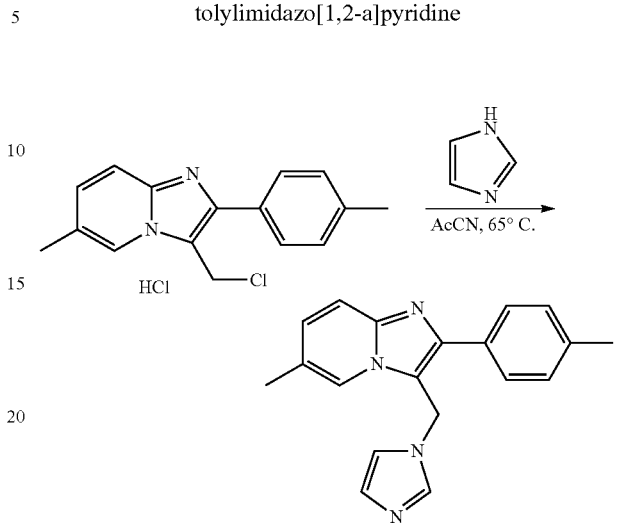

A mixture of 3-(chloromethyl)-6-methyl-2-p-tolylimidazo[1,2-a]pyridine hydrochloride (0.10 mmol), 1H-imidazole (0.20 mmol, 2.0 eq) in AcCN (1 ml) was heated at 65° C. overnight. The mixture was basified with sat. $NaHCO_3$ (5 ml), extracted with ethyl acetate or $CH_2Cl_2$ (2×5 ml). The combined organic solution was dried with $Na_2SO_4$, evaporated under vacuum. The product was purified by silica gel column chromatography (12 g silica gel RediSep column, eluted first with 10% ethyl acetate in hexane, then 20-50% acetone in hexane), to afford the product as a white solid. The product shows up as violet spot on TLC plate under UV light. m/e$^+$ 303.4 for $C_{19}H_{19}N_4$ (M+H)$^+$; $^1$H-NMR (400 MHz, $CDCl_3$, δ) 7.60-7.50 (m, 5H), 7.26 (d, J=8.065 Hz, 2H), 7.11 (m, 2H), 6.883 (s, 1H), 5.51 (s, 2H), 2.39 (s, 3H), 2.285 (s, 3H) ppm; $^{13}$C-NMR (100 MHz, $CDCl_3$, δ) 146.681, 144.944, 138.582, 136.512, 130.787, 130.484, 129.832, 128.937, 128.330, 123.341, 120.710, 118.845, 117.396, 112.315, 40.969, 21.512, 18.608 ppm.

Example 2

6-Methyl-3-((2-methyl-1H-imidazol-1-yl)methyl)-2-p-tolylH-imidazo[1,2-a]pyridine (2)

The title compound was prepared according to Method A and the experimentals described for compound 1 from 3-(chloromethyl)-6-methyl-2-p-tolylimidazo[1,2-a]pyridine hydrochloride and 2-methyl-1H-imidazole. 35% yield; m/e$^+$ 317.4 for $C_{20}H_{21}N_4$ (M+H)$^+$; $^1$H-NMR (400 MHz, $CDCl_3$, δ) 7.61 (d, J=9.16 Hz, 1H), 7.53 (d, J=8.064 Hz, 2H), 7.46 (s, 1H), 7.25 (d, J=8.064 Hz, 2H), 7.13 (dd, $J_1$=9.164 Hz, $J_2$=1.466 Hz, 1H), 6.887 (s, 1H), 6.56 (d, J=1.466 Hz, 1H), 5.344 (s, 2H), 2.481 (s, 3H), 2.299 (s, 3H), 1.248 (s, 3H) ppm.

Example 3

3-((4,5-Dichloro-1H-imidazol-1-yl)methyl)-6-methyl-2-p-tolylH-imidazo[1,2-a]pyridine (3)

The title compound was prepared according to Method A and the experimentals described for compound 1 from 3-(chloromethyl)-6-methyl-2-p-tolylimidazo[1,2-a]pyridine hydrochloride and 4,5-dichloro-1H-imidazole m/e+ 371.2 (100%), 373.2 (65%) for $C_{19}H_{17}Cl_2N_4$ (M+H)+; 1H-NMR (400 MHz, CDCl3, δ) 7.618 (d, 1H), 7.53 (m, 3H), 7.27 (d, J=7.698 Hz, 2H), 7.17 (d, J=8.432 Hz, 1H), 6.995 (s, 1H), 5.393 (s, 2H, D, CH2), 2.399 (s, 3H, D, CH3), 2.337 (s, 3H, D, CH3) ppm.

Example 4

3-((2-Ethyl-1H-imidazol-1-yl)methyl)-6-methyl-2-p-tolylH-imidazo[1,2-a]pyridine (4)

The title compound was prepared according to Method A and the experimentals described for compound 1 from 3-(chloromethyl)-6-methyl-2-p-tolylimidazo[1,2-a]pyridine hydrochloride and 2-ethyl-1H-imidazole. m/e+ 3314 for $C_{21}H_{23}N_4$ (M+H)+; 1H-NMR (400 MHz, CDCl3, δ) 7.59 (d, J=9.164 Hz, 1H), 7.48 (d, J=8.064 Hz, 2H), 7.457 (s, 1H), 7.24 (d, J=8.065 Hz, 2H), 7.12 (d, J=9.163 Hz, 1H), 6.91 (d, J=5.132 Hz, 2H), 6.552 (s, 1H), 5.341 (s, 2H, D, CH2), 2.76 (m, 2H, D, CH2), 2.385 (s, 3H, D, CH3), 2.285 (s, 3H, D, CH3), 1.38 (t, 3H, D, CH3) ppm.

Example 5

3-((2-Isopropyl-1H-imidazol-1-yl)methyl)-6-methyl-2-p-tolylH-imidazo[1,2-a]pyridine (5)

The title compound was prepared according to Method A and the experimentals described for compound 1 from 3-(chloromethyl)-6-methyl-2-p-tolylimidazo[1,2-a]pyridine hydrochloride and 2-isopropyl-1H-imidazole. m/e+ 335.4 for $C_{22}H_{25}N_4$ (M+H)+; 1H-NMR (400 MHz, CDCl3, δ) 7.60 (d, J=9.531 Hz, 1H), 7.52 (d, J=8.065 Hz, 2H), 7.469 (s, 1H), 7.24 (d, J=8.431 Hz, 1H), 7.14 (dd, $J_1$=9.165 Hz, $J_2$=1.467 Hz, 1H), 6.92 (d, J=1.099 Hz, 1H), 6.51 (d, J=1.099 Hz), 5.376 (s, 2H, D, CH2), 3.15 (m, 1H, D, CH), 2.392 (s, 3H, D, CH3), 2.289 (s, 3H, D, CH3), 1.40 (d, J=6.965 Hz, 6H, D, 2×CH3) ppm.

Example 6

3-((1H-1,2,3-triazol-1-yl)methyl)-6-methyl-2-p-tolylH-imidazo[1,2-a]pyridine (6)

The title compound was prepared according to Method A and the experimentals described for compound 1 from 3-(chloromethyl)-6-methyl-2-p-tolylimidazo[1,2-a]pyridine hydrochloride and 1H-1,2,3-triazole. m/e+ 304.5 for $C_{18}H_{18}N_5$ (M+H)+; 1H-NMR (400 MHz, CDCl3, δ) 7.81 (s, 1H), 7.66 (s, 1H), 7.59 (d, J=8.06 Hz, 2H), 7.55 (d, J=9.16 Hz, 1H), 7.37 (s, 1H), 7.27 (d, 8.06 Hz, 2H), 7.11 (dd, $J_1$=9.17 Hz, $J_2$=1.1 Hz, 2H), 5.97 (s, 1H), 2.39 (s, 3H), 2.28 (s, 3H) ppm.

Example 7

3-((1H-1,2,4-triazol-1-yl)methyl)-6-methyl-2-p-tolylH-imidazo[1,2-a]pyridine (7)

The title compound was prepared according to Method A and the experimentals described for compound 1 from 3-(chloromethyl)-6-methyl-2-p-tolylimidazo[1,2-a]pyridine hydrochloride and 1H-1,2,4-triazole in 48% yield; m/e+ 304.5 for (M+H)+; 1H-NMR (400 MHz, CDCl3, δ) 7.99 (s, 1H), 7.94 (s, 1H), 7.85 (s, 1H), 7.57 (m, 3H), 7.20 (d, J=7.70 Hz, 2H), 7.13 (d, J=9.16 Hz, 1H), 5.70 (s, 2H), 2.39 (s, 3H), 2.31 (s, 3H) ppm.

Example 8

3-((1H-pyrazol-1-yl)methyl)-6-methyl-2-p-tolylH-imidazo[1,2-a]pyridine (8)

The title compound was prepared according to Method A and the experimentals described for compound 1 from 3-(chloromethyl)-6-methyl-2-p-tolylimidazo[1,2-a]pyridine hydrochloride and 1H-pyrazole. m/e+ 303.4 for $C_{19}H_{19}N_4$ (M+H)−, 303.4; 1H-NMR (400 MHz, CDCl3, δ) 7.80 9s, 1H), 7.64 (d, J=8.06 Hz, 2H), 7.59 (d, J=2.2 Hz, 1H), 7.56 (s, 1H), 7.25 (m, 3H), 7.10 (dd, $J_1$=9.164, $J_2$=1.47 Hz, 1H), 6.26 (m, 1H), 5.73 (s, 1H), 2.41 (s, 3H), 2.30 (s, 3H) ppm.

Example 9

6-Methyl-3-((3,5-dimethyl-1H-pyrazol-1-yl)methyl)-2-p-tolylH-imidazo[1,2-a]pyridine (9)

The title compound was prepared according to Method A and the experimentals described for compound 1 from 3-(chloromethyl)-6-methyl-2-p-tolylimidazo[1,2-a]pyridine hydrochloride and 3,5-dimethyl-1H-pyrazole. m/e+ 331.4 for $C_{21}H_{23}N_4$ (M+H)+, 1H-NMR (400 MHz, CDCl3, δ) 8.249 (s, 1H), 7.58 (d, J=7.698 Hz, 2H), 7.49 (d, J=9.165 Hz, 1H), 7.27 (d, J=8.064 Hz, 2H), 7.04 (dd, $J_1$=9.164 Hz, $J_2$=1.466 Hz, 1H), 5.692 (s, 1H), 5.635 (s, 2H, D, CH2), 2.403 (s, 3H, D, CH3), 0.2285 (s, 3H, D, CH3), 2.201 (s, 3H, D, CH3), 1.696 (s, 3H, D, CH3) ppm.

Example 10

2-(6-Methyl-2-p-tolyl-imidazo[1,2-a]pyridin-3-ylmethyl)-2H-[1,2,4]triazole-3-carboxylic acid methyl ester (10)

and

Example 11

1-(6-Methyl-2-p-tolyl-imidazo[1,2-a]pyridin-3-ylmethyl)-1H-[1,2,4]triazole-3-carboxylic acid methyl ester (11)

The title compound was prepared according to Method A and the experimentals described for compound 1 from 3-(chloromethyl)-6-methyl-2-p-tolylimidazo[1,2-a]pyridine hydrochloride and methyl 1H-1,2,4-triazole-5-carboxylate. The two isomers were separated by silica gel chromatography eluted with 20% acetone to flash out the less polar spot and 50% acetone to flash out the second spot (more polar spot). Compound 10: m/e+ 362 for $C_{20}H_{20}N_5O_2$ [M+H]+; 1H-NMR (400 MHz, CDCl3) δ 7.95 (s, 2H), 7.65 (d, J=8.0 Hz, 2H), 7.56 (d, J=9.1 Hz, 1H), 7.23 (d, J=8.0 Hz, 2H), 7.10 (dd, J=1.4, 9.1 Hz, 1H), 6.15 (s, 2H), 3.98 (s, 3H), 2.38 (s, 3H), 2.31 (s, 3H) ppm; Compound 11: m/e+ 362 for $C_{20}H_{20}N_5O_2$ [M+H]+; 1H-NMR (400 MHz, CDCl3) δ 7.91 (s, 1H), 7.74 (s, 1H), 7.58 (d, J=9.5 Hz, 1H), 7.54 (d, J=7.7 Hz, 2H), 7.24 (d, J=7.7 Hz, 2H), 7.14 (d, J=9.5 Hz, 1H), 5.81 (s, 2H), 3.98 (s, 3H), 2.37 (s, 3H), 2.29 (s, 3H) ppm.

Example 12

1-(6-Methyl-2-p-tolyl-imidazo[1,2-a]pyridin-3-ylmethyl)-1H-imidazole-2-carboxylic acid ethyl ester (12)

The title compound was prepared according to Method A and the experimentals described for compound 1 from 3-(chloromethyl)-6-methyl-2-p-tolylimidazo[1,2-a]pyridine hydrochloride and ethyl 1H-imidazole-2-carboxylate. m/e⁺ 375 for $C_{22}H_{23}N_4O_2$ [M+H]⁺; ¹H-NMR (300 MHz, CDCl₃) δ 7.63 (m, 4H), 7.24 (m, 4H), 6.73 (d, J=0.9 Hz, 1H), 6.07 (s, 2H), 4.39 (m, 2H), 2.39 (s, 3H), 2.29 (s, 3H), 1.43 (m, 3H) ppm.

Example 13

6-Methyl-3-((2-phenyl-1H-imidazol-1-yl)methyl)-2-p-tolylH-imidazo[1,2-a]pyridine (13)

The title compound was prepared according to Method A and the experimentals described for compound 1 from 3-(chloromethyl)-6-methyl-2-p-tolylimidazo[1,2-a]pyridine hydrochloride and 2-phenyl-1H-imidazole. m/e⁺ 379.4 for $C_{25}H_{23}N_4$ (M+H)⁺.

Example 14

2-Methyl-1-((6-methyl-2-p-tolylH-imidazo[1,2-a]pyridin-3-yl)methyl)-1H-benzo[d]imidazole (14)

The title compound was prepared according to Method A and the experimentals described for compound 1 from 3-(chloromethyl)-6-methyl-2-p-tolylimidazo[1,2-a]pyridine hydrochloride and 2-methyl-1H-benzo[d]imidazole. m/e⁺ 367.4 for $C_{24}H_{23}N_4$ (M+H)⁺.

Example 15

1-((6-Methyl-2-p-tolylH-imidazo[1,2-a]pyridin-3-yl)methyl)-1H-imidazo[4,5-b]pyridine (15)

The title compound was prepared according to Method A and the experimentals described for compound 1 from 3-(chloromethyl)-6-methyl-2-p-tolylimidazo[1,2-a]pyridine hydrochloride and 2-methyl-1H-imidazo[4,5-b]pyridine. m/e⁺ 354.4 for $C_{22}H_{20}N_5$ (M+H)⁺; ¹H-NMR (400 MHz, CDCl₃, δ) 8.526 (dd, J₁=4.765 Hz, J₂=1.1 Hz, 1H), 8.10 (dd, J₁=8.065 Hz, J₂=1.1 Hz, 1H), 7.900 (s, 1H), 7.716 (s, 1H), 7.67 (d, J=8.065 Hz, 2H), 7.58 (d, J=9.164 Hz, 1H), 7.31 (m, 2H), 7.10 (d, J₁=9.165 Hz, J₂=1.467 Hz, 1H), 5.90 (s, 2H), 2.416 (s, 3H, D, CH₃), 2.223 (s, 3H, D, CH₃) ppm.

Example 16

1-((6-Methyl-2-p-tolyl-H-imidazo[1,2-a]pyridin-3-yl)methyl)-1H-benzo[d]imidazole (16)

The title compound was prepared according to Method A and the experimentals described for compound 1 from 3-(chloromethyl)-6-methyl-2-p-tolylimidazo[1,2-a]pyridine hydrochloride and 1H-benzo[d]imidazole. m/e⁺ 353.4 for $C_{23}H_{21}N_4$ (M+H)⁺; ¹H-NMR (400 MHz, CDCl₃, δ) 7.85-7.12 (m, 12H), 5.68 (s, 2H), 2.387 (s, 3H, D, CH₃), 2.23 (s, 3H, D, CH₃) ppm.

Example 17

N,N-Dimethyl-9-((6-methyl-2-p-tolylH-imidazo[1,2-a]pyridin-3-yl)methyl)-9H-purin-6-amine (17)

The title compound was prepared according to Method A and the experimentals described for compound 1 from 3-(chloromethyl)-6-methyl-2-p-tolylimidazo[1,2-a]pyridine hydrochloride and N,N-dimethyl-9H-purin-6-amine. m/e⁺ 398.4 for $C_{23}H_{24}N_7$ (M+H)⁺; ¹H-NMR (400 MHz, CD₃OD, δ) 8.453 (s, 1H), 7.956 (s, 1H), 7.66 (d, J=8.065 Hz, 2H), 7.56 (d, J=9.164 Hz, 1H), 7.368 (s, 1H), 7.28 (d, J=7.698 Hz, 2H), 7.07 (dd, J₁=9.164 Hz, J₂=1.466 Hz, 1H), 5.765 (s, 2H, D, CH₂), 3.51 (broad, 6H, D, 2×CH₃), 2.414 (s, 3H, D, CH₃), 2.239 (s, 3H, D, CH₃) ppm.

Example 18

3-((1H-1,2,4-triazol-1-yl)methyl)-6-chloro-2-(4-chlorophenyl)H-imidazo[1,2-a]pyridine (18)

The title compound was prepared according to Method A and the experimentals described for compound 1 from 6-chloro-3-(chloromethyl)-2-(4-chlorophenyl)imidazo[1,2-a]pyridine hydrochloride and 1H-1,2,4-triazole. m/e⁺ 344.3 (100%), 346.3 (60%), 345.39 (20%), 347.29 (10%) for $C_{16}H_{12}Cl_2N_5$(M+H)⁺; ¹H-NMR (400 MHz, CDCl₃, δ) 8.31 (s, 1H), 8.058 (s, 1H), 8.004 (s, 1H), 7.62 (m, 3H), 7.46 (dd, J₁=9.531 Hz, J₂=0.733 Hz, 1H), 7.44 (dd, J₁=6.598 Hz, J₂=1.832 Hz, 2H), 7.26 (dd, J₁=6.598 Hz, J₂=1.833 Hz, 2H), 7.27 (d, J=9.531 Hz, 1H), 5.685 (s, 2H, D, CH₂) ppm.

Example 19

3-((1H-1,2,3-triazol-1-yl)methyl)-6-chloro-2-(4-chlorophenyl)H-imidazo[1,2-a]pyridine (19)

The title compound was prepared according to Method A and the experimentals described for compound 2 from 6-chloro-3-(chloromethyl)-2-(4-chlorophenyl)imidazo[1,2-a]pyridine hydrochloride and 1H-1,2,3-triazole. m/e⁺ 344.3 (100%), 346.3 (60%) for $C_{16}H_{12}Cl_2N_5$ (M+H)⁺; ¹H-NMR (400 MHz, CDCl₃, δ) 8.23 (d, J=1.1 Hz, 1H), 7.74 (d, J=1.1 Hz, 1H), (s, 1H), 7.65 (m, 3H), 7.45 (m, 3H), 7.30 (d, J=7.698 Hz, 1H), 5.965 (s, 2H, D, CH₂) ppm.

Example 20

Methyl 1-((6-chloro-2-(4-chlorophenyl)H-imidazo[1,2-a]pyridin-3-yl)methyl)-1H-1,2,4-triazole-3-carboxylate (20)

and

Example 21

Methyl 2-((6-chloro-2-(4-chlorophenyl)H-imidazo[1,2-a]pyridin-3-yl)methyl)-2H-1,2,4-triazole-3-carboxylate (21)

The title compound was prepared according to Method A and the experimentals described for compound 1 from 6-chloro-3-(chloromethyl)-2-(4-chlorophenyl)imidazo[1,2-a]pyridine hydrochloride and methyl 1H-1,2,4-triazole-5-carboxylate. The two isomers were separated by silica gel chromatography (eluted with 20% acetone/hexane to flush out the less polar isomer and then flashed with 50% acetone to get the second compound off the column. Compound 20: m/e⁺ 402.3 (100%), 404.2 (65%) for $C_{18}H_{14}Cl_2N_5O_2$ (M+H)⁺; ¹H-NMR (300 MHz, CDCl₃, δ), 8.41 (d, J=2.1 Hz, 1H), 8.03 (s, 1H), 7.81 (d, 2H), 7.77 (d, J=9.3 Hz, 1H), 7.48 (d, 2H), 7.30 (d, 1H), 6.21 (s, 2H), 4.07 (s, 3H) ppm. Compound 21: m/e⁺ 402.3 (100%), 404.2 (65%) for $C_{18}H_{14}Cl_2N_5O_2$ (M+H)⁺; ¹H-NMR (400 MHz, CDCl₃, δ) 8.37 (d, J=1.1 Hz, 1H), 8.00 (s, 1H), 7.76 (dd, J₁=6.598 Hz, J₂=1.833 Hz, 2H), 7.62 (dd, J₁=9.531 Hz, J₂=0.733 Hz, 1H), 7.44 (dd, $J_1$=6.598 Hz, $J_2$=1.832 Hz, 2H), 7.26 (dd, $J_1$=9.531 Hz, $J_2$=1.833 Hz, 1H), 6.18 (s, 2H, D, $CH_2$), 4.035 (s, 3H, D, $CH_3$) ppm. $^{13}$C-NMR (100 MHz, $CDCl_3$, δ) 159.025, 151.670, 146.916, 144.345, 144.201, 135.033, 131.94, 130.256, 129.953, 129.187, 127.451, 122.385, 121.604, 118.329, 114.272, 53.769, 44.245 ppm.

Example 22

1-[6-Chloro-2-(4-chloro-phenyl)-imidazo[1,2-a]pyridin-3-ylmethyl]-1H-imidazole-2-carboxylic acid ethyl ester (22)

The title compound was prepared according to Method A and the experimentals described for compound 1 from 6-chloro-3-(chloromethyl)-2-(4-chlorophenyl)imidazo[1,2-a]pyridine hydrochloride and ethyl 1H-imidazole-2-carboxylate. m/e$^+$ 416 for $C_{20}H_{17}Cl_2N_4O_2$ [M+H]$^+$; $^1$H-NMR (300 MHz, $CDCl_3$) δ 8.04 (dd, J=0.9, 6.3 Hz, 1H), 7.60 (m, 3H), 7.42 (dd, J=6.3, 8.1 Hz, 2H), 7.27 (m, 1H), 7.11 (m, 1H), 6.67 (dd, J=2.1, 3.3 Hz, 1H), 6.07 (d, J=2.1 Hz, 2H), 4.48 (q, J=7.2 Hz, 2H), 1.48 (t, J=7.2 Hz, 3H) ppm; $^{13}$C-NMR (75 MHz, $CDCl_3$, δ) 160.222, 135.309, 130.815, 130.735, 129.653, 129.593, 127.897, 123.336, 123.283, 122.261, 121.647, 121.573, 118.475, 62.384, 53.016, 41.598, 41.544, 14.534 ppm.

Example 23

2-[6-Chloro-2-(4-chloro-phenyl)-imidazo[1,2-a]pyridin-3-ylmethyl]-2H-[1,2,4]triazole-3-carboxylic acid isopropyl ester (23)

The title compound was prepared according to Method A and the experimentals described for compound 1 from 6-chloro-3-(chloromethyl)-2-(4-chlorophenyl)imidazo[1,2-a]pyridine hydrochloride and isopropyl 1H-1,2,4-triazole-5-carboxylate. m/e$^+$ 430 for $C_{20}H_{18}Cl_2N_5O_2$ [M+H]$^+$; $^1$H-NMR (300 MHz, $CDCl_3$) δ 8.41 (dd, J=0.9, 1.8 Hz, 1H), 8.01 (s, 1H), 7.82 (dd, J=2.1, 6.6 Hz, 2H), 7.64 (dd, J=0.9, 9.3 Hz, 1H), 7.46 (dd, J=2.1, 6.6 Hz, 2H), 7.28 (dd, J=1.8, 9.3 Hz, 1H), 6.21 (s, 2H), 5.38 (m, 1H), 1.50 (d, J=6.0 Hz, 6H) ppm; $^{13}$C-NMR (75 MHz, $CDCl_3$, δ) 158.353, 151.649, 146.894, 144.844, 144.190, 135.015, 132.017, 130.301, 129.199, 127.410, 122.448, 121.573, 118.355, 114.495, 71.973, 44.202, 21.946 ppm.

Example 24

2-[2-(4-Chloro-phenyl)-imidazo[1,2-a]pyridin-3-ylmethyl]-2H-[1,2,4]triazole-3-carboxylic acid methyl ester (24)

and

Example 25

1-[2-(4-Chloro-phenyl)-imidazo[1,2-a]pyridin-3-ylmethyl]-1H-[1,2,4]triazole-3-carboxylic acid methyl ester (25)

The title compound was prepared according to Method A and the experimentals described for compound 1 from 3-(chloromethyl)-2-(4-chlorophenyl)imidazo[1,2-a]pyridine hydrochloride and methyl 1H-1,2,4-triazole-3-carboxylate. The two isomers were separated by silica gel chromatography (eluted with 20% acetone/hexane to flush out the less polar isomer and then flashed with 50% acetone to get the second compound off the column. Compound 24: m/e$^+$ 368 for $C_{18}H_{15}ClN_5O_2$ [M+H]$^+$; $^1$H-NMR (400 MHz, $CDCl_3$) δ 8.24 (d, J=6.6 Hz, 1H), 7.95 (s, 1H), 7.76 (d, J=8.8 Hz, 2H), 7.65 (d, J=9.1 Hz, 1H), 7.42 (d, J=8.8 Hz, 2H), 7.27 (m, 1H), 6.86 (m, 1H), 6.19 (s, 2H), 4.00 (s, 3H) ppm; Compound 25: m/e$^+$ 368 for $C_{18}H_{15}ClN_5O_2$ [M+H]$^+$; $^1$H-NMR (400 MHz, $CDCl_3$) δ 8.06 (d, J=6.6 Hz, 1H), 8.00 (s, 1H), 7.62 (m, 3H), 7.44 (m, 2H), 7.29 (m, 1H), 6.89 (d, J=5.8 Hz, 1H), 5.83 (s, 2H), 3.95 (s, 3H) ppm.

Example 26

Ethyl 1-((2-(4-chlorophenyl)H-imidazo[1,2-a]pyridin-3-yl)methyl)-1H-imidazole-2-carboxylate (26)

The title compound was prepared according to Method A and the experimentals described for compound 1 from 3-(chloromethyl)-2-p-tolylimidazo[1,2-a]pyridine hydrochloride and ethyl 1H-imidazole-2-carboxylate. m/e+ 375 for C22H23N4O2 [M+H]+; 1H-NMR (300 MHz, CDCl3 7.90 (d, J=6.8 Hz, 1H), 7.69 (d, J=8.8 Hz, 1H), 7.63 (d, J=8.4 Hz, 2H), 7.42 (d, J=8.4 Hz, 2H), 7.30 (t, J=7.2 Hz, 1H), 7.08 (s, 1H), 6.86 (t, J=6.8 Hz, 1H), 6.66 (s, 1H), 6.10 (s, 2H), 4.51 (q, J=6.8 Hz, 2H), 1.47 (t, J=6.8 Hz, 3H) ppm; m/e 381.

Example 27

2-(4-chlorophenyl)-3-((2-(3-methyl-1,2,4-oxadiazol-5-yl)-1H-imidazol-1-yl)methyl)H-imidazo[1,2-a]pyridine (27)

The title compound was prepared according to Method A and the experimentals described for compound 1 from 3-(chloromethyl)-2-(4-chlorophenyl)imidazo[1,2-a]pyridine hydrochloride and 5-(1H-imidazol-2-yl)-3-methyl-1,2,4-oxadiazole and 5-(1H-imidazol-2-yl)-3-methyl-1,2,4-oxadiazole. $^1$H-NMR ($CDCl_3$, 400 MHz, δ) 7.87 (d, J=6.4 mg, 1H), 7.73 (d, J=8.8 Hz, 2H), 7.68 (d, J=10 Hz, 2H), 7.44 (t, J=1.6 Hz, 1H), 7.33 (m, 2H), 6.88 (t, J=6.8 Hz, 1H), 6.20 (s, 2H), 2.52 (s, 3H) ppm;

Example 28

Ethyl 1-((2-(4-chlorophenyl)imidazo[1,2-a]pyridin-3-yl)methyl)-3-methyl-1H-pyrazole-5-carboxylate (28)

and

Example 29 ethyl 1-((2-(4-chlorophenyl)imidazo[1,2-a]pyridin-3-yl)methyl)-5-methyl-1H-pyrazole-3-carboxylate (29)

The title compound was prepared according to Method A and the experimentals described for compound 1 from 3-(chloromethyl)-2-(4-chlorophenyl)imidazo[1,2-a]pyridine hydrochloride and ethyl 3-methyl-1H-pyrazole-5-carboxylate. The regioisomers were separated by silica gel chromatography. Compound 28: M/e$^+$ 395 for $C_{21}H_{20}ClN_4O_2$ (M+H)$^+$; $^1$H-NMR (400 MHz, $CDCl_3$) δ 8.24 (d, J=6.9 Hz, 1H), 7.82 (d, J=8.4 Hz, 2H), 7.61 (d, J=8.8 Hz, 1H), 7.36 (d, J=8.4 Hz, 2H), 7.17 (td, J=6.6, 1.1 Hz, 1H), 6.78 (td, J=6.6, 1.1 Hz, 1H), 6.50 (s, 1H), 6.01 (s, 2H), 4.30 (q, J=7.3 Hz, 2H), 2.26 (s, 3H), 1.30 (q, J=7.3 Hz, 3H) ppm; Compound 29: M/e$^+$ 395 for $C_{21}H_{20}ClN_4O_2$ (M+H)$^+$; $^1$H-NMR (400 MHz, CDCl$_3$) δ 8.47 (d, J=6.6 Hz, 1H), 7.64 (d, J=8.4 Hz, 2H), 7.63 (m, 1H), 7.48 (d, J=8.4 Hz, 2H), 7.24 (t, J=6.6 Hz, 1H), 6.84 (t, J=6.6 Hz, 1H), 6.44 (s, 1H), 5.84 (s, 2H), 4.36 (q, J=7.3 Hz, 2H), 1.73 (s, 3H), 1.37 (t, J=3H) ppm.

Example 30

Ethyl 1-((2-(4-chlorophenyl)imidazo[1,2-a]pyridin-3-yl)methyl)-5-(furan-2-yl)-1H-pyrazole-3-carboxylate (30)

and

Example 31

Ethyl 1-((2-(4-chlorophenyl)imidazo[1,2-a]pyridin-3-yl)methyl)-3-(furan-2-yl)-1H-pyrazole-5-carboxylate (31)

The title compound was prepared according to Method A and the experimentals described for compound 1 from 3-(chloromethyl)-2-(4-chlorophenyl)imidazo[1,2-a]pyridine hydrochloride and ethyl 5-(furan-2-yl)-1H-pyrazole-3-carboxylate. The regioisomers were separated silica gel chromatography. Compound 30: M/e$^+$ 447 for C$_{24}$H$_{20}$ClN$_4$O$_3$ (M+H)$^+$; $^1$H-NMR (400 MHz, CDCl$_3$) δ 8 7.93 (d, J=6.2 Hz, 1H), 7.67 (d, J=7.7 Hz, 2H), 7.56 (d, J=9.1 Hz, 1H), 7.34 (d, J=7.7 Hz, 2H), 7.25 (d, J=2.9 Hz, 1H), 7.17 (m, 1H), 6.98 (s, 1H), 6.81 (t, J=6.6 Hz, 1H), 6.62 (s, 1H), 6.09 (s, 1H), 4.40 (m, 4H), 1.39 (t, J=6.9 Hz, 3H) ppm; Compound 31: M/e$^+$ 447 for C$_{24}$H$_{20}$ClN$_4$O$_3$ (M+H)$^+$; $^1$H-NMR (400 MHz, CDCl$_3$) δ 8.37 (d, J=6.9 Hz, 1H), 7.90 (d, J=8.4 Hz, 2H), 7.65 (d, J=9.1 Hz, 1H), 7.42 (m, 3H), 7.24 (m, 1H), 7.09 (s, 1H), 6.84 (td, J=6.6, 1.1 Hz, 1H), 6.58 (d, J=3.3 Hz, 1H), 6.40 (dd, J=3.3, 1.8 Hz, 1H), 6.15 (s, 2H), 4.36 (q, J=7.3 Hz, 2H), 1.39 (t, J=7.3 Hz, 3H) ppm.

Example 3

3-((1H-1,2,4-triazol-1-yl)methyl)-2-(4-chlorophenyl)imidazo[1,2-b]pyridazine (32)

The title compound was prepared according to Method A and the experimentals described for compound 1 from 3-(chloromethyl)-2-(4-chlorophenyl)imidazo[1,2-a]pyridine hydrochloride and 1H-1,2,4-triazole. $^1$H-NMR (CDCl$_3$, 400 MHz, δ) 8.74 (s, 1H) 8.07 (d, J=8.5 Hz, 2H), 8.07 (d, J=8.5 Hz, 2H), 8.01 (dd, J=1.3, 9.2 Hz, 1H), 7.95 (s, 1H), 7.51 (m, 2H), 7.17 (dd, J=4.5, 9.2 Hz, 1H), 5.85 (s, 2H) ppm; [M+H]+ 311

Example 33

Methyl 4-((2-(4-chlorophenyl)imidazo[1,2-a]pyridin-3-yl)methyl)-4H-furo[3,2-b]pyrrole-5-carboxylate (33)

The title compound was prepared according to Method A and the experimentals described for compound 1 from 3-(chloromethyl)-2-(4-chlorophenyl)imidazo[1,2-a]pyridine hydrochloride methyl 4H-furo[3,2-b]pyrrole-5-carboxylate. M/e$^+$ 406 for C$_{22}$H$_{17}$ClN$_3$O$_3$ (M+H)$^+$; $^1$H-NMR (400 MHz, CDCl$_3$) δ 9.18 (s, 1H), 7.95 (d, J=7.71 Hz, 1H), 7.71 (d, J=8.4 Hz, 2H), 7.63 (d, J=8.8 Hz, 1H), 7.39 (d, J=8.4 Hz, 2H), 7.22 (m, 2H), 6.82 (t, J=6.6 Hz, 1H), 5.98 (s, 1H), 4.45 (s, 2H), 3.83 (s, 3H) ppm.

Example 34

Methyl 1-((2-(4-chlorophenyl)imidazo[1,2-a]pyridin-3-yl)methyl)-1H-indazole-3-carboxylate (34)

The title compound was prepared according to Method A and the experimentals described for compound 1 from 3-(chloromethyl)-2-(4-chlorophenyl)imidazo[1,2-a]pyridine hydrochloride methyl 1H-indazole-3-carboxylate. M/e$^+$ 417 for C$_{23}$H$_{18}$ClN$_4$O$_2$ (M+H)$^+$; $^1$H-NMR (400 MHz, CDCl$_3$) δ 8.22 (d, J=6.9 Hz, 1H), 8.03 (d, J=6.6 Hz, 1H), 7.83 (d, J=8.4 Hz, 2H), 7.68 (dd, J=8.8, 1.8 Hz, 2H), 7.41 (d, J=8.4 Hz, 2H), 7.30 (m, 2H), 7.24 (m, 1H), 6.81 (t, J=6.2 Hz, 1H), 6.47 (s, 2H), 4.03 (s, 3H) ppm.

Example 35

Methyl 1-((2-(4-chlorophenyl)imidazo[1,2-a]pyridin-3-yl)methyl)indoline-2-carboxylate (35)

The title compound was prepared according to Method A and the experimentals described for compound 1 from 3-(chloromethyl)-2-(4-chlorophenyl)imidazo[1,2-a]pyridine hydrochloride and methyl indoline-2-carboxylate. M/e$^+$ 418 for C$_{24}$H$_{21}$ClN$_3$O$_2$ (M+H)$^+$; $^1$H-NMR (400 MHz, CDCl$_3$) δ 8.33 (d, J=6.9 Hz, 1H), 7.69 (d, J=8.4 Hz, 2H), 7.64 (d, J=9.1 Hz, 1H), 7.64 (d, J=8.4 Hz, 2H), 7.25 (t, J=6.9 Hz, 1H), 7.09 (t, J=7.7 Hz, 1H), 7.04 (d, J=6.9 Hz, 1H), 6.83 (t, J=6.6 Hz, 1H), 6.75 (t, J=7.7 Hz, 1H), 6.60 (d, J=7.7 Hz, 1H), 4.90 (d, J=14.7 Hz, 1H), 4.62 (d, J=14.7 Hz, 1H), 3.85 (t, J=8.4 Hz, 1H), 3.26 (m, 1H), 3.23 (s, 3H), 2.96 (dd, J=15.7, 8.0 Hz, 1H) ppm.

Example 36

1-((2-(4-chlorophenyl)imidazo[1,2-a]pyridin-3-yl)methyl)-N-methyl-1H-benzo[d]imidazole-2-carboxamide (36)

The title compound was prepared according to Method A and the experimentals described for compound 1 from 3-(chloromethyl)-2-(4-chlorophenyl)imidazo[1,2-a]pyridine hydrochloride and N-methyl-1H-benzo[d]imidazole-2-carboxamide. M/e$^+$ 416 for C$_{23}$H$_{19}$ClN$_5$O (M+H)$^+$; $^1$H-NMR (400 MHz, CDCl$_3$) δ 8.40 (d, J=6.9 Hz, 1H), 7.90 (d, J=4.7 Hz, 1H), 7.76 (d, J=8.4 Hz, 2H), 7.62 (dd, J=13.1, 8.0 Hz, 2H), 7.51 (d, J=8.4 Hz, 2H), 7.18 (dd, J=8.4, 1.1 Hz, 2H), 6.98 (m, 1H), 6.73 (m, 1H), 6.67 (s, 2H) 3.12 (d, J=5.1 Hz, 3H) 1.83 (s, 1H) ppm.

Example 37

Ethyl 1-((2-(4-chlorophenyl)imidazo[1,2-a]pyridin-3-yl)methyl)-1H-indole-2-carboxylate (37)

The title compound was prepared according to Method A and the experimentals described for compound 1 from 3-(chloromethyl)-2-(4-chlorophenyl)imidazo[1,2-a]pyridine hydrochloride and ethyl 1H-indole-2-carboxylate. M/e$^+$ 430 for C$_{25}$H$_{21}$ClN$_3$O$_2$ (M+H)$^+$; $^1$H-NMR (400 MHz, CD$_3$OD) δ 8.13 (d, J=6.6 Hz, 1H), 7.70 (dd, J=8.4, 2.2 Hz, 2H), 7.55 (d, J=9.1 Hz, 1H), 7.42 (d, J=8.4, 2.5 Hz, 2H), 7.33 (d, J=8.4 Hz, 1H), 7.25 (t, J=6.6 Hz, 1H), 7.10 (t, J=6.6 Hz, 1H), 6.79 (m, 1H), 6.67 (m, 1H), 6.61 (m, 2H), 5.03 (s, 2H), 4.44 (q, J=6.9 Hz, 2H), 1.39 (t, J=6.9 Hz, 3H) ppm.

Example 38

Methyl 1-((2-(4-chlorophenyl)imidazo[1,2-a]pyridin-3-yl)methyl)-1H-indole-3-carboxylate (38)

The title compound was prepared according to Method A and the experimentals described for compound 1 from 3-(chloromethyl)-2-(4-chlorophenyl)imidazo[1,2-a]pyridine hydrochloride and methyl 1H-indole-3-carboxylate. M/e$^+$ 430 for $C_{25}H_{21}ClN_3O_2$ (M+H)$^+$; $^1$H-NMR (400 MHz, CDCl$_3$) δ 8.24 (dd, J=5.8, 2.5 Hz, 1H), 7.74 (d, J=9.1 Hz, 2H), 7.66 (d, J=8.4 Hz, 1H), 7.64 (m, 1H), 7.51 (s, 1H), 7.48 (m, 1H), 7.42 (d, J=8.4 Hz, 2H), 7.31 (m, 2H), 7.29 (t, J=5.8 Hz, 1H), 6.80 (t, J=6.9 Hz, 1H), 5.67 (s, 2H), 3.83 (s, 3H) ppm.

Example 39

2-(4-Chloro-phenyl)-3-[1,2,3]triazol-2-ylmethyl-imidazo[1,2-a]pyridine (39)

and

Example 40

2-(4-Chloro-phenyl)-3-[1,2,3]triazol-1-ylmethyl-imidazo[1,2-a]pyridine (40)

The title compound was prepared according to Method A and the experimentals described for compound 1 from 3-(chloromethyl)-2-(4-chlorophenyl)imidazo[1,2-a]pyridine hydrochloride and 1H-1,2,3-triazole. The two isomers were separated by silica gel chromatography (eluted with 20% acetone/hexane to flush out the less polar isomer and then flashed with 50% acetone to get the second compound off the column. Compound 39: m/e$^+$ 310 for $C_{16}H_{13}ClN_5$ [M+H]$^+$; $^1$H-NMR (400 MHz, CDCl$_3$) δ 8.55 (d, J=6.9 Hz, 1H), 8.06 (d, J=8.4 Hz, 2H), 7.66 (t, J=5.1 Hz, 2H), 7.51 (d, J=8.4 Hz, 2H), 7.28 (m, 1H), 7.26 (s, 1H), 6.91 (m, 1H), 5.97 (s, 2H) ppm. Compound 40: m/e$^+$ 310 for $C_{16}H_{13}ClN_5$ [M+H]$^+$; $^1$H-NMR (400 MHz, CDCl$_3$) δ 8.12 (d, J=6.6 Hz, 1H), 7.70 (m, 4H), 7.48 (d, J=8.8 Hz, 2H), 7.41 (d, J=0.7 Hz, 1H), 7.31 (m, 1H), 6.89 (dt, J=1.1, 6.6 Hz, 1H), 6.01 (s, 2H) ppm.

Example 41

3-((1H-tetrazol-1-yl)methyl)-2-(4-chlorophenyl)imidazo[1,2-a]pyridine (41)

The title compound was prepared according to Method A and the experimentals described for compound 1 from 3-(chloromethyl)-2-(4-chlorophenyl)imidazo[1,2-a]pyridine hydrochloride and 1H-tetrazole. M/e$^+$ 311 for $C_{15}H_{12}ClN_6$ (M+H)$^+$; $^1$H-NMR (400 MHz, CDCl$_3$) δ 8.45 (s, 1H), 8.12 (d, J=6.9 Hz, 1H), 7.73 (d, J=9.1 Hz, 1H), 7.64 (d, J=8.4 Hz, 2H), 7.50 (d, J=8.4 Hz, 2H), 7.37 (td, J=6.9, 1.1 Hz, 1H), 6.97 (m, 1H), 6.03 (s, 2H) ppm.

Example 42

1-((2-(4-chlorophenyl)H-imidazo[1,2-a]pyridin-3-yl)methyl)-1H-benzo[d][1,2,3]triazole (42)

and

Example 43

2-((2-(4-chlorophenyl)H-imidazo[1,2-a]pyridin-3-yl)methyl)-2H-benzo[d][1,2,3]triazole (43)

The title compound was prepared according to Method A and the experimentals described for compound 1 from 3-(chloromethyl)-2-(4-chlorophenyl)imidazo[1,2-a]pyridine hydrochloride and 1H-benzo[d][1,2,3]triazole. The two regioisomers were separated by silica gel chromatography. Compound 42: 1H-NMR (CDCl$_3$, 400 MHz, δ) 8.29 (d, J=6.9 Hz, 1H), 7.97 (m, 1H), 7.75 (d, J=8.5 Hz, 2H), 7.61 (d, J=9.1 Hz, 1H), 7.52 (d, J=8.5 Hz, 2H), 7.25 (m, 3H), 6.81 (m, 2H), 6.26 (s, 2H) ppm; [M+H]+ 360; Compound 43: 1H-NMR (CDCl$_3$, 400 MHz, δ) 8.65 (d, J=6.9 Hz, 1H), 8.15 (d, J=8.5 Hz, 2H), 7.88 (m, 2H), 7.69 (d, J=9.1 Hz, 1H), 7.54 (d, J=8.5 Hz, 2H), 7.43 (m, 2), 7.30 (m, 1H), 6.94 (m, 1H), 6.25 (s, 2H) ppm; [M+H]+ 360.

Example 44

2-(6-Chloro-2-phenyl-imidazo[1,2-a]pyridin-3-ylmethyl)-2H-[1,2,4]triazole-3-carboxylic acid methyl ester (44)

and

Example 45

1-(6-Chloro-2-phenyl-imidazo[1,2-a]pyridin-3-ylmethyl)-1H-[1,2,4]triazole-3-carboxylic acid methyl ester (45)

The title compound was prepared according to Method A and the experimentals described for compound 1 from 6-chloro-3-(chloromethyl)-2-phenylimidazo[1,2-a]pyridine hydrochloride and methyl 1H-1,2,4-triazole-3-carboxylate. The two isomers were separated by silica gel chromatography (eluted with 20% acetone/hexane to flush out the less polar isomer (44) and then flashed with 50% acetone to get the second compound off the column (45). Compound 44: m/e$^+$ 368 for $C_{18}H_{15}ClN_5O_2$ [M+H]$^-$; $^1$H-NMR (400 MHz, CDCl$_3$) δ 8.35 (d, J=1.1 Hz, 1H), 7.98 (s, 1H), 7.76 (dd, J=1.4, 8.0 Hz, 2H), 7.61 (d, J=9.5 Hz, 1H), 7.42 (m, 3H), 7.24 (m, 1H), 6.17 (s, 2H), 3.97 (s, 3H) ppm; Compound 45: m/e$^+$ 368 for $C_{18}H_{15}ClN_5O_2$ [M+H]$^+$; $^1$H-NMR (400 MHz, CDCl$_3$) δ 8.18 (d, J=1.1 Hz, 1H), 7.99 (s, 1H), 7.63 (m, 3H), 7.44 (m, 3H), 7.25 (m, 1H), 5.82 (s, 2H), 3.97 (s, 3H) ppm.

Example 46

1-((6-chloro-2-phenylH-imidazo[1,2-a]pyridin-3-yl)methyl)-1H-benzo[d][1,2,3]triazole (46)

and

Example 47

2-((6-chloro-2-phenylH-imidazo[1,2-a]pyridin-3-yl)methyl)-2H-benzo[d][1,2,3]triazole (47)

The title compound was prepared according to Method A and the experimentals described for compound 1 from 6-chloro-3-(chloromethyl)-2-phenylimidazo[1,2-a]pyridine hydrochloride and 1H-benzo[d][1,2,3]triazole. The two regioisomers were separated by silica gel chromatography. Compound 46: 1H-NMR (CDCl3, 400 MHz, δ) 8.42 (d, J=1.3 Hz, 1H), 7.97 (d, J=7.3 Hz, 1H), 7.52 (m, 4H), 7.24 (m, 2H), 7.17 (dd, J=1.9, 9.5 Hz, 1H), 6.98 (dd, J=4.6, −147.3 Hz, 1H), 6.23 (s, 2H) ppm; [M+H]+ 360; Compound 47: $^1$H-NMR (CDCl$_3$, 400 MHz, δ) 8.74 (s, 1H), 8.13 (d, J=7.2 Hz, 2H), 7.91 (m, 2H), 7.63 (d, J=9.5 Hz, 1H), 7.57 (m, 2H), 7.48 (d, J=7.4 Hz, 1H), 7.41 (m, 2H), 7.26 (dd, J=7.4 Hz, 1H), 6.25 (s, 2H) ppm; [M+H]+ 360.

Example 48

3-((1H-1,2,3-triazol-1-yl)methyl)-2-(4-fluorophenyl) H-imidazo[1,2-a]pyridine (48)

and

Example 49

3-((2H-1,2,3-triazol-2-yl)methyl)-2-(4-fluorophenyl) H-imidazo[1,2-a]pyridine (49)

The title compound was prepared according to Method A and the experimentals described for compound 1 from 3-(chloromethyl)-2-(4-fluorophenyl)imidazo[1,2-a]pyridine hydrochloride and 1H-1,2,3-triazole. The two regioisomers were separated by chromatography. Compound 48: $^1$H-NMR (CDCl$_3$, 400 MHz, δ) 8.51 (d, J=6.9 Hz, 1H), 7.7 (m, 3H), 7.39 (s, 1H), 7.30 (m, 2H), 7.20 (t, J=8.5 Hz, 2H), 6.88 (t, J=6.8 Hz, 1H), 6.0 (s, 2H) ppm; m/e 294 (M+H)$^+$; Compound 49: $^1$H-NMR (CDCl$_3$, 400 MHz, δ) 8.52 (d, J=6.8 Hz, 1H), 8.07 (t, J=6.4 Hz, 2H), 7.63 (m, 3H), 7.22 (m, 3H), 6.88 (m, 1H), 5.90 (s, 2H) ppm; m/e 294 (M+H)

Example 50

3-((1H-1,2,3-triazol-1-yl)methyl)-2-phenylH-imidazo[1,2-a]pyridine (50)

and

Example 51

3-((2H-1,2,3-triazol-2-yl)methyl)-2-phenylH-imidazo[1,2-a]pyridine (51)

The title compound was prepared according to Method A and the experimentals described for compound 1 from 3-(chloromethyl)-2-phenylimidazo[1,2-a]pyridine hydrochloride and 1H-1,2,3-triazole. The two regioisomers were separated by chromatography. Compound 50: $^1$H-NMR (CDCl$_3$, 400 MHz, δ) 8.11 (d, J=6.9 Hz, 1H), 7.74 (d, J=7.1 Hz, 2H), 7.70 (d, J=6.5 Hz, 2H), 7.51 (t, J=7.4 Hz, 2H), 7.46 (d, J=7.3 Hz, 1H), 7.40 (s, 1H), 7.30 (t, J=7.9 Hz, 1H), 6.87 (t, J=6.4 Hz, 1H), 6.03 (s, 2H) ppm. m/e 276 (M+H)$^+$; Compound 51: $^1$H-NMR (CDCl$_3$, 400 MHz, δ) 8.1 (d, J=6.9 Hz, 1H), 8.08 (d, J=7.3 Hz, 2H), 7.65 (m, 3H), 7.51 9m, 2H), 7.41 (m, 1H), 8.07 (t, J=6.4 Hz, 1H), 6.86 (t, J=6.8 Hz, 1H), 6.0 (s, 2H) ppm. m/e 276 (M+H)$^+$.

Example 52

Methyl 1-((6-fluoro-2-(4-fluorophenyl)imidazo[1,2-a]pyridin-3-yl)methyl)-1H-1,2,4-triazole-3-carboxylate (52)

and

Example 53

Methyl 1-((6-fluoro-2-(4-fluorophenyl)imidazo[1,2-a]pyridin-3-yl)methyl)-1H-1,2,4-triazole-5-carboxylate (53)

The title compound was prepared according to Method A and the experimentals described for compound 1 from 3-(chloromethyl)-6-fluoro-2-(4-fluorophenyl)imidazo[1,2-a]pyridine hydrochloride and methyl 1H-1,2,4-triazole-5-carboxylate. The two isomers were separated by silica gel chromatography eluted with 20% acetone to flash out the less polar spot and 50% acetone to flash out the second spot (more polar spot). m/e$^-$ 370 for C18H14F2N5O2 (M+H)$^-$.

Example 54

3-((1H-1,2,4-triazol-1-yl)methyl)-2-(4-fluorophenyl) H-imidazo[1,2-a]pyridine (54)

The title compound was prepared according to Method A and the experimentals described for compound 1 from 2-(4-flurophenyl)-3-(chloromethyl)imidazo[1,2-a]pyridine hydrochloride and 1H-1,2,4-triazole. $^1$H-NMR (CDCl$_3$, 400 MHz, δ) 8.20 (dd, J=10.4, 11.7 Hz, 1H), 8.09 (s, 1H), 7.96 (dd, J=10.3, 25.7 Hz, 2H), 7.68 (m, 3H), 7.30 (t, J=7.9 Hz, 1H), 7.17 (m, 2H), 5.72 (s, 2H) ppm; m/e 294 (M+H)$^+$

Example 55

3-((1H-1,2,4-triazol-1-yl)methyl)-2-(4-chlorophenyl)-6-fluoroH-imidazo[1,2-a]pyridine (55)

The title compound was prepared according to Method A and the experimentals described for compound 1 from 3-(chloromethyl)-2-(4-chlorophenyl)-6-fluoroimidazo[1,2-a]pyridine hydrochloride and 1H-1,2,4-triazole. $^1$H-NMR (CDCl$_3$, 400 MHz, δ) 8.23 (t, J=3.1 Hz, 1H), 8.04 (s, 1H), 7.99 (s, 1H), 7.64 (m, 3H), 7.46 (d, J=8.5 Hz, 2H), 7.23 (m, 1H), 5.68 (s, 2H) ppm, [M+H]+ 312.

Example 56

3-((2H-1,2,3-triazol-2-yl)methyl)-2-(4-chlorophenyl)-6-fluoroH-imidazo[1,2-a]pyridine (56)

and

Example 57

3-((1H-1,2,3-triazol-1-yl)methyl)-2-(4-chlorophenyl)-6-fluoroH-imidazo[1,2-a]pyridine (57)

The title compound was prepared according to Method A and the experimentals described for compound 1 from 3-(chloromethyl)-2-(4-chlorophenyl)-6-fluoroimidazo[1,2-a]pyridine hydrochloride and 1H-1,2,3-triazole. The two regioisomers were separated by silica gel chromatography. Compound 56: $^1$H-NMR (CDCl$_3$, 400 MHz, δ) 8.56 (dd, J=2.3, 4.0 Hz, 1H), 8.03 (d, J=8.5 Hz, 2H), 7.68 (s, 1H), 7.63 (dd, J=5.1, 9.8 Hz, 1H), 7.51 (d, J=8.5 Hz, 2H), 7.20 (m, 1H), 5.93 (s, 2H) ppm; [M+H]+ 328; Compound 57: $^1$H-NMR (CDCl$_3$, 400 MHz, δ) 8.19 (m, 1H), 7.64 (d, J=67.0 Hz, 1H), 7.65 (m, 2H), 7.51 (m 1H), 7.48 (m, 1H), 7.44 (m, 1H), 7.22 (m, 1H), 5.96 (s, 2H) ppm; m/e 328, 330.

Example 58

1-((2-(4-chlorophenyl)-6-fluoroH-imidazo[1,2-a]pyridin-3-yl)methyl)-1H-benzo[d][1,2,3]triazole (58)

and

Example 59

2-((2-(4-chlorophenyl)-6-fluoroH-imidazo[1,2-a]pyridin-3-yl)methyl)-2H-benzo[d][1,2,3]triazole (59)

The title compound was prepared according to Method A and the experimentals described for compound 1 from 3-(chloromethyl)-2-(4-chlorophenyl)-6-fluoroimidazo[1,2-a]pyridine hydrochloride and 1H-benzo[d][1,2,3]triazole. The two regioisomers were separated by silica gel chromatography. Compound 58: 1H-NMR (CDCl3, 400 MHz, δ) 8.30 (m, 1H), 7.99 (m, 2H), 7.71 (d, J=8.5 Hz, 2H), 7.59 (dd, J=5.0, 9.8 Hz, 1H), 7.51 (d, J=8.4 Hz, 2H), 7.28 (m, 2H), 7.16 (m, 1H), 6.86 (m, 1H), 6.20 (s, 2H) ppm; [M+H]+ 378; Compound 59: 1H-NMR (CDCl3, 400 MHz, δ) 8.69 (m, 1H), 8.12 (d, J=8.5 Hz, 2H), 7.90 (m, 2H), 7.64 (dd, J=5.1, 9.8 Hz, 1H), 7.55 (d, J=-8.5 Hz, 2H), 7.40 (m, 2H), 7.22 (m, 1H), 6.21 (s, 2H); [M+H]+ 378, 380.

Example 60

3-((2H-1,2,3-triazol-2-yl)methyl)-6-fluoro-2-(4-fluorophenyl)H-imidazo[1,2-a]pyridine (60)

and

Example 61

3-((1H-1,2,3-triazol-1-yl)methyl)-6-fluoro-2-(4-fluorophenyl)H-imidazo[1,2-a]pyridine (61)

The title compound was prepared according to Method A and the experimentals described for compound 1 from 3-(chloromethyl)-6-fluoro-2-(4-fluorophenyl)imidazo[1,2-a]pyridine hydrochloride and 1H-1,2,3-triazole. The two regioisomers were separated by silica gel chromatography. Compound 60: $^1$H-NMR (CDCl3, 400 MHZ, δ) 8.54 (dd, J=2.4, 3.9 Hz, 1H), 8.04 (m, 2H), 7.66 (s, 1H), 7.60 (dd, J=5.1, 9.9 Hz, 1H), 7.20 (m, 3H), 5.91 (s, 2H) ppm; [M+H]+ 312; Compound 61: $^1$H-NMR (CDCl$_3$, 400 MHz, δ) 8.14 (m, 1H), 7.2 (m, 2H), 7.65 (m, 1H), 7.44 (s, 1H), 7.21 (m, 3H), 5.98 (s, 2H) ppm, {M+H]+ 312.

Example 62

3-((1H-1,2,4-triazol-1-yl)methyl)-6-chloro-2-(4-fluorophenyl)H-imidazo[1,2-a]pyridine (62)

The title compound was prepared according to Method A and the experimentals described for compound 1 from 6-chloro-3-(chloromethyl)-2-(4-fluorophenyl)imidazo[1,2-a]pyridine hydrochloride and 1H-1,2,3-triazole. $^1$H-NMR (CDCl$_3$, 400 MHz, δ) 8.30 (d, J=1.2 Hz, 1H), 8.04 (s, 1H), 7.99 (s, 1H), 7.66 (m, 3H), 7.60 (d, J=9.6 Hz, 1), 7.26 (dd, J=2 Hz, 10 Hz, 1H), 7.17 (m, 2H), 5.67 (s, 2H) ppm; [M+H]+ 328.

Example 63

3-((1H-1,2,4-triazol-1-yl)methyl)-2-(4-fluorophenyl)-6-methylH-imidazo[1,2-a]pyridine (63)

The title compound was prepared according to Method A and the experimentals described for compound 1 from 3-(chloromethyl)-2-(4-fluorophenyl)-6-methylimidazo[1,2-a]pyridine hydrochloride and 1H-1,2,3-triazole. $^1$H-NMR (CDCl$_3$, 400 MHz, δ) 7.92 (d, J=4.4 Hz, 1H), 7.80 (s, 1H), 7.63 (m, 2H), 7.48 (d, J=9.2 Hz, 1H), 7.09 (m, 3H), 5.62 (s, 2H), 2.24 (s, 3H) ppm; [M+H]+ 308.

Example 64

3-((1H-1,2,4-triazol-1-yl)methyl)-2-(4-bromophenyl)H-imidazo[1,2-a]pyridine (64)

The title compound was prepared according to Method A and the experimentals described for compound 1 from 2-(4-bromophenyl)-3-(chloromethyl)imidazo[1,2-a]pyridine hydrochloride and 1H-1,2,4-triazole. $^1$H-NMR (CDCl$_3$, 400 MHz, δ) 8.16 (d, J=6.9 Hz, 1H), 8.1 (s, 1H), 7.99 (d, J=11.8 Hz, 2H), 7.67 (m, 3H), 7.30 (t, J=7.9 Hz, 1H), 7.17 (m, 1H), 6.91 (m, 1H), 5.72 (s, 2H) ppm; m/e 355 (M+H)+

Example 65

3-((1H-pyrazol-1-yl)methyl)-6,8-dichloro-2-p-tolylimidazo[1,2-a]pyridine (65)

The title compound was prepared according to Method A and the experimentals described for compound 1 from 6,8-dichloro-3-(chloromethyl)-2-p-tolylimidazo[1,2-a]pyridine hydrochloride and 1H-pyrazole. m/e+ 357 for $C_{18}H_{15}Cl_2N_4$ [M+H]+; $^1$H-NMR (300 MHz, CDCl$_3$) δ 8.28 (d, J=2.1 Hz, 1H), 7.67 (d, J=7.8 Hz, 2H), 7.60 (d, J=1.5 Hz, 1H), 7.35 (d, J=7.8 Hz, 2H), 7.30 (m, 2H), 6.31 (t, J=2.7 Hz, 1H), 5.71 (s, 2H), 2.44 (s, 3H) ppm.

Example 66

6-Chloro-2-phenyl-3-[1,2,3]triazol-1-ylmethyl-imidazo[1,2-a]pyridine (66)

The title compound was prepared according to Method A and the experimentals described for compound 1 from 2-(biphenyl-4-yl)-6-chloro-3-(chloromethyl)imidazo[1,2-a]pyridine hydrochloride and 1H-1,2,3-triazole. (m, 3H), 7.62 (dd, J=0.7, 9.5 Hz, 1H), 7.52 (m, 2H), 7.46 (m, 2H), 7.26 (m, 1H), 5.99 (s, 2H) ppm.

Example 67

3-((1H-1,2,4-triazol-1-yl)methyl)-2-(4-chlorophenyl)imidazo[1,2-a]pyridine (67)

The title compound was prepared according to Method A and the experimentals described for compound 1 from 3-(chloromethyl)-2-(4-chlorophenyl)imidazo[1,2-b]pyridazine hydrochloride and 1H-1,2,3-triazole. $^1$H-NMR (400 MHz, CDCl$_3$, δ) 8.17 (d, J=6.8 Hz, 1H), 8.00 (s, 1H), 7.68 (m, 3H), 7.52 (m, 2H), 7.33 (m, 1H), 7.26 (m, 1H), 6.93 (m, 1H), 5.74 (s, 2H) ppm; m/e 310.

Example 68

2-(6-Methyl-2-p-tolyl-imidazo[1,2-a]pyridin-3-ylmethyl)-2H-[1,2,4]triazole-3-carboxylic acid methylamide (68)

Methyl 1-((6-methyl-2-p-tolylimidazo[1,2-a]pyridin-3-yl)methyl)-1H-1,2,4-triazole-5-carboxylate was treated with excess methylamine in methanol in a sealed tube at 80° C. for several hours until the reaction was completed as judged by TLC or LC analysis. Solvent was evaporated and the crude product was purified by chromatography (SiO$_2$ column, eluted with 50% acetone). m/e+ 361 for $C_{20}H_{21}N_6O$ [M+H]+; $^1$H-NMR (300 MHz, CDCl$_3$) δ 8.13 (d, J=0.6 Hz, 1H), 7.87 (d, J=8.1 Hz, 2H), 7.65 (s, 1H), 7.57 (d, J=9.3 Hz, 1H), 7.27 (d, J=8.1 Hz, 2H), 7.08 (dd, J=1.2, 9.3 Hz, 1H), 6.32 (s, 2H), 3.06 (d, J=5.1 Hz, 3H), 2.50 (bs, 1H), 2.41 (s, 3H), 2.31 (s, 3H) ppm; $^{13}$C-NMR (75 MHz, CDCl$_3$, δ) 158.440, 150.38, 146.788, 146.587, 138.174, 131.289, 129.586, 129.413, 128.819, 128.612, 122.655, 122.094, 117.100, 113.447, 44.395, 26.393, 21.605, 18.714 ppm.

Example 69

2-(6-Methyl-2-p-tolyl-imidazo[1,2-a]pyridin-3-ylmethyl)-2H-[1,2,4]triazole-3-carboxylic acid amide (69)

The title compound was prepared according to the procedure described for compound 68 from methyl 1-((6-methyl-2-p-tolylimidazo[1,2-a]pyridin-3-yl)methyl)-1H-1,2,4-triazole-5-carboxylate and ammonia. m/e⁻ 347 for $C_{19}H_{19}N_6O$ [M+H]⁺; ¹H-NMR (300 MHz, CDCl$_3$) δ 8.10 (s, 1H), 7.87 (d, J=6.9 Hz, 2H), 7.61 (d, J=9.3 Hz, 1H), 7.41 (d, J=9.3 Hz, 1H), 7.30 (d, J=6.9 Hz, 2H), 7.12 (dd, J=1.2, 9.3 Hz, 1H), 6.32 (s, 2H), 6.03 (bs, 2H), 2.43 (s, 3H), 2.34 (s, 3H) ppm.

Example 70

2-(6-Methyl-2-p-tolyl-imidazo[1,2-a]pyridin-3-ylmethyl)-2H-[1,2,4]triazole-3-carboxylic acid dimethylamide (70)

The title compound was prepared according to the procedure described for compound 68 from methyl 1-((6-methyl-2-p-tolylimidazo[1,2-a]pyridin-3-yl)methyl)-1H-1,2,4-triazole-5-carboxylate and dimethylamine. m/e 375 for $C_{21}H_{23}N_6O$ [M+H]⁺; ¹H-NMR (300 MHz, CDCl$_3$) δ 8.35 (s, 2H), 7.87 (d, J=2.1 Hz, 1H), 7.72 (d, J=7.8 Hz, 2H), 7.54 (d, J=9.0 Hz, 1H), 7.26 (d, J=7.8 Hz, 2H), 7.10 (d, J=9.0 Hz, 1H), 6.00 (s, 1H), 3.06 (s, 3H), 3.00 (s, 3H), 2.40 (s, 3H), 2.35 (s, 3H) ppm; ¹³C-NMR (75 MHz, CDCl$_3$, δ) 158.440, 150.213, 147.869, 146.313, 144.771, 138.154, 131.236, 131.236, 129.600, 128.812, 128.725, 122.609, 116.939, 113.480, 43.481, 38.888, 35.781, 21.585, 18.727 ppm.

Example 71

N,N-Dimethyl-1-((6-methyl-2-p-tolylH-imidazo[1,2-a]pyridin-3-yl)methyl)-1H-imidazole-2-carboxamide (71)

The title compound was prepared according to Method A and the experimentals described for compound 68 from 3-(chloromethyl)-6-methyl-2-p-tolylimidazo[1,2-a]pyridine hydrochloride and N,N-dimethyl-1H-imidazole-2-carboxamide. The reagent N,N-dimethyl-1H-imidazole-2-carboxamide was prepared from the treatment of 1H-imidazole-2-carboxylic acid with thionyl chloride followed by the reaction of the resulting 1H-imidazole-2-carbonyl chloride with dimethyl amine in CH$_2$Cl$_2$. m/e⁺ 374.2 for $C_{22}H_{24}N_5O$ (M+H)⁺; ¹H-NMR (400 MHz, CDCl$_3$, δ) 8.131 (s, 1H), 7.60 (d, J=7.698 Hz, 2H), 7.53 (d, J=9.165 Hz, 1H), 7.24 (d, J=8.064 Hz, 2H), 7.07 (dd, J$_1$=9.164 Hz, J$_2$=1.1 Hz, 1H), 6.944 (s, 1H), 6.635 (s, 1H), 5.924 (s, 2H, D, CH$_2$), 3.399 (s, 3H, D, CH$_3$), 3.146 (s, 3H, D, CH$_3$), 2.409 (s, 3H, D, CH$_3$), 2.37 (s, 3H, D, CH3) ppm; ¹³C-NMR (100 MHz, CDCl$_3$, δ) 161.399, 146.066, 144.861, 139.818, 138.370, 131.030, 129.794, 129.028, 128.361, 128.254, 123.053, 122.310, 120.967, 116.895, 113.680, 40.840, 39.680, 36.162, 21.520, 18.638 ppm.

Example 72

1-((2-(4-chlorophenyl)imidazo[1,2-a]pyridin-3-yl)methyl)-1H-1,2,4-triazole-3-carboxamide (72)

The title compound was prepared according to the procedure described for compound 68 from methyl 1-((2-(4-chlorophenyl)imidazo[1,2-a]pyridin-3-yl)methyl)-1H-1,2,4-triazole-3-carboxylate and ammonia. ¹H-NMR (D6-DMSO, 400 MHZ, d) 8.60 (d, J=6.9 Hz, 1H), 8.41 (s, 1H), 8.17 (s, 1H), 8.03 (s, 1H), 7.83 (d, J=8.5 Hz, 2H), 7.65 (d, J=9.1 Hz, 1H), 7.50 (d, J=8.5 Hz, 2H), 7.35 (t, J=7.9 Hz, 1H), 7.00 (t, J=6.8 Hz, 1H), 6.32 (s, 2H) ppm; m/e 353, 355.

Example 73

1-((2-(4-chlorophenyl)imidazo[1,2-a]pyridin-3-yl)methyl)-N-methyl-1H-1,2,4-triazole-3-carboxamide (73)

The title compound was prepared according to the procedure described for compound 68 from methyl 1-((2-(4-chlorophenyl)imidazo[1,2-a]pyridin-3-yl)methyl)-1H-1,2,4-triazole-3-carboxylate and methylamine. 1H-NMR (400 MHz, CDCl3, δ) 8.42 (d, J=6.8 Hz, 1H), 7.98 (d, J=8.5 Hz, 2H), 7.85 (s, 1H), 7.69 (d, J=9.1 Hz, 1H), 7.50 (broad, 1H), 7.45 (d, J=8.5 Hz, 2H), 7.29 (m, 1H), 6.87 (m, 1H), 6.34 (s, 2H), 3.08 (d, J=5.1 Hz, 3H) ppm; m/e 367, 369.

Example 74

1-((2-(4-chlorophenyl)imidazo[1,2-a]pyridin-3-yl)methyl)-N,N-dimethyl-1H-1,2,4-triazole-5-carboxamide (74)

The title compound was prepared according to the procedure described for compound 68 from methyl 1-((2-(4-chlorophenyl)imidazo[1,2-a]pyridin-3-yl)methyl)-1H-1,2,4-triazole-5-carboxylate and dimethylamine. ¹H-NMR (400 MHz, CDCl$_3$, δ) 8.21 (d, J=6.9 Hz, 1H), 7.97 (s, 1H), 7.71 (d, J=9.2 Hz, 1H), 7.68 (d, J=8.5 Hz, 2H), 7.49 (d, J=8.4 Hz, 1H), 7.34 (m, 1H), 6.94 (m, 1H), 5.80 (s, 2H), 3.21 (s, 3H), 3.13 (s, 3H) ppm; m/e 241, 243.

Example 75

1-((2-(4-chlorophenyl)imidazo[1,2-a]pyridin-3-yl)methyl)-N,N-dimethyl-1H-1,2,4-triazole-3-carboxamide (75)

The title compound was prepared according to the procedure described for compound 68 from methyl 1-((2-(4-chlorophenyl)imidazo[1,2-a]pyridin-3-yl)methyl)-1H-1,2,4-triazole-3-carboxylate and dimethylamine. ¹H-NMR (400 MHz, CDCl$_3$, δ) 8.65 (d, J=6.9 Hz, 1H), 7.88 (s, 1H), 7.85 (d, J=8.5 Hz, 2H), 7.66 (d, J=9.1 Hz, 1H), 7.45 (d, J=8.5 Hz, 2H), 7.28 (m, 1H), 6.89 (m, 1H), 6.04 (s, 2H), 3.15 (s, 3H), 3.06 (s, 3H) ppm; m/e 381, 383.

Example 76

1-((2-(4-chlorophenyl)H-imidazo[1,2-a]pyridin-3-yl)methyl)-1H-imidazole-2-carboxamide (76)

The title compound was prepared according to the procedure described for compound 68 from methyl 1-((2-(4-chlorophenyl)imidazo[1,2-a]pyridin-3-yl)methyl)-1H-imidazole-2-carboxylate and ammonia. ¹H-NMR (300 MHz, CDCl$_3$) 8.10 (d, J=6.9 Hz, 1H), 7.70 (d, J=8.4 Hz, 2H), 7.46 (d, J=8.5 Hz, 2H), 7.36 (broad, 1H), 7.29 (t, J=7.9 Hz, 1H), 6.96 (s, 1H), 6.85 (t, J=6.8 Hz, 1H), 6.63 (s, 1H), 6.27 (s, 2H). m/e 352.

Example 77

1-((2-(4-chlorophenyl)H-imidazo[1,2-a]pyridin-3-yl)
methyl)-N-methyl-1H-imidazole-2-carboxamide
(77)

The title compound was prepared according to the procedure described for compound 68 from methyl 1-((2-(4-chlorophenyl)imidazo[1,2-a]pyridin-3-yl)methyl)-1H-imidazole-2-carboxylate and methylamine. 1H-NMR (400 MHz, CDCl3) 8.15 (d, J=6.9 Hz, 1H), 7.69 (m, 2H), 7.47 (m, 2H), 7.25 (m, 1H), 6.91 (s, 1H), 6.85 (m, 1H), 6.60 (s, 1H), 6.30 (s, 2H), 3.49 (s, 2H), 3.04 (d, J=5.1 Hz, 3H) ppm; m/e 366, 368.

Example 78

1-((2-(4-chlorophenyl)H-imidazo[1,2-a]pyridin-3-yl)
methyl)-N-(2-(dimethylamino)ethyl)-1H-imidazole-
2-carboxamide (78)

The title compound was prepared according to the procedure described for compound 68 from 3-(chloromethyl)-2-(4-chlorophenyl)imidazo[1,2-a]pyridine hydrochloride and N1,N1-dimethylethane-1,2-diamine. H-NMR (CDCl$_3$, 400 MHz, δ) 8.11 (d, J=6.8 Hz, 1H), 7.82 (t, J=4.8 Hz, 1H), 7.65 (m, 2H), 7.42 (m, 2H), 7.24 (m, 1H), 6.89 (s, 1H), 6.89 (m, 1H), 6.55 (s, 1H), 6.24 (s, 2H), 3.5 (m, 2H), 3.25 (broad, 1H), 2.54 (m, 2H), 2.27 (s, 6H) ppm; m/e 423 (M+H)$^+$

Example 79

1-((2-(4-chlorophenyl)imidazo[1,2-a]pyridin-3-yl)
methyl)-N,3-dimethyl-1H-pyrazole-5-carboxamide
(79)

The title compound was prepared according to the procedure described for compound 68 from 3 methyl 1-((2-(4-chlorophenyl)imidazo[1,2-a]pyridin-3-yl)methyl)-3-methyl-1H-pyrazole-5-carboxylate and methylamine. M/e$^+$ 380 for C$_{20}$H$_{19}$ClN$_5$O (M+H)$^+$; $^1$H-NMR (400 MHz, CDCl$_3$) δ 8.29 (d, J=6.6 Hz, 1H), 7.85 (d, J=8.4 Hz, 2H), 7.64 (d, J=8.8 Hz, 1H), 7.42 (d, J=8.4 Hz, 2H), 7.23 (m, 1H), 6.82 (t, J=6.9 Hz, 1H), 6.66 (s, 1H), 6.05 (s, 2H), 3.84 (s, 3H), 2.19 (s, 3H) 1.57 (s, 1H), ppm;

Example 80

1-((2-(4-chlorophenyl)imidazo[1,2-a]pyridin-3-yl)
methyl)-N,5-dimethyl-1H-pyrazole-3-carboxamide
(80)

The title compound was prepared according to the procedure described for compound 68 from methyl 1-((2-(4-chlorophenyl)imidazo[1,2-a]pyridin-3-yl)methyl)-5-methyl-1H-pyrazole-3-carboxylate and methylamine. M/e$^+$ 381 for C$_{20}$H$_{19}$ClN$_5$O (M+H)$^+$; $^1$H-NMR (400 MHz, CDCl$_3$) δ 8.20 (d, J=6.9 Hz, 1H), 7.68 m, 1H), 7.65 (d, J=8.4 Hz, 2H), 7.47 (d, J=8.4 Hz, 2H), 7.28 (m, 1H), 6.86 (td, J=6.9, 1.1 Hz, 1H), 6.62 (m, 1H), 6.52 (s, 1H), 5.64 (s, 2H), 2.93 (d, J=5.1 Hz, 3H), 1.99 (s, 3H) ppm.

Example 81

2-[6-Chloro-2-(4-chloro-phenyl)-imidazo[1,2-a]pyri-
din-3-ylmethyl]-2H-[1,2,4]triazole-3-carboxylic acid
methylamide (81)

The title compound was prepared according to the procedure described for compound 68 from ethyl 1-(((6-chloro-2-(4-chlorophenyl)imidazo[1,2-a]pyridin-3-myl)methyl)-1H-1,2,4-triazole-5-carboxylate and methylamine. m/e$^+$ 401 for C$_{18}$H$_{15}$Cl$_2$N$_6$O [M+H]$^+$; $^1$H-NMR (400 MHz, CDCl$_3$) δ 8.55 (s, 1H), 7.96 (d, J=8.4 Hz, 2H), 7.86 (s, 1H), 7.60 (d, J=9.5 Hz, 1H), 7.45 (d, J=8.4 Hz, 2H), 7.45 (s, 1H), 6.31 (s, 2H), 3.08 (s, 3H) 1.20 (bs, 1H) ppm.

Example 82

2-[6-Chloro-2-(4-chloro-phenyl)-imidazo[1,2-a]pyri-
din-3-ylmethyl]-2H-[1,2,4]triazole-3-carboxylic acid
methoxy-methyl-amide (82)

The title compound was prepared according to the procedure described for compound 68 from 1-((6-chloro-2-(4-chlorophenyl)imidazo[1,2-a]pyridin-3-yl)methyl)-N-methoxy-N-methyl-1H-1,2,4-triazole-5-carboxamide and methoxymethanamine. m/e$^-$ 431 for C$_{19}$H$_{17}$Cl$_2$N$_6$O$_2$ [M+H]$^+$; $^1$H-NMR (300 MHz, CDCl$_3$) δ 8.90 (s, 1H), 7.74 (m, 3H), 7.51 (m, 4H), 6.02 (s, 2H), 3.33 (s, 3H), 3.20 (s, 3H) ppm.

Example 83

1-((6-fluoro-2-(4-fluorophenyl)imidazo[1,2-a]pyri-
din-3-yl)methyl)-1H-1,2,4-triazole-3-carboxamide
(83)

The title compound was prepared according to the procedure described for compound 68 from methyl 1-((6-fluoro-2-(4-fluorophenyl)imidazo[1,2-a]pyridin-3-yl)methyl)-1H-1,2,4-triazole-3-carboxylate and ammonia. m/e+ 355 for C17H13F2N6O (M+H)+.

Example 84

1-((6-fluoro-2-(4-fluorophenyl)imidazo[1,2-a]pyri-
din-3-yl)methyl)-1H-1,2,4-triazole-5-carboxamide
(84)

The title compound was prepared according to the procedure described for compound 68 from methyl 1-((6-fluoro-2-(4-fluorophenyl)imidazo[1,2-a]pyridin-3-yl)methyl)-1H-1,2,4-triazole-5-carboxylate and ammonia. m/e+ 355 for C17H13F2N6O (M+H)+.

Example 85

1-((6-fluoro-2-(4-fluorophenyl)imidazo[1,2-a]pyri-
din-3-yl)methyl)-N-methyl-1H-1,2,4-triazole-5-car-
boxamide (85)

The title compound was prepared according to the procedure described for compound 68 from methyl 1-((6-fluoro-2-(4-fluorophenyl)imidazo[1,2-a]pyridin-3-yl)methyl)-1H-1,2,4-triazole-5-carboxylate and methylamine. m/e+ 368 for C18H15F2N6O (M+H)+.

Example 86

1-((6-fluoro-2-(4-fluorophenyl)imidazo[1,2-a]pyri-
din-3-yl)methyl)-1H-1,2,4-triazole-5-carbohydrazide
(86)

The title compound was prepared according to the procedure described for compound 68 from methyl 1-((6-fluoro-2-

(4-fluorophenyl)imidazo[1,2-a]pyridin-3-yl)methyl)-1H-1,2,4-triazole-5-carboxylate and hydrazine hydrate. m/e+ 370 for C17H14F2N7O (M+H)+.

Example 87

1-((2-(4-chlorophenyl)imidazo[1,2-b]pyridazin-3-yl)methyl)-1H-imidazole-2-carboxamide (87)

The title compound was prepared according to the procedure described for compound 68 from methyl 1-((2-(4-chlorophenyl)imidazo[1,2-b]pyridazin-3-yl)methyl)-1H-imidazole-2-carboxylate and ammonia. $^1$H-NMR (CDCl$_3$, 400 MHz, δ) 8.59 (d, J=4.4 Hz, 1H), 8.23 (d, J=9.2 Hz, 1H), 7.87 (s, 1H), 7.75 (d, J=8.5 Hz, 2H), 7.57 (s, 1H), 7.50 (d, J=8.4 Hz, 2H), 7.36 (dd, J=4.4, 9.2 Hz, 1H), 6.87 (s, 1H), 6.21 (s, 2H) ppm; m/e 353 (M+H)$^+$.

Example 88

1-((2-(4-chlorophenyl)imidazo[1,2-b]pyridazin-3-yl)methyl)-N-methyl-1H-imidazole-2-carboxamide (88)

The title compound was prepared according to the procedure described for compound 68 from methyl 1-((2-(4-chlorophenyl)imidazo[1,2-b]pyridazin-3-yl)methyl)-1H-imidazole-2-carboxylate and methylamine $^1$H-NMR (CDCl$_3$, 400 MHz, δ) 8.54 (d, J=4.4 Hz, 1H), 8.09 (d, J=9.3 Hz, 1H), 7.87 (s, 1H), 7.64 (d, J=8.0 Hz, 2H), 7.51 (s, 1H), 7.47 (d, J=7.9 Hz, 2H), 7.37 (dd, J=4.5, 9.2 Hz, 1H), 6.93 (s, 1H), 6.90 (s, 1H), 6.31 (s, 2H), 2.91 (s, 3H) ppm; m/e 367 (M+H)$^+$.

Example 89

1-((2-(4-chlorophenyl)imidazo[1,2-b]pyridazin-3-yl)methyl)-1H-1,2,4-triazole-5-carboxamide (89)

The title compound was prepared according to the procedure described for compound 68 from methyl 1-((2-(4-chlorophenyl)imidazo[1,2-b]pyridazin-3-yl)methyl)-1H-1,2,4-triazole-5-carboxylate and ammonia. $^1$H-NMR (CDCl$_3$, 400 MHz, δ) 8.74 (s, 1H), 8.56 (dd, J=1.4, 4.5 Hz, 1H), 8.08 (dd, J=1.5, 9.3 Hz, 1H), 8.02 (d, J=8.5 Hz, 2H), 7.57 (d, J=8.5 Hz, 2H), 7.37 (dd, J=4.5, 9.2 Hz, 1H), 6.01 (s, 2H) ppm; m/e 354 (M+H)$^-$.

Example 90

1-((2-(4-chlorophenyl)imidazo[1,2-b]pyridazin-3-yl)methyl)-N-methyl-1H-1,2,4-triazole-5-carboxamide (90)

The title compound was prepared according to the procedure described for compound 68 from methyl 1-((2-(4-chlorophenyl)imidazo[1,2-b]pyridazin-3-yl)methyl)-1H-1,2,4-triazole-5-carboxylate and methylamine. $^1$H-NMR (CDCl$_3$, 400 MHz, δ) 8.42 (dd, J=1.5, 4.4 Hz, 1H), 8.31 (s, 1H), 8.04 (dd, J=1.5, 9.2 Hz, 1H), 7.95 (d, J=8.5 Hz, 2H), 7.52 (d, J=8.5 Hz, 2H), 7.20 (dd, J=4.5, 9.2 Hz, 1H), 7.06 (broad, 1H), 5.91 (s, 2H), 3.00 (d, J=5.1 Hz, 3H) ppm; m/e 368 (M+H)$^+$.

General Procedure for Imidazopyridinylmethyllactams (Formula III, Method B from 1d)

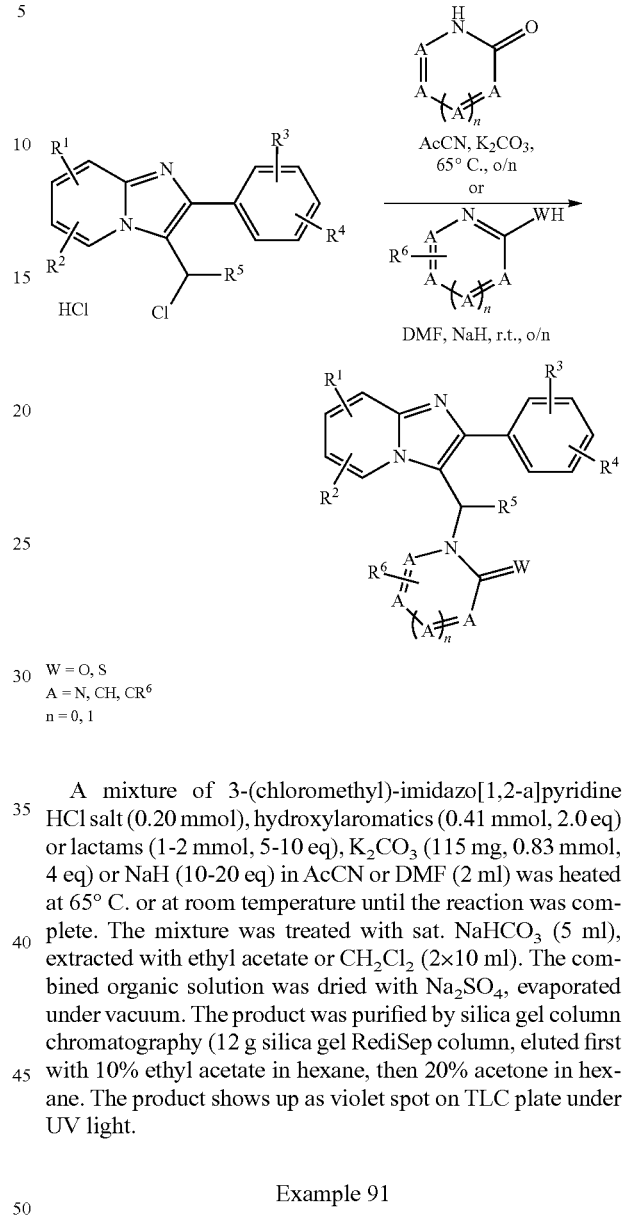

W = O, S
A = N, CH, CR$^6$
n = 0, 1

A mixture of 3-(chloromethyl)-imidazo[1,2-a]pyridine HCl salt (0.20 mmol), hydroxylaromatics (0.41 mmol, 2.0 eq) or lactams (1-2 mmol, 5-10 eq), K$_2$CO$_3$ (115 mg, 0.83 mmol, 4 eq) or NaH (10-20 eq) in AcCN or DMF (2 ml) was heated at 65° C. or at room temperature until the reaction was complete. The mixture was treated with sat. NaHCO$_3$ (5 ml), extracted with ethyl acetate or CH$_2$Cl$_2$ (2×10 ml). The combined organic solution was dried with Na$_2$SO$_4$, evaporated under vacuum. The product was purified by silica gel column chromatography (12 g silica gel RediSep column, eluted first with 10% ethyl acetate in hexane, then 20% acetone in hexane. The product shows up as violet spot on TLC plate under UV light.

Example 91

1,2-dihydro-3-methyl-1-((6-methyl-2-p-tolyl-H-imidazo[1,2-a]pyridin-3-yl)methyl)pyrazol-5-one (91)

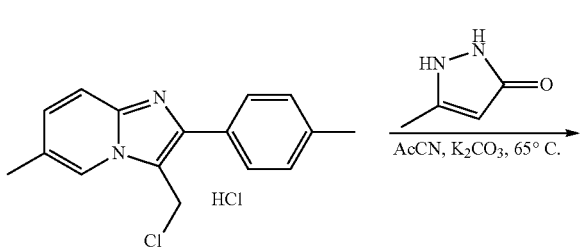

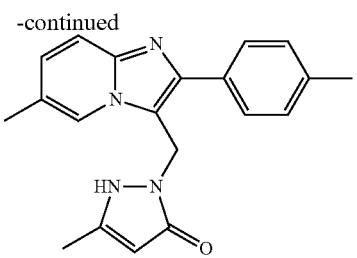

A mixture of 3-(chloromethyl)-6-methyl-2-p-tolylimidazo[1,2-a]pyridine hydrochloride (0.20 mmol), 5-methyl-1H-pyrazol-3(2H)-one (2 mmol, 10 eq) K$_2$CO$_3$ (115 mg, 0.83 mmol, 4 eq) in AcCN (2 ml) was heated at 65° C. 12-36 hr. The mixture was treated with sat. NaHCO$_3$ (5 ml), extracted with ethyl acetate or CH$_2$Cl$_2$ (2×10 ml). The combined organic solution was dried with Na$_2$SO$_4$, evaporated under vacuum. The product was purified by silica gel column chromatography (12 g silica gel RediSep column, eluted first with 10% ethyl acetate in hexane, then 20% acetone in hexane. The product shows up as violet spot on TLC plate under UV light. m/e$^+$ 333.4 for C$_{20}$H$_{21}$N$_4$O (M+H)$^+$, $^1$H-NMR (400 MHz, CDCl$_3$, δ) 8.211 (s, 1H), 7.97 (d, J=7.698 Hz, 2H), 7.53 (d, J=9.165 Hz, 1H), 7.28 (d, J=7.698 Hz, 2H), 7.07 (d, J=8.798 Hz, 1H), 5.156 (s, 2H, D, CH$_2$), 2.406 (s, 3H, D, CH$_3$), 2.347 (s, 3H, D, CH$_3$), 2.067 (s, 3H, D, CH$_3$) ppm.

Example 92

1-methyl-3-((6-methyl-2-p-tolylH-imidazo[1,2-a]pyridin-3-yl)methyl)imidazolidin-2-one (92)

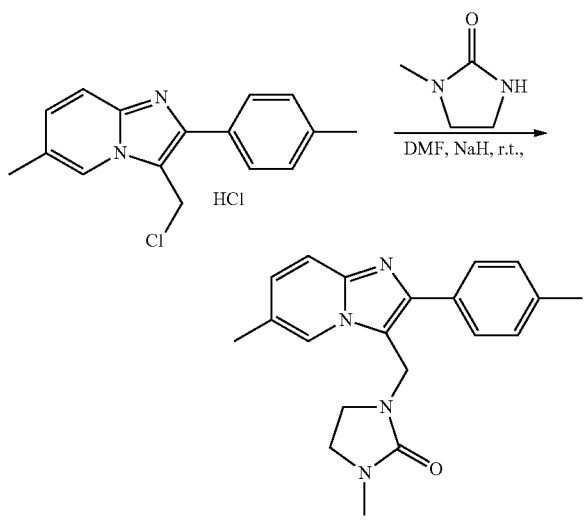

To a mixture of 3-(chloromethyl)-6-methyl-2-p-tolylimidazo[1,2-a]pyridine hydrochloride (0.20 mmol), 1-methylimidazolidin-2-one (10 eq) in DMF (4 ml) at 0° C. was added NaH (20 eq). The reaction was exothermic, and gas was evolved. The mixture was stirred at room temperature over night. The reaction was quenched by addition of water after the reaction was complete as judged by LC-Mass analysis. The mixture was extracted with ethyl acetate (2×10 ml). The combined organic solution was washed with brine and dried with Na$_2$SO$_4$, evaporated under vacuum. The product was purified by silica gel column chromatography (12 g silica gel RediSep column, eluted first with 10% ethyl acetate in hexane, then 20% acetone in hexane and finally flashed with 50% acetone in hexane if necessary to get the product out off the column. The product shows up as violet spot on TLC plate under UV light. m/e$^+$ 335.4 for C$_{20}$H$_{23}$N$_4$O (M+H)$^+$; $^1$H-NMR (400 MHz, CDCl$_3$, δ) 8.149 (s, 1H), 7.61 (d, J=7.699 Hz, 2H), 7.52 (d, J=8.798 Hz, 1H), 7.25 (d, J=8.064 Hz, 2H), 7.07 (d, J=9.164 Hz, 1H), 4.857 (s, 2H), 3.18 (m, 2H), 3.02 (m, 2H), 2.814 (s, 3H, D, CH$_3$), 2.398 (s, 3H, D, CH$_3$), 2.347 (s, 3H, D, CH$_3$) ppm; $^{13}$C-NMR (100 MHz, CDCl$_3$, δ) 161.535, 145.414, 144.444, 137.809, 131.735, 129.513, 128.702, 128.308, 122.810, 122.310, 116.767, 115.205, 45.079, 42.4768, 38.080, 31.612, 21.504, 18.699 ppm; UV 242.0, 310.0 nm.

Example 93

3-ethyl-4-methyl-1-((6-methyl-2-p-tolyl-H-imidazo[1,2-a]pyridin-3-yl)methyl)-1H-pyrrol-2(5H)-one (93)

The title compound was prepared according to Method B and the experimentals described for compound 91 from 3-(chloromethyl)-6-methyl-2-p-tolylimidazo[1,2-a]pyridine hydrochloride and 3-ethyl-4-methyl-1H-pyrrol-2(5H)-one in 84% yield; m/e$^+$ 360.4 for C$_{23}$H$_{26}$N$_3$O (M+H)$^+$; $^1$H-NMR (400 MHz, CDCl$_3$, δ) 8.119 (s, 1H), 7.63 (d, J=8.065 Hz, 2H), 7.49 (d, J=8.798 Hz, 1H), 7.25 (d, J=8.065 Hz, 2H), 7.04 (d, J=9.165 Hz, 1H), 5.071 (s, 2H, D, CH$_2$), 3.428 (s, 2H, D, CH$_2$), 2.384 (s, 3H, D, CH$_3$), 2.294 (s, 3H, D, CH$_3$), 2.26 (q, 2H, D, CH$_2$), 1.821 (s, 3H, D, CH$_3$), 1.03 (t, J=7.698 Hz, 3H, D, CH$_3$) ppm.

Example 94

4-methoxy-1-((6-methyl-2-p-tolyl-H-imidazo[1,2-a]pyridin-3-yl)methyl)-1H-pyrrol-2(5H)-one (94)

The title compound was prepared according to Method B and the experimentals described for compound 91 from 3-(chloromethyl)-6-methyl-2-p-tolylimidazo[1,2-a]pyridine hydrochloride and 3-ethyl-4-methyl-1H-pyrrol-2(5H)-one in 84% yield; m/e$^+$ 360.4 for C$_{23}$H$_{26}$N$_3$O (M+ and 4-methoxy-1H-pyrrol-2(5H)-one. m/e$^+$ 348 for C$_{21}$H$_{22}$N$_3$O$_2$ (M+H)$^+$; $^1$H-NMR (400 MHz, CDCl$_3$, δ) 8.166 (s, 1H), 7.61 (d, J=8.064 Hz, 2H), 7.53 (d, J=9.165 Hz, 1H), 7.27 (d, J=8.798 Hz, 2H), 7.07 (dd, J$_1$=9.164 Hz, J$_2$=1.466 Hz, 1H), 5.053 (s, 2H, D, CH$_2$), 5.053 (s, 1H), 3.718 (s, 3H, D, CH$_3$), 3.551 (s, 2H, D, CH$_2$), 2.405 (s, 3H, D, CH$_3$), 2.337 (s, 3H, D, CH$_3$) ppm.

Example 95

1-((6-methyl-2-p-tolyl-H-imidazo[1,2-a]pyridin-3-yl)methyl)piperidin-2-one (95)

The title compound was prepared according to Method B and the experimentals described for compound 91 from 3-(chloromethyl)-6-methyl-2-p-tolylimidazo[1,2-a]pyridine hydrochloride and piperidin-2-one in 39% yield; m/e$^+$ 334.4 for C$_{21}$H$_{24}$N$_3$O (M+H)$^+$; $^1$H-NMR (400 MHz, CDCl$_3$, δ) 8.162 (s, 1H), 7.59 (d, J=8.065 Hz, 2H), 7.51 (d, J=9.165 Hz, 1H), 7.26 (d, J=8.065 Hz, 2H), 7.07 (dd, J$_1$=9.164 Hz, J$_2$=1.466 Hz, 1H), 5.174 (s, 2H, D, CH$_2$), 2.83 (m, 2H), 2.40 (s, 3H, D, CH$_3$), 2.33 (s, 3H, D, CH$_3$), 1.90 (m, 2H, D, CH$_2$), 1.70 (m, 2H, D, CH$_2$), 1.60 (m, 2H, D, CH$_2$) ppm.

Example 96

1-((6-methyl-2-p-tolyl-H-imidazo[1,2-a]pyridin-3-yl)methyl)pyridin-2(1H)-one (96)

The title compound was prepared according to Method B and the experimentals described for compound 91 from 3-(chloromethyl)-6-methyl-2-p-tolylimidazo[1,2-a]pyridine hydrochloride and pyridin-2-ol in 76.4% yield; m/e$^+$ 330.5 for $C_{21}H_{20}N_3O$ (M+H)$^+$; $^1$H-NMR (400 MHz, CDCl$_3$, δ) 8.00 (s, 1H), 7.60 (d, J=8.065 Hz, 2H), 7.53 (d, J=9.165 Hz, 1H), 7.24 (m, 3H), 7.08 (d, J$_1$=9.146 Hz, J$_2$=1.1 Hz, 1H), 6.82 (dd, J=6.965 Hz, J$_2$=2.199, 1H), 6.60 (d, J=8.799 Hz, 1H), 5.97 (m, 1H), 5.638 (s, 2H, D, CH$_2$), 2.384 (s, 3H, D, CH$_3$), 2.290 (s, 3H, D, CH$_3$) ppm; $^{13}$C-NMR (100 MHz, CDCl$_3$, δ) 163.074, 147.029, 144.891, 139.773, 138.491, 135.557, 131.060, 129.900, 129.028, 128.535, 123.091, 122.272, 121.051, 117.047, 113.976, 107.045, 39.885, 21.542, 18.638 ppm.

Example 97

3-methyl-1-((6-methyl-2-p-tolylH-imidazo[1,2-a]pyridin-3-yl)methyl)pyridin-2(1H)-one (97)

The title compound was prepared according to Method B and the experimentals described for compound 91 from 3-(chloromethyl)-6-methyl-2-p-tolylimidazo[1,2-a]pyridine hydrochloride and 3-methylpyridin-2-ol in 63% yield; m/e$^+$ 344.3 for $C_{22}H_{22}N_3O$ (M+H)$^+$; $^1$H-NMR (400 MHz, CDCl$_3$, δ) 7.954 (s, 1H), 7.60 (d, J=8.065 Hz, 2H), 7.54 (d, J=9.164, 1H), 7.26 (d, J=8.064, 2H), 7.13 (d, J=6.599 Hz, 1H), 7.09 (dd, J=9.164 Hz, J$_2$=1.1 Hz, 1H), 6.31 (t, J=6.866 Hz, 1H), 5.649 (s, 2H, D, CH$_2$), 2.388 (s, 3H, D, CH$_3$), 2.312 (s, 3H, D, CH$_3$), 2.291 (s, 3H, D, CH$_3$) ppm.

Example 98

4,5-dichloro-2-((6-methyl-2-p-tolylH-imidazo[1,2-a]pyridin-3-yl)methyl)pyridazin-3(2H)-one (98)

The title compound was prepared according to Method B and the experimentals described for compound 91 from 3-(chloromethyl)-6-methyl-2-p-tolylimidazo[1,2-a]pyridine hydrochloride and 4,5-dichloropyridazin-3(2H)-one. (68.5 mg, 88.2% yield); m/e$^+$ 399.3, 401.3 (M+H)$^+$; $^1$H-NMR (400 MHz, CDCl$_3$, δ) 7.995 (s, 1H), 7.75 (d, J=8.064 Hz, 2H), 7.74 (s, 1H), 7.46 (d, J=9.164 Hz, 1H), 7.20 (d, J=7.699 Hz, 2H), 7.10 (d, J=9.165 Hz, 1H), 5.670 (s, 2H, D, CH$_2$), 2.334 (s, 3H, D, CH$_3$), 2.287 (s, 3H, D, CH$_3$) ppm; $^{13}$C-NMR (100 MHz, CDCl$_3$, δ) 157.410, 156.295, 146.779, 144.459, 138.446, 137.27, 136.77, 130.598, 129.506, 129.263, 128.671, 123.25, 122.173, 116.433, 113.491, 45.216, 21.375, 18.502 ppm.

Example 99

3-((6-methyl-2-p-tolylH-imidazo[1,2-a]pyridin-3-yl)methyl)pyrimidin-4(3H)-one (99)

The title compound was prepared according to Method B and the experimentals described for compound 91 from 3-(chloromethyl)-6-methyl-2-p-tolylimidazo[1,2-a]pyridine hydrochloride and pyrimidin-4(3H)-one (or pyrimidin-4-ol) (41.3 mg, 64% yield); m/e$^-$ 331.4 for $C_{20}H_{19}N_4O$ (M+H)$^+$; $^1$H-NMR (400 MHz, CDCl$_3$, δ) 8.026 (s, 1H), 7.80 (d, J=6.598 Hz, 1H), 7.648 (s, 1H), 7.57 (m, 3H), 7.29 (d, J=8.065 Hz, 2H), 7.13 (d, J=9.165 Hz, 1H), 6.47 (d, J=6.598 Hz, 1H), 5.638 (s, 2H, D, CH$_2$), 2.416 (s, 3H, D, CH$_3$), 2.340 (s, 3H, D, CH$_3$) ppm; $^{13}$C-NMR (100 MHz, CDCl$_3$, δ) 161.437, 153.528, 150.381, 147.393, 145.050, 138.817, 130.772, 130.044, 129.210, 128.634, 123.356, 122.044, 117.275, 115.902, 113.021, 37.906, 21.542, 18.653 ppm; UV 244 nm.

Example 100

1-((6-methyl-2-p-tolylH-imidazo[1,2-a]pyridin-3-yl)methyl)pyrimidin-2(1H)-one (100)

The title compound was prepared according to Method B and the experimentals described for compound 91 from 3-(chloromethyl)-6-methyl-2-p-tolylimidazo[1,2-a]pyridine hydrochlorid and 2-hydroxypyrimidine. M/e$^+$ 331.4 for $C_{20}H_{19}N_4O$ (M+H)$^+$; $^1$H-NMR (400 MHz, CDCl$_3$, δ) 8.54 (dd, J$_1$=4.032 Hz, J$_2$=3.299 Hz, 1H), 7.989 (s, 1H), 7.59 (d, J=8.063 Hz, 2H), 7.58 (d, J=9.531 Hz, 1H), 7.29 (d, J=8.065 Hz, 1H), 7.16 (m, 2H), 6.15 (dd, J$_1$=6.595 Hz, J$_2$=4.032 Hz, 1H), 5.646 (s, 2H, D, CH$_2$), 2.416 (s, 3H, D, CH$_3$), 2.337 (s, 3H, D, CH$_3$) ppm. $^{13}$C-NMR (75 MHz, CDCl$_3$, δ) 166.318, 156.976, 147.675, 145.818, 145.284, 138.921, 130.688, 130.093, 129.519, 128.424, 123.723, 121.934, 117.306, 112.372, 105.120, 42.327, 21.574, 18.649 ppm; UV 240, 306 nm.

Example 101

5,5-dimethyl-3-((6-methyl-2-p-tolylH-imidazo[1,2-a]pyridin-3-yl)methyl)oxazolidine-2,4-dione (101)

The title compound was prepared according to Method B and the experimentals described for compound 91 from 3-(chloromethyl)-6-methyl-2-p-tolylimidazo[1,2-a]pyridine hydrochlorid and 5,5-dimethyloxazolidine-2,4-dione. m/e$^-$ 364.4 for $C_{21}H_{22}N_3O_3$ (M+H)$^+$; $^1$H-NMR (400 MHz, CDCl$_3$, δ) 8.08 (s, 1H), 7.74 (d, J=8.0 Hz, 2H), 7.56 (d, J=9.1 Hz, 1H), 7.28 (d, J=8.0 Hz, 2H), 7.10 (d, J=9.1 Hz, 1H), 5.14 (s, 2H, D, CH$_2$), 2.40 (s, 3H, D, CH$_3$), 2.35 (s, 3H, D, CH$_3$), 1.48 (s, 6H, D, 2×CH$_3$) ppm.

Example 102

1-methyl-3-((6-methyl-2-p-tolylH-imidazo[1,2-a]pyridin-3-yl)methyl)imidazolidine-2,4-dione (102)

The title compound was prepared according to Method B and the experimentals described for compound 91 from 3-(chloromethyl)-6-methyl-2-p-tolylimidazo[1,2-a]pyridine hydrochlorid and 1-methylimidazolidine-2,4-dione. m/e$^+$ 349.4 for $C_{20}H_{21}N_4O_2$ (M+H)$^+$; $^1$H-NMR (400 MHz, CDCl$_3$, δ) 8.23 (s, 1H), 7.81 (d, J=7.7 Hz, 2H), 7.54 (d, J=9.1 Hz, 1H), 7.28 (d, J=7.7 Hz, 2H), 7.08 (dd, J$_1$=9.1 Hz, J$_2$=1.1, 1H), 5.12 (s, 2H, D, CH$_2$), 3.81 (s, 2H, D, CH$_2$), 2.95 (s, 3H, D, CH$_3$), 2.40 (s, 3H, D, CH$_3$), 2.36 (s, 3H, D, CH$_3$) ppm.

Example 103

1-(6-Methyl-2-p-tolyl-imidazo[1,2-a]pyridin-3-ylmethyl)-1H-pyrimidine-2-thione (103)

The title compound was prepared according to Method B and the experimentals described for compound 91 from 3-(chloromethyl)-6-methyl-2-p-tolylimidazo[1,2-a]pyridine hydrochloride and pyrimidine-2(1H)-thione. m/e$^+$ 367 for $C_{20}H_{19}N_4S$ [M+H]$^+$; $^1$H-NMR (300 MHz, CDCl$_3$) δ 8.54 (d, J=4.8 Hz, 2H), 7.94 (d, J=4.8 Hz, 1H), 7.74 (m, 2H), 7.56 (d, J=9.0 Hz, 1H), 7.27 (dd, J=4.2, 7.8 Hz, 2H), 7.05 (m, 2H), 4.94 (s, 2H), 2.40 (s, 3H), 2.33 (s, 3H) ppm.

Example 104

1-((6-chloro-2-(4-chlorophenyl)H-imidazo[1,2-a]pyridin-3-yl)methyl)pyridin-2(1H)-one (104)

The title compound was prepared according to Method B and the experimentals described for compound 91 from 6-chloro-3-(chloromethyl)-2-(4-chlorophenyl)imidazo[1,2-a]pyridine hydrochloride and pyridin-2(1H)-one or pyridin-2-ol in 71% yield; m/e$^+$ 370.2 (100%), 372.2 (60%), 374.2 (20%) for $C_{19}H_{14}C_{l2}N_3O$ (M+H)$^+$; $^1$H-NMR (400 MHz, CDCl$_3$, δ) 8.54 (d, J=0.733 Hz, 1H), 7.67 (d, J=8.065 Hz, 2H), 7.58 (d, J=9.531 Hz, 1H), 7.48 (d, J=8.431 Hz, 2H), 7.25 (m, 2H), 6.78 (dd, J$_1$=6.598 Hz, J$_2$=1.833 Hz, 1H), 6.54 (d, J=9.164 Hz, 1H), 6.03 (t, 6.965 Hz, 1H), 5.64 (s, 2H, D, CH$_2$) ppm; $^{13}$C-NMR (100 MHz, CDCl$_3$, δ) 162.915, 146.506, 144.193, 140.008, 135.534, 135.109, 132.053, 130.067, 129.566, 127.701, 123.242, 121.817, 121.392, 118.086, 115.986, 107.409, 39.597 ppm. UV 226, 308 nm.

Example 105

1-((2-(4-chlorophenyl)imidazo[1,2-a]pyridin-3-yl)methyl)-4-methylpyrimidin-2(1H)-one (105)

The title compound was prepared according to Method B and the experimentals described for compound 91 from 3-(chloromethyl)-2-(4-chlorophenyl)imidazo[1,2-a]pyridine hydrochloride and 4-methylpyrimidin-2(1H)-one or 4-methylpyrimidin-2-ol. m/e$^+$ 351 for C19H16ClN4O (M+H)$^+$.

Example 106

4-amino-1-((2-(4-chlorophenyl)imidazo[1,2-a]pyridin-3-yl)methyl)pyrimidin-2(1H)-one (106)

The title compound was prepared according to Method B and the experimentals described for compound 91 3-(chloromethyl)-2-(4-chlorophenyl)imidazo[1,2-a]pyridine hydrochloride and 4-methylpyrimidin-2(1H)-one. m/e$^+$ 352 for C18H15ClN5O (M+H)$^+$.

Example 107

1-((6-chloro-2-(4-chlorophenyl)H-imidazo[1,2-a]pyridin-3-yl)methyl)-6-methylpyridin-2(1H)-one (107)

The title compound was prepared according to Method B and the experimentals described for compound 91 from 6-chloro-3-(chloromethyl)-2-(4-chlorophenyl)imidazo[1,2-a]pyridine hydrochloride and 6-methylpyridin-2(1H)-one. m/e$^+$ 384.3 (100%), 386.3 (60%), 387.3 (10%) for $C_{20}H_{16}Cl_2N_3O$ (M+H)$^+$; $^1$H-NMR (400 MHz, CDCl$_3$, δ) 8.85 (d, J=1.466 Hz, 1H), 7.57 (d, J$_1$=8.432 Hz, J$_2$=1.833 Hz, 2H), 7.47 (d, J=8.431 Hz, 2H), 7.18 (m, 2H), 6.57 (d, J=9.164 Hz, 1H), 6.89 (d, J=6.965 Hz, 1H), 5.85 (s, 2H, D, CH$_2$), 1.757 (s, 3H, D, CH$_3$) ppm; UV 242, 310 nm.

Example 108

5-chloro-1-((6-chloro-2-(4-chlorophenyl)H-imidazo[1,2-a]pyridin-3-yl)methyl)pyridin-2(1H)-one (108)

The title compound was prepared according to Method B and the experimentals described for compound 91 from 6-chloro-3-(chloromethyl)-2-(4-chlorophenyl)imidazo[1,2-a]pyridine hydrochloride and 5-chloropyridin-2(1H)-one in 88% yield; m/e$^+$ 404.2 (96%), 406.2 (100%), 408.2 (30%), 407.2 (20%) for $C_{19}H_{13}Cl_3N_3O$ (M+H)$^+$; $^1$H-NMR (400 MHz, CDCl$_3$, δ) 8.44 (d, J=1.1 Hz, 1H), 7.62 (d, J=8.431 Hz, 2H), 7.58 (d, J=9.531 Hz, 1H), 7.48 (m, 2H), 7.21 (m, 2H), 6.74 (d, J=2.932 Hz, 1H), 6.58 (d, J=9.898 Hz, 1H), 5.57 (s, 2H, D, CH$_2$) ppm; $^{13}$C-NMR (100 MHz, CDCl$_3$, δ) 161.323, 146.878, 144.330, 141.130, 135.352, 133.077, 131.773, 130.082, 129.672, 127.906, 123.007, 122.158, 122.037, 118.253, 115.341, 113.779, 39.946 ppm. UV 226, 308 nm.

Example 109

1-((6-chloro-2-(4-chlorophenyl)H-imidazo[1,2-a]pyridin-3-yl)methyl)-3-methylpyridin-2(1H)-one (109)

The title compound was prepared according to Method B and the experimentals described for compound 91 from 6-chloro-3-(chloromethyl)-2-(4-chlorophenyl)imidazo[1,2-a]pyridine hydrochloride and 3-methylpyridin-2(1H)-one in 85% yield; m/e$^+$ 384.3 (100%), 386.3 (60%), 347.3 (15%) for $C_{20}H_{16}Cl_2N_3O$ (M+H)$^+$; $^1$H-NMR (400 MHz, CDCl$_3$, δ) 8.47 (d, J=1.838 Hz, 1H), 7.64 (d, J=8.431 Hz, 2H), 7.55 (t, J=9.531 Hz, 1H), 7.44 (d, J=8.431 Hz, 2H), 7.22 (dd, J$_1$=9.531 Hz, J$_2$=1.833 Hz, 1H), 7.13 (d, J=6.598 Hz, 1H), 6.65 (d, J=6.965 Hz, 1H), 5.93 (t, J=6.599 Hz, 1H), 5.625 (s, 2H, D, CH$_2$), 2.175 (s, 3H, D, CH$_3$) ppm; $^{13}$C-NMR (100 MHz, CDCl$_3$, δ) 163.332, 146.453, 144.163, 137179, 135.041, 132.683, 132.069, 130.514, 130.036, 129.513, 127.602, 123.212, 121.756, 118.063, 116.084, 107.030, 39.968, 17.713 ppm. UV 226, 308 nm.

Example 110

2-((6-chloro-2-(4-chlorophenyl)H-imidazo[1,2-a]pyridin-3-yl)methyl)-6-methylpyridazin-3(2H)-one (110)

The title compound was prepared according to Method B and the experimentals described for compound 91 from 6-chloro-3-(chloromethyl)-2-(4-chlorophenyl)imidazo[1,2-a]pyridine hydrochloride and 6-methylpyridazin-3(2H)-one in 28% yield; m/e$^-$ 385.3 (100%), 387.3 (60%), 386.3 (20%), 388.3 (14%), 389.29 (10%) for $C_{19}H_{15}Cl_2N_4O$ (M+H)$^+$; $^1$H-NMR (400 MHz, CDCl$_3$, δ) 8.78 (d, J$_1$=1.833 Hz, J$_2$=0.733 Hz, 1H), 8.09 (dd, J$_1$=6.965 Hz, J$_2$=2.199 Hz, 2H), 7.54 (dd, J$_1$=9.531 Hz, J$_2$=0.733 Hz, 1H), 7.46 (d, J=8.431 Hz, 2H), 7.20 (dd, J$_1$=9.531 Hz, J$_2$=2.2 Hz, 1H), 7.09 (d, J=9.531 Hz, 1H), 6.95 (d, J=9.531 Hz, 1H), 5.674 (s, 2H, D, CH$_2$), 2.277 (s, 3H, D, CH$_3$) ppm; $^{13}$C-NMR (100 MHz, CDCl$_3$, δ) 160.087, 146.499, 145.611, 143.807, 134.639, 133.775, 132.448, 130.514, 130.431, 128.982, 127.011, 123.712, 121.149, 117.912, 116.676, 43.214, 21.087 ppm. UV 226, 308 nm.

Example 111

3-((6-chloro-2-(4-chlorophenyl)H-imidazo[1,2-a]pyridin-3-yl)methyl)oxazolidin-2-one (111)

The title compound was prepared according to Method B and the experimentals described for compound 91 from 6-chloro-3-(chloromethyl)-2-(4-chlorophenyl)imidazo[1,2-a]pyridine hydrochloride and oxazolidin-2-one. m/e$^+$ 362.3 (100%), 364.3 (65%) for $C_{17}H_{14}Cl_2N_3O_2$ (M+H)$^+$; $^1$H-NMR (400 MHz, CDCl$_3$, δ) 8.44 (d, J=1.1 Hz, 1H), 7.64 (dd, J$_1$=8.431 Hz, J$_2$=1.832 Hz, 2H), 7.59 (d, J=9.531 Hz, 1H), 7.446 (dd, J$_1$=6.598 Hz, J$_2$=1.833 Hz, 2H), 7.26 (dd, J$_1$=9.531 Hz, J$_2$=1.833 Hz, 1H), 4.933 (s, 2H, D, CH$_2$), 4.27 (t, J=7.698 Hz, 2H), 3.29 (t, J=8.065 Hz, 2H) ppm.

Example 112

1-((6-chloro-2-(4-chlorophenyl)H-imidazo[1,2-a]pyridin-3-yl)methyl)pyrrolidin-2-one (112)

The title compound was prepared according to Method B and the experimentals described for compound 91 from 6-chloro-3-(chloromethyl)-2-(4-chlorophenyl)imidazo[1,2-a]pyridine hydrochloride and pyrrolidin-2-one. m/e$^+$ 360.3 (100%), 362.3 (65%) for C$_{18}$H$_{16}$Cl$_2$N$_3$O (M+H)$^+$; $^1$H-NMR (400 MHz, CDCl$_3$, δ) 8.48 (d, J=1.1 Hz, 1H), 7.66 (d, J$_1$=8.431 Hz, 2H), 7.57 (d, J=9.531 Hz, 1H), 7.45 (d J$_1$=8.431 Hz, 2H), 7.21 (dd, J$_1$=9.531 Hz, J$_2$=1.833 Hz, 1H), 4.928 (s, 2H, D, CH$_2$), 3.09 (t, J=6.965 Hz, 2H), 2.43 (t, J=8.065 Hz, 2H), 1.92 (m, 2H) ppm.

Example 113

1-[6-Chloro-2-(4-chloro-phenyl)-imidazo[1,2-a]pyridin-3-ylmethyl]-azetidin-2-one (113)

The title compound was prepared according to Method B and the experimentals described for compound 91 from 6-chloro-3-(chloromethyl)-2-(4-chlorophenyl)imidazo[1,2-a]pyridine hydrochloride and azetidin-2-one. m/e$^+$ 346 for C$_{17}$H$_{14}$Cl$_2$N$_3$O$_4$ [M+H]$^+$; $^1$H-NMR (400 MHz, CDCl$_3$) δ 8.44 (s, 1H), 7.65 (d, J=8.4 Hz, 2H), 7.59 (d, J=9.5 Hz, 1H), 7.46 (d, J=8.4 Hz, 2H), 7.25 (m, 1H), 4.79 (s, 2H), 3.18 (t, J=4.0 Hz, 2H), 3.00 (t, J=4.0 Hz, 2H) ppm; $^{13}$C-NMR (100 MHz, CDCl$_3$, δ) 168.269, 145.293, 143.807, 134.791, 132.129, 129.877, 129.324, 127.269, 122.325, 121.771, 118.185, 115.333, 39.400, 37.512, 35.449 ppm.

Example 114

1-((6-chloro-2-(4-chlorophenyl)H-imidazo[1,2-a]pyridin-3-yl)methyl)-4-methoxy-1H-pyrrol-2(5H)-one (114)

The title compound was prepared according to Method B and the experimentals described for compound 91 from 6-chloro-3-(chloromethyl)-2-(4-chlorophenyl)imidazo[1,2-a]pyridine hydrochloride and 4-methoxy-1H-pyrrol-2(5H)-one. m/e$^+$ 388.3 (100%), 390.3 (65%) for C$_{19}$H$_{16}$Cl$_2$N$_3$O$_2$ (M+H)$^+$; $^1$H-NMR (400 MHz, CDCl$_3$, δ) 8.58 (d, J=1.1 Hz, 1H), 7.66 (d, J=8.431 Hz, 2H), 7.56 (d, J=9.531 Hz, 1H), 7.46 (d, J=8.431 Hz, 2H), 7.22 (dd, J$_1$=9.531 Hz, J$_2$=1.466 Hz, 1H), 5.082 (s, 1H), 5.038 (s, 2H, D, CH$_2$), 3.742 (s, 3H, D, CH$_3$), 3.562 (s, 2H, D, CH$_2$) ppm.

Example 115

1-(6-Chloro-2-phenyl-imidazo[1,2-a]pyridin-3-ylmethyl)-azetidin-2-one (115)

The title compound was prepared according to Method B and the experimentals described for compound 91 from 6-chloro-3-(chloromethyl)-2-phenylimidazo[1,2-a]pyridine hydrochloride and azetidin-2-one. m/e$^+$ 312 for C$_{17}$H$_{15}$ClN$_3$O [M+H]$^+$; $^1$H-NMR (400 MHz, CDCl$_3$) δ 8.45 (d, J=1.4 Hz, 1H), 7.72 (d, J=1.4, 3.3 Hz, 2H), 7.62 (d, J=9.5 Hz, 1H), 7.49 (m, 2H), 7.25 (dd, J=2.5, 9.5 Hz, 2H), 4.81 (t, J=4.0 Hz, 2H), 3.20 (t, J=4.0 Hz, 2H), 3.00 (t, J=4.0 Hz, 2H) ppm.

Example 116

1-(6,8-Dichloro-2-p-tolyl-imidazo[1,2-a]pyridin-3-ylmethyl)-pyrrolidin-2-one (116)

The title compound was prepared according to Method B and the experimentals described for compound 91 from 6,8-dichloro-3-(chloromethyl)-2-p-tolylimidazo[1,2-a]pyridine hydrochloride and pyrrolidin-2-one. m/e$^+$ 374 for C$_{19}$H$_{18}$Cl$_2$N$_3$O [M+H]$^+$; $^1$H-NMR (300 MHz, CDCl$_3$) δ 8.49 (d, J=1.5 Hz, 1H), 7.63 (d, J=8.1 Hz, 2H), 7.33 (m, 3H), 4.93 (s, 2H), 3.11 (t, J=6.9 Hz, 2H), 2.43 (m, 5H), 1.92 (m, 2H) ppm.

Example 117

2-(6,8-Dichloro-2-p-tolyl-imidazo[1,2-a]pyridin-3-ylmethyl)-6-methyl-2H-pyridazin-3-one (117)

The title compound was prepared according to Method B and the experimentals described for compound 91 from 6,8-dichloro-3-(chloromethyl)-2-p-tolylimidazo[1,2-a]pyridine hydrochloride and 6-methylpyridazin-3(2H)-one. m/e$^+$ 399 for C$_{20}$H$_{17}$Cl$_2$N$_4$O [M+H]$^+$; $^1$H-NMR (300 MHz, CDCl$_3$) δ 8.72 (d, J=1.8 Hz, 1H), 8.01 (d, J=8.1 Hz, 2H), 7.30 (m, 3H), 7.10 (d, J=9.3 Hz, 1H), 6.96 (d, J=9.3 Hz, 1H), 5.70 (s, 2H), 2.43 (s, 3H), 2.29 (s, 3H) ppm.

Example 118

2-((2-(4-chlorophenyl)imidazo[1,2-a]pyridin-3-yl)methyl)-1H-indazol-3(2H)-one (118)

The title compound was prepared according to Method B and the experimentals described for compound 91 from 3-(chloromethyl)-2-(4-chlorophenyl)imidazo[1,2-a]pyridine hydrochloride and 1H-indazol-3(2H)-one. M/e$^+$ 375 for C$_{21}$H$_{16}$ClN$_4$O (M+H)$^+$; $^1$H-NMR (400 MHz, CDCl$_3$) δ 11.11 (bs, 1H), 8.16 (d, J=6.9 Hz, 1H), 8.01 (d, J=7.7 Hz, 1H), 7.64 (m, 1H), 7.55 (d, J=8.4 Hz, 2H), 7.50 (d, J=8.4 Hz, 1H), 7.30 (t, J=7.3 Hz, 1H), 7.15 (d, J=8.4 Hz, 2H), 6.75 (t, J=7.7 Hz, 1H), 6.60 (t, J=7.7 Hz, 1H), 6.27 (d, J=8.4 Hz, 1H), 5.34 (s, 2H) ppm.

Example 119

2-((2-(4-chlorophenyl)imidazo[1,2-a]pyridin-3-yl)methyl)-[1,2,4]triazolo[4,3-a]pyridin-3(2H)-one (119)

The title compound was prepared according to Method B and the experimentals described for compound 91 from 3-(chloromethyl)-2-(4-chlorophenyl)imidazo[1,2-a]pyridine hydrochloride and [1,2,4]triazolo[4,3-a]pyridin-3(2H)-one. M/e$^+$ 376 for C$_{20}$H$_{15}$ClN$_5$O (M+H)$^+$; $^1$H-NMR (400 MHz, CDCl$_3$) δ 8.68 (d, J=6.9 Hz, 1H), 8.18 (d, J=8.4 Hz, 2H), 7.80 (d, J=7.3 Hz, 1H), 7.63 (d, J=9.1 Hz, 1H), 7.50 (d, J=8.4 Hz, 2H), 7.25 (m, 1H), 7.09 (dd, J=4.0, 2.9 Hz, 2H), 6.89 (m, 1H), 6.52 (m, 1H), 5.54 (s, 2H) ppm.

Example 120

1-((2-(4-chlorophenyl)-6-fluoroimidazo[1,2-a]pyridin-3-yl)methyl)-6-methylpyridin-2(1H)-one (120)

The title compound was prepared according to Method B and the experimentals described for compound 91 from 3-(chloromethyl)-2-(4-chlorophenyl)-6-fluoroimidazo[1,2-a]pyridine hydrochloride and 6-methylpyridin-2(1H)-one. $^1$H-NMR (CDCl$_3$, 400 MHz, δ) 8.75 (dd, J=2.2, 4.6 Hz, 1H), 7.55 (m, 3H), 7.45 (m, 2H), 7.16 (m, 2H), 6.55 (d, J=9.1 Hz, 1H), 5.87 (d, J=6.8 Hz, 1H), 5.84 (s, 2H), 1.74 (s, 3H) ppm; m/e 368 (M+H)$^+$

Example 121

1-((2-(4-chlorophenyl)-6-fluoroimidazo[1,2-a]pyridin-3-yl)methyl)-3-methylpyridin-2(1H)-one (121)

The title compound was prepared according to Method B and the experimentals described for compound 91 from 3-(chloromethyl)-2-(4-chlorophenyl)-6-fluoroimidazo[1,2-a]pyridine hydrochloride and 3-methylpyridin-2(1H)-one. $^1$H-NMR (CDCl$_3$, 400 MHz, δ) 8.43 (dd, J=2.4, 4.1 Hz, 1H), 7.64 (d, J=8.5 Hz, 2H), 7.58 (dd, J=5.0, 9.6 Hz, 1H), 7.45 (d, J=8.6 Hz, 2H), 7.17 (m, 1 h), 7.13 (m, 1H), 6.65 (dd, J=1.4, 6.9 Hz, 1H), 5.93 (t, J=6.8 Hz, 1H), 5.63 (s, 2H), 2.16 (s, 3H) ppm; m/e368 (M+H)$^+$

Example 122

1-((2-(4-chlorophenyl)-6-fluoroimidazo[1,2-a]pyridin-3-yl)methyl)pyridin-2(1H)-one (122)

The title compound was prepared according to Method B and the experimentals described for compound 91 from 3-(chloromethyl)-2-(4-chlorophenyl)-6-fluoroimidazo[1,2-a]pyridine hydrochloride and pyridin-2-ol. $^1$H-NMR (CDCl$_3$, 400 MHz, δ) 8.45 (dd, J=2.4, 4.0 Hz, 1H), 7.65 (d, J=8.4 Hz, 2H), 7.58 (dd, J=5.1, 9.8 Hz, 1H), 7.46 (d, J=8.4 Hz, 1H), 7.24 (m, 1H), 7.16 (m, 1H), 6.76 (dd, J=1.9, 6.9 Hz, 1H), 6.59 (d, J=9.1 Hz, 1H), 6.00 (m, 1H), 5.62 (s, 2H) ppm; me/354 (M+H)$^+$

Example 123

1-((2-(4-chlorophenyl)imidazo[1,2-a]pyridin-3-yl)methyl)pyrimidine-2,4(1H,3H)-dione (123)

The title compound was prepared according to Method B and the experimentals described for compound 91 from 3-(chloromethyl)-2-(4-chlorophenyl)imidazo[1,2-a]pyridine hydrochloride and pyrimidine-2,4(1H,3H)-dione. M/e$^+$ 353 for C$_{18}$H$_{14}$ClN$_4$O$_2$ (M+H)$^+$; $^1$H-NMR (400 MHz, CDCl$_3$) δ 8.33 (d, J=5.8 Hz, 1H), 8.10 (s, 1H), 7.81 (d, J=8.4 Hz, 1H), 7.63 (d, J=8.4 Hz, 2H), 7.51 (d, J=8.4 Hz, 2H), 7.39 (td, J=6.9, 1.1 Hz, 1H), 7.00 (td, J=6.9, 1.1 Hz, 1H), 6.66 (d, J=8.0 Hz, 1H), 5.58 (d, J=8.0 Hz, 1H), 5.45 (s, 2H) ppm.

Example 124

4-((2-(4-chlorophenyl)imidazo[1,2-a]pyridin-3-yl)methyl)-2H-benzo[b][1,4]oxazin-3(4H)-one (124)

The title compound was prepared according to Method B and the experimentals described for compound 92 from 3-(chloromethyl)-2-(4-chlorophenyl)imidazo[1,2-a]pyridine hydrochloride and 2H-benzo[b][1,4]oxazin-3(4H)-one. M/e$^+$ 390 for C$_{22}$H$_{17}$ClN$_3$O$_2$ (M+H)$^+$; $^1$H-NMR (400 MHz, CDCl$_3$) δ 8.32 (d, J=6.9 Hz, 1H), 7.61 (d, J=8.4 Hz, 2H), 7.53 (m, 3H), 7.19 (ddd, J=9.1, 6.9, 1,1 Hz, 1H), 6.82 (m, 3H), 6.48 (m, 1H), 6.26 (d, J=7.7 Hz, 1H), 5.68 (s, 2H), 4.60 (s, 2H) ppm.

Example 125

1-((2-(4-chlorophenyl)imidazo[1,2-a]pyridin-3-yl)methyl)-3-methylpyrimidine-2,4(1H,3H)-dione (125)

The title compound was prepared according to Method B and the experimentals described for compound 92 from 3-(chloromethyl)-2-(4-chlorophenyl)imidazo[1,2-a]pyridine hydrochloride and 3-methylpyrimidine-2,4(1H,3H)-dione. M/e$^+$ 367 for C$_{19}$H$_{16}$ClN$_4$O$_2$ (M+H)$^+$; $^1$H-NMR (400 MHz, CDCl$_3$) δ 8.22 (d, J=5.8 Hz, 1H), 7.66 (d, J=8.4 Hz, 2H), 7.45 (d, J=8.4 Hz, 2H), 7.30 (m, 1H), 6.91 (t, J=6.6 Hz, 1H), 6.63 (d, J=8.0 Hz, 1H), 5.56 (d, J=8.0 Hz, 1H), 5.45 (s, 2H), 5.26 (d, J=0.7 Hz, 1H), 3.34 (s, 3H) ppm.

Example 126

Ethyl 1-((2-(4-chlorophenyl)imidazo[1,2-a]pyridin-3-yl)methyl)-2,4-dioxo-1,2,3,4-tetrahydropyrimidine-5-carboxylate (126)

The title compound was prepared according to Method B and the experimentals described for compound 92 from 3-(chloromethyl)-2-(4-chlorophenyl)imidazo[1,2-a]pyridine hydrochloride and ethyl 2,4-dioxo-1,2,3,4-tetrahydropyrimidine-5-carboxylate. M/e$^+$ 425 for C$_{21}$H$_{18}$ClN$_4$O$_4$ (M+H)$^+$; $^1$H-NMR (400 MHz, CDCl$_3$) δ 9.72 (s, 1H), 8.32 (d, J=6.9 Hz, 1H), 7.67 (m, 4H), 7.48 (d, J=8.4 Hz, 2H), 7.31 (t, J=7.3 Hz, 1H), 6.93 (t, J=6.96 Hz, 1H), 5.49 (s, 2H), 4.10 (q, J=6.9 Hz, 2H), 1.16 (t, J=6.9 Hz, 3H) ppm.

Example 127

1-((2-(4-chlorophenyl)imidazo[1,2-a]pyridin-3-yl)methyl)-5-fluoropyrimidine-2,4(1H,3H)-dione (127)

The title compound was prepared according to Method B and the experimentals described for compound 92 from 3-(chloromethyl)-2-(4-chlorophenyl)imidazo[1,2-a]pyridine hydrochloride and 5-fluoropyrimidine-2,4(1H,3H)-dione. M/e$^+$ 371 for C$_{18}$H$_{13}$ClFN$_4$O$_2$ (M+H)$^+$; $^1$H-NMR (400 MHz, CDCl$_3$) δ 8.22 (d, J=6.9 Hz, 1H), 7.71 (d, J=8.8 Hz, 1H), 7.67 (d, J=8.4 Hz, 2H), 7.52 (d, J=8.4 Hz, 2H), 7.36 (m, 1H), 6.96 (m, 1H), 6.69 (d, J=5.5 Hz, 1H), 5.45 (s, 2H) ppm.

Example 128

6-chloro-1-((2-(4-chlorophenyl)imidazo[1,2-a]pyridin-3-yl)methyl)pyrimidine-2,4(1H,3H)-dione (128)

The title compound was prepared according to Method B and the experimentals described for compound 92 from 3-(chloromethyl)-2-(4-chlorophenyl)imidazo[1,2-a]pyridine hydrochloride and 6-chloropyrimidine-2,4(1H,3H)-dione. M/e$^+$ 387 for C$_{18}$H$_{13}$Cl$_2$N$_4$O$_2$ (M+H)$^+$; $^1$H-NMR (400 MHz, CDCl₃) δ 9.35 (bs, 1H), 8.44 (d, J=6.23 Hz, 1H), 7.66 (d, J=9.1 Hz, 1H), 7.55 (d, J=8.4 Hz, 2H), 7.45 (d, J=8.4 Hz, 2H), 7.29 (m, 2H), 6.90 (t, J=6.9 Hz, 1H), 5.74 (d, J=8.0 Hz, 2H) ppm.

Example 129

3-Methylsulfanyl-4-(6-methyl-2-p-tolyl-imidazo[1,2-a]pyridin-3-ylmethyl)-4H-[1,2,4]thiadiazole-5-thione (129)

The title compound was prepared according to Method A and the experimentals described for compound 92 from 3-(chloromethyl)-6-methyl-2-p-tolylimidazo[1,2-a]pyridine hydrochloride and 3-(methylthio)-1,2,4-thiadiazole-5(4H)-thione. m/e⁺ 399 for $C_{19}H_{19}N_4S_3$ [M+H]⁺; ¹H-NMR (400 MHz, CDCl₃) δ 7.96 (s, 1H), 7.67 (d, J=7.7 Hz, 2H), 7.57 (d, J=9.1 Hz, 1H), 7.27 (d, J=8.0 Hz, 2H), 7.11 (d, J=9.1 Hz, 1H), 5.04 (s, 2H), 2.67 (s, 3H), 2.39 (s, 3H), 2.36 (s, 3H) ppm; ¹³C-NMR (100 MHz, CDCl₃, δ) 186.346, 171.423, 145.801, 144.701, 138.203, 130.870, 129.680, 128.573, 128.300, 122.825, 121.733, 117.047, 111.982, 29.739, 21.444, 18.577, 14.968, ppm.

Example 130

4,5-Dimethyl-3-(6-methyl-2-p-tolyl-imidazo[1,2-a]pyridin-3-ylmethyl)-3H-thiazole-2-thione (130)

The title compound was prepared according to Method A and the experimentals described for compound 92 from 3-(chloromethyl)-6-methyl-2-p-tolylimidazo[1,2-a]pyridine hydrochloride and 4,5-dimethylthiazole-2(3H)-thione. m/e⁺ 380 for $C_{21}H_{22}N_3S_2$ [M+H]⁺; ¹H-NMR (400 MHz, CDCl₃) δ 7.96 (s, 1H), 7.65 (d, J=8.0 Hz, 2H), 7.55 (d, J=8.8 Hz, 1H), 7.26 (d, J=8.0 Hz, 2H), 7.08 (dd, J=1.4, 9.1 Hz, 1H), 4.83 (s, 2H), 2.39 (s, 3H), 2.35 (s, 3H), 2.29 (s, 3H), 2.28 (s, 3H) ppm; ¹³C-NMR (100 MHz, CDCl₃, δ) 156.250, 149.085, 145.149, 144.391, 137.642, 131.159, 129.347, 128.748, 128.217, 127.929, 122.090, 121.794, 116.828, 113.612, 30.301, 21.308, 18.449, 14.688, 11.374 ppm.

Example 131

3-((6-Methyl-2-p-tolylH-imidazo[1,2-a]pyridin-3-yl)methyl)thiazole-2(3H)-thione (131)

The title compound was prepared according to Method A and the experimentals described for compound 92 from 3-(chloromethyl)-6-methyl-2-p-tolylimidazo[1,2-a]pyridine hydrochloride and thiazole-2(3H)-thione. m/e⁺ 352 for $C_{19}H_{18}N_3S_2$ [M+H]⁺; ¹H-NMR (400 MHz, CDCl₃) δ 7.96 (s, 1H), 7.73 (d, J=3.3 Hz, 1H), 7.68 (d, J=8.0 Hz, 2H), 7.56 (d, J=9.1 Hz, 1H), 7.27 (m, 3H), 7.08 (dd, J=1.1, 9.1 Hz, 1H), 4.97 (s, 2H), 2.39 (s, 3H), 2.34 (s, 3H) ppm; ¹³C-NMR (100 MHz, CDCl₃, δ) 162.749, 145.233, 144.444, 142.927, 137.779, 131.022, 129.430, 128.164, 128.096, 122.310, 121.643, 120.225, 116.850, 112.983, 29.808, 21.300, 18.426 ppm.

Example 132

1-((2-(4-chlorophenyl)imidazo[1,2-a]pyridin-3-yl)methyl)-4-(ethylamino)pyrimidin-2(1H)-one (132)

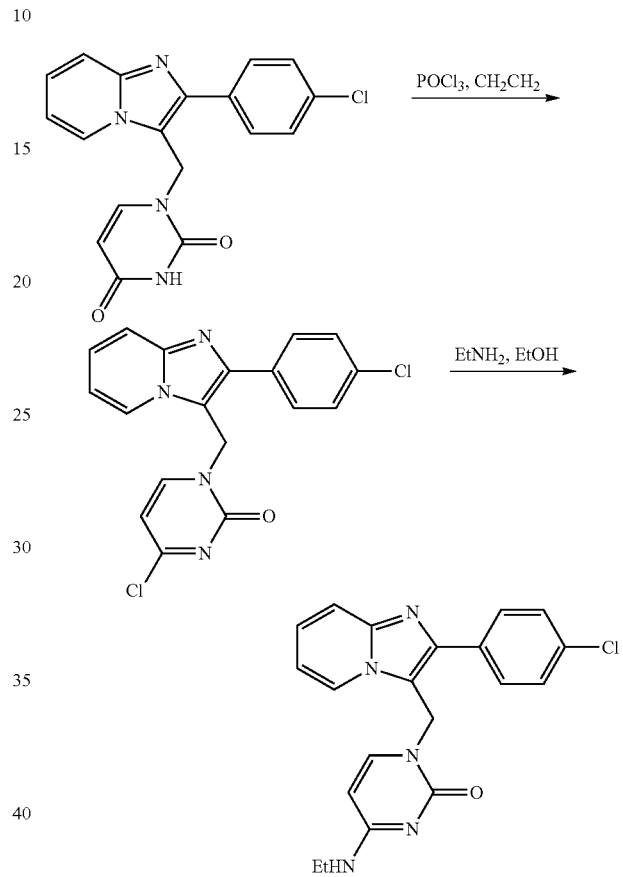

Step 1: To a solution of 1-((2-(4-chlorophenyl)imidazo[1,2-a]pyridin-3-yl)methyl)pyrimidine-2,4(1H,3H)-dione (500 mg, 1.42 mmol) in CH₂Cl₂ (10 mL) at 0° C. was added POCl₃ (0.3 ml). The mixture was refluxed for 4 hours and cooled to room temperature and poured onto ice-water (10 ml). The mixture was neutralized with aqueous ammonia hydroxide to pH~7-8 and extracted with CH₂Cl₂ (3×20 mL). The combined organic solution was washed with water, sat. NaHCO₃ and brine, dried and evaporated. The crude product was purified by silica gel chromatography. m/e⁺ 372 for C18H13N4O [M+H]⁺.

Step 2: A mixture of 4-chloro-1-((2-(4-chlorophenyl)imidazo[1,2-a]pyridin-3-yl)methyl)pyrimidin-2(1H)-one (50 mg, 0.13 mmol) and ethylamine (30 μl) in ethanol (2 ml) in a sealed tube was heated at 70° C. for 4 hours. Excess reagent was evaporated under reduced pressure. Crude product was dissolved in CH₂Cl₂ (10 mL) was washed with water, sat. NaHCO₃ and brine, dried and evaporated. The crude product was purified by silica gel chromatography. M/e⁺ 380 for $C_{20}H_{19}ClN_5O$ (M+H)⁺; ¹H-NMR (400 MHz, CDCl₃) δ 8.42 (d, J=6.6 Hz, 1H), 7.68 (d, J=8.4 Hz, 2H), 7.64 (d, J=9.1 Hz, 1H), 7.47 (d, J=8.4 Hz, 2H), 7.29 (d, J=7.7 Hz, 1H), 6.87 (t, J=6.9 Hz, 1H), 6.65 (d, J=7.3 Hz, 1H), 5.37 (d, J=7.3 Hz, 2H), 4.97 (s, 1H), 3.51 (m, 2H), 3.18 (s, 1H), 1.18 (t, J=7.3 Hz, 3H) ppm.

Example 133

1-((2-(4-chlorophenyl)imidazo[1,2-a]pyridin-3-yl) methyl)-4-(methylamino)pyrimidin-2(1H)-one (133)

The title compound was prepared according to the experimental for compound 132 from 4-chloro-1-((2-(4-chlorophenyl)imidazo[1,2-a]pyridin-3-yl)methyl)pyrimidin-2(1H)-one and methylamine. M/e⁻ 366 for $C_{19}H_{17}ClN_5O$ (M+H)⁺; ¹H-NMR (400 MHz, CDCl₃) δ 8.42 (d, J=6.6 Hz, 1H), 7.68 (d, J=8.4 Hz, 2H), 7.62 (m, 1H), 7.46 (d, 8.4 Hz, 2H), 7.28 (d, J=7.7 Hz, 1H), 6.86 (t, J=6.9 Hz, 1H), 6.64 (d, J=7.3 Hz, 1H), 5.51 (s, 2H), 5.41 (d, J=7.3 Hz, 1H), 5.24 (bs, 1H), 2.98 (s, 3H) ppm.

Example 134

1-((2-(4-chlorophenyl)imidazo[1,2-a]pyridin-3-yl) methyl)-4-(2-(dimethylamino)ethylamino)pyrimidin-2(1H)-one (134)

The title compound was prepared according to the experimental for compound 132 from 4-chloro-1-((2-(4-chlorophenyl)imidazo[1,2-a]pyridin-3-yl)methyl)pyrimidin-2(1H)-one and $N^1,N^1$-dimethylethane-1,2-diamine. M/e⁺ 423 for $C_{22}H_{24}ClN_6O$ (M+H)⁺; ¹H-NMR (400 MHz, CDCl₃) δ 8.42 (d, J=6.9 Hz, 1H), 7.68 (dd, J=8.4, 2.2 Hz, 2H), 7.64 (dd, J=9.1, 1.1 Hz, 1H), 7.47 (dd, J=8.4, 2.2 Hz, 2H), 7.28 (d, J=7.7 Hz, 1H), 6.86 (t, J=6.6 Hz, 1H), 6.65 (dd, J=7.3, 2.2 Hz, 1H), 6.49 (bs, 1H), 5.54 (d, J=1.8 Hz, 2H), 5.46 (dd, J=7.3, 1.8 Hz, 1H), 3.59 (m, 2H), 2.61 (m, 2H), 2.16 (s, 6H) ppm.

Example 135

1-((2-(4-chlorophenyl)imidazo[1,2-a]pyridin-3-yl) methyl)-4-(dimethylamino)pyrimidin-2(1H)-one (135)

The title compound was prepared according to the experimental for compound 132 from 4-chloro-1-((2-(4-chlorophenyl)imidazo[1,2-a]pyridin-3-yl)methyl)pyrimidin-2(1H)-one and dimethylamine. M/e⁺ 380 for $C_{20}H_{19}ClN_5O$ (M+H)⁺; ¹H-NMR (400 MHz, CDCl₃) δ 8.44 (d, J=6.9 Hz, 1H), 7.67 (d, J=8.4 Hz, 2H), 7.63 (d, J=8.8 Hz, 1H), 7.47 (d, J=8.4 Hz, 2H), 7.28 (d, J=6.9 Hz, 1H), 6.86 (t, J=6.6 Hz, 1H), 6.75 (d, J=7.7 Hz, 1H), 5.63 (d, J=7.7 Hz, 1H), 5.56 (s, 2H), 3.18 (s, 3H), 2.96 (s, 3H) ppm.

Example 136

1-((2-(4-chlorophenyl)imidazo[1,2-a]pyridin-3-yl) methyl)-4-(pyrrolidin-1-yl)pyrimidin-2(1H)-one (136)

The title compound was prepared according to the experimental for compound 132 from 4-chloro-1-((2-(4-chlorophenyl)imidazo[1,2-a]pyridin-3-yl)methyl)pyrimidin-2(1H)-one and pyrrolidine. M/e⁺ 406 for $C_{22}H_{21}ClN_5O$ (M+H)⁺; ¹H-NMR (400 MHz, CDCl₃) δ 8.44 (d, J=6.6 Hz, 1H), 7.69 (d, J=8.4 Hz, 2H), 7.63 (d, J=8.8 Hz, 1H), 7.47 (d, J=8.4 Hz, 2H), 7.28 (m, 1H), 6.86 (td, J=6.9, 1.1 Hz, 1H), 6.73 (d, J=7.3 Hz, 1H), 5.57 (s, 2H), 5.49 (d, J=7.7 Hz, 1H), 3.65 (t, J=6.6 Hz, 2H), 3.28 (t, J=6.6 Hz, 2H), 1.90 (m, 4H) ppm.

Example 137

1-((2-(4-chlorophenyl)imidazo[1,2-a]pyridin-3-yl) methyl)-4-ethoxypyrimidin-2(1H)-one (137)

The title compound was prepared according to the experimental for compound 132 from 4-chloro-1-((2-(4-chlorophenyl)imidazo[1,2-a]pyridin-3-yl)methyl)pyrimidin-2(1H)-one and NaOEt in EtOH. M/e⁺ 381 for $C_{20}H_{18}ClN_4O_2$ (M+H)⁺; ¹H-NMR (400 MHz, CDCl₃) δ 8.36 (d, J=7.0 Hz, 1H), 8.17 (s, 1H), 7.66 (d, J=8.4 Hz, 2H), 7.48 (d, J=8.4 Hz, 2H), 7.30 (m, 1H), 6.92 (m, 1H), 6.89 (d, J=6.9 Hz, 1H), 5.71 (d, J=6.9 Hz, 1H), 5.60 (s, 2H), 4.40 (q, J=6.9 Hz, 2H), 1.32 (t, J=6.9 Hz, 3H) ppm.

Example 138

1-((2-(4-chlorophenyl)imidazo[1,2-a]pyridin-3-yl) methyl)-4-(1H-1,2,4-triazol-1-yl)pyrimidin-2(1H)-one (138)

The title compound was prepared according to the experimental for compound 132 from 4-chloro-1-((2-(4-chlorophenyl)imidazo[1,2-a]pyridin-3-yl)methyl)pyrimidin-2(1H)-one and 1H-1,2,4-triazole in DMF. M/e⁺ 404 for $C_{20}H_{15}ClN_7O$ (M+H)⁺; ¹H-NMR (400 MHz, CDCl₃) δ 9.24 (d, J=1.8 Hz, 1H), 8.33 (d, J=6.6 Hz, 1H), 8.18 (d, J=1.8 Hz, 2H), 8.06 (d, J=1.8 Hz, 1H), 7.67 (m, 1H), 7.66 (dd, J=8.4, 1.8 Hz, 1H), 7.49 (dd, J=8.4, 1.8 Hz, 2H), 7.34 (m, 1H), 6.95 (t, J=6.6 Hz, 1H), 6.90 (dd, J=7.3, 1.8 Hz, 1H), 5.27 (s, 2H) ppm.

General Procedures for Formula IV, Method A

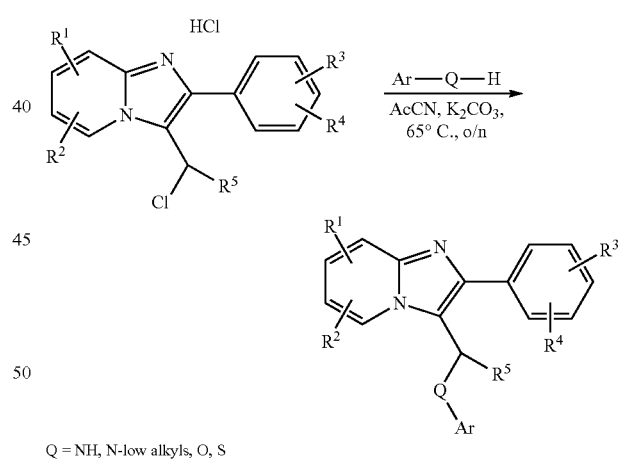

Q = NH, N-low alkyls, O, S

A mixture of 3-(chloromethyl)-imidazo[1,2-a]pyridine HCl salt (0.20 mmol), hetereoaromatic amines or ArQH (Q=O or S) (0.42 mmol, 2.0 eq) in AcCN (1-2 ml) and K₂CO₃ (4 eq) was heated at 65° C. overnight. The mixture was treated with sat. NaHCO₃ (5 ml), extracted with CH₂Cl₂ (10 ml). The organic solution was dried with Na₂SO₄, evaporated under vacuum. The crude product was purified by silica gel column chromatography (12 g silica gel RediSep column, eluted first with 10% ethyl acetate in hexane, then 20% acetone in hexane to afford a white solid. The product shows up as violet spot on TLC plate under UV light. For larger scale reaction (>1 g), the corresponding HCl salt can be obtained by the following simplified work up procedures: After the reaction was complete as judged by LC-mass analysis, the mixture was cooled down to room temperature and the white solid was collected by filtration. Then the solid was suspended in 30-40 ml of EtOH (for 1 gram os starting material) and stirred at 50° C. for a few hours. After being cooled by ice water, the white solid was collected by filtration and rinsed with cool ethanol. The product was dried under reduced pressure.

Example 139

N-((6-methyl-2-p-tolylH-imidazo[1,2-a]pyridin-3-yl)methyl)pyrimidin-2-amine (139)

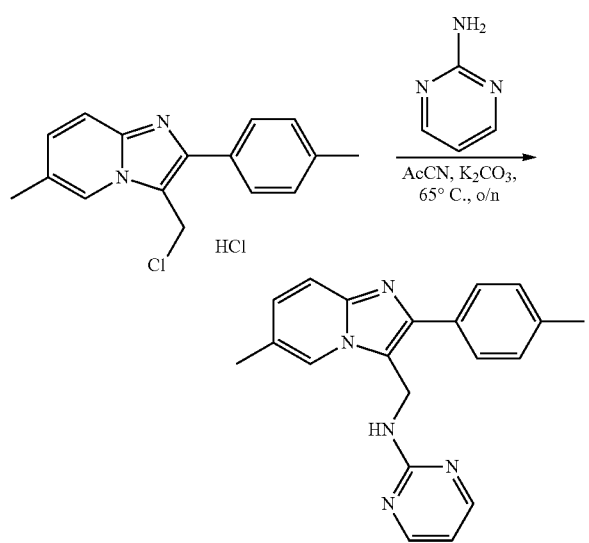

A mixture of 3-(chloromethyl)-6-methyl-2-p-tolylimidazo[1,2-a]pyridine hydrochloride (0.20 mmol), pyrimidin-2-amine (0.42 mmol, 2.0 eq) in AcCN (2 ml) and $K_2CO_3$ (4 eq) was heated at 65° C. overnight. The mixture was treated with sat. $NaHCO_3$ (5 ml), extracted with $CH_2Cl_2$ (10 ml). The organic solution was dried with $Na_2SO_4$, evaporated under vacuum. The crude product was purified by silica gel column chromatography (12 g silica gel RediSep column, eluted first with 10% ethyl acetate in hexane, then 20% acetone in hexane to afford a white solid. The product shows up as violet spot on TLC plate under UV light. m/e$^+$ 330.5 for $C_{20}H_{20}N_5$ (M+H)$^+$; $^1$H-NMR (400 MHz, CDCl$_3$, δ) 8.05 (broad, 1H), 7.902 (s, 1H), 7.66 (d, J=8.065 Hz, 2H), 7.53 (d, J=9.164 Hz, 1H), 7.23 (d, J=7.698 Hz, 2H), 7.03 (dd, $J_1$=9.164 Hz, $J_2$=1.466 Hz, 1H), 6.47 (t, J=5.132 Hz, 1H), 6.32 (t, J=4.399 Hz, 1H, D, NH), 5.00 (d, J=4.765 Hz, 2H, D, CH$_2$). 2.383 (s, 3H, D, CH$_3$), 2.263 (s, 3H, D, CH$_3$) ppm; $^{13}$C-NMR (100 MHz, CDCl$_3$, δ) 162.347 (C=NH, D, Pyrimidine), 158.100 (2 C=N, Pyrimidine), 144.499 (Tolyl C=N, imidazopyridine), 144.375 (N—C—N, imidazopyridine) 137.869, 131.500, 129.612, 128.452, 128.103, 122.188, 122.097, 116.956, 116.304, 111.307 (CH, D, pyrimidine), 35.707 (CH$_2$), 21.520 (CH$_3$), 18.600 (CH$_3$) ppm.

Example 140

N-((6-methyl-2-p-tolylH-imidazo[1,2-a]pyridin-3-yl)methyl)pyridin-2-amine (140)

The title compound was prepared according to Method A and the experimentals described for compound 139 from 3-(chloromethyl)-6-methyl-2-p-tolylimidazo[1,2-a]pyridine hydrochloride and pyridin-2-amine. m/e$^+$ 329.4 for $C_{21}H_{21}N_4$ (M+H)$^+$; $^1$H-NMR (400 MHz, CDCl$_3$, δ); 0.8.19 (dd, J=4.032 Hz, $J_2$=0.733 Hz, 1H), 7.926 (s, 1H), 7.66 (d, J=8.065 Hz, 2H), 7.53 (d, J=9.164 Hz, 1H), 7.23 (d, J=8.065 Hz, 2H), 7.06 (dd, $J_1$=9.164 Hz, $J_2$=1.466 Hz, 1H), 6.67 (d, J=6.232 Hz, $J_2$=5.132 Hz, 1H), 6.47 (d, J=8.431 Hz, 1H), 4.95 (d, J=4.766 Hz, 2H, D, CH$_2$), 4.56 (t, 1H, D, J=4.398 Hz, 1H, D, NH), 2.385 (s, 3H, D, CH$_3$), 2.295 (s, 3H, D, CH$_3$) ppm; $^{13}$C-NMR (100 MHz, CDCl$_3$, δ) 158.631, 148.174, 144.466, 144.262, 137.627, 137.551, 131.379, 129.506, 128.209, 127.997, 122.082, 116.744, 116.463, 113.582, 108.645, 35.980, 21.497, 18.532 ppm.

Example 141

5-bromo-N-((6-methyl-2-p-tolylH-imidazo[1,2-a]pyridin-3-yl)methyl)pyrimidin-2-amine (141)

The title compound was prepared according to Method A and the experimentals described for compound 139 from 3-(chloromethyl)-6-methyl-2-p-tolylimidazo[1,2-a]pyridine hydrochloride and 5-bromopyrimidin-2-amine. m/e$^+$ 408 (100%), 410 (98%) for $C_{20}H_{19}BrN_5$ (M+H)$^+$.

Example 142

4,6-dichloro-N-((6-methyl-2-p-tolylH-imidazo[1,2-a]pyridin-3-yl)methyl)pyrimidin-2-amine (142)

The title compound was prepared according to Method A and the experimentals described for compound 139 from 3-(chloromethyl)-6-methyl-2-p-tolylimidazo[1,2-a]pyridine hydrochloride and 4,6-dichloropyrimidin-2-amine. m/e$^+$ 398.3, 3 (100%), 399.3 (65%) for $C_{20}H_{18}Cl_2N_5$ (M+H)$^+$; $^1$H-NMR (400 MHz, CDCl$_3$, δ) 8.072 (s, 1H), 7.63 (d, J=8.064 Hz, 2H), 7.55 (d, J=9.531 Hz, 1H), 7.27 (d, J=8.432, 2H), 7.08 (d, J=9.165 Hz, 1H), 6.707 (s, 1H), 5.544 (t, 1H, D, NH), 5.02 (d, J=5.499 Hz, 2H, D, CH$_2$), 2.406, (s, 3H, D, CH$_3$), 2.350 (s, 3H, D, CH$_3$) ppm.

Example 143

4-methyl-N-((6-methyl-2-p-tolylH-imidazo[1,2-a]pyridin-3-yl)methyl)pyrimidin-2-amine (143)

The title compound was prepared according to Method A and the experimentals described for compound 139 from 3-(chloromethyl)-6-methyl-2-p-tolylimidazo[1,2-a]pyridine hydrochloride and 4-methylpyrimidin-2-amine (52.9 mg, 79% yield). M/e$^+$ 344.4 for $C_{21}H_{22}N_5$ (M+H)$^+$; $^1$H-NMR (400 MHz, CDCl$_3$, δ) 7.938 (s, 1H), 7.64 (d, J=8.065 Hz, 2H), 7.49 (d, J=9.165 Hz, 1H), 7.20 (d, J=7.698, 2H), 7.00 (d, J=9.165 Hz, 1H), 6.35 (d, J=4.766 Hz, 1H), 6.10 (broad, 1H, D, NH), 4.97 (d, J=4.765 Hz, 2H, D, CH$_2$), 2.358 (s, 3H, D, CH$_3$), 2.221 (s, 3H, D, CH$_3$) ppm; $^{13}$C-NMR (100 MHz, CDCl$_3$, δ) 168.344, 162.256, 157.56, 144.770, 144.262, 137.771, 131.52, 129.544, 128.444, 127.989, 122.219, 122.037, 116.827, 116.585, 111.004, 35.684, 24.204, 21.489, 18.577 ppm. UV 244.0, 306.0 nm.

Example 144

N-((6-methyl-2-p-tolylH-imidazo[1,2-a]pyridin-3-yl)methyl)pyrazin-2-amine (144)

The title compound was prepared according to Method A and the experimentals described for compound 139 from 3-(chloromethyl)-6-methyl-2-p-tolylimidazo[1,2-a]pyridine hydrochloride and pyrazin-2-amine. m/e+ 330.4 for $C_{20}H_{20}N_5$ (M+H)+; 1H-NMR (400 MHz, CDCl3, δ) 8.07 (d, J=3.66 Hz, 2H), 7.86 (d, J=2.566 Hz, 1H), 7.73 (s, 1H), 7.51 (d, J=8.064 Hz, 2H), 7.45 (d, J=9.164 Hz, 1H), 7.12 (d, J=8.065, 2H), 7.00 (d, J=9.165 Hz, 1H), 5.58 (t, 1H, D, NH), 4.88 (d, J=4.765 Hz, 2H, D, CH2), 2.34 (s, 3H, D, CH3), 2.253 (s, 3H, D, CH3) ppm; 13C-NMR (100 MHz, CDCl3, δ) 154.900, 144.436, 144.239, 142.184, 141.903, 137.665, 133.873, 133.024, 130.954, 129.483, 128.148, 127.913, 122.287, 121.809, 116.638, 115.819, 35.153, 21.451, 18.539 ppm.

Example 145

(6-Methyl-2-p-tolyl-imidazo[1,2-a]pyridin-3-ylmethyl)-[1,2,4]triazin-3-yl-amine (145)

The title compound was prepared according to Method A and the experimentals described for compound 139 from 3-(chloromethyl)-6-methyl-2-p-tolylimidazo[1,2-a]pyridine hydrochloride and 1,2,4-triazin-3-amine. m/e+ 331 for $C_{19}H_{19}N_6$ [M+H]+; 1H-NMR (400 MHz, CDCl3) δ 8.60 (d, J=2.2 Hz, 1H), 8.04 (s, 1H), 8.00 (d, J=2.2 Hz, 1H), 7.86 (s, 1H), 7.64 (d, J=8.0 Hz, 2H), 7.53 (d, J=9.1 Hz, 1H), 7.22 (d, J=8.0 Hz, 2H), 7.05 (dd, J=1.4, 9.1 Hz, 1H), 5.11 (s, 2H), 2.37 (s, 3H), 2.27 (s, 3H) ppm.

Example 146

(6-Methyl-2-p-tolyl-imidazo[1,2-a]pyridin-3-ylmethyl)-[1,3,5]triazin-2-yl-amine (146)

The title compound was prepared according to Method A and the experimentals described for compound 139 from 3-(chloromethyl)-6-methyl-2-p-tolylimidazo[1,2-a]pyridine hydrochloride and 1,3,5-triazin-2-amine. M/e+ 331 for $C_{19}H_{19}N_6$ (M+H)+; 1H-NMR (400 MHz, CDCl3) δ 8.71 (s, 1H), 8.51 (s, 1H), 8.24 (s, 1H), 7.94 (s, 1H), 7.65 (d, J=9.1 Hz, 1H), 7.58 (d, J=8.4 Hz, 2H), 7.26 (d, J=8.4 Hz, 2H), 7.14 (dd, J=9.1, 1.4 Hz, 1H), 5.06 (d, J=5.1 Hz, 2H), 2.39 (s, 3H), 2.32 (s, 3H) ppm.

Example 147

4-chloro-6-methyl-N-((6-methyl-2-p-tolylimidazo[1,2-a]pyridin-3-yl)methyl)pyrimidin-2-amine (147)

The title compound was prepared according to Method A and the experimentals described for compound 139 from 3-(chloromethyl)-6-methyl-2-p-tolylimidazo[1,2-a]pyridine hydrochloride and 1,3,5-triazin-2-amine. m/e+ m/e+ 378.1 for $C_{21}H_{20}ClN_5$ (M+H)+; 1H-NMR (400 MHz, CDCl3, δ) 8.095 (s, 1H), 7.65 (d, J=8.064 Hz, 2H), 7.55 (d, J=9.164 Hz, 1H), 7.16 (d, J=7.698 Hz, 2H), 7.07 (d, J=9.165 Hz, 1H), 6.533 (s, 1H), 5.396 (broad s, 1H, D, NH), 5.02 (d, J=5.132 Hz, 2H), CH2), 2.396 (s, 3H, D, CH3), 2.322 (s, s, 6H, D, 2CH3) ppm.

Example 148

4,6-dimethyl-N-((6-methyl-2-p-tolylH-imidazo[1,2-a]pyridin-3-yl)methyl)pyrimidin-2-amine (148)

The title compound was prepared according to Method A and the experimentals described for compound 139 from 3-(chloromethyl)-6-methyl-2-p-tolylimidazo[1,2-a]pyridine hydrochloride and 4,6-dimethylpyrimidin-2-amine. (49.3 mg, 70% yield) m/e+ 358.3 for $C_{22}H_{24}N_5$ (M+H)+; 1H-NMR (400 MHz, CDCl3, δ) 8.11 (s, 1H), 7.68 (d, J=8.065 Hz, 2H), 7.23 (d, J=8.065 Hz, 1H), 7.00 (d, J=9.165 Hz, 2H), 6.35 (s, 1H), 5.35 (broad s, 1H, D, NH), 5.03 (d, J=5.132 Hz, 2H, D, CH2), 2.383 (s, 3H, D, CH3), 2.275 (s, 6H, D, 2CH3) ppm.

Example 149

N-((6-methyl-2-p-tolylH-imidazo[1,2-a]pyridin-3-yl)methyl)isoxazole-3-amine (149)

The title compound was prepared according to Method A and the experimentals described for compound 139 from 3-(chloromethyl)-6-methyl-2-p-tolylimidazo[1,2-a]pyridine hydrochloride and isoxazol-3-amine. m/e+ 319.4 for $C_{19}H_{19}N_4O$ (M+H)+; 1H-NMR (400 MHz, CDCl3, δ) 8.11 (d, J=1.833 Hz, 1H), 7.828 (s, 1H), 7.56 (d, J=8.065 Hz, 2H), 7.479 (d, J=9.164 Hz, 1H), 7.17 (d, J=7.698 Hz, 2H), 7.03 (dd, J1=9.164 Hz, J2=1.466 Hz, 1H), 5.92 (d, J=1.833 Hz, 1H), 4.78 (d, J=5.132 Hz, 2H, D, CH2), 4.38 (t, 1H, D, NH), 2.366 (s, 3H, D, CH3), 2.301 (s, 3H, D, CH3) ppm; 13C-NMR (100 MHz, CDCl3, δ) 163.820, 158.512, 144.683, 144.436, 137.919, 131.188, 129.613, 128.317, 128.204, 122.414, 121.934, 116.899, 115.971, 96.620, 38.000, 21.520, 18.595 ppm; UV 244.0, 312.0 nm.

Example 150

N-((6-methyl-2-p-tolylH-imidazo[1,2-a]pyridin-3-yl)methyl)thiazole-2-amine (150)

The title compound was prepared according to Method A and the experimentals described for compound 139 from 3-(chloromethyl)-6-methyl-2-p-tolylimidazo[1,2-a]pyridine hydrochloride and thiazol-2-amine. m/e+ 335.4 (100%), 336.3 (20%) for $C_{19}H_{19}N_4S$ (M+H)+; 1H-NMR (400 MHz, CDCl3, δ) δ) 7.802 (s, 1H, D, H), 7.56 (d, J=8.064 Hz, 2H, D, 2×H), 7.49 (d, J=9.164 Hz, 1H), 7.17 (d, J=8.065 Hz, 2H), 7.04 (m, 2H), 6.238 (broad, 1H, D, NH), 4.848 (s, 2H, D, CH2), 2.363 (s, 3H, D, CH3), 2.269 (s, 3H, D, CH3) ppm; 13C-NMR (100 MHz, CDCl3, δ) 169.376, 144.974, 144.451, 139.181, 137.900, 131.060, 129.597, 128.361, 128.239, 122.476, 121.893, 116.911, 115.121, 107.622, 39.415, 21.504, 18.562 ppm; UV 246.0, 312.0 nm.

Example 151

3-methyl-N-((6-methyl-2-p-tolylH-imidazo[1,2-a]pyridin-3-yl)methyl)isothiazol-5-amine (151)

The title compound was prepared according to Method A and the experimentals described for compound 139 from 3-(chloromethyl)-6-methyl-2-p-tolylimidazo[1,2-a]pyridine hydrochloride and 3-methylisothiazol-5-amine. 31.2 mg, 45.5% yield); m/e+ 349.3 for $C_{20}H_{21}N_4S$ (M+H)+; 1H-NMR (400 MHz, CDCl3, δ) 7.541 (s, 1H), 7.38 (d, J=9.165 Hz, 1H), 7.35 (d, J=8.065 Hz, 2H), 7.04 (d, J=8.064 Hz, 2H), 6.97 (d, J=9.164 Hz, 1H), 6.127 (s, 1H), 6.03 (t, 1H, D, NH), 4.41 (d, J=4.4 Hz, 2H, D, CH2), 2.335 (s, 3H, D, CH3), 2.320 (s, 3H, D, CH3), 2.231 (s, 3H, D, CH3) ppm; 13C-NMR (100 MHz, CDCl3, δ) 173.425, 167.154, 144.512, 144.284, 137.809, 130.537, 129.536, 128.452, 127.799, 122.589, 121.483, 116.706, 114.659, 102.382, 41.235, 21.482, 19.715, 18.547 ppm; UV 242 nm.

Example 152

(6-methyl-2-p-tolylH-imidazo[1,2-a]pyridin-3-yl)-N-(4H-1,2,4-triazol-4-yl)methanamine (152)

The title compound was prepared according to Method A and the experimentals described for compound 139 from 3-(chloromethyl)-6-methyl-2-p-tolylimidazo[1,2-a]pyridine hydrochloride and 4H-1,2,4-triazol-4-amine (36.5 mg, 58.9% yield); m/e⁺ 319.4 for $C_{18}H_{19}N_6$ (M+H)⁺; ¹H-NMR (400 MHz, CDCl₃, δ) 7.541 (s, 1H), 7.96 (m, 2H), 7.910 (s, 1H), 7.37 (m 2H), 7.16 (m, 2H), 7.07 (m, 3H), 4.47 (s, 2H), 3.98 (broad, 1H), 2.276 (s, 3H, D, CH₃), 2.247 (s, 3H, D, CH₃) ppm; ¹³C-NMR (100 MHz, CDCl₃, δ) 146.180, 144.391, 142.897, 138.385, 130.271, 129.430, 129.248, 128.421, 123.083, 121.877, 116.281, 113.658, 46.831, 21.186, 18.282 ppm; UV 242, 308 nm.

Example 153

N-((6-methyl-2-p-tolyl-H-imidazo[1,2-a]pyridin-3-yl)methyl)-1H-imidazol-2-amine (153)

The title compound was prepared according to Method A and the experimentals described for compound 139 from 3-(chloromethyl)-6-methyl-2-p-tolylimidazo[1,2-a]pyridine hydrochloride and 1H-imidazol-2-amine. m/e⁺ 318.4 for $C_{19}H_{20}N_5$(M+H)⁺; ¹H-NMR (400 MHz, CD₃OD, δ) 8.141 (s, 1H), 7.60 (d, J=8.065 Hz, 2H), 7.48 (d, J=9.164 Hz, 1H), 7.27 (d, J=8.432 Hz, 2H), 7.24 (d, J₁=9.164 Hz, J₂=1.467 Hz, 1H), 6.716 (s, 2H), 4.905 (s, 2H, D, NH₂), 4.787 (s, 2H, D, CH₂), 2.377 (s, 3H, D, CH₃), 2.342 (s, 3H, D, CH₃) ppm; ¹³C-NMR (100 MHz, CD₃OD, δ), 149.850, 144.140, 144.034, 138.135, 130.787, 129.195, 129.028, 128.307, 123.037, 122.446, 116.736, 116.403, 115.364, 37.163, 20.109, 17.016 ppm.

Example 154

1-methyl-N-((6-methyl-2-p-tolylH-imidazo[1,2-a]pyridin-3-yl)methyl)-1H-benzo[d]imidazol-2-amine (154)

The title compound was prepared according to Method A and the experimentals described for compound 139 from 3-(chloromethyl)-6-methyl-2-p-tolylimidazo[1,2-a]pyridine hydrochloride and 1-methyl-1H-benzo[d]imidazol-2-amine. m/e⁺ 382.4 for $C_{24}H_{24}N_5$ (M+H)⁺; ¹H-NMR (400 MHz, CDCl₃, δ) 8.107 (s, 1H), 8.061 (s, 1H), 7.66 (d, J=8.065 Hz, 2H), 7.57 (d, J=7.698 Hz, 1H), 7.53 (d, J=9.164 Hz, 1H), 7.24 (d, J=8.065 Hz, 2H), 7.15 (m, 2H), 7.13 (dd, J₁=4.032 Hz, J₂=0.733 Hz, 2H), 7.07 (dd, J₁=9.165 Hz, J₂=1.467 Hz, 1H), 5.21 (d, J=4.66 Hz, 2H), 3.504 (s, 3H), 2.394 (s, 3H, D, CH₃), 2.284 (s, 3H, D, CH₃) ppm; UV 218, 244, 266 nm.

Example 155

2-Methyl-3-[(6-methyl-2-p-tolyl-imidazo[1,2-a]pyridin-3-ylmethyl)-amino]-3H-quinazolin-4-one (155)

The title compound was prepared according to Method A and the experimentals described for compound 139 from 3-(chloromethyl)-6-methyl-2-p-tolylimidazo[1,2-a]pyridine hydrochloride and 3-amino-2-methylquinazolin-4(3H)-one. m/e⁺ 410 for $C_{25}H_{24}N_5O$ [M+H]⁺; ¹H-NMR (400 MHz, CDCl₃) δ 8.31 (s, 1H), 8.22 (t, J=1.1 Hz, 1H), 7.71 (m, 1H), 7.68 (d, J=8.0 Hz, 2H), 7.58 (d, J=8.0 Hz, 1H), 7.53 (d, J=9.1 Hz, 1H), 7.44 (t, J=8.0 Hz, 1H), 7.11 (d, J=8.0 Hz, 2H), 7.06 (dd, J=1.1, 9.1 Hz, 1H), 5.86 (t, J=4.8 Hz, 2H), 4.53 (bs, 1H), 2.42 (s, 3H), 2.33 (s, 3H), 2.29 (s, 3H) ppm; ¹³C-NMR (100 MHz, CDCl₃, δ) 161.838, 155.787, 147.287, 146.870, 144.648, 137.968, 134.753, 131.113, 129.377, 128.399, 128.361, 127.246, 126.736, 126.457, 122.711, 121.779, 120.763, 117.161, 114.044, 43.949, 21.906, 21.459, 18.646 ppm.

Example 156

N-((6-chloro-2-(4-chlorophenyl)H-imidazo[1,2-a]pyridin-3-yl)methyl)pyrimidin-2-amine hydrochloride (156)

The title compound was prepared according to Method A and the experimentals described for compound 139 from 6-chloro-3-(chloromethyl)-2-(4-chlorophenyl)imidazo[1,2-a]pyridine hydrochloride and pyrimidin-2-amine. m/e⁺ 300.3 (100%), 372.3 (65%) for $C_{18}H_{14}Cl_2N_5$ (M+H)⁺; ¹H-NMR (400 MHz, CD₃OD, δ) 9.324 (m, 1H), 8.35 (d, J=5.132 Hz, 2H), 8.06 (dd, J₁=9.531 Hz, J₂=1.833 Hz, 1H), 7.96 (d, J=9.531 Hz, 1H), 7.86 (dd, J₁=6.599 Hz, J₂=1.833 Hz, 2H), 7.67 (dd, J₁=6.598 Hz, J₂=1.833 Hz, 2H), 6.79 (t, 1H, D, J=5.132 Hz, 1H), 5.10 (s, 2H, D, CH₂) ppm. ¹³C-NMR (100 MHz, DMSO-d₆-CD₃OD) 159.707, 157.599, 138.203, 135.337, 134.305, 133.282, 130.628, 129.066, 125.858, 125.638, 123.856, 120.490, 33.774 ppm; UV 246, 312 nm. The salt dissolved slowly under heating in DMSO, MeOH. It is not very soluble in CDCl₃, CH₂Cl₂.

Example 157

[2-(4-Chloro-phenyl)-imidazo[1,2-a]pyridin-3-ylmethyl]-(4-methyl-pyrimidin-2-yl)-amine (157)

The title compound was prepared according to Method A and the experimentals described for compound 139 from 3-(chloromethyl)-2-(4-chlorophenyl)imidazo[1,2-a]pyridine hydrochloride and 4-methylpyrimidin-2-amine. m/e⁺ 350 for $C_{19}H_{17}ClN_5$[M+H]⁺; ¹H-NMR (400 MHz, CDCl₃) δ 8.18 (d, J=6.9 Hz, 1H), 7.95 (s, 1H), 7.73 (d, J=8.4 Hz, 2H), 7.62 (d, J=8.8 Hz, 1H), 7.40 (d, J=8.4 Hz, 2H), 7.20 (m, 1H), 6.76 (dt, J=1.1, 6.9 Hz, 1H), 6.42 (d, J=5.1 Hz, 1H), 5.95 (s, 1H), 5.03 (d, J=5.1 Hz, 2H) 2.28 (s, 3H) ppm.

Example 158

(6-Chloro-2-phenyl-imidazo[1,2-a]pyridin-3-ylmethyl)-(4-methyl-pyrimidin-2-yl)-amine (158)

The title compound was prepared according to Method A and the experimentals described for compound 139 from 6-chloro-3-(chloromethyl)-2-phenylimidazo[1,2-a]pyridine hydrochloride 4-methylpyrimidin-2-amine. m/e⁺ 350 for $C_{19}H_{17}ClN_5$ [M+H]⁺; ¹H-NMR (400 MHz, CDCl₃) δ 8.61 (s, 1H), 8.13 (d, J=4.0 Hz, 1H), 7.77 (d, J=6.9 Hz, 2H), 7.57 (d, J=9.5 Hz, 1H), 7.47 (m, 2H), 7.39 (s, 1H), 7.17 (dd, J=2.2, 9.5 Hz, 1H), 6.50 (d, J=5.1 Hz, 1H), 5.48 (s, 1H), 5.06 (d, J=5.8 Hz, 2H), 2.37 (s, 3H) ppm.

Example 159

4-chloro-N-((2-(4-chlorophenyl)imidazo[1,2-a]pyridin-3-yl)methyl)-6-methylpyrimidin-2-amine (159)

The title compound was prepared according to Method A and the experimentals described for compound 139 from 3-(chloromethyl)-2-(4-chlorophenyl)imidazo[1,2-a]pyridine hydrochloride and 4-chloro-6-methylpyrimidin-2-amine. M/e+, 384.1, 386 for C19H15C12N5. $^1$H-NMR (400 MHz, CDCl$_3$, δ) 8.25 (m, 1H), 7.74 (d, J=6.598 Hz, 2H), 7.63 (m, 1H), 7.42 (d, J=6.599 Hz, 2H), 7.24 (m, 1H), 6.84 (m, 1H), 6.55 (s, 1H), 5.41 (s, NH), 5.05 (d, J=5.13 Hz, 2H, D, CH2), 2.318 (s, 3H, D, CH3) ppm.

Example 160

4-chloro-N-((2-(4-fluorophenyl)-6-methylimidazo[1,2-a]pyridin-3-yl)methyl)-6-methylpyrimidin-2-amine (160)

The title compound was prepared according to Method A and the experimentals described for compound 139 from 3-(chloromethyl)-2-(4-fluorophenyl)-6-methylimidazo[1,2-a]pyridine hydrochloride and 4-chloro-6-methylpyrimidin-2-amine. H-NMR (400 MHz, CDCl3) 8.021 (s, 1H), 7.73 (m, 2H), 7.51 (d, J=9.164 Hz, 1H), 7.10 (m, 2H), 6.50 (s, 1H), 5.28 (broad, 1H, D, NH), 4.98 (d, J=5.032 Ha, 2H, D, CH2), 2.29 (s, 3H, D, CH3), 2.26 (s, 3H) ppm; m/e+ 382.0, 384.1 for C20H17ClFN5 (M+H)+

Example 161

4-(6-chloro-3-((4-chloro-6-methylpyrimidin-2-ylamino)methyl)imidazo[1,2-a]pyridin-2-yl)benzonitrile (161)

The title compound was prepared according to Method A and the experimentals described for compound 139 from 4-(6-chloro-3-(chloromethyl)imidazo[1,2-a]pyridin-2-yl)benzonitrile hydrochloride and 4-chloro-6-methylpyrimidin-2-amine. m/e+ 409.0, 411.0 for C20H14Cl2N6; H-NMR (400 MHz, CDCl3) 8.80 (s, 1H), 7.953 (d, J=8.277 Hz, 2H), 7.750 (d, J=8.093 Hz, 2H), 7.593 (d, J=9.533 Hz, 1H), 7.234 (d, J=9.551 Hz, 1H), 6.545 (s, 1H), 5.257 (s, NH), 5.03 (d, J=5.498 Hz, 2H, D, CH2), 2.311 (s, 6H, D, 2CH3) ppm.

Example 162

4-chloro-N-((6-chloro-2-(4-fluorophenyl)imidazo[1,2-a]pyridin-3-yl)methyl)-6-methylpyrimidin-2-amine (162)

The title compound was prepared according to Method A and the experimentals described for compound 139 from 6-chloro-3-(chloromethyl)-2-(4-fluorophenyl)imidazo[1,2-a]pyridine hydrochloride and 4-chloro-6-methylpyrimidin-2-amine. m/e+ 402.0, 404.0 for C19H14C12FN5.

Example 163

6-Methyl-3-phenylsulfanylmethyl-2-p-tolyl-imidazo[1,2-a]pyridine (163)

The title compound was prepared according to Method A and the experimentals described for compound 139 from 3-(chloromethyl)-6-methyl-2-p-tolylimidazo[1,2-a]pyridine hydrochloride and benzenethiol. m/e$^+$ 345 for C$_{22}$H$_{21}$N$_2$ (M+H)$^+$; $^1$H NMR (400 MHz, CDCl$_3$) δ 7.81 (s, 1H), 7.59 (d, J=8.0 Hz, 2H), 7.54 (d, J=9.1 Hz, 1H), 7.35 (d, J=1.8 Hz, 2H), 7.32 (m, 5H), 7.07 (d, J=9.1 Hz, 1H), 4.54 (s, 2H), 2.39 (s, 3H), 2.34 (s, 3H) ppm.

Example 164

4,6-difluoro-N-((2-phenylimidazo[1,2-a]pyridin-3-yl)methyl)pyrimidin-2-amine (164)

The title compound was prepared according to Method A and the experimentals described for compound 139 from 3-(chloromethyl)-2-phenylimidazo[1,2-a]pyridine hydrochloride and 4,6-difluoropyrimidin-2-amine. (0.10 g, 17% yield), M/e$^-$ 338.2 for C$_{18}$H$_{13}$F$_2$N$_5$ (M+H)$^+$

Example 165

N-((6-chloro-2-phenylimidazo[1,2-a]pyridin-3-yl)methyl)-6-methoxypyridazin-3-amine (165)

The title compound was prepared according to Method A and the experimentals described for compound 139 from 3-(chloromethyl)-6-fluoro-2-(4-fluorophenyl)imidazo[1,2-a]pyridine hydrochloride and 6-methoxypyridazin-3-amine compound. M/e$^+$ 366 for C$_{19}$H$_{17}$ClN$_5$O (M+H)$^+$; $^1$H-NMR (400 MHz, CDCl$_3$) δ 8.16 (t, J=0.7 Hz, 1H), 7.68 (dd, J=8.4, 1.4 Hz, 2H), 7.52 (d, J=9.5 Hz, 1H), 7.39 (m, 3H), 7.16 (dd, J=9.5, 1.8 Hz, 1H), 6.84 (q, J=9.5 Hz, 2H), 5.07 (d, J=4.7 Hz, 2H), 4.06 (s, 3H), 1.62 (bs, 1H) ppm.

Example 166

4,6-difluoro-N-((2-(4-fluorophenyl)-6-methylimidazo[1,2-a]pyridin-3-yl)methyl)pyrimidin-2-amine (166)

The title compound was prepared according to Method A and the experimentals described for compound 139 from 3-(chloromethyl)-2-(4-fluorophenyl)-6-methylimidazo[1,2-a]pyridine hydrochloride and 4,6-difluoropyrimidin-2-amine. (0.23 g, 39% yield), M/e$^+$ 370.1 for C$_{19}$H$_{14}$F$_3$N$_5$ (M+H)$^+$.

Example 167

N-((2-(4-chlorophenyl)imidazo[1,2-a]pyridin-3-yl)methyl)-4,6-difluoropyrimidin-2-amine (167)

The title compound was prepared according to Method A and the experimentals described for compound 139 from 3-(chloromethyl)-2-(4-chlorophenyl)imidazo[1,2-a]pyridine hydrochloride and 4,6-difluoropyrimidin-2-amine. (0.100 g, 34% yield); $^1$H-NMR (300 MHz, CDCl$_3$, δ) 8.08 (d, J=6.9 Hz, 1H), 7.64-7.85 (m, 3H) 7.37-7.33 (m, 2H), 7.25-7.20 (m, 1H), 6.85-6.80 (m, 1H), 6.07 (t, J=9.3 Hz, 1H), 5.86-5.85 (m, 1H), 5.99 (d, J=5.4 Hz, 2H).

Example 168

N-((6-chloro-2-phenylimidazo[1,2-a]pyridin-3-yl)methyl)-4,6-difluoropyrimidin-2-amine (168)

The title compound was prepared according to Method A and the experimentals described for compound 139 from 6-chloro-3-(chloromethyl)-2-phenylimidazo[1,2-a]pyridine hydrochloride and 4,6-difluoropyrimidin-2-amine. ((0.26 g, 43% yield), M/e+ 372.2 for $C_{18}H_{12}ClF_2N_5$ (M+H)+.

Example 169

N-((6-Chloro-2-(4-fluorophenyl)imidazo[1,2-a]pyridin-3-yl)methyl)-4,6-difluoropyrimidin-2-amine (169)

The title compound was prepared according to Method A and the experimentals described for compound 139 from 6-chloro-3-(chloromethyl)-2-(4-fluorophenyl)imidazo[1,2-a]pyridine hydrochloride and 4,6-difluoropyrimidin-2-amine. (0.42 g, 45% yield). M/e+ 390.2 for $C_{18}H_{11}ClF_3N_5$ (M+H)+.

Example 170

4-chloro-N-((6-chloro-2-(4-chlorophenyl)imidazo[1,2-a]pyridin-3-yl)methyl)-6-methylpyrimidin-2-amine (170)

The title compound was prepared according to Method A and the experimentals described for compound 139 from 6-chloro-3-(chloromethyl)-2-(4-chlorophenyl)imidazo[1,2-a]pyridine hydrochloride and 4-chloro-6-methylpyrimidin-2-amine. 1H-NMR (400 MHz, CDCl3) δ 8.56 (s, 1H), 7.69 (d, J=8.4 Hz, 2H), 7.55 (d, J=9.5 Hz, 1H), 7.40 (d, J=8.5 Hz, 2H), 7.18 (dd, J=1.8, 9.5 Hz, 1H), 6.55 (s, 1H), 5.59 (broad, 1H), 4.99 (d, J=5.6 Hz, 2H), 2.34 (s, 3H); m/e+ 419 for C19H14Cl3N5 [M+H]+.

Example 171

(6,8-Dichloro-2-p-tolyl-imidazo[1,2-a]pyridin-3-ylmethyl)-(1H-imidazol-2-yl)-amine (171)

The title compound was prepared according to Method A and the experimentals described for compound 139 from 6,8-dichloro-3-(chloromethyl)-2-p-tolylimidazo[1,2-a]pyridine hydrochloride and 1H-imidazol-2-amine. m/e+ 372 for $C_{18}H_{16}Cl_2N_5$ [M+H]+; 1H-NMR (300 MHz, CDCl3) δ 8.10 (s, 1H), 7.27 (m, 4H), 6.92 (d, J=6.6 Hz, 2H), 6.76 (s, 2H), 4.67 (s, 2H), 4.50 (bs, 1H), 2.31 (s, 3H) ppm.

Example 172

(6,8-Dichloro-2-p-tolyl-imidazo[1,2-a]pyridin-3-ylmethyl)-(4,6-dimethyl-pyrimidin-2-yl)-amine (172)

The title compound was prepared according to Method A and the experimentals described for compound 139 from 6,8-dichloro-3-(chloromethyl)-2-p-tolylimidazo[1,2-a]pyridine hydrochloride and 4,6-dimethylpyrimidin-2-amine. m/e+ 412 for $C_{21}H_{20}Cl_2N_5$ [M+H]+; 1H-NMR (400 MHz, CDCl3) δ 8.85 (d, J=1.4 Hz, 1H), 7.64 (d, J=8.0 Hz, 2H), 7.48 (d, J=7.7 Hz, 1H), 7.25 (d, J=8.0 Hz, 2H), 7.14 (d, J=7.7 Hz, 1H), 6.41 (s, 1H), 5.02 (s, 2H), 2.40 (s, 3H), 2.36 (s, 3H), 2.33 (s, 3H) ppm.

Example 173

2-((6-methyl-2-p-tolylH-imidazo[1,2-a]pyridin-3-yl)methoxy)isoindoline-1,3-dione (173)

The title compound was prepared according to Method A and the experimentals described for compound 139 from 3-(chloromethyl)-6-methyl-2-p-tolylimidazo[1,2-a]pyridine hydrochloride and 2-hydroxyisoindoline-1,3-dione. m/e+ 398.3 for $C_{24}H_{20}N_3O_3$ (M+H)+; 1H-NMR (400 MHz, CDCl3, δ) 8.542 (s, 1H), 7.8-7.6 (m, 7H), 7.26-7.22 (m, 3H), 5.523 (s, 2H, D, CH2), 2.475 (s, 3H, D, CH3), 2.351 (s, 3H, D, CH3) ppm.

Example 174

1-((6-methyl-2-p-tolylH-imidazo[1,2-a]pyridin-3-yl)methoxy)-1H-benzo[d][1,2,3]triazole (174)

The title compound was prepared according to Method A and the experimentals described for compound 139 from 3-(chloromethyl)-6-methyl-2-p-tolylimidazo[1,2-a]pyridine hydrochloride and 1H-benzo[d][1,2,3]triazol-1-ol. m/e+ 370.5 for $C_{22}H_{20}N_5O$ (M+H)+; 1H-NMR (400 MHz, CDCl3, δ) 8.030 (s, 1H), 7.91 (d, J=8.798 Hz, 1H), 7.63 (d, J=7.698 Hz, 2H), 7.56 (d, J=9.164 Hz, 1H), 7.35 (d, J=8.065 Hz, 2H), 7.28 (m, 2H), 7.12 (d, J=9.165 Hz, 1H), 6.72 (dd, J1=7.331 Hz, J=5.865 Hz, 1H), 6.007 (s, 2H, D, CH2), 2.456 (s, 3H, D, CH3), 2.339 (s, 3H, D, CH3) ppm.

Example 175

6-Methyl-3-(pyridin-3-yloxymethyl)-2-p-tolyl-imidazo[1,2-a]pyridine (175)

The title compound was prepared according to Method A and the experimentals described for compound 139 from 3-(chloromethyl)-6-methyl-2-p-tolylimidazo[1,2-a]pyridine hydrochloride and 1H-benzo[d][1,2,3]triazol-1-ol. and pyridin-3-ol. m/e+ 350 for $C_{21}H_{20}N_3O$ [M+H]+; 1H-NMR (400 MHz, CDCl3) δ 8.38 (d, J=1.8 Hz, 1H), 8.27 (dd, J=1.8, 4.4 Hz, 1H), 8.21 (d, J=2.5 Hz, 1H), 8.02 (d, J=4.4 Hz, 1H), 7.91 (s, 1H), 7.59 (dd, J=1.4, 8.0 Hz, 2H), 7.23 (d, J=1.4, 8.0 Hz, 2H), 7.15 (m, 2H), 5.42 (s, 2H), 2.36 (s, 3H), 2.35 (s, 3H) ppm.

Example 176

3-((4-methyl-4H-1,2,4-triazol-3-ylthio)methyl)-6-methyl-2-p-tolylH-imidazo[1,2-a]pyridine (176)

The title compound was prepared according to Method A and the experimentals described for compound 139 from 3-(chloromethyl)-6-methyl-2-p-tolylimidazo[1,2-a]pyridine hydrochloride and 4-methyl-4H-1,2,4-triazole-3-thiol. m/e+ 350 for $C_{19}H_{20}N_5S$ [M+H]+; 1H-NMR (400 MHz, CDCl3, δ) 8.55 (s, 1H), 7.96 (d, J=8.0 Hz, 2H), 7.79 (s, 1H), 7.67 (d, J=9.1 Hz, 1H), 7.30 (d, J=8.0 Hz, 2H), 7.16 (d, J=9.1 Hz, 1H), 5.77 (s, 2H, D, CH2), 3.65 (s, 3H, D, CH3), 2.41 (s, 3H, D, CH3), 2.36 (s, 3H, D, CH3) ppm.

Example 177

6-Methyl-2-p-tolyl-3-(1H-[1,2,4]triazol-3-ylsulfanyl-methyl)-imidazo[1,2-a]pyridine (177)

The title compound was prepared according to Method A and the experimentals described for compound 139 from 3-(chloromethyl)-6-methyl-2-p-tolylimidazo[1,2-a]pyridine hydrochloride and 1H-1,2,4-triazole-3-thiol. m/e+ 336 for C18H18N5S (M+H)+; 1H NMR (400 MHz, CDCl3) δ 8.10 (s, 1H), 7.90 (s, 1H), 7.57 (m, 3H), 7.21 (d, J=7.7 Hz, 2H), 7.11 (dd, J=1.1, 9.1 Hz, 1H), 4.78 (s, 2H), 2.36 (s, 3H), 2.33 (s, 3H) 0.90 (bs, 1H) ppm.

Example 178

6-Methyl-3-(thiophen-2-ylsulfanylmethyl)-2-p-tolyl-imidazo[1,2-a]pyridine (178)

The title compound was prepared according to Method A and the experimentals described for compound 139 from 3-(chloromethyl)-6-methyl-2-p-tolylimidazo[1,2-a]pyridine hydrochloride and thiophene-2-thiol. m/e⁺ 351 for $C_{20}H_{19}N_2S_2$ [M+H]⁺; ¹H-NMR (400 MHz, CDCl₃) δ 7.75 (s, 1H), 7.53 (s, 1H), 7.50 (d, J=8.0 Hz, 2H), 7.29 (dd, J=1.1, 5.1 Hz, 1H), 7.20 (d, J=8.0 Hz, 2H), 7.04 (dd, J=1.4, 9.1 Hz, 1H), 6.95 (dd, J=1.1, 3.6 Hz, 1H), 6.87 (dd, J=3.6, 5.5 Hz, 1H), 4.40 (s, 2H), 2.37 (s, 3H), 2.33 (s, 3H) ppm; ¹³C-NMR (100 MHz, CDCl₃, δ) 145.528, 144.436, 137.718, 135.777, 132.167, 131.485, 131.098, 129.437, 128.391, 128.057, 127.944, 122.074, 121.711, 117.032, 114.621, 33.849, 21.527, 18.699 ppm.

Example 170

6-Methyl-3-(5-methyl-[1,3,4]thiadiazol-2-ylsulfanylmethyl)-2-p-tolyl-imidazo[1,2-a]pyridine (179)

The title compound was prepared according to Method A and the experimentals described for compound 139 from 3-(chloromethyl)-6-methyl-2-p-tolylimidazo[1,2-a]pyridine hydrochloride and 5-methyl-1,3,4-thiadiazole-2-thiol. m/e⁻ 367 for $C_{19}H_{19}N_4S_2$ [M+H]⁺; ¹H-NMR (400 MHz, CDCl₃) δ 8.27 (s, 1H), 7.86 (d, J=8.0 Hz, 2H), 7.55 (d, J=9.1 Hz, 1H), 7.28 (d, J=8.0 Hz, 2H), 7.09 (dd, J=1.4, 9.1 Hz, 1H), 5.83 (s, 2H), 2.40 (s, 3H), 2.37 (s, 3H), 2.33 (s, 3H) ppm; ¹³C-NMR (100 MHz, CDCl₃, δ) 186.983, 156.637, 146.840, 144.588, 138.165, 131.265, 129.597, 128.800, 128.649, 122.931, 122.787, 116.971, 113.923, 44.131, 21.557, 18.638, 16.606 ppm.

Example 180

6-Methyl-3-([1,3,4]thiadiazol-2-ylsulfanylmethyl)-2-p-tolyl-imidazo[1,2-a]pyridine (180)

The title compound was prepared according to Method A and the experimentals described for compound 139 from 3-(chloromethyl)-6-methyl-2-p-tolylimidazo[1,2-a]pyridine hydrochloride and 1,3,4-thiadiazole-2-thiol. m/e⁺ 353 for $C_{18}H_{17}N_4S_2$ [M+H]⁺; ¹H-NMR (300 MHz, CDCl₃) δ 8.22 (d, J=10.2 Hz, 2H), 7.82 (dd, J=1.8, 6.3 Hz, 2H), 7.57 (d, J=9 Hz, 1H), 7.27 (d, J=9 Hz, 2H), 7.12 (dd, J=1.5, 9.0 Hz, 1H), 5.91 (s, 2H), 2.41 (s, 3H), 2.34 (s, 3H) ppm.

Example 181

3-((4,6-dimethylpyrimidin-2-ylthio)methyl)-6-methyl-2-p-tolylH-imidazo[1,2-a]pyridine (181)

The title compound was prepared according to Method A and the experimentals described for compound 139 from 3-(chloromethyl)-6-methyl-2-p-tolylimidazo[1,2-a]pyridine hydrochloride and 4,6-dimethylpyrimidine-2-thiol. m/e⁺ 375.3 for $C_{22}H_{23}N_4S$ [M+H]⁺; ¹H-NMR (400 MHz, CDCl₃) δ 8.00 (s, 1H), 7.77 (d, J=8 Hz, 2H), 7.54 (d, J=9.2 Hz, 1H), 7.27 (d, J=8 Hz, 2H), 7.05 (d, J=9.2 Hz, 1H), 6.74 (s, 1H), 4.95 (s, 2H), 2.40 (s, 6H), 2.39 (s, 3H), 2.31 (s, 3H) ppm; ¹³C-NMR (100 MHz, CDCl₃, δ) 170.64, 167.50, 144.89, 144.50, 137.71, 131.70, 129.57, 128.53, 127.88, 122.13, 122.07, 116.99, 116.36, 114.08, 26.19, 24.06, 21.52, 18.68 ppm.

Example 182

4,6-Difluoro-N-((6-fluoro-2-(4-fluorophenyl)imidazo[1,2-a]pyridin-3-yl)methyl)pyrimidin-2-amine (182)

The title compound was prepared according to Method A and the experimentals described for compound 139 from 3-(chloromethyl)-6-fluoro-2-(4-fluorophenyl)imidazo[1,2-a]pyridine hydrochloride and 4,6-difluoropyrimidin-2-amine. (0.35 g, 39% yield). M/e⁺ 374.2 for $C_{18}H_{11}F_4N_5$ (M+H)⁺.

General Procedure for Chloro Displacement with Nucleophiles (RONa, RSNa or R₃R₄NH)

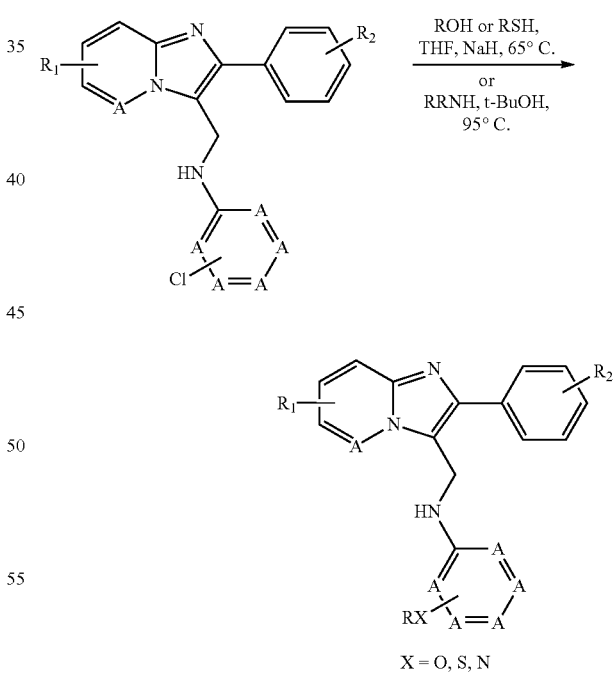

X = O, S, N

Starting material and 5-10 eq of ROH or RSH (in THF, with 1-2 eq of NaH) or R₁R₂NH (neat or in t-BuOH) was heated from 65° C. to 95° C. until the reaction was completed. The mixture was diluted with ethyl acetate and the resulting mixture was washed with saturated NaHCO₃ and brine, dried over Na₂SO₄ and concentrated by evaporation. The crude product was purified by silica gel chromatography (methanol/methylene chloride gradient) to obtain the desired product)

Example 183

(R)—N-((6-chloro-2-(4-fluorophenyl)imidazo[1,2-a]pyridin-3-yl)methyl)-4-(1-methylpyrrolidin-3-yloxy)pyrimidin-2-amine (183)

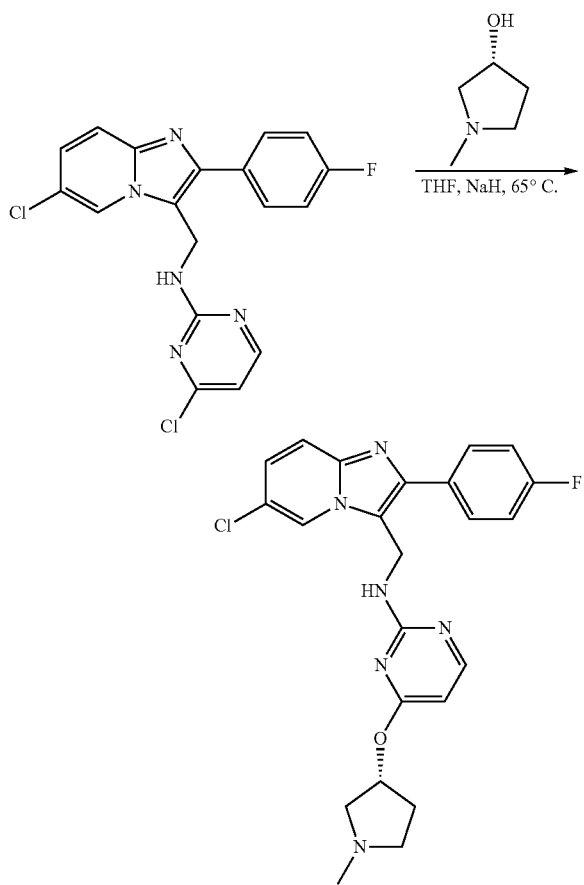

To a solution of (R)-1-methylpyrrolidin-3-ol (66 mg, 0.65 mmol) in THF (3 ml) was added NaH (25 mg, 65% in mineral oil). The mixture was stirred for 30 min and 4-chloro-N-((6-chloro-2-(4-fluorophenyl)imidazo[1,2-a]pyridin-3-yl)methyl)pyrimidin-2-amine (50 mg, 0.13 mmol) was added. The mixture was heated from 65 to 95° C. until the reaction was completed. The mixture was diluted with ethyl acetate and the resulting mixture was washed with saturated NaHCO$_3$ and brine, dried over Na$_2$SO$_4$ and concentrated by evaporation. The crude product was purified by silica gel chromatography (methanol/methylene chloride gradient) to obtain the desired product. $^1$H-NMR (CDCl$_3$, 400 MHz, δ) 8.23 (s, 1H), 7.69 (m, 2H), 7.52 (d, J=9.5 Hz, 1H), 7.12 (m, 3H), 5.97 (s, 1H), 5.36 (s, 1H), 4.96 (d, J=4.7 Hz, 2H), 2.80 (m, 3H), 2.68 (m, 1H), 2.34 (s, 3H), 2.25 (m, 2H), 1.96 (m, 1H) ppm; m/e 453 (M+H)$^+$.

Example 184

(S)—N-((6-chloro-2-(4-fluorophenyl)imidazo[1,2-a]pyridin-3-yl)methyl)-4-(1-methylpyrrolidin-3-yloxy)pyrimidin-2-amine (184)

The title compound was prepared in the same fashion as that described for compound 183 from 4-chloro-N-((6-chloro-2-(4-fluorophenyl)imidazo[1,2-a]pyridin-3-yl)methyl)pyrimidin-2-amine and (S)-1-methylpyrrolidin-3-ol. $^1$H-NMR (CDCl$_3$, 400 MHz, δ) 8.20 (s, 1H), 7.65 (m, 1H), 7.50 (d, J=9.5 Hz, 1H), 9.10 (m, 3H), 5.93 (s, 1H), 5.34 (s, 1H), 4.93 (d, J=4.9 Hz, 2H), 2.75 (m, 4H), 2.33 (s, 3H), 2.25 (m, 2H), 1.95 (m, 1H) ppm; m/e 453 (M+H)$^+$.

Example 185

N-((2-(4-chlorophenyl)imidazo[1,2-a]pyridin-3-yl)methyl)-2-(2-(methylamino)ethoxy)pyrimidin-4-amine (185)

The title compound was prepared in the same fashion as that described for compound 183 from 2-chloro-N-((2-(4-chlorophenyl)imidazo[1,2-a]pyridin-3-yl)methyl)pyrimidin-4-amine and 2-(methylamino)ethanol. M/e$^+$ 409 for C$_{21}$H$_{22}$ClN$_6$O (M+H)$^+$; $^1$H-NMR (400 MHz, CD$_3$OD) δ 8.61 (s, 1H), 7.74 (d, J=8.4 Hz, 2H), 7.68 (d, J=6.2 Hz, 1H), 7.50 (t, J=7.3 Hz, 2H), 7.43 (d, J=7.3 Hz, 1H), 7.39 (m, 1H), 5.84 (d, J=6.2 Hz, 2H), 5.08 (d, J=8.8 Hz, 2H), 3.74 (m, 2H), 3.17 (s, 3H) ppm.

Example 186

2-(4-chlorophenyl)-3-((6-(pyrrolidin-3-yloxy)pyrazin-2-yl)methyl)imidazo[1,2-a]pyridine (186)

The title compound was prepared according to the experimental for compound 183 from 2-(4-chlorophenyl)-3-((6-chloropyrazin-2-yl)methyl)imidazo[1,2-a]pyridine and pyrrolidin-3-ol. M/e$^+$ 406 for C$_{22}$H$_{21}$ClN$_5$O (M+H)$^-$; $^1$H-NMR (400 MHz, CDCl$_3$) δ 8.20 (d, J=6.9 Hz, 1H), 7.91 (dd, J=6.6, 1.8 Hz, 2H), 7.75 (d, J=8.4 Hz, 2H), 7.62 (d, J=9.1 Hz, 1H), 7.42 (d, J=8.4 Hz, 2H), 7.20 (m, 1H), 6.79 (td, J=6.9, 1.1 Hz, 1H), 4.59 (s, 1H), 4.35 (s, 2H), 3.54 (m, 3H), 2.09 (m, 2H), 1.55 (s, 1H) ppm

Example 187

1-(2-((6-chloro-2-phenylimidazo[1,2-a]pyridin-3-yl)methylamino)pyrimidin-4-yl)-4-methylpiperidin-4-ol (187)

A mixture of 4-chloro-N-((6-chloro-2-phenylimidazo[1,2-a]pyridin-3-yl)methyl)pyrimidin-2-amine (50 mg, 0.135 mmol) and 4-methylpiperidin-4-ol (200 mg, 1.74 mmol) in t-BuOH (0.5 ml) was heated 95° C. until the reaction was completed. The mixture was diluted with ethyl acetate and the resulting mixture was washed with saturated NaHCO$_3$ and brine, dried over Na$_2$SO$_4$ and concentrated by evaporation. The crude product was purified by silica gel chromatography (methanol/methylene chloride gradient) to title compound. M/e$^+$ 449 for C$_{24}$H$_{26}$ClN$_6$O (M+H)$^+$; $^1$H-NMR (400 MHz, CDCl$_3$) δ 8.47 (s, 1H), 7.89 (d, J=5.8 Hz, 1H), 7.76 (d, J=6.9 Hz, 2H), 7.57 (d, J=9.5 Hz, 1H), 7.47 (m, 3H), 7.39 (d, J=7.7 Hz, 1H), 7.16 (dd, J=9.5, 1.8 Hz, 1H), 5.99 (d, J=6.2 Hz, 1H), 5.05 (d, J=5.5 Hz, 2H), 5.00 (bs, 1H), 4.00 (m, 2H), 3.40 (m, 2H), 1.62 (m, 4H), 1.29 (s, 3H) ppm.

Example 188

(R)-(1-(2-((6-chloro-2-phenylimidazo[1,2-a]pyridin-3-yl)methylamino)pyrimidin-4-yl)pyrrolidin-2-yl)methanol (188)

The title compound was prepared in the same fashion as that described for compound 187 from 4-chloro-N-((6- chloro-2-phenylimidazo[1,2-a]pyridin-3-yl)methyl)pyrimidin-2-amine and (R)-pyrrolidin-2-ylmethanol. m/e 435 (M+H)$^+$.

Example 189

1-(2-((6-chloro-2-(4-fluorophenyl)imidazo[1,2-a]pyridin-3-yl)methylamino)pyrimidin-4-yl)pyrrolidin-3-ol (189)

The title compound was prepared in the same fashion as that described for compound 187 from N-((6-chloro-2-(4-fluorophenyl)imidazo[1,2-a]pyridin-3-yl)methyl)pyrimidin-2-amine and pyrrolidin-3-ol. $^1$H-NMR (CDCl$_3$, 400 MHz, δ) 8.72 (d, J=11.6 Hz, 1H), 8.32 (s, 1H), 7.78 (dd, J=5.7, 8.3 Hz, 2H), 7.66 (s, 1H), 7.61 (d, J=9.6 Hz, 2H), 7.41 (d, J=9.6 Hz, 1H), 7.26 (t, J=8.7 Hz, 2H), 6.13 (dd, J=6.3, 21.2 Hz, 1H), 5.10 (s, 2H), 4.88 (, 1H), 4.48 (d, J=36.5 Hz, 1H), 3.60 (m, 1H), 3.52 (m, 1H), 3.42 (m, 1H), 2.42 (m, 2H) ppm; m/e 439 (M+H)$^+$.

Example 190

N1-(6-((2-(4-chlorophenyl)imidazo[1,2-a]pyridin-3-yl)methyl)pyrazin-2-yl)-N2,N2-dimethylethane-1,2-diamine (190)

The title compound was prepared in the same fashion as that described for compound 187 from 2-(4-chlorophenyl)-3-((6-chloropyrazin-2-yl)methyl)imidazo[1,2-a]pyridine and N$^1$,N$^1$-dimethylethane-1,2-diamine. M/e$^+$ 407 for C$_{22}$H$_{24}$ClN$_6$ (M+H)$^+$; $^1$H-NMR (400 MHz, CDCl$_3$) δ 8.12 (d, J=6.9 Hz, 1H), 7.85 (d, J=8.8 Hz, 2H), 7.78 (s, 1H), 7.63 (d, J=8.4 Hz, 2H), 7.42 (d, J=8.4 Hz, 2H), 7.20 (m, 1H), 6.78 (m, 1H), 5.30 (s, 1H), 4.34 (s, 2H), 3.29 (q, J=5.5 Hz, 2H), 2.46 (t, J=5.5 Hz, 2H), 2.21 (s, 6H) ppm.

Example 191

1-(6-((2-(4-chlorophenyl)imidazo[1,2-a]pyridin-3-yl)methyl)pyrazin-2-yl)pyrrolidin-3-ol (191)

The title compound was prepared according to the experimental for compound 187 from 2-(4-chlorophenyl)-3-((6-chloropyrazin-2-yl)methyl)imidazo[1,2-a]pyridine and pyrrolidin-3-ol. M/e$^+$ 406 for C$_{22}$H$_{21}$ClN$_5$O (M+H)$^-$; $^1$H-NMR (400 MHz, CDCl$_3$) δ 8.20 (d, J=6.2 Hz, 1H), 7.89 (d, J=8.4 Hz, 2H), 7.71 (d, J=10.6 Hz, 2H), 7.59 (dd, J=9.1, 0.7 Hz, 1H), 7.41 (d, J=8.4 Hz, 2H), 7.16 (m, 1H), 6.77 (t, J=6.9 Hz, 1H), 4.56 (s, 1H), 4.32 (s, 2H), 4.06 (m, 1H), 3.53 (m, 3H), 3.00 (bs, 1H), 2.04 (m, 2H) ppm.

Example 192

2-((6-((2-(4-chlorophenyl)imidazo[1,2-a]pyridin-3-yl)methyl)pyrazin-2-yl)(methyl)amino)ethanol (192)

The title compound was prepared according to the experimental for compound 187 from 2-(4-chlorophenyl)-3-((6-chloropyrazin-2-yl)methyl)imidazo[1,2-a]pyridine and 2-(methylamino)ethanol. M/e$^+$ 394 for C$_{21}$H$_{21}$ClN$_5$O (M+H)$^+$; $^1$H-NMR (400 MHz, CDCl$_3$) δ 8.06 (d, J=6.6 Hz, 1H), 7.89 (s, 1H), 7.78 (d, J=8.4 Hz, 2H), 7.70 (s, 1H), 7.60 (dd, J=8.4, 0.7 Hz, 1H), 7.40 (d, J=8.4 Hz, 2H), 7.17 (m, 1H), 6.77 (t, J=6.9 Hz, 1H), 4.34 (s, 2H), 3.64 (t, J=5.1 Hz, 2H), 3.54 (t, J=5.1 Hz, 2H), 3.05 (s, 3H) ppm.

Example 193

2-(4-chlorophenyl)-3-((6-(2-methylhydrazinyl)pyrazin-2-yl)methyl)imidazo[1,2-a]pyridine (193)

The title compound was prepared according to the experimental for compound 187 from 2-(4-chlorophenyl)-3-((6-chloropyrazin-2-yl)methyl)imidazo[1,2-a]pyridine and methylhydrazine. M/e$^+$ 365 for C$_{19}$H$_{18}$ClN$_6$ (M+H)$^+$; $^1$H-NMR (400 MHz, CDCl$_3$) δ 8.41 (s, 1H), 8.12 (d, J=6.9 Hz, 1H), 7.83 (d, J=8.4 Hz, 2H), 7.73 (s, 1H), 7.63 (d, J=9.1 Hz, 1H), 7.41 (d, J=8.4 Hz, 2H), 7.19 (m, 1H), 6.78 (t, J=6.9 Hz, 1H), 4.36 (s, 2H), 3.88 (bs, 2H), 3.18 (s, 3H) ppm.

Example 194

Tert-butyl 2-(2-((6-chloro-2-(4-fluorophenyl)imidazo[1,2-a]pyridin-3-yl)methylamino)pyrimidin-4-yl)pyrrolidine-1-carboxylate (194)

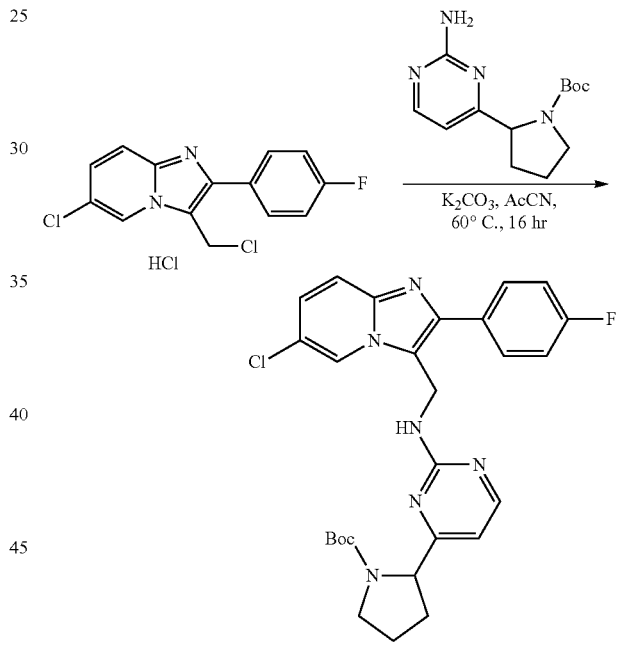

To a solution of 6-chloro-3-(chloromethyl)-2-(4-fluorophenyl)imidazo[1,2-a]pyridine hydrochloride (100 mg, 0.35 mmol) in acetonitrile (25 mL) was added tert-butyl 2-(2-aminopyrimidin-4-yl)pyrrolidine-1-carboxylate (prepared according to the procedures described in WO 2007/09117 A1)(190 mg, 0.71 mmol) and freshly ground potassium carbonate (150 mg, 1.1 mmol) and the reaction mixture was heated to 60° C. for 16 h. After this time the reaction mixture was cooled to room temperature, diluted with ethyl acetate (20 mL) and washed with brine (2×20 mL). The organic layer was separated, dried over Na$_2$SO$_4$, concentrated and purified by column chromatography (methanol/methylene chloride) to afford the desired product. (0.10 g, 54% yield). M/e$^+$ 523.1 for C$_{27}$H$_{28}$ClFN$_6$O$_2$ (M+H)$^+$, $^1$H-NMR (500 MHz, CDCl$_3$, δ) 8.45 (d, J=1.0 Hz, 1H), 8.28 (s, 1H), 7.77-7.74 (m, 2H), 7.58 (d, J=9.5 Hz, 1H), 7.20-7.15 (m, 3H), 6.55 (d, J=5.0 Hz, 1H), 5.18 (s, 1H), 5.07-5.01 (m, 2H), 4.62 (s, 1H), 3.61-3.52

(m, 2H), 2.34 (m, 1H), 1.98-1.94 (m, 1H), 1.91-1.86 (m, 2H), 1.26 (s, 9H) and signals due to a minor tautomer (ca. 44%): 4.77 (d, J=5.0 Hz), 1.46 (s).

Example 195

N-((6-chloro-2-(4-fluorophenyl)imidazo[1,2-a]pyridin-3-yl)methyl)-4-(pyrrolidin-2-yl))pyrimidin-2-amine (195)

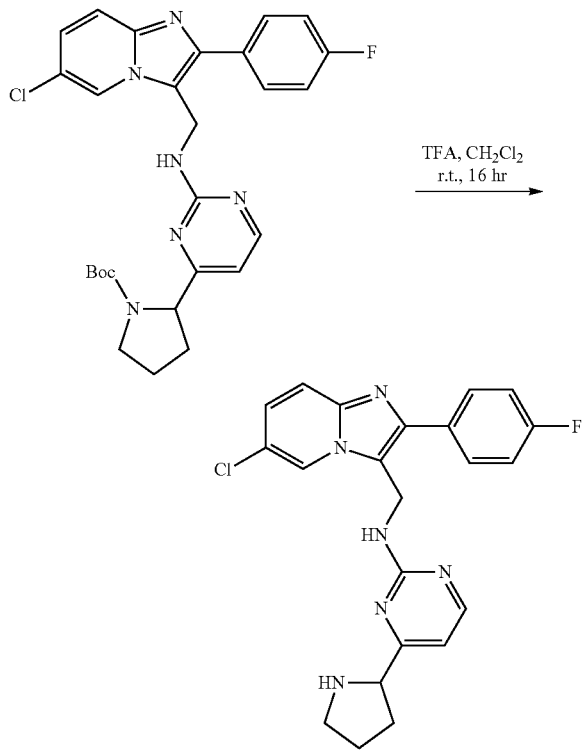

To a solution of tert-butyl 2-(2-((6-chloro-2-(4-fluorophenyl)imidazo[1,2-a]pyridin-3-yl)methylamino)pyrimidin-4-yl)pyrrolidine-1-carboxylate (64 mg, 120 mmol) in methylene chloride (5 mL) was added trifluoroacetic acid (2 mL) and the reaction was stirred at room temperature for 16 h. After this time the reaction was concentrated and purified by reverse phase preparatory HPLC (acetonitrile/water gradient) to afford the desired product. (0.045 g, 88% yield). M/e+ 423.1 for $C_{22}H_{20}ClFN_6$ (M+H)+, $^1$H-NMR (500 mHz, CDCl$_3$, δ), 8.45 (d, J=1.0 Hz, 1H), 8.29 (d, J=5.5 Hz, 1H), 7.77-7.75 (m, 2H), 7.58 (d, J=9.5 Hz, 1H), 7.20-7.15 (m, 3H), 6.72 (d, J=5.0 Hz, 1H), 5.06 (d, J=6.0 Hz, 2H), 4.13 (t, J=14.5 Hz, 1H), 3.19-3.14 (m, 1H), 3.06-3.01 (m, 1H), 2.26-2.22 (m, 1H), 1.88-1.72 (m, 3H).

Example 196

4-((ethylamino)methyl)-N-((2-(4-fluorophenyl)-6-methylimidazo[1,2-a]pyridin-3-yl)methyl)pyrimidin-2-amine (196)

To a suspension of 2-((6-chloro-2-(4-fluorophenyl)imidazo[1,2-a]pyridin-3-yl)methylamino)pyrimidine-4-carbaldehyde (110 mg, 0.29 mmol) in CH$_2$Cl$_2$ (5 mL) was added acetic acid (0.5 mL) until the reaction became clear. Ethylamine (0.87 mmol, 3.0 eq) and Na(OAc)$_3$BH (0.58 mmol, 2.0 eq) were added and the reaction mixture was stirred for 18 h at room temperature. After this time the reaction was diluted with CH$_2$Cl$_2$ (20 mL) and quenched by the addition of satd. aq. NaHCO$_3$ (10 mL). After stirring for 10 min the layers were separated and the organic layer was dried over Na$_2$SO$_4$, filtered, concentrated and purified by reverse phase preparatory HPLC (silica gel, acetonitrile/water w/0.05% TFA) to afford the desired product. (0.060 g, 37% yield). M/e+ 411.1 for $C_{21}H_{20}ClFN_6$ (M+H)+; $^1$H-NMR (500 MHz, CDCl$_3$, δ) 8.48 (d, J=1.5 Hz, 1H), 8.29 (d, J=5.0 Hz, 1H), 7.78-7.75 (m, 2H), 7.58 (d, J=9.5 Hz, 1H), 7.21-7.15 (m, 3H), 6.70 (d, J=5.5 Hz, 1H), 5.24 (br s, 1H), 5.05 (d, J=5.5 Hz, 2H), 3.77 (s, 2H), 2.72 (q, J=7.5 Hz, 2H), 1.15 (t, J=7.5 Hz, 3H).

Example 197

4-((ethyl(methyl)amino)methyl)-N-((2-(4-fluorophenyl)-6-methylimidazo[1,2-a]pyridin-3-yl)methyl)pyrimidin-2-amine (197)

The title compound was prepared in the same fashion as that described for compound 196 from 2-((6-chloro-2-(4-fluorophenyl)imidazo[1,2-a]pyridin-3-yl)methylamino)pyrimidine-4-carbaldehyde and N-methylethanamine. (0.068 g, 40% yield). M/e+ 425.1 for $C_{22}H_{22}ClFN_6$ (M+H)+; $^1$H-NMR (500 MHz, CDCl$_3$, δ) 8.55 (s, 1H), 8.30 (d, J=5.0 Hz, 1H), 7.78-7.75 (m, 2H), 7.57 (d, J=9.5 Hz, 1H), 7.20-7.15 (m, 3H), 6.83 (d, J=5.0 Hz, 1H), 5.26 (br s, 1H), 5.05 (d, J=6.0 Hz, 2H), 3.48 (s, 2H), 2.51 (q, J=7.0 Hz, 2H), 2.28 (s, 3H), 1.11 (t, J=7.0 Hz, 3H)

Example 198

N-((6-chloro-2-(4-fluorophenyl)imidazo[1,2-a]pyridin-3-yl)methyl)-4-(pyrrolidin-1-ylmethyl)pyrimidin-2-amine (198)

The title compound was prepared in the same fashion as that described for compound 196 from 2-((6-chloro-2-(4-fluorophenyl)imidazo[1,2-a]pyridin-3-yl)methylamino)pyrimidine-4-carbaldehyde and pyrrolidine. (0.040 g, 33% yield). M/e+ 437.1 for $C_{23}H_{22}ClFN_6$ (M+H)+; $^1$H-NMR (500 MHz, CDCl$_3$, δ) 8.54 (s, 1H), 8.30 (d, J=5.0 Hz, 1H), 7.77-7.75 (m, 2H), 7.57 (dd, J=9.5. 0.5 Hz, 1H), 7.20-7.15 (m, 3H), 6.81 (d, J=5.0 Hz, 1H), 5.32-5.26 (m, 1H), 5.05 (d, J=5.5 Hz, 2H), 3.64 (s, 2H), 2.64 (br s, 4H), 1.84 (br s, 4H).

Example 199

6-fluoro-2-(4-fluorophenyl)-3-((1-methyl-1H-imidazol-2-yl)methyl)imidazo[1,2-a]pyridine (199)

Step 1: To a solution of 1-methyl-1H-imidazole (2.6 eq) in THF (5 mL) at −78° C. was added n-butyllithium (2.5 M) dropwise. After 15 min, the solution was warmed to 0° C. for 15 min. The solution was cooled back to −78° C. and the 6-fluoro-2-(4-fluorophenyl)imidazo[1,2-a]pyridine-3-carbaldehyde (1 eq) was added portion wise as a solid. The mixture was warmed to room temperature and stirred overnight, quenched with saturated NaHCO$_3$ (15 mL) and the solvents were removed under vacuum. The residue was triturated with diethyl ether or acetonitrile and the resulting solid was collected by filtration and washed with ether and water. The crude product was purified by chromatographed (silica gel, heptanes/ethyl acetate). m/e+ 341 (M+H)+.

Step 2: A Teflon-capped high-pressure glass bottle was charged with (6-fluoro-2-(4-fluorophenyl)imidazo[1,2-a]pyridin-3-yl)(1-methyl-1H-imidazol-2-yl)methanol (2.2 g, 6.4 mmoles, 1.0 eq.), dry CH$_2$Cl$_2$ (60 ml) and solid P$_2$I$_4$ (7.3 g, 12.9 mmoles, 2.0 eq.). The bottle was flushed with N$_2$ and heated at 40° C. for 60 hours. The reaction was quenched with NaHCO$_3$ (200 ml, 1.0 M in water), extracted (3×200 ml CH$_2$Cl$_2$), the organic layer was dried with MgSO$_4$ and concentrated on rotary evaporator. The crude residue was purified by flash chromatography (30%→70% gradient of 10% MeOH/90% EtOAc in hexanes on a 330 g silica gel column). The purified product was crystallized from hot EtOAc. Yield: 1.1 g (53%). Repeated crystallization provided additional 0.7 g (34%) having equal purity. (0.19 g, 53% yield). M/e$^+$ 325 for C$_{18}$H$_{15}$F$_2$N$_4$ (M+H)$^+$; $^1$H-NMR (400 MHz, CDCl$_3$) δ 8.35 (d, J=1.8 Hz, 1H), 7.68 (dd, J=7.7, 5.5 Hz, 2H), 7.57 (dd, J=9.9, 5.1 Hz, 1H), 7.25 (d, J=1.1 Hz, 1H), 7.18 (t, J=8.4 Hz, 1H), 7.11 (t, J=7.7 Hz, 1H), 6.92 (s, 1H), 6.74 (s, 1H), 4.50 (s, 2H), 3.19 (s, 3H) ppm.

Example 200

6-fluoro-2-(4-fluorophenyl)-3-((1-methyl-1H-1,2,4-triazol-5-yl)methyl)imidazo[1,2-a]pyridine (200)

The title compound was prepared according to Method C and the experimentals described for compound 199 from 6-fluoro-2-(4-fluorophenyl)imidazo[1,2-a]pyridine-3-carbaldehyde and 1-methyl-1H-1,2,4-triazole. (0.19 g, 53% yield). M/e+ 326.2 for C$_{17}$H$_{14}$F$_2$N$_5$ (M+H)$^+$; $^1$H-NMR (500 MHz, DMSO-d6, δ) 8.55 (dd, J=5.0, 2.0 Hz, 1H), 7.72-7.68 (m, 4H), 7.40-7.36 (m, 1H), 7.31-7.27 (m, 2H), 4.64 (s, 2H), 3.86 (s, 3H).

Example 201

3-((6-fluoro-2-(4-fluoropnyl)imidazo[1,2-a]pyridin-3-yl)methyl)-5-methyl-1,2,4-oxadiazole (201)

The title compound was prepared according to Method C and the experimentals described for compound 199 from 6-fluoro-2-(4-fluorophenyl)imidazo[1,2-a]pyridine-3-carbaldehyde and 5-methyl-1,2,4-oxadiazole. M/e$^+$ 327 for C$_{17}$H$_{13}$F$_2$N$_4$O (M+H)$^+$; $^1$H-NMR (400 MHz, CDCl$_3$) δ 8.22 (4.0, 2.2 Hz, 1H), 7.90 (dd, J=8.8, 5.5 Hz, 2H), 7.63 (dd, J=9.9, 5.1 Hz, 1H), 7.17 (m, 3H), 4.38 (s, 2H), 2.58 (s, 3H) ppm.

Example 202

3-((2-(4-chlorophenyl)imidazo[1,2-a]pyridin-3-yl)methyl)-5-methyl-1,2,4-oxadiazole (202)

The title compound was prepared according to Method C and the experimentals described for compound 199 from 2-(4-chlorophenyl)imidazo[1,2-a]pyridine-3-carbaldehyde and 5-methyl-1,2,4-oxadiazole. M/e$^+$ 325 for C$_{17}$H$_{14}$ClN$_4$O (M+H)$^+$; $^1$H-NMR (400 MHz, CDCl$_3$) δ 8.22 (d, J=6.9 Hz, 1H), 7.91 (d, J=8.4 Hz, 2H), 7.66 (d, J=8.8 Hz, 1H), 7.47 (d, J=8.4 Hz, 2H), 7.23 (m, 1H), 6.88 (t, J=6.9 Hz, 1H), 4.42 (d, J=0.7 Hz, 2H), 2.56 (s, 3H) ppm.

Example 203

2-((2-(4-chlorophenyl)-6-methylimidazo[1,2-a]pyridin-3-yl)methyl)-5-methyl-1,3,4-oxadiazole (203)

The title compound was prepared according to Method C and the experimentals described for compound 199 from 2-(4-chlorophenyl)-6-methylimidazo[1,2-a]pyridine-3-carbaldehyde and 2-methyl-1,3,4-oxadiazole. M/e$^+$ 339 for C$_{18}$H$_{16}$ClN$_4$O (M+H)$^+$; $^1$H-NMR (400 MHz, CDCl$_3$) δ 7.95 (s, 1H), 7.76 (d, J=8.4 Hz, 2H), 7.56 (d, J=9.1 Hz, 1H), 7.45 (d, J=8.4 Hz, 2H), 7.10 (dd, J=9.1, 1.4 Hz, 1H), 4.54 (s, 2H), 2.49 (s, 3H), 2.35 (s, 3H) ppm.

Example 204

2-((2-(4-chlorophenyl)imidazo[1,2-a]pyridin-3-yl)methyl)-5-methyl-1,3,4-oxadiazole (204)

The title compound was prepared according to Method C and the experimentals described for compound 199 from 2-(4-chlorophenyl)imidazo[1,2-a]pyridine-3-carbaldehyde and 2-methyl-1,3,4-oxadiazole. M/e$^+$ 325 for C$_{17}$H$_{14}$ClN$_4$O (M+H)$^+$; $^1$H-NMR (400 MHz, CDCl$_3$) δ 8.22 (d, J=6.6 Hz, 1H), 7.80 (d, J=8.4 Hz, 2H), 7.67 (d, J=9.1 Hz, 1H), 7.47 (d, J=8.4 Hz, 2H), 7.27 (t, J=6.9 Hz, 1H), 6.91 (d, J=6.6 Hz, 1H), 4.58 (s, 2H), 2.50 (s, 3H) ppm.

Example 205

2-((6-chloro-2-phenylimidazo[1,2-a]pyridin-3-yl)methyl)-5-methyl-1,3,4-oxadiazole (205)

The title compound was prepared according to Method C and the experimentals described for compound 199 from 6-chloro-2-phenylimidazo[1,2-a]pyridine-3-carbaldehyde and 2-methyl-1,3,4-oxadiazole. M/e$^+$ 325 for C$_{17}$H$_{14}$ClN$_4$O (M+H)$^+$; $^1$H-NMR (400 MHz, CDCl$_3$) δ 8.25 (d, J=1.4 Hz, 1H), 7.81 (d, J=8.4 Hz, 2H), 7.61 (d, J=9.5 Hz, 1H), 7.51 (d, J=8.4 Hz, 2H), 7.43 (d, J=7.3 Hz, 1H), 7.22 (dd, J=9.5, 1.8 Hz, 1H), 4.58 (s, 2H), 2.52 (s, 3H) ppm.

Example 206

2-(4-chlorophenyl)-3-((1-methyl-1H-imidazol-2-yl)methyl)imidazo[1,2-a]pyridine (206)

The title compound was prepared according to Method C and the experimentals described for compound 199 from 2-(4-chlorophenyl)imidazo[1,2-a]pyridine-3-carbaldehyde and 1-methyl-1H-imidazole. (21.6 mg, 19% yield). M/e$^+$ 323.1 for C$_{18}$H$_{15}$ClN$_4$ (M+H)$^+$; $^1$H-NMR (300 MHz, DMSO, δ) 8.25 (d, J=6.9 Hz, 1H), 7.75 (dd, J=8.7, 2.1 Hz, 2H), 7.61 (d, J=9.0 Hz, 1H), 7.51 (dd, J=8.4, 1.8 Hz, 2H), 7.28 (t, J=2.1 Hz, 1H), 7.08 (d, J=0.9 Hz, 1H), 6.91 (t, J=6.9 Hz, 1H), 6.68 (d, J=0.9 Hz, 1H), 4.53 (s, 2H), 3.58 (s, 3H).

Example 207

2-(4-Chlorophenyl)-3-((1-methyl-1H-1,2,4-triazol-5-yl)methyl)imidazo[1,2-a]pyridine (207)

The title compound was prepared according to Method C and the experimentals described for compound 199 from 2-(4-chlorophenyl)imidazo[1,2-a]pyridine-3-carbaldehyde and 1-methyl-1H-1,2,4-triazole. (0.22 g, 89% yield). M/e$^+$ 324.1 for C$_{17}$H$_{14}$ClN$_5$ (M+H)$^+$; $^1$H-NMR (300 MHz, DMSO-d$_6$, δ) 8.26 (d, J=6.9 Hz, 1H), 7.74-7.70 (m, 3H), 7.65-7.61 (m, 1H), 7.54-7.51 (m, 2H), 7.33-7.28 (m, 1H), 6.93 (td, J=6.8, 1.2 Hz, 1H), 4.68 (s, 2H), 3.87 (s, 3H).

Example 208

2-(4-chlorophenyl)-3-((1-vinyl-1H-imidazol-2-yl) methyl)imidazo[1,2-a]pyridine (208)

The title compound was prepared according to Method C and the experimentals described for compound 199 from 2-(4-chlorophenyl)imidazo[1,2-a]pyridine-3-carbaldehyde and 1-vinyl-1H-imidazole. (34 mg, 18%). $m/e^+=335$ $(M+H^+)$. $^1$H-NMR (400 MHz, CDCl$_3$, δ): 8.28 (d, 1H, D, J=7.0 Hz), 7.66 (d, 2H, D, J=10.2 Hz), 7.61 (d, 1H, D, J=9.2 Hz), 7.46 (d, 2H, D, J=8.5 Hz), 7.19 (t, 1H, D, J=7.9 Hz), 7.08 (d, 1H), 6.96 (d, 1H), 6.80 (t, 1H, D, J=7.0 Hz), 6.46 (m, 1H), 5.03 (m, 1H), 4.62 (m, 1H), 4.56 (s, 2H).

Example 209

6-fluoro-2-(4-fluorophenyl)-3-((1-vinyl-1H-1,2,4-triazol-5-yl)methyl)imidazo[1,2-a]pyridine (209)

The title compound was prepared according to Method C and the experimentals described for compound 199 from 6-fluoro-2-(4-fluorophenyl)imidazo[1,2-a]pyridine-3-carbaldehyde and 1-vinyl-1H-1,2,4-triazole. (55 mg, 36%). $m/e^+=338$ $(M+H^+)$.

Example 210

3-((1H-1,2,4-triazol-5-yl)methyl)-6-fluoro-2-(4-fluorophenyl)imidazo[1,2-a]pyridine (210)

To a solution of mercuric trifluroacetate (128 mg, 0.30 mmol) in 0.3 mL of water was added 0.3 mL of THF. The yellow suspension thus formed was mled to 0° C., and 6-fluoro-2-(4-fluorophenyl)-3-((1-vinyl-1H-1,2,4-triazol-5-yl)methyl)imidazo[1,2-a]pyridine (101 mg, 0.30 mmol) was added portion wise. After the addition was over, the reaction mixture was allowed to warm to room temperature and stirred for 12 h. After cooling to 0° C., 0.3 mL of 3 N NaOH followed by 0.3 mL of 0.5 M NaBH$_4$ in 3 N NaOH was added to the mixture. The mercury was allowed to settle, and the supernatant liquid decanted and extracted with CH2CH2. The extract was dried over anhydrous Na$_2$SO$_4$ and concentrated to give the crude product which was purified silica gel chromatography. 28 mg, 30% yield. $m/e^+=312$ $(M+H^+)$. $^1$H-NMR (400 MHz, CD$_3$OD, δ): 8.41 (m, 1H), 8.33 (s, 1H), 7.79 (m, 2H), 7.60 (m, 1H), 7.33 (m, 1H), 7.21 (m, 2H), 4.53 (s, 2H).

Example 211

3-((1H-1,2,4-triazol-5-yl)methyl)-2-(4-chlorophenyl) imidazo[1,2-a]pyridine (211)

The title compound was prepared according to the experimentals described for compound 210 from 2-(4-chlorophenyl)-3-((1-vinyl-1H-1,2,4-triazol-5-yl)methyl)imidazo[1,2-a]pyridine. $m/e^+$ 310 for C16H13ClN5 $(M+H)^+$.

Example 212

Ethyl 3-((2-(4-chlorophenyl)imidazo[1,2-a]pyridin-3-yl)methyl)-1,2,4-oxadiazole-5-carboxylate (212)

Step 1: 2-(2-(4-chlorophenyl)imidazo[1,2-a]pyridin-3-yl)acetonitrile 30.0 g of molecular sieves were activated under vacuum, at 100° C., for 1 h. 5.00 g of 3-(chloromethyl)-2-(4-chlorophenyl)imidazo[1,2-a]pyridine hydrochloride (15.94 mmol, 1 eq), 9.38 g of NaCN (191.3 mmol, 12 eq), 428 mg of Bu$_4$NCN (1.59 mmol, 0.1 eq), 9.56 g of NaI (63.77 mmol, 4 eq) and 150 mL of ACN were added. The mixture were stirred at RT, O/N. Sieves were filtered and washed with EtOAc. The filtrate was washed twice with NaHCO$_3$, dried on MgSO$_4$, filtered and concentrated to give 4.95 g of crude. It was purified by silica gel chromatography (MeOH/CH$_2$Cl$_2$, 0 to 5%) and gave two batches: batch #01 (very pure)=3.90 g, batch #02 (some impurities) was purified on activated carbon to give 0.90 g. Total yield=82%. $m/e^+=268$ $(M+H^+)$.

Step 2: 2-(2-(4-chlorophenyl)imidazo[1,2-a]pyridin-3-yl)-N'-hydroxyacetimidamide To a suspension of 2-(2-(4-chlorophenyl)imidazo[1,2-a] pyridin-3-yl)acetonitrile (0.13 mol, 34.0 g) in absolute EtOH (300 mL) was added NH$_2$OH.HCl (0.32 mol, 22.1 g) and K$_2$CO$_3$ (0.32 mol, 44.1 g), respectively. The mixture was stirred at r.t. overnight, filtrated, and washed with EtOH for 3 times. The EtOH-filtrate was concentrated to small volume, and the precipitation was collected by filtration, to give one partial products. The solid was dispersed into water, sonicated for 10 mins, filtrated, washed with water, and dried in vacuo, to give another partial products. Combined two portions products added up to 25.0 g (65.4%). $m/e^+=301$ $(M+H^+)$.

Step 3: ethyl 3-((2-(4-chlorophenyl)imidazo[1,2-a] pyridin-3-yl)methyl)-1,2,4-oxadiazole-5-carboxylate To a suspension of 2-(2-(4-chlorophenyl)imidazo[1,2-a] pyridin-3-yl)-N'-hydroxyacetimidamide (83.3 mmol, 25.0 g) in dry CHCl$_3$ (600 mL) was cooled to −40° C. in an ice/EtOH bath under N$_2$ atmosphere, Py. (100.0 mmol, 8.1 mL) was added in one portion, and followed by slowly adding ethyl 2-chloro-2-oxoacetate (166.6 mmol, 18.6 mL). After that, the reaction mixture was allowed to slowly rise up to r.t., and kept stirring for 1.0 H, D, then heated to 80 C for another 2 hs. The reaction mixture was cooled to r.t. and filtered, and the filtrate was evaporated under reduced pressure to give the brown residue, which was applied to C.C.eluted by petroleum/acetone (4:1, 2:1, 1:1, and 0:1). The acetone portion was concentrated in vacuo to give the solid, which was washed with acetone for 3 times, to obtain the product, 18.0 g (58.0%), as a white solid. $m/e^+=383$ $(M+H^+)$.

Example 213

Ethyl 3-((2-(4-chlorophenyl)-6-fluoroimidazo[1,2-a] pyridin-3-yl)methyl)-1,2,4-oxadiazole-5-carboxylate (213)

The title compound was prepared according to the experimentals described for compound 212 from 3-(chloromethyl)-2-(4-chlorophenyl)-6-fluoroimidazo[1,2-a]pyridine hydrochloride. $m/e^+$ 401 for C19H15ClFN4O3 $(M+H)^+$.

Example 214

Ethyl 3-((6-fluoro-2-(4-fluorophenyl)imidazo[1,2-a] pyridin-3-yl)methyl)-1,2,4-oxadiazole-5-carboxylate (214)

The title compound was prepared according to the experimentals described for compound 212 from 3-(chloromethyl)-

2-(4-chlorophenyl)-6-fluoroimidazo[1,2-a]pyridine hydrochloride. m/e⁺ 385 for C19H15F2N4O3 (M+H)⁺.

Example 215

3-((2-(4-chlorophenyl)imidazo[1,2-a]pyridin-3-yl)methyl)-1,2,4-oxadiazole-5-carbohydrazide (215)

To a solution of ethyl 3-((2-(4-chlorophenyl)imidazo[1,2-a]pyridin-3-yl)methyl)-1,2,4-oxadiazole-5-carboxylate (10.5 mmol, 4.0 g) in MeOH (50 mL) was cooled to 0° C., and 99% $NH_2NH_2 \cdot H_2O$ (62.8 mmol, 3.2 g) was then added dropwise. In the period of addition, lots of white precipitate was generated, kept stirring for 15 mins, the white solid was collected by filtration. The white solid was dispersed into MeOH again, sonicated for 10 mins, filtered, to give the final product (3.3 g, 86.0%). m/e⁺=369 (M+H⁺). ¹H NMR (400 MHz, in DMSO-$d_6$): δ 10.9-10.5 (1H, D, brd, NH), δ 8.44-8.42 (1H, D, d, J=6.8 Hz, ArH), δ 7.87-7.85 (2H, D, dd, J=6.4, 1.6 Hz, ArH), δ 7.67-7.64 (1H, D, d, J=9.2 Hz, ArH), δ 7.56-7.54 (2H, D, dd, J=6.4, 1.6 Hz, ArH), δ 7.38-7.25 (1H, D, m, ArH), δ 5.01-4.75 (2H, D, brd, NH₂), δ 4.75 (2H, D, s, CH₂).

Example 216

3-((2-(4-chlorophenyl)-6-fluoroimidazo[1,2-a]pyridin-3-yl)methyl)-1,2,4-oxadiazole-5-carbohydrazide (216)

The title compound was prepared in the same fashion as that for compound 215 from ethyl 3-((2-(4-chlorophenyl)-6-fluoroimidazo[1,2-a]pyridin-3-yl)methyl)-1,2,4-oxadiazole-5-carboxylate and hydrazine hydrate. m/e⁺=387 (M+H⁺). ¹H NMR (400 MHz, in DMSO-$d_6$): δ 10.75 (1H, D, brs, NH), δ 8.70-8.68 (1H, D, dd, J=4.4, 2.0 Hz, ArH), δ 7.83-7.80 (2H, D, d, J=8.4 Hz, ArH), δ 7.75-7.71 (1H, D, dd, J=10.0, 5.2 Hz, ArH), δ 7.55-7.53 (2H, D, d, J=8.4 Hz, ArH), δ 7.47-7.42 (1H, D, dt, J=8.4, 2.4 Hz, ArH), δ 5.01-4.75 (2H, D, brd, NH₂), δ 4.74 (2H, D, s, CH₂).

Example 217

3-((2-(4-chlorophenyl)-6-fluoroimidazo[1,2-a]pyridin-3-yl)methyl)-1,2,4-oxadiazole-5-carboxamide (217)

The title compound was prepared in the same fashion as that for compound 215 from ethyl 3-((2-(4-chlorophenyl)-6-fluoroimidazo[1,2-a]pyridin-3-yl)methyl)-1,2,4-oxadiazole-5-carboxylate and saturated ammonia in MeOH. (47 mg, 90.0%), as a white solid. m/e⁺=372 (M+H⁺). ¹H NMR (300 MHz, in DMSO-$d_6$): δ 8.68 (2H, D, brd, NH₂), δ 8.39 (1H, D, s, ArH), δ 7.82-7.80 (2H, D, d, J=8.4 Hz, ArH), δ 7.75-7.71 (1H, D, dd, J=9.6, 5.2 Hz, ArH), δ 7.55-7.53 (2H, D, d, J=8.4 Hz, ArH), δ 7.47-7.44 (1H, D, m, ArH), and δ 4.74 (2H, D, s, CH₂).

Example 218

3-((2-(4-fluorophenyl)-6-chloroimidazo[1,2-a]pyridin-3-yl)methyl)-1,2,4-oxadiazole-5-N-methyl-carboxamide (218)

The title compound was prepared in the same fashion as that for compound 215 from ethyl 3-((2-(4-chlorophenyl)-6-fluoroimidazo[1,2-a]pyridin-3-yl)methyl)-1,2,4-oxadiazole-5-carboxylate and methylamine. m/e⁺=386 (M+H⁺). ¹H NMR (400 MHz, in DMSO-$d_6$): δ 9.25 (H, D, brd, NH), δ 8.69-8.67 (1H, D, d, J=5.2, 2.0 Hz, ArH), δ 7.81-7.79 (2H, D, dd, J=9.2, 5.6 Hz, ArH), δ 7.75-7.71 (1H, D, dd, J=9.6, 5.2 Hz, ArH), δ 7.55-7.53 (1H, D, dt, J=9.6, 2.0 Hz, ArH), δ 7.47-7.42 (1H, D, t, J=8.8, ArH), δ 4.75 (2H, D, s, CH₂), and 2.77 (3H, D, s, CH₃).

Example 219

3-((2-(4-chlorophenyl)-6-fluoroimidazo[1,2-a]pyridin-3-yl)methyl)-1,2,4-oxadiazole-5-N,N-dimethyl-carboxamide (219)

The title compound was prepared in the same fashion as that for compound 215 from ethyl 3-((2-(4-chlorophenyl)-6-fluoroimidazo[1,2-a]pyridin-3-yl)methyl)-1,2,4-oxadiazole-5-carboxylate and dimethylamine. m/e⁺=400 (M+H⁺). ¹H NMR (400 MHz, in DMSO-$d_6$): δ 8.76-8.74 (1H, D, m, ArH), δ 7.83-7.81 (2H, D, d, J=8.4 Hz, ArH), δ 7.75-7.71 (1H, D, m, ArH), δ 7.56-7.54 (2H, D, d, J=8.6 Hz, ArH), δ 7.47-7.42 (1H, D, m, ArH), and δ 4.78 (2H, D, s, CH₂), 3.09 (3H, D, s, CH₃), 3.02 (3H, D, s, CH₃).

Example 220

3-((2-(4-fluorophenyl)-6-fluoroimidazo[1,2-a]pyridin-3-yl)methyl)-1,2,4-oxadiazole-5-N-methyl-carboxamide (220)

The title compound was prepared in the same fashion as that for compound 215 from ethyl 3-((6-fluoro-2-(4-fluorophenyl)imidazo[1,2-a]pyridin-3-yl)methyl)-1,2,4-oxadiazole-5-carboxylate and saturated ammonia in MeOH. m/e⁺=356 (M+H⁺). ¹H NMR (300 MHz, in DMSO-$d_6$): δ 8.68 (2H, D, brd, NH₂), δ 8.39 (1H, D, s, ArH), δ 7.84-7.80 (2H, D, d, J=8.4 Hz, ArH), δ 7.75-7.71 (1H, D, dd, J=9.6, 5.2 Hz, ArH), δ 7.46-7.41 (1H, D, m, ArH), δ 7.34-7.30 (2H, D, m, ArH), and δ 4.73 (2H, D, s, CH₂).

Example 221

3-((6-fluoro-2-(4-fluorophenyl)imidazo[1,2-a]pyridin-3-yl)methyl)-N-methyl-1,2,4-oxadiazole-5-carboxamide (221)

The title compound was prepared in the same fashion as that for compound 215 from ethyl 3-((6-fluoro-2-(4-fluorophenyl)imidazo[1,2-a]pyridin-3-yl)methyl)-1,2,4-oxadiazole-5-carboxylate and methylamine. m/e⁺=370 (M+H⁻). ¹H NMR (400 MHz, in DMSO-$d_6$): δ 9.23 (H, D, brd, NH), δ 8.66-8.65 (1H, D, dd, J=5.2, 2.0 Hz, ArH), δ 7.81-7.78 (2H, D, m, ArH), δ 7.45-7.40 (1H, D, dd, J=9.6, 5.2 Hz, ArH), δ 7.32-7.28 (2H, D, m, ArH), δ 4.72 (2H, D, s, CH₂), and 2.76 (3H, D, s, CH₃).

Example 222

3-((2-(4-chlorophenyl)-6-fluoroimidazo[1,2-a]pyridin-3-yl)methyl)-N-hydroxy-1,2,4-oxadiazole-5-carboxamide (222)

To a solution of ethyl 3-((2-(4-chlorophenyl)-6-fluoroimidazo[1,2-a]pyridin-3-yl)methyl)-1,2,4-oxadiazole-5-carboxylate (0.125 mmol, 50.0 mg) in EtOH (10 mL) was added NH₂OH·HCl (0.75 mmol, 52.1 mg) and K₂CO₃ (0.375 mmol, 51.8 mg) at r.t. The reaction mixture was stirred for 30 mins at r.t., and filtered. The filtrate was concentrated under reduced pressure, to give the title product (30 mg, 60.0%), as a white solid. m/e⁺=388 (M+H⁺). ¹H NMR (300 MHz, in DMSO-d₆): δ 12.14 (1H, D, brd, OH), δ 9.87 (1H, D, brd, NH), δ 8.69-8.68 (1H, D, dd, J=5.2, 2.4 Hz, ArH), δ 7.81-7.79 (2H, D, d, J=8.4 Hz, ArH), δ 7.74-7.71 (1H, D, dd, J=9.6, 5.2 Hz, ArH), δ 7.55-7.53 (2H, D, d, J=8.4 Hz, ArH), δ 7.47-7.41 (1H, D, m, ArH), and δ 4.73 (2H, D, s, CH₂).

Example 223

3-((2-(4-fluorophenyl)-6-fluoroimidazo[1,2-a]pyridin-3-yl)methyl)-N-hydroxy-1,2,4-oxadiazole-5-carboxamide (223)

The title compound was prepared in the same fashion as that for compound 222 from ethyl ethyl 3-((6-fluoro-2-(4-fluorophenyl)imidazo[1,2-a]pyridin-3-yl)methyl)-1,2,4-oxadiazole-5-carboxylate and hydroxylamine hydrochloride. m/e⁺=372 (M+H⁺). ¹H NMR (400 MHz, in DMSO-d₆): δ 8.68-8.67 (1H, D, dd, J=5.2, 2.0 Hz, ArH), δ 7.84-7.79 (2H, D, dd, J=9.2, 5.6 Hz, ArH), δ 7.73-7.70 (1H, D, dd, J=9.6, 5.2 Hz, ArH), δ 7.45-7.40 (1H, D, dt, J=9.6, 2.0 Hz, ArH), δ 7.34-7.29 (1H, D, t, J=8.8, ArH), and δ 4.70 (2H, D, s, CH₂).

Example 224

3-((2-(4-fluorophenyl)-6-fluoroimidazo[1,2-a]pyridin-3-yl)methyl)-N-methyoxy-1,2,4-oxadiazole-5-carboxamide (224)

The title compound was prepared in the same fashion as that for compound 222 from ethyl ethyl 3-((6-fluoro-2-(4-fluorophenyl)imidazo[1,2-a]pyridin-3-yl)methyl)-1,2,4-oxadiazole-5-carboxylate and O-methylhydroxylamine hydrochloride. m/e⁺=386 (M+H⁺). ¹H NMR (400 MHz, in DMSO-d₆): δ 8.55-8.53 (1H,m, ArH), δ 7.88-7.84 (2H, D, dd, J=9.2, 5.6 Hz, ArH), δ 7.67-7.63 (1H, D, dd, J=9.6, 5.2 Hz, ArH), δ 7.43-7.38 (2H, D, m ArH), δ 7.30-7.25 (1H, D, m, ArH), and δ 4.59 (2H, D, s, CH₂). δ 3.77 (3H, D, s, CH₃).

Example 225

3-((6-fluoro-2-(4-fluorophenyl)imidazo-[1,2-a]pyridin-3-yl)methyl)-N-hydroxy-N-methyl-1,2,4-oxadiazole-5-carboxamide (225)

The title compound was prepared in the same fashion as that for compound 222 from ethyl ethyl 3-((6-fluoro-2-(4-fluorophenyl)imidazo[1,2-a]pyridin-3-yl)methyl)-1,2,4-oxadiazole-5-carboxylate and N-methylhydroxylamine hydrochloride. m/e⁺=386 (M+H⁺). ¹H NMR (400 MHz, in DMSO-d₆): δ 10.97 (1H,s, OH),δ 8.84 (1H,m, ArH), δ 7.85-7.78 (3H,m, ArH), δ 7.58-7.39 (1H,m, ArH), δ 7.39-7.34 (2H, D, m ArH), δ 7.30-7.25 (1H, D, m, ArH), and δ 4.80 (2H, D, s, CH₂). δ 3.28 (3H, D, s, CH₃).

Example 226

N-hydroxy-3-((2-phenylimidazo[1,2-a]pyridin-3-yl)methyl)-1,2,4-oxadiazole-5-carboxamide (226)

The title compound was prepared in the same fashion as that for compound 222 from ethyl 3-((2-(4-chlorophenyl)imidazo[1,2-a]pyridin-3-yl)methyl)-1,2,4-oxadiazole-5-carboxylate and hydroxylamine hydrochloride. m/e⁺=370 (M+H⁺). ¹H NMR (400 MHz, in DMSO-d₆): δ 8.43-8.41 (1H, D, d, J=7.2 Hz, ArH), δ 8.31 (1H, D, s, ArH), δ 7.88-7.86 (2H, D, d, J=8.4 Hz, ArH), δ 7.65-7.62 (1H, D, d, J=9.2 Hz, ArH), δ 7.57-7.54 (1H, D, d, J=8.4 Hz, ArH), δ 7.35-7.31 (1H, D, t, J=8.0, ArH), δ 7.04-7.00 (1H, D, t, J=8.0, ArH), and δ 4.62 (2H, D, s, CH₂).

Example 227

3-((2H-1,2,3-triazol-4-yl)methyl)-6-chloro-2-(4-chlorophenyl)imidazo[1,2-a]pyridine (227)

Step 1: To a suspension of 6-chloro-3-(chloromethyl)-2-(4-chlorophenyl)imidazo[1,2-a]pyridine hydrochloride (1.7-2.9 mmol, 1.0 eq) in THF (20-40 mL) at −40° C. was added propynyl magnesium bromide (1.7-2.9 mmol, 1.0 eq) dropwise. After 10 min, more Grignard reagent (1.7-2.9 mmol, 1.0 eq) was added dropwise and the reaction was warmed to −20° C. for 30 min, followed by addition of more Grignard reagent (0.85-1.4 mmol, 0.5 eq). After this time the reaction mixture was warmed to 0° C. for 2H, D and then quenched with 1 M HCl (10 mL). The reaction mixture was neutralized with satd. aq. NaHCO₃ and extracted with ethyl acetate (50 mL). The organic layer was washed with brine, dried, concentrated, and purified by chromatography (silica gel, heptanes/ethyl acetate gradient) to afford.6-chloro-2-(4-chlorophenyl)-3-(prop-2-ynyl)imidazo[1,2-a]pyridine. (0.66 g, 73% yield). M/e⁺ 301.1 for C₁₆H₁₀Cl₂N₂ (M+H)⁺; ¹H-NMR (500 MHz, CDCl₃, δ) 8.19 (d, J=1.5 Hz, 1H), 7.71-7.69 (m, 2H), 7.61 (d, J=9.5 Hz, 1H), 7.48-7.46 (m, 2H), 7.22 (dd, J=2.0, 9.5 Hz, 1H), 3.93 (d, J=3.0 Hz, 2H), 2.19 (t, J=3.0 Hz, 1H).

Step 2: A mixture of 6-chloro-2-(4-chlorophenyl)-3-(prop-2-ynyl)imidazo[1,2-a]pyridine alkyne (0.8 mmol, 1.0 eq) and trimethylsilylazide (20 eq) was stirred in a microwave (300 W, 170° C.) for 5 hours. After this time the reaction mixture was diluted with CH₂Cl₂ (25 mL) and 1 M NaOH (5 mL) and stirred at room temperature for 18 hours. The reaction mixture was concentrated and used without further purification or characterization. An aliquot of the crude products was purified by reverse phase preparatory HPLC (silica gel, acetonitrile/water gradient) to obtain the desired product. M/e⁺ 344.1 for C₁₆H₁₁Cl₂N₅ (M+H)⁺; ¹H-NMR (300 MHz, DMSO-d₆, δ) 14.83 (s, 1H), 8.67 (d, J=1.2 Hz, 1H), 7.89-7.86 (m, 3H), 7.70-7.66 (m, 1H), 7.56-7.53 (m, 2H), 7.35 (dd, J=9.5, 2.0 Hz, 1H), 4.57 (s, 2H).

Example 228

6-chloro-2-(4-chlorophenyl)-3-((5-methyl-2H-1,2,3-triazol-4-yl)methyl)imidazo[1,2-a]pyridine (228)

The title compound was prepared according to the experimental described for compound 227 from 6-chloro-3-(chloromethyl)-2-(4-chlorophenyl)imidazo[1,2-a]pyridine hydrochloride and prop-1-ynylmagnesium bromide. m/e⁺ 359 for C17H14Cl2N5 (M+H)⁺.

Example 229

6-Chloro-2-(4-chlorophenyl)-3-((2,5-dimethyl-2H-1,2,3-triazol-4-yl)methyl)imidazo[1,2-a]pyridine (229)

To a suspension of the 6-chloro-2-(4-chlorophenyl)-3-((5-methyl-2H-1,2,3-triazol-4-yl)methyl)imidazo[1,2-a]pyridine (0.6-1.7 mmol, 1.0 eq) in DMF or THF (5-20 mL) was added potassium carbonate (3-5 eq) and either methyliodide or ethyliodide (3-5 eq) and the reaction mixture was heated at 75-85° C. for 18 h. After this time the reaction mixture was cooled and diluted with water (20-50 mL) and ethyl acetate (20-50 mL) and the layers were separated. The aqueous layer was extracted with ethyl acetate (10-30 mL) and the combined organic layers were dried over $Na_2SO_4$, concentrated and the residue was purified by chromatography (silica gel, heptane/ethyl acetate gradient) or reverse phase preparatory HPLC (acetonitrile/water gradient) to obtain the desired product. (0.14 g, 26% yield). M/e$^+$ 372.1 for $C_{18}H_{15}Cl_2N_5$ (M+H)$^+$; $^1$H-NMR (500 MHz, CDCl$_3$, δ) 8.09 (d, J=2.0 Hz, 1H), 7.69-7.67 (m, 2H), 7.58 (d, J=9.5 Hz, 1H), 7.45-7.44 (m, 2H), 7.17 (dd, J=9.5, 2.0 Hz, 1H), 4.33 (s, 2H), 4.05 (s, 3H), 2.01 (s, 3H).

Example 230

2-(4-chlorophenyl)-3-((5-(pyridin-2-yl)-4H-1,2,4-triazol-3-yl)methyl)imidazo[1,2-a]pyridine (230)

Step 1: A mixture of ethyl 2-(2-(4-chlorophenyl)imidazo [1,2-a]pyridin-3-yl)acetate (prepared from 2-(4-chlorophenyl)imidazo[1,2-a]pyridine and ethyl 2-oxoacetate by reluxing in toluene with catalytic amount of pTSA followed by dehydroxylation with P2I4 as illustrated in WO 2005/044818) (100 mg) was treated with hydrazine hydrate (0.5 ml) until the reacyion was complete. Excess hydrazine was removed under reduced pressure. The residue was dissolved in $CH_2Cl_2$ (10 mL) and was washed with sat. NaHCO$_3$, brine, dried with $Na_2SO_4$ and concentrated. m/e$^+$ 301 for C15H14N4O (M+H)$^+$.

Step 2: A mixture of 2-(2-(4-chlorophenyl)imidazo[1,2-a] pyridin-3-yl)acetohydrazide (0.55 mmol, 1.0 eq) in DMF (1-2 ml) and picolinimidamide hydrochloride (1.5 eq) was heated at 120° C. for 3 h. The mixture was cooled to rt, treated with sat. NaHCO$_3$ (5 ml), extracted with $CH_2Cl_2$ (10 ml). The organic solution was dried with $Na_2SO_4$, evaporated under vacuum. The crude product was purified by HPLC. M/e$^+$ 387 for $C_{21}H_{16}ClN_6$ (M+H)$^+$; $^1$H-NMR (400 MHz, CD$_3$OD) δ 9.11 (d, J=1.4 Hz, 1H), 8.56 (d, J=3.7 Hz, 1H), 8.36 (d, J=6.2 Hz, 2H), 7.77 (d, J=8.4 Hz, 2H), 7.70 (dt, J=8.4, 2.9 Hz, 2H), 7.36 (m, 2H), 6.99 (m, 2H), 4.64 (s, 2H) ppm.

Example 231

2-(4-chlorophenyl)-3-((5-isopropyl-4H-1,2,4-triazol-3-yl)methyl)imidazo[1,2-a]pyridine (231)

The title compound was prepared according to the experimental described for compound 230 from 2-(2-(4-chlorophenyl)imidazo[1,2-a]pyridin-3-yl)acetohydrazide and isobutyrimidamide hydrochloride. M/e$^+$ 352 for $C_{19}H_{19}ClN_5$ (M+H)$^+$; $^1$H-NMR (400 MHz, CDCl$_3$) δ 8.05 (m, 1H), 7.61 (d, J=8.4 Hz, 2H), 7.27 (m, 4H), 7.04 (t, J=7.3 Hz, 1H), 6.75 (t, J=6.6 Hz, 1H), 4.42 (s, 2H), 3.12 (m, 1H), 1.39 (s, 3H), 1.37 (s, 3H) ppm.

Example 232

6-chloro-3-((5-isopropyl-4H-1,2,4-triazol-3-yl)methyl)-2-phenylimidazo[1,2-a]pyridine (232)

The title compound was prepared according to the experimental described for compound 230 from 2-(6-chloro-2-phenylimidazo[1,2-a]pyridin-3-yl)acetohydrazide and isobutyrimidamide hydrochloride. M/e$^+$ 352 for $C_{19}H_{19}ClN_5$ (M+H)$^+$; $^1$H-NMR (400 MHz, CDCl$_3$) δ 8.23 (s, 1H), 7.72 (d, J=8.4 Hz, 2H), 7.29 (m, 5H), 7.00 (dd, J=9.5, 1.8 Hz, 1H), 4.40 (s, 2H), 3.03 (m, 1H), 1.29 (s, 3H), 1.28 (s, 3H) ppm.

Example 233

2-(4-chlorophenyl)-3-((5-methyl-4H-1,2,4-triazol-3-yl)methyl)imidazo[1,2-a]pyridine (233)

The title compound was prepared according to the experimental described for compound 230 from 2-(2-(4-chlorophenyl)imidazo[1,2-a]pyridin-3-yl)acetohydrazide and acetimidamide hydrochloride. M/e$^-$ 324 for $C_{17}H_{15}ClN_5$ (M+H)$^+$; $^1$H-NMR (400 MHz, CD$_3$OD) δ 8.27 (d, J=6.6 Hz, 1H), 7.76 (d, J=8.4 Hz, 2H), 7.58 (d, J=9.1 Hz, 1H), 7.46 (d, J=8.4 Hz, 2H), 7.35 (t, J=6.9 Hz, 1H), 6.95 (t, J=6.2 Hz, 1H), 4.46 (s, 2H), 2.37 (s, 3H) ppm.

Example 234

6-chloro-3-((5-methyl-4H-1,2,4-triazol-3-yl)methyl)-2-phenylimidazo[1,2-a]pyridine (234)

The title compound was prepared according to the experimental described for compound 230 from 2-(6-chloro-2-phenylimidazo[1,2-a]pyridin-3-yl)acetohydrazide and acetimidamide hydrochloride. M/e$^-$ 324 for $C_{17}H_{15}ClN_5$ (M+H)$^+$; $^1$H-NMR (400 MHz, CD$_3$OD) δ 8.43 (s, 1H), 7.74 (d, J=8.4 Hz, 2H), 7.63 (m, 1H), 7.57 (d, J=9.9 Hz, 1H), 7.46 (d, J=8.4 Hz, 2H), 7.39 (m, 2H), 4.46 (s, 2H), 2.38 (s, 3H) ppm.

Example 235

5-((2-(4-chlorophenyl)imidazo[1,2-a]pyridin-3-yl) methyl)-N-methyl-1,3,4-thiadiazol-2-amine (235)

A solution of 2-(2-(4-chlorophenyl)imidazo[1,2-α]pyridin-3-yl)acetohydrazide (0.1 g, 0.33 mmol) in EtOH (1 mL) was treated with isothiocyanatomethane (0.023 mL, 0.33 mmol) and refluxed for 3 h. The precipitated thiosemicarbazide was filtered and dissolved in concentrated sulfuric acid. The reaction mixture was stirred for 30 min at rt. The mixture was poured into cold water and the precipitated product was filtered in vacuo and washed with ditilled water. The crude product was recrystallized in EtOH to provide the title product as a yellow solid. M/e$^+$ 356 for $C_{17}H_{15}ClN_5S$ (M+H)$^+$; $^1$H-NMR (400 MHz, CDCl$_3$) δ 8.15 (d, J=6.9 Hz, 1H), 7.71 (d, J=8.4 Hz, 2H), 7.63 (d, J=9.1 Hz, 1H), 7.45 (d, J=8.4 Hz, 2H), 7.22 (m, 2H), 6.84 (t, J=6.6 Hz, 1H), 4.65 (s, 2H), 2.98 (s, 3H) ppm.

Example 236

3-((6-fluoro-2-(4-fluorophenyl)imidazo[1,2-a]pyridin-3-yl)methyl)-1,2,4-oxadiazol-5(4H)-one (236)

A solution of 2-(6-fluoro-2-(4-fluorophenyl)imidazo[1,2-α]pyridin-3-yl)-N'-hydroxyacetimidamide (0.040 g, 0.13 mmol) and triethylamine (0.025 mL, 0.198 mmol) in CHCl$_3$ (1 mL) was treated with phenyl carbonochloridate (0.018 mL, 0.19 mmol) and stirred for 1 h. The reaction mixture was washed with water (30 mL) and dichloromethane (30 mL). The organic solution was dried with $Na_2SO_4$, evaporated under vacuum. The crude product was purified by HPLC to provide the title product. M/e$^+$ 329 for $C_{16}H_{11}F_2N_4O_2$ (M+H)$^+$; $^1$H-NMR (400 MHz, CDCl$_3$) δ 8.69 (dd, J=4.0, 2.2

Hz, 1H), 7.77 (dd, J=9.9, 4.7 Hz, 1H), 7.69 (m, 2H), 7.62 (m, 2H), 7.29 (m, 2H), 4.45 (s, 2H) ppm.

Example 237

1-((2-(4-chlorophenyl)imidazo[1,2-a]pyridin-3-yl) methyl)-4-(2-(dimethylamino)ethylamino)-1H-pyrrol-2(5H)-one (237)

Step 1: A mixture of (2-(4-chlorophenyl)imidazo[1,2-a] pyridin-3-yl)methanamine (850 mg, 3.31 mmol), 380 uL of (Z)-methyl 4-chloro-3-methoxybut-2-enoate (3.31 mmol, 1 eq), 1.37 g of potassium carbonate (9.94 mmol, 3 eq), and 50 mg of sodium iodide (0.331 mmol, 0.1 eq) in 15 mL of CAN was heated to 60° C. and refluxed for 2 h. LCMS showed a mixture of the product, and the next step product (cyclization). Let the reaction go until no more Z-methyl 4-chloro-3-methoxybut-2-enoate was detedted. After cooled to room temperature, the mixture was filtere to remove the solid. The filtrate was concentrated under vacuum. The crude was used in next step without further purification. (1.07 g, 84%). m/e$^+$=386 (M+H$^+$).

Step 2: A mixture of 1.19 g of (Z)-methyl 4-((2-(4-chlorophenyl)imidazo[1,2-a]pyridin-3-yl)methylamino)-3-methoxybut-2-enoate (2.75 mmol, 1 eq) in 12 mL acetic acid (excess) was stirred at 90° C. and refluxed for 2H, D, then diluted with EtOAc, washed with an excess of NaHCO$_3$ (aq, sat), dried on MgSO$_4$, filtered and concentrated to give 788 mg of a yellow solid. The product was then purified by a silica gel chromatography (EtOAc/Hexane, 2 to 100%) (420 mg, 43%). m/e$^+$=354 (M+H$^+$).

Step 3: To a mixture of 100 mg of 1-((2-(4-chlorophenyl) imidazo[1,2-a]pyridin-3-yl)methyl)-4-methoxy-1H-pyrrol-2 (5H)-one (0.251 mmol, 1 eq) in 1 mL of N,N-dimethylethane-1,2-diamine in a sealed tube, one drop of HCl was added. The solution was heated at 140° C., O/N. The mixture was then diluted with EtOAc, washed with an excess of NaHCO$_3$ (aq, sat), dried on MgSO$_4$, filtered and concentrated. The crude was purified on silica gel chromatography (MeOH:NH$_4$OH (95:5)/EtOAc, 0 to 15%). The product was then washed with ether to give a white solid. (37 mg, 32%) m/e$^+$=410 (M+H$^+$). $^1$H-NMR (400 MHz, CDCl$_3$, δ): 8.51 (d, 1H, D, J=6.6 Hz), 7.72 (d, 2H, D, J=8.6 Hz), 7.61 (d, 1H, D, J=9.2 Hz), 7.45 (d, 2H, D, J=8.4 Hz), 7.24 (t, 1H, D, J=8.8 Hz), 6.85 (t, 1H, D, J=6.4 Hz), 5.06 (s, 2H), 4.89 (m, 1H), 4.67 (s, 1H), 3.56 (s, 2H), 2.99 (m, 2H), 2.42 (m, 2H), 2.15 (s, 6H).

Example 238

1-((2-(4-chlorophenyl)imidazo[1,2-a]pyridin-3-yl) methyl)-4-(4-methylpiperazin-1-yl)-1H-pyrrol-2 (5H)-one (238)

The title compound was prepared according to the experimental for compound 237 from 1-((2-(4-chlorophenyl)imidazo[1,2-a]pyridin-3-yl)methyl)-4-methoxy-1H-pyrrol-2 (5H)-one and 1-methylpiperazine. (56 mg, 47%) m/e$^+$=422 (M+H$^+$). $^1$H-NMR (400 MHz, CDCl$_3$, δ): 8.47 (d, 1H, D, J=7.0 Hz), 7.73 (d, 2H, D, J=8.4 Hz), 7.62 (d, 1H, D, J=9.1 Hz), 7.47 (d, 2H, D, J=8.4 Hz), 7.25 (t, 1H, D, J=7.3 Hz), 6.85 (t, 1H, D, J=6.4 Hz), 5.09 (s, 2H), 4.74 (s, 1H), 3.57 (s, 2H), 3.03 (m, 4H), 2.36 (m, 4H), 2.27 (s, 3H).

Example 239

1-((2-(4-chlorophenyl)imidazo[1,2-a]pyridin-3-yl) methyl)-4-(piperidin-1-yl)-1H-pyrrol-2(5H)-one (239)

The title compound was prepared according to the experimental for compound 237 from 1-((2-(4-chlorophenyl)imidazo[1,2-a]pyridin-3-yl)methyl)-4-methoxy-1H-pyrrol-2 (5H)-one and piperidine. (62 mg, 54%) m/e$^+$=407 (M+H$^+$). $^1$H-NMR (400 MHz, CDCl$_3$, δ): 8.49 (d, 1H, D, J=7.0 Hz), 7.73 (d, 2H, D, J=8.4 Hz), 7.62 (d, 1H, D, J=9.2 Hz), 7.47 (d, 2H, D, J=8.4 Hz), 7.25 (t, 1H, D, J=7.3 Hz), 6.85 (t, 1H, D, J=7.3 Hz), 5.09 (s, 2H), 4.69 (s, 1H), 3.56 (s, 2H), 2.99 (m, 4H), 1.63 (m, 2H), 1.53 (m, 4H).

Example 240

1-((2-(4-chlorophenyl)imidazo[1,2-a]pyridin-3-yl) methyl)-4-(3-hydroxypyrrolidin-1-yl)-1H-pyrrol-2 (5H)-one (240)

The title compound was prepared according to the experimental for compound 237 from 1-((2-(4-chlorophenyl)imidazo[1,2-a]pyridin-3-yl)methyl)-4-methoxy-1H-pyrrol-2 (5H)-one and pyrrolidin-3-ol. (33 mg, 32%) m/e$^+$=409 (M+H$^+$). $^1$H-NMR (400 MHz, CDCl$_3$, δ): 8.46 (d, 1H, D, J=7.0 Hz), 7.73 (d, 2H, D, J=8.4 Hz), 7.61 (d, 1H, D, J=9.1 Hz), 7.46 (d, 2H, D, J=8.4 Hz), 7.25 (t, 1H, D, J=7.3 Hz), 6.84 (t, 1H, D, J=7.3 Hz), 5.09 (s, 2H), 4.57 (s, 1H), 4.53 (m, 1H), 3.55 (s, 2H), 3.2 (m, 4H), 2.1 (m, 3H).

Example 241

1-((2-(4-chlorophenyl)imidazo[1,2-a]pyridin-3-yl) methyl)-4-(4-hydroxypiperidin-1-yl)-1H-pyrrol-2 (5H)-one (241)

The title compound was prepared according to the experimental for compound 237 from 1-((2-(4-chlorophenyl)imidazo[1,2-a]pyridin-3-yl)methyl)-4-methoxy-1H-pyrrol-2 (5H)-one and piperidin-4-ol. (49 mg, 41%) m/e$^+$=423 (M+H$^+$). $^1$H-NMR (400 MHz, CDCl$_3$, δ): 8.47 (d, 1H, D, J=7.0 Hz), 7.73 (d, 2H, D, J=8.4 Hz), 7.62 (d, 1H, D, J=9.2 Hz), 7.47 (d, 2H, D, J=8.8 Hz), 7.25 (t, 1H, D, J=7.3 Hz), 6.85 (t, 1H, D, J=7.3 Hz), 5.09 (s, 2H), 4.73 (s, 1H), 3.87 (m, 1H), 3.57 (s, 2H), 3.25 (m, 2H), 2.87 (m, 2H), 1.7 (m, 4H).

Example 242

Preparation of 1-((2-(4-bromophenyl)imidazo[1,2-a] pyridin-3-yl)methyl)-4-(2-(dimethylamino)ethylamino)-1H-pyrrol-2(5H)-one (242)

The title compound was prepared according to the experimental for compound 237 from (2-(4-bromophenyl)imidazo [1,2-a]pyridin-3-yl)methanamine. m/e$^+$=454 (M+H$^+$). $^1$H-NMR (400 MHz, CDCl$_3$, δ): 8.51 (d, 1H, D, J=5.8 Hz), 7.63 (m, 5H), 7.26 (m, 1H), 6.85 (t, 1H, D, J=6.6 Hz), 5.06 (s, 2H), 4.88 (m, 1H), 4.67 (s, 1H), 3.55 (s, 2H), 2.99 (m, 2H), 2.42 (m, 2H), 2.16 (s, 6H).

Example 243

N$^1$-(6-((2-(4-chlorophenyl)imidazo[1,2-a]pyridin-3-yl)methyl)pyrimidin-4-yl)-N$^2$,N$^2$-dimethylethane-1, 2-diamine (243)

Step 1: 6-((2-(4-chlorophenyl)imidazo[1,2-a]pyridin-3-yl)methyl)pyrimidin-4-ol

To 20 mL of ACN were added 500 mg of 2-(2-(4-chlorophenyl)imidazo[1,2-a]pyridin-3-yl)acetonitrile (1.87 mmol, 1 eq), 1.12 g of 4,6-dichloropyrimidine (7.47 mmol, 4 eq) and 840 mg of KOBu (7.47 mmol, 4 eq). The mixture was stirred at RT, O/N. The solution was then diluted with EtOAc, washed with NaHCO$_3$, dried on MgSO$_4$, filtered and concentrated to give 1.32 g of a crude nitrile intermediate (m/e$^+$=380). This intermediate was dissolved in a mixture of 36 mL of TFA and 360 uL of water. It was heated to 150° C. under microwaves for 5 min. Excess TFA was then removed by blowing a steam of N$_2$ over the solution. The residue was diluted with EtOAc, washed with NaHCO$_3$, dried on MgSO$_4$, filtered and concentrated to give 840 mg of the final crude. It was purified by silica gel chromatography (MeOH/CH$_2$Cl$_2$, 1 to 5%) (360 mg, 57%). m/e$^+$=337 (M+H$^+$).

Step 2: 2-(4-chlorophenyl)-3-((6-chloropyrimidin-4-yl)methyl)imidazo[1,2-a]pyridine To a mixture of 360 mg of 6-((2-(4-chlorophenyl)imidazo[1,2-a]pyridin-3-yl)methyl)pyrimidin-4-ol (1.07 mmol, 1 eq) in 5 mL of ACN was added 0.98 mL of POCl$_3$ (10.7 mmol. 10 eq). The mixture was heated to 65° C. and stirred for 1 h. The solution was then diluted with EtOAc, washed with NaHCO$_3$, dried on MgSO$_4$, filtered and concentrated (210 mg, 55%) m/e$^+$=355 (M+H$^+$).

Step 3: N1-(6-((2-(4-chlorophenyl)imidazo[1,2-a]pyridin-3-yl)methyl)pyrimidin-4-yl)N2,N2-dimethylethane-1,2-diamine A mixture of 100 mg of 2-(4-chlorophenyl)-3-((6-chloropyrimidin-4-yl)methyl)imidazo[1,2-a]pyridine (0.282 mmol, 1 eq) in 1 mL of N,N-dimethylethane-1,2-diamine (excess) in a sealed tube was heated to 95° C. for 2 h. The solution was then diluted with EtOAc, washed with water, dried on MgSO$_4$, filtered and concentrated. The crude was purified by silica gel chromatography (MeOH:NH$_4$OH (95:5)/EtOAc, 0 to 15%). The product was finally washed with ether (33 mg, 29%) m/e$^+$=407 (M+H$^+$). $^1$H-NMR (400 MHz, CDCl$_3$, δ): 8.55 (s, 1H), 7.90 (d, 1H, D, J=6.6 Hz), 7.73 (d, 2H, D, J=8.4 Hz), 7.67 (d, 1H, D, J=9.2 Hz), 7.42 (d, 2H, D, J=8.8 Hz), 7.25 (t, 1H, D, J=7.7 Hz), 6.81 (t, 1H, D, 7.7 Hz), 5.86 (s, 1H), 4.38 (s, 2H), 2.43 (m, 2H), 2.17 (s, 6H).

Example 244

2-(4-chlorophenyl)-3-((6-(4-methylpiperazin-1-yl)pyrimidin-4-yl)methyl)imidazo[1,2-a]pyridine (244)

The title compound was prepared according to Method D and the experimental for compound 243 from 2-(4-chlorophenyl)-3-((6-chloropyrimidin-4-yl)methyl)imidazo[1,2-a]pyridine and 1-methylpiperazine. (59 mg, 45%) m/e$^+$=419 (M+H$^+$). $^1$H-NMR (400 MHz, CDCl$_3$, δ): 8.57 (s, 1H), 7.93 (d, 1H, D, J=7.0 Hz), 7.73 (d, 2H, D, J=8.4 Hz), 7.67 (d, 1H, D, J=8.8 Hz), 7.42 (d, 2H, D, J=8.8 Hz), 7.25 (t, 1H, D, J=7.7 Hz), 6.81 (t, 1H, D, 7.7 Hz), 6.05 (s, 1H), 4.39 (s, 2H), 3.48 (m, 4H), 2.37 (m, 4H), 2.28 (s, 3H).

As previously stated, the Examples included herein are for illustrative purposes only, and the invention is in no way limited to the embodiments prepared in the Examples.

Example 245

Compounds of the invention were assessed for their binding to the benzodiazepine receptor by the test of Speth et al. [*Life Sci.* 24, 351 (1979)] for central benzodiazepine receptors and LeFur et al. [*Life Sci.* 33, 449 (1983)] for peripheral receptors. The compounds were tested first at 1.0E-09, 1.0E-07 and 1.0E-05 M in single determination. In the assays where a compound showed a % inhibition higher than 50% at either concentration, it was tested further at five concentrations in duplicate to obtain competition curves. The specific ligand binding to the receptor is defined as the difference between the total binding and the nonspecific binding determined in the presence of an excess of unlabelled ligand. In each experiment, the respective reference compound was tested concurrently with the test compounds in order to assess the assay suitability. It was tested at several concentrations (for IC$_{50}$ value determination), and the data were compared with historical values. The assay was rendered valid if suitability criteria were met.

BZD central binding data for the compounds is provided in Table 3, wherein is provided the percent inhibition of central BZD in the presence of 1000 nM of the compound. The sign "++" indicates that percentage of inhibition of central BZD site binding is greater than 80% in the presence of 1000 nM of the compound; the sign "+" indicates that percentage of inhibition of central BZD site binding is greater than 50% but less than 80% in the presence of 1000 nM of the compound; the sign "−" indicates that percentage of inhibition of central BZD site binding is less than 50% in the presence of 1000 nM of the compound.

TABLE 3

| Compound Index | % Inhibition at 1000 nM for CBZD |
| --- | --- |
| 1 | ++ |
| 2 | ++ |
| 3 | + |
| 4 | ++ |
| 5 | ++ |
| 6 | ++ |
| 7 | ++ |
| 8 | ++ |
| 9 | ++ |
| 10 | ++ |
| 11 | ++ |
| 12 | ++ |
| 13 | + |
| 14 | − |
| 15 | ++ |
| 16 | ++ |
| 17 | ++ |
| 18 | ++ |
| 19 | ++ |
| 21 | ++ |
| 22 | ++ |
| 23 | ++ |
| 24 | ++ |
| 26 | ++ |
| 27 | ++ |
| 28 | ++ |
| 29 | ++ |
| 30 | + |
| 31 | + |
| 32 | ++ |
| 33 | ++ |
| 34 | + |
| 35 | + |
| 36 | + |
| 37 | − |
| 38 | ++ |
| 39 | ++ |
| 40 | ++ |
| 41 | ++ |
| 43 | ++ |
| 44 | ++ |
| 45 | + |
| 46 | ++ |
| 47 | + |
| 48 | ++ |
| 49 | ++ |
| 50 | + |

TABLE 3-continued

| Compound Index | % Inhibition at 1000 nM for CBZD |
|---|---|
| 51 | ++ |
| 54 | ++ |
| 55 | ++ |
| 56 | ++ |
| 57 | ++ |
| 58 | ++ |
| 59 | + |
| 60 | ++ |
| 61 | ++ |
| 62 | ++ |
| 63 | ++ |
| 64 | ++ |
| 65 | ++ |
| 67 | ++ |
| 68 | ++ |
| 69 | ++ |
| 70 | + |
| 71 | + |
| 72 | ++ |
| 74 | ++ |
| 75 | ++ |
| 76 | ++ |
| 77 | ++ |
| 78 | ++ |
| 79 | + |
| 80 | ++ |
| 81 | ++ |
| 82 | ++ |
| 87 | + |
| 88 | ++ |
| 89 | ++ |
| 90 | ++ |
| 91 | ++ |
| 92 | ++ |
| 93 | ++ |
| 94 | ++ |
| 95 | ++ |
| 96 | ++ |
| 97 | ++ |
| 101 | ++ |
| 102 | + |
| 104 | ++ |
| 107 | ++ |
| 108 | ++ |
| 109 | ++ |
| 111 | ++ |
| 112 | ++ |
| 113 | ++ |
| 115 | ++ |
| 116 | ++ |
| 117 | ++ |
| 118 | ++ |
| 119 | ++ |
| 120 | ++ |
| 121 | ++ |
| 122 | ++ |
| 123 | ++ |
| 124 | ++ |
| 125 | ++ |
| 126 | − |
| 127 | + |
| 128 | ++ |
| 129 | ++ |
| 130 | ++ |
| 131 | ++ |
| 132 | ++ |
| 133 | ++ |
| 134 | ++ |
| 135 | ++ |
| 136 | ++ |
| 137 | ++ |
| 138 | ++ |
| 139 | ++ |
| 140 | ++ |
| 143 | ++ |
| 144 | ++ |
| 146 | ++ |
| 147 | ++ |
| 148 | ++ |
| 149 | ++ |
| 150 | ++ |
| 151 | ++ |
| 152 | + |
| 153 | ++ |
| 154 | ++ |
| 155 | + |
| 156 | ++ |
| 157 | ++ |
| 158 | ++ |
| 159 | ++ |
| 160 | ++ |
| 161 | ++ |
| 162 | ++ |
| 163 | ++ |
| 164 | ++ |
| 165 | ++ |
| 166 | ++ |
| 167 | ++ |
| 168 | ++ |
| 169 | ++ |
| 170 | ++ |
| 171 | ++ |
| 172 | ++ |
| 173 | ++ |
| 174 | ++ |
| 175 | ++ |
| 176 | ++ |
| 177 | + |
| 178 | + |
| 179 | ++ |
| 180 | ++ |
| 181 | ++ |
| 183 | ++ |
| 184 | ++ |
| 185 | ++ |
| 186 | ++ |
| 187 | ++ |
| 188 | ++ |
| 189 | ++ |
| 190 | ++ |
| 191 | ++ |
| 192 | ++ |
| 193 | ++ |
| 194 | + |
| 195 | ++ |
| 196 | ++ |
| 198 | ++ |
| 199 | ++ |
| 200 | ++ |
| 201 | ++ |
| 202 | ++ |
| 203 | ++ |
| 204 | ++ |
| 205 | ++ |
| 206 | ++ |
| 207 | ++ |
| 210 | ++ |
| 227 | ++ |
| 229 | ++ |
| 230 | ++ |
| 231 | ++ |
| 232 | ++ |
| 233 | ++ |
| 234 | ++ |
| 235 | + |
| 236 | ++ |
| 237 | ++ |
| 238 | ++ |
| 239 | ++ |
| 240 | ++ |
| 241 | ++ |
| 242 | ++ |

TABLE 3-continued

| Compound Index | % Inhibition at 1000 nM for CBZD |
|---|---|
| 243 | ++ |
| 244 | ++ |

The results of these in vitro tests are accepted by persons of skill in the art as predictive of therapeutic utility in vivo.

Example 246

Electrophysiology protocol: Oocytes were prepared from adult female *Xenopus laevis* frogs. cRNA encoding human α1, α2, α3, α5, β3 and γ2L GABA$_A$ receptor subunits was injected into the cytoplasm of stage 5 or 6 oocytes using the Robocyte Robot (Multi Channel Systems, Reutlingen, Germany). Two-electrode voltage clamp recordings were made in 96-well plates using the Robocyte Robot. Oocytes were impaled using recording heads with two glass electrodes containing 1.5 M potassium acetate and 0.5 M KCl and held at a membrane potential of −80 mV. Oocytes were continually perfused with a ND96 solution (96 mM NaCl, 2 mM KCl, 0.1 mM CaCl$_2$, and 5 mM HEPES, pH 7.5) using a Gilson 222 XL Liquid Handler and Gilson Minipuls 3 Peristaltic Pump (Gilson Medical Electronics, Middleton, Wis., USA). The protocol consisted of three 20-s applications of GABA that gave a 20% of the maximum response (EC$_{20}$: 60 μM) to allow for headroom to determine a baseline GABA response. To assess the potentiation, oocytes were first exposed to a single 1 μM chlordiazepoxide (CDP) as a potentiation standard. Oocytes with insufficient expression levels (currents below threshold) or insufficient γ2L subunit incorporation (judged by rapid desensitization upon GABA application, or by insufficient potentiation by CDP) were not included in analysis. Following this control application, a given oocyte was exposed to test compounds at 100 nM concentrations. Only one concentration of one compound was tested per oocyte. Results are displayed in Table 4. The sign "++" indicates that percentage of potentiation is greater than or equal to 50% in the presence of 100 nM of the compound; the sign "+" indicates that percentage of potentiation is greater than or equal to 10% but less than 50% in the presence of 100 nM of the compound; the sign "0" indicates that percentage of potentiation is between about 10% to about −10%; the sign "−" indicates that percentage of potentiation is less than or equal to −10% in the presence of 100 nM of the compound. One skilled in the art will recognize that subtypes contribute to the effects of GABA-A modulators. Such that compounds favoring different subtypes can have different therapeutic effects. The magnitude of modulation, for example, partial modulators can influence the effects in vivo. "++" indicates a greater modulation that "+" so that at any given subtype "++" inducates a greater amount of modulation for that subtype. In some embodiments, modulation favoring alpha 1 relative to alpha2 and/or alpha 3 can have sedative hypnotic effects. In other embodiments, compounds with reduced selectivity of alpha 1 can express anxiolytic effects with less sedation. Compounds with selectivity for alpha 5 can have memory/cognition enhancing effects.

TABLE 4

Percentage of potentiations of compounds for α1, α2, α3 and α5 subtype containing GABA-A receptors

| Compound Index | alpha1 | alpha2 | alpha3 | alpha5 |
|---|---|---|---|---|
| 2 | + | + | | |
| 4 | + | 0 | | |
| 6 | + | + | | |
| 7 | + | + | | |
| 8 | ++ | + | | |
| 9 | + | + | | |
| 15 | + | + | + | 0 |
| 17 | + | + | 0 | 0 |
| 19 | + | + | | |
| 21 | + | + | + | 0 |
| 23 | + | + | + | 0 |
| 25 | + | ++ | | |
| 27 | + | + | | |
| 29 | ++ | ++ | | |
| 32 | + | + | | |
| 39 | + | + | + | 0 |
| 40 | 0 | + | | |
| 42 | + | + | | |
| 43 | 0 | + | | |
| 44 | 0 | 0 | | |
| 46 | + | 0 | | |
| 47 | 0 | 0 | | |
| 49 | 0 | + | | |
| 56 | + | ++ | | |
| 57 | + | ++ | | |
| 58 | + | + | 0 | 0 |
| 59 | 0 | 0 | | |
| 60 | 0 | + | | |
| 61 | + | + | ++ | |
| 62 | + | 0 | | |
| 63 | + | 0 | | |
| 64 | + | + | | |
| 72 | + | ++ | + | 0 |
| 73 | + | + | | |
| 76 | 0 | + | | |
| 77 | 0 | + | | |
| 78 | + | + | | |
| 81 | + | + | | |
| 88 | 0 | + | | |
| 90 | + | + | | |
| 105 | + | + | | |
| 106 | + | + | | |
| 114 | ++ | + | + | 0 |
| 115 | + | + | | |
| 118 | + | ++ | | |
| 119 | 0 | + | 0 | 0 |
| 120 | ++ | ++ | | |
| 121 | ++ | ++ | | |
| 123 | + | + | | |
| 125 | 0 | + | | |
| 127 | 0 | + | | |
| 128 | 0 | + | 0 | + |
| 133 | + | ++ | 0 | 0 |
| 135 | | ++ | | |
| 136 | + | ++ | | |
| 137 | + | + | | |
| 138 | + | + | | |
| 139 | + | + | 0 | 0 |
| 145 | ++ | + | | |
| 147 | ++ | | | |
| 150 | 0 | + | | |
| 157 | + | | | |
| 158 | 0 | + | + | 0 |
| 159 | + | + | | |
| 160 | + | + | | |
| 162 | + | | | |
| 165 | + | + | | |
| 170 | + | + | + | 0 |
| 179 | 0 | 0 | | |
| 183 | ++ | ++ | 0 | |
| 184 | + | + | | |
| 187 | − | 0 | | |
| 188 | ++ | ++ | | |
| 189 | ++ | ++ | | |
| 191 | + | + | | |

TABLE 4-continued

Percentage of potentiations of compounds for α1, α2,
α3 and α5 subtype containing GABA-A receptors

| Compound Index | alpha1 | alpha2 | alpha3 | alpha5 |
|---|---|---|---|---|
| 192 | + | + | | |
| 193 | + | + | | |
| 195 | ++ | ++ | | |
| 196 | ++ | ++ | | |
| 198 | ++ | ++ | | |
| 200 | + | ++ | | |
| 204 | 0 | + | | |
| 205 | 0 | 0 | 0 | 0 |
| 206 | ++ | ++ | | |
| 207 | + | + | | |
| 211 | + | ++ | | |
| 215 | 0 | + | | |
| 216 | + | ++ | + | 0 |
| 217 | + | ++ | | |
| 218 | + | ++ | | |
| 220 | 0 | + | 0 | 0 |
| 221 | 0 | + | | |
| 222 | 0 | ++ | | |
| 223 | − | + | | |
| 224 | 0 | + | | |
| 225 | − | + | | |
| 227 | ++ | | | |
| 229 | + | + | | |
| 230 | + | + | + | + |
| 233 | + | ++ | | |
| 234 | + | ++ | | |
| 237 | 0 | + | | |
| 238 | + | + | | |
| 240 | ++ | + | 0 | 0 |
| 242 | + | + | 0 | |
| 243 | + | + | | |

Example 247

Stress-Induced Hyperthermia (SIH) protocol: The stress-induced hyperthermia (SIH) test is based on the principle that animal's have a natural hyperthermic response to stress. The test involves taking two measures of rectal temperature in the same animal within a 10 minute interval. The two sequential rectal temperature measurements reveal the animal's basal temperature (T1) and 10 minutes later, an enhanced body temperature (T2) due to the stress of the first rectal temperature. The difference T2-T1 (delta T) is the SIH response. When anxiolytic drugs are administered prior to recording temperature, they reduce the stress response.

Adult male 129SVEV mice (6 weeks old) from Taconic Laboratories (Germantown, N.Y.) were used in these studies. Upon receipt, mice were assigned unique identification numbers (tail marked) and were group housed in OptiMICE ventilated racks. All animals remained group housed during the remainder of the study unless indicated otherwise. All mice were acclimated to the colony room for at least two weeks prior to testing and were subsequently tested at 8 weeks of age. During the period of acclimation, mice were examined on a regular basis, handled, and weighed to assure adequate healtH, D and suitability. Mice were maintained on a 12/12 light/dark cycle with the light on at 7:00 a.m. The room temperature was maintained between 20 and 23° C. with a relative humidity maintained between 30% and 70%. Chow and water were provided ad libitum for the duration of the study. Animals were not disturbed between test days.

On the day prior to testing, the mice were brought to the experimental room one hour before scheduled lights out and singly housed overnight with food and water ad libitum. On the morning of the experiment, mice were orally dosed via gavage with vehicle, CDP (10 mg/kg) or compounds of the present invention (3, 10 or 30 mg/kg) and placed back in the cages. One hour after oral gavage, each animal was removed from the holding cage and held in a supine position and rectal temperature was measured. The rectal probe was attached to a PhysiTemp digital thermometer (Fisher Scientific) which provides temperature readings at 0.1° C. accuracy. The probe remained inside the animal for approximately 5 seconds or until body temperature reached stability. This temperature was recorded as the baseline rectal temperature (T1). The animal was immediately placed back to the holding cage and after a 10-min interval the $2^{nd}$ rectal temperature (T2) was taken using the same procedure as in measuring T1. Before each insertion, the rectal probe was cleaned with an alcohol pad and lubricated with sterile K-Y jelly.

Chlordiazepoxide (10 mg/kg) was used as the positive control. Compounds of the present invention, vehicle (45% hydroxypropyl beta-cyclodextrin) and chlordiazepoxide were administered orally to all groups (n=10 mice per group) 60 minutes prior to behavioral testing. All data were analyzed using an analysis of variance (ANOVA) followed by Fisher's PLSD post hoc test. An effect was considered significance if $p<0.05$. Statistical outliers above or below 2 standard deviations from the mean in any of the temperature measures were removed from the final analysis. Results are displayed in Table 5. The results showed that following administration of compounds of the present invention, the SIH response was significantly smaller than when vehicle alone was administered. The data indicate that when the compounds of the present invention are administered, the stress response is significantly reduced.

TABLE 5

Effects of compounds in the mouse SIH test

| Treatment | Dose (mg/kg, PO) | Change in Temperature (T2 − T1) ° C. Mean ± S.E.M. |
|---|---|---|
| 72 | 0 | 0.69 ± 0.07 |
| | 3 | 0.21 ± 0.11* |
| | 10 | 0.32 ± 0.05* |
| | 30 | 0.44 ± 0.10 |
| Chlordiazepoxide | 10 | −0.25 ± 0.15* |
| 200 | 0 | 0.74 ± 0.09 |
| | 3 | −0.13 ± 0.11* |
| | 10 | −0.50 ± 0.15* |
| | 30 | −0.66 ± 0.13* |
| Chlordiazepoxide | 10 | −0.66 ± 0.10* |
| 211 | 0 | 0.79 ± 0.09 |
| | 3 | 0.37 ± 0.08* |
| | 10 | 0.33 ± 0.09* |
| | 30 | 0.37 ± 0.09* |
| Chlordiazepoxide | 10 | −0.37 ± 0.09* |
| 32 | 0 | 0.60 ± 0.05 |
| | 3 | 0.26 ± 0.04* |
| | 10 | 0.28 ± 0.10* |
| | 30 | 0.37 ± 0.06* |
| Chlordiazepoxide | 10 | −0.2 ± 0.07* |
| 77 | 0 | 0.70 ± 0.10 |
| | 3 | 0.37 ± 0.15 |
| | 10 | 0.55 ± 0.11 |
| | 30 | 0.55 ± 0.12 |
| Chlordiazepoxide | 10 | −0.56 ± 0.23* |

*p value < 0.05

Example 248

Conflict protocol: The conflict procedure is a well established operant conditioning approach to evaluate anxiolytic-like effects of test compounds. In this procedure, positively-reinforced behavior is suppressed by response-contingent administration of a noxious stimulus (i.e., mild electric shock). Compounds with anxiolytic effects in humans (e.g., benzodiazepines) characteristically increase rates of responding that are suppressed by shock and are referred to as anti-conflict or anxiolytic-like effects. The conflict procedure has good predictive validity and positive correlations between the potency of benzodiazepines to produce anti-conflict effects and clinical efficacy have been demonstrated (Cook and Davidson, 1973; Kleven and Koek, 1999; Rowlett et al. 2006). In addition to anxiolytic-like effects, conflict procedures also provide an assessment of the ability of the animal to perform operant lever pressing. This is typically assessed by including lever pressing in the absence of the noxious stimulus. Most anxiolytic compounds will decrease rates of responding in the absence of shock at doses higher than those that induce anxiolytic-like effects. The effects contributing to anxiolytic-induced decreases in non-suppressed responding are not well understood, but likely consist of a combination of motor co-ordination deficits and sedative effects.

Adult rhesus monkeys were used in these studies (n=1-4). Weights of the monkeys ranged from 6.2 to 10.5 kg. The animals had been previously trained using the conflict procedure. Animals were maintained at 85-95% of their free-feeding weights by manipulation of food intake. Monkeys were individually housed with water available ad libitum, and maintained on a 12 hour lights-on/12 hour lights-off cycle (lights on at 0600 a.m.). Monkeys received Harlan Teklad diet (15% Primate Diet) as well as supplemental feeding (fruits, vegetables, and commercially available primate treats) daily. They were also given toys and video enrichment when not in an experimental session. Each animal was prepared prior to the study with a chronic indwelling venous catheter for drug delivery. A polyvinyl chloride catheter was implanted in a jugular, femoral or brachial vein under isoflurane anesthesia and aseptic conditions. The proximal end of the catheter terminated above the right atrium, and the distal end was passed subcutaneously to exit in the midscapular region. Experimental sessions began 5-7 days following surgery. Catheters had been implanted approximately 3 months to 1 year prior to the initiation of the study. During experimental sessions, monkeys were seated in primate chairs that were placed in ventilated sound-attenuating chambers. A single response lever was mounted on the wall of the chamber in front of the monkey. Each press of a lever produced an audible click and was recorded as a response via electromechanical equipment, a computer interface, and PC with specialized software. Food pellets could be delivered into a tray located next to the lever. Mild electric shock could be delivered to the bottom of the feet via brass electrodes that were fitted to shoes. Red and green lights mounted above the levers could be illuminated to serve as visual stimuli.

Monkeys were trained under a multiple schedule of food reinforcement adapted from Spealman (1979). A daily session consisted of 4 cycles, each preceded by a 10-min time out period in which all lights in the chamber were off and responding had no programmed consequences. Each cycle consisted of two components, component 1 and 2. Component 1 was signaled by red stimulus lights and consisted of an 18-response schedule (FR18) of food pellet delivery (i.e., the animal receives a food pellet following 18 responses). Component 2, signaled by green stimulus lights, followed immediately and consisted of the FR18 schedule of food delivery combined with a FR20 schedule of foot shock delivery (1.5-3.0 mA, adjusted for each monkey based on individual performance, 0.25 sec duration). Delivery of a food pellet (FR18 schedule) was followed by a 10 sec time out in which responses had no programmed consequences. Both components were 5 min in duration, or ended after the monkey obtained 5 food pellets or received 3 foot shocks, whichever occurred first.

Sessions were conducted 5 days per week at approximately the same time each day. During training sessions, monkeys received i.v. injections of saline (0.1 ml/kg) in the $5^{th}$ minute of each 10-min time out. For individual monkeys, performance was considered stable if the average rates of responding (responses/second) for component 1 and component 2 did not vary by ±20% over five consecutive sessions, with no upward or downward trends. Test sessions were initiated once performance was stable, and continued as long as the stability criteria were met on interceding training sessions. No training or test sessions were conducted the day after a test session.

During test sessions (conducted once or twice per week), i.v. injections of vehicle or compound were administered in the $5^{th}$ minute of each time out. Volume of vehicle matched the highest concentration of compound administered (~0.5 ml/kg) and as described above, different volumes of compound were administered followed by a 2ml injection of saline. In successive cycles, increasing doses of the test compound were administered using a cumulative dosing procedure, in which the dose of compound was increased in ½ $log_{10}$ units.

Data were expressed as the mean number of responses/second (±S.E.M.). All data were analyzed using a repeated measures analysis of variance (ANOVA) followed by Fisher's PLSD post hoc test. An effect was considered significance if $p<0.05$. The results are displayed in Table 6.

TABLE 6

Effects of exemplary compounds in the rhesus monkey conflict test

| Treatment<br>Dose<br>(mg/kg, IV) | | Non-Suppressed Response<br>Rates (Responses/Second)<br>Mean ± S.E.M. | Suppressed Response<br>Rates (Responses/Second)<br>Mean ± S.E.M. |
|---|---|---|---|
| Alpra-<br>zolam | 0 | 2.55 ± 0.27 | 0.02 ± 0.01 |
| | 0.003 | 2.18 ± 0.26 | 0.04 ± 0.02 |
| | 0.01 | 2.62 ± 0.32 | 0.76 ± 0.26 |
| | 0.03 | 2.38 ± 0.36 | 2.28 ± 0.55* |
| | 0.1 | 1.16 ± 0.26* | 1.44 ± 0.57* |
| 200 | 0.3 | 3.2 | 0.02 |
| | 1 | 2.9 | 0.02 |
| | 1.8 | 2.4 | 1.4* |
| | 3 | 3.1 | 1.2* |
| | 5.6 | 3.3 | 1.9* |
| 105 | 0 | 2.62 ± 0.36 | 0.06 ± 0.04 |
| | 0.1 | 2.68 ± 0.37 | 0.02 ± 0.01 |
| | 0.3 | 2.68 ± 0.39 | 0.47 ± 0.44 |
| | 1 | 2.78 ± 0.36 | 0.79 ± 0.45 |
| | 3 | 1.02 ± 0.57* | 0.46 ± 0.32 |
| 32 | 0 | 2.38 ± 0.37 | 0.02 ± 0.01 |
| | 0.1 | 2.50 ± 0.29 | 0.03 ± 0.01 |
| | 0.3 | 2.58 ± 0.44 | 0.24 ± 0.17 |
| | 1 | 1.82 ± 0.67 | 1.1 ± 0.67 |
| | 3 | 1.77 ± 0.64 | 1.19 ± 0.36* |

*p value < 0.05

Example 248

Four Plate Test (FPT) Protocol: The four plate test (FPT) is an animal model of anxiety in which simple ongoing behavior (exploration of novel surroundings) is suppressed by the delivery of mild electric foot-shock contingent to quadrant crossing (Aron, et al., 1971). Clinically effective classes of anxiolytic compounds such as benzodiazepines, selective serotonin reuptake inhibitors, or 5-$HT_{1A}$ receptor agonists produce a marked anti-punishment effect (an increase in punished crossings), which is thought to indicate anxiolytic activity (Aron, et al., 1971; Bourin, et al., 1992; Hascoet, et al., 2000; Ring, et al., 2006). The four plate apparatus (Bioseb, Chaville France) consists of a cage (18×25×16 cm) floored by four identical rectangular metal plates (8×11 cm) separated from one another by a gap of 4 mm. The plates are connected to a shocker unit that can generate electric foot shocks.

Male Swiss Webster (CFW) mice from Charles River (Wilmington, Mass.) were used for the FPT. Mice were received at 3-weeks of age. Upon receipt, mice were assigned unique identification numbers (tail marked) and were group housed with 4 mice per cage in mouse ventilated racks. All animals remained housed in groups of four during the remainder of the study. All mice were acclimated to the colony room for at least one week prior to testing and were subsequently tested at an average age of 4 weeks of age. During the period of acclimation, mice and rats were examined on a regular basis, handled, and weighed to assure adequate healtH, D and suitability. Animals were maintained on a 12/12 light/dark cycle. The room temperature was maintained between 20 and 23° C. with a relative humidity maintained between 30% and 70%. Chow and water were provided ad libitum for the duration of the study. In each test, animals were randomly assigned across treatment groups. Alprazolam (0.3 mg/kg) was used as the positive control. Compounds of the present invention, vehicle (45% hydroxypropyl beta-cyclodextrin) and alprazolam were administered orally to all groups (n=10 mice per group) 30 minutes prior to behavioral testing. Following pretreatment, mice were gently placed in the four plate chamber and allowed to explore the enclosure for 18 seconds. After the exploration period, every time the mouse crossed from one plate to another, the experimenter, blind to the dosing conditions, administered a mild electric foot-shock, and referred to as a punished crossing. The intensity and duration of the foot-shock were 0.5 mA for 0.5 seconds. The number of punished crossings was recorded during the 2 min test session. The plates were thoroughly cleaned with 70% ethanol immediately after each mouse. All data were analyzed using an analysis of variance (ANOVA) followed by Fisher's PLSD post hoc test. An effect was considered significance if p<0.05. Statistical outliers above or below 2 standard deviations from the mean in any of the temperature measures were removed from the final analysis. Results are displayed in Table 7.

TABLE 7

Effects of compounds in the mouse four plate test

| Treatment Dose (mg/kg, PO) | | Number of Punished Crossings Mean ± S.E.M. |
|---|---|---|
| 211 | 0 | 4.9 ± 0.23 |
|  | 3 | 7.8 ± 0.59* |
|  | 10 | 8.6 ± 0.85* |
|  | 30 | 8.9 ± 0.57* |
| Alprazolam | 0.3 | 12.5 ± 1.17* |
| 76 | 0 | 4.8 ± 0.25 |
|  | 3 | 6.7 ± 0.45* |
|  | 10 | 6.9 ± 0.35* |
|  | 30 | 6.3 ± 0.62* |
| Alprazolam | 0.3 | 11.9 ± 0.46* |
| 60 | 0 | 6.2 ± 0.36 |
|  | 3 | 6.3 ± 0.45 |
|  | 10 | 6.3 ± 0.70 |
|  | 30 | 6.0 ± 0.30 |
| Alprazolam | 0.3 | 11.6 ± 0.65* |
| 72 | 0 | 4.9 ± 0.46 |
|  | 3 | 5.8 ± 0.63 |
|  | 10 | 5.2 ± 0.47 |
|  | 30 | 4.8 ± 0.36 |

TABLE 7-continued

Effects of compounds in the mouse four plate test

| Treatment Dose (mg/kg, PO) | | Number of Punished Crossings Mean ± S.E.M. |
|---|---|---|
| Alprazolam | 0.3 | 12.1 ± 0.94* |
| 200 | 0 | 5.8 ± 0.29 |
|  | 3 | 7.2 ± 0.52* |
|  | 10 | 8.6 ± 0.43* |
|  | 30 | 7.5 ± 0.39* |
| Alprazolam | 0.3 | 12.4 ± 0.42* |
| 77 | 0 | 4.8 ± 0.20 |
|  | 3 | 4.3 ± 0.26 |
|  | 10 | 4.6 ± 0.31 |
|  | 30 | 5.0 ± 0.37 |
| Alprazolam | 0.3 | 9.6 ± 0.65* |
| 32 | 0 | 5.7 ± 0.94 |
|  | 3 | 6.6 ± 0.72 |
|  | 10 | 6.6 ± 0.67 |
|  | 30 | 5.7 ± 0.94 |
| Alprazolam | 0.3 | 12.0 ± 0.58* |
| 105 | 0 | 5.4 ± 0.22 |
|  | 3 | 6.7 ± 0.34 |
|  | 10 | 5.5 ± 0.60 |
|  | 30 | 5.6 ± 0.52 |
| Alprazolam | 0.3 | 9.4 ± 0.41* |

*p value < 0.05

Example 249

Vogel Conflict Test Protocol: The Vogel conflict test is an animal model of anxiety described by Vogel et al. (1971). In this test, water deprived animals are placed in a cage with free access to a drinking bottle. Whenever the animal drinks, an electric shock is administered. Animals punished during drinking rapidly cease to drink. Anxiolytic drugs decrease the effect of punishment and increase the number of shocks accepted by the rats in this conflict situation. Male Wistar rats were used in these studies. Rats were deprived of water for approximately 48 hours and then placed individually into a transparent Plexiglas enclosure with a floor consisting of stainless steel bars spaced 1 cm apart. The back wall of the enclosure was made of opaque Plexiglas thereby concealing the observer from the experimental animal. In the center of the opposite wall, 5 cm above the floor, a metal water spout protruded into the cage and was connected to one pole of a shock generator. The other pole of the shock generator was connected to the metal grid floor. The rat is left to explore until it finds the water spout. Then, every time it drinks, it receives an electric shock (1.7 mA, 1 sec duration) 2 seconds after it starts drinking The number of punished drinks is counted during a 3 minute test. Ten rats are studied per treatment group. Clobazam (64 mg/kg) was used as the positive control. Compounds of the present invention, vehicle (45% hydroxypropyl beta-cyclodextrin) and clobazam were administered orally to all groups (n=10 mice per group) 60 minutes prior to behavioral testing. All data were analyzed using unpaired Student's t-tests. An effect was considered significance if p<0.05. Results are displayed in Table 8.

TABLE 8

Effects of compounds in the rat Vogel conflict test

| Treatment Dose (mg/kg, PO) | | Number of Shocks Mean ± S.E.M. |
|---|---|---|
| 32 | 0 | 4.2 ± 0.5 |
|  | 3 | 3.8 ± 0.6 |
|  | 10 | 3.8 ± 0.7 |
|  | 30 | 6.6 ± 2.3 |

TABLE 8-continued

Effects of compounds in the rat Vogel conflict test

| Treatment | Dose (mg/kg, PO) | Number of Shocks Mean ± S.E.M. |
|---|---|---|
| Clobazam | 64 | 8.3 ± 1.2* |
| 105 | 0 | 5.3 ± 1.1 |
|  | 3 | 5.1 ± 0.6 |
|  | 10 | 5.8 ± 0.8 |
|  | 30 | 8.2 ± 1.8 |
| Clobazam | 64 | 10.1 ± 1.2* |
| 211 | 0 | 5.2 ± 0.8 |
|  | 3 | 3.9 ± 0.5 |
|  | 10 | 5.3 ± 0.8 |
|  | 30 | 5.0 ± 1.1 |
| Clobazam | 64 | 8.9 ± 0.8* |
| 200 | 0 | 4.0 ± 0.5 |
|  | 3 | 8.4 ± 2.1 |
|  | 10 | 8.9 ± 2.3* |
|  | 30 | 9.5 ± 2.1* |
| Clobazam | 64 | 9.2 ± 0.7* |
| 40 | 0 | 3.0 ± 0.4 |
|  | 1 | 2.4 ± 0.4 |
|  | 3 | 3.4 ± 0.7 |
|  | 10 | 4.4 ± 0.7 |
| Clobazam | 64 | 6.6 ± 1.0* |
| 170 | 0 | 4.6 ± 0.6 |
|  | 0.3 | 5.1 ± 0.9 |
|  | 1 | 5.6 ± 0.9 |
|  | 3 | 6.5 ± 1.0 |
| Clobazam | 64 | 8.4 ± 1.3* |

*p value < 0.05

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound having the structure:

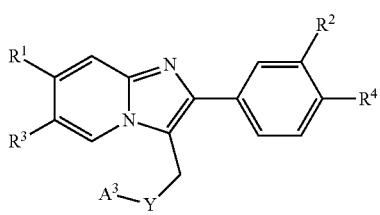

wherein:

$R^1$, $R^2$, $R^3$ and $R^4$ are each members independently selected from H, D, halogen, hydroxyl, dialkylamino, cyano, sulfonamide, acyl, substituted alkyl, substituted or unsubstituted alkoxy, substituted or unsubstituted heterocycloalkyl, substituted or unsubstituted aryl and substituted or unsubstituted heteroaryl; wherein substituents on said substituted alkyl, substituted alkoxy, substituted heterocycloalkyl, substituted aryl and substituted heteroaryl are chosen from —OR', =O, =NR', —NR'R", —SR', -halogen, —OC(O)R', —C(O)R', —CO$_2$R'—NR"C(O)R', —NR'—C(O)NR"R'", —S(O)R', —S(O)$_2$R', —S(O)$_2$NR'R", —NRSO$_2$R', —CN and —NO$_2$; wherein R, R', R" and R'" are chosen independently from H, alkyl and aryl; and substituents on said substituted aryl and substituted heteroaryl may additionally be alkyl;

Y is a member selected from a single bond, NH, ND, S, and O; and $A^3$ is selected from:

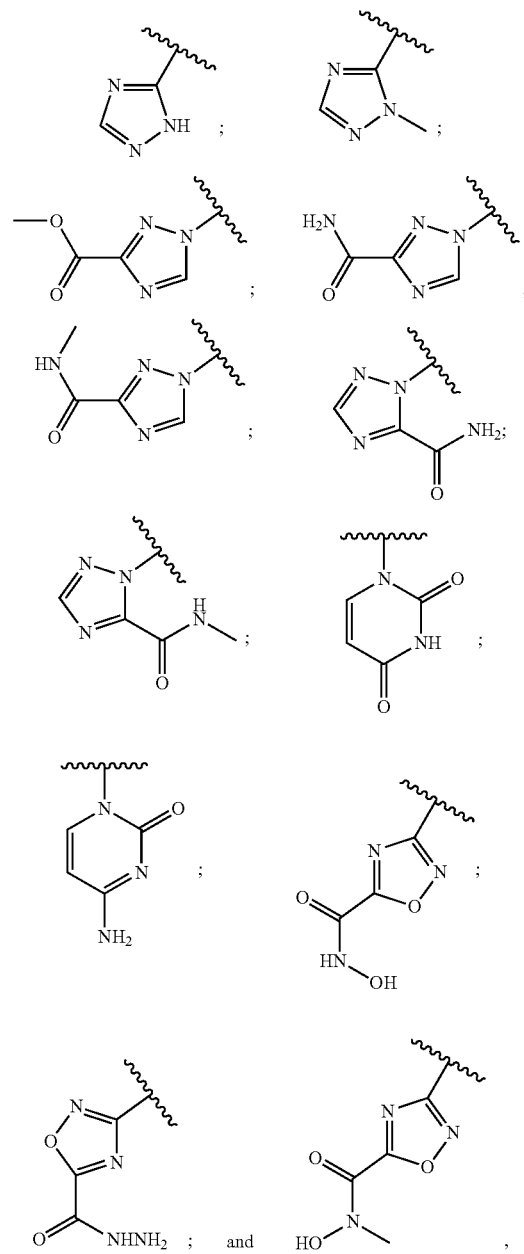

or a pharmaceutically acceptable salt thereof.

2. The compound of claim 1, wherein $R^1$, $R^2$, $R^3$ and $R^4$ are independently selected from H, D, halogen, substituted alkyl and substituted or unsubstituted alkoxy.

3. The compound of claim 1, wherein $R^1$ and $R^2$ are H and $R^3$ and $R^4$ are selected from chlorine, fluorine, bromine and hydrogen.

4. The compound of claim 3 having the formula:

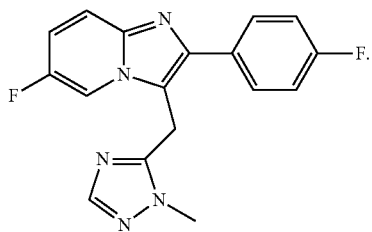 [SMILES: Cn1ncnc1Cc1c(-c2ccc(F)cc2)nc2ccc(F)cn12]

5. The compound of claim 3 having the formula:

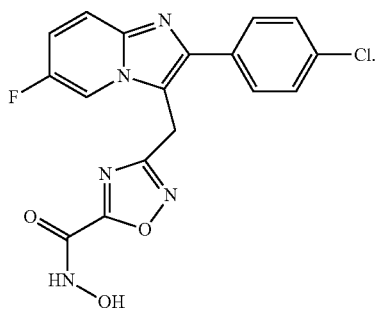 [SMILES: O=C(NO)c1nc(Cc2c(-c3ccc(Cl)cc3)nc3ccc(F)cn23)no1]

6. The compound of claim 3 having the formula:

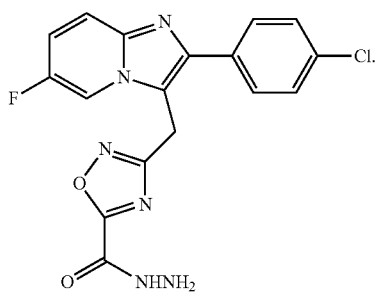 [SMILES: NNC(=O)c1nc(Cc2c(-c3ccc(Cl)cc3)nc3ccc(F)cn23)no1]

7. The compound of claim 3 having the formula:

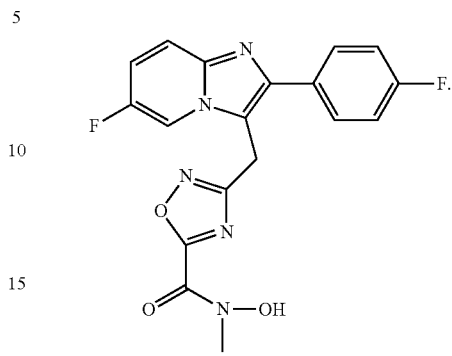

8. The compound having the formula:

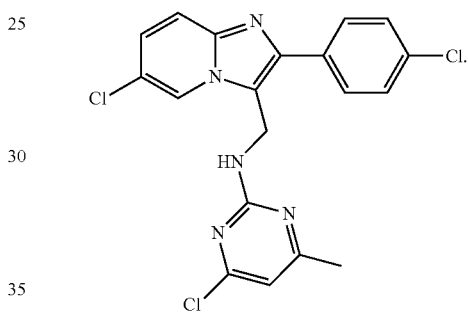

9. The compound according to claim 1 as a pharmaceutically acceptable salt.

10. A pharmaceutical composition comprising a compound according to claim 1 and a pharmaceutically acceptable carrier.

* * * * *